United States Patent
Li et al.

(10) Patent No.: US 9,133,204 B2
(45) Date of Patent: Sep. 15, 2015

(54) 5-MEMBERED HETEROCYCLIC AMIDES AND RELATED COMPOUNDS

(71) Applicant: H. Lundbeck A/S, Valby (DK)

(72) Inventors: Hongbin Li, Madson, CT (US); Jun Yuan, Boston, MA (US); Rajagopal Bakthavatchalam, Madison, CT (US); Kevin J Hodgetts, Framingham, MA (US); Qin Guo, Waterford, CT (US); Scott M. Capitosti, Perry, OH (US); Jianmin Mao, Winchester, MA (US); David J. Wustrow, Los Gatos, CA (US)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 14/480,979

(22) Filed: Sep. 9, 2014

(65) Prior Publication Data

US 2015/0005293 A1    Jan. 1, 2015

Related U.S. Application Data

(63) Continuation of application No. 12/669,308, filed as application No. PCT/US2008/070613 on Jul. 21, 2008, now abandoned.

(60) Provisional application No. 60/950,625, filed on Jul. 19, 2007.

(51) Int. Cl.
| | |
|---|---|
| *C07D 403/04* | (2006.01) |
| *C07D 487/04* | (2006.01) |
| *C07D 231/14* | (2006.01) |
| *C07D 277/56* | (2006.01) |
| *C07D 333/38* | (2006.01) |
| *C07D 401/04* | (2006.01) |
| *C07D 401/14* | (2006.01) |
| *C07D 403/06* | (2006.01) |
| *C07D 403/12* | (2006.01) |
| *C07D 403/14* | (2006.01) |
| *C07D 405/12* | (2006.01) |
| *C07D 409/04* | (2006.01) |
| *C07D 417/14* | (2006.01) |
| *C07D 401/12* | (2006.01) |

(52) U.S. Cl.
CPC ............ *C07D 487/04* (2013.01); *C07D 231/14* (2013.01); *C07D 277/56* (2013.01); *C07D 333/38* (2013.01); *C07D 401/04* (2013.01); *C07D 401/12* (2013.01); *C07D 401/14* (2013.01); *C07D 403/04* (2013.01); *C07D 403/06* (2013.01); *C07D 403/12* (2013.01); *C07D 403/14* (2013.01); *C07D 405/12* (2013.01); *C07D 409/04* (2013.01); *C07D 417/14* (2013.01)

(58) Field of Classification Search
USPC ....................................... 544/122; 514/235.8
See application file for complete search history.

(56) References Cited

U.S. PATENT DOCUMENTS

| | | |
|---|---|---|
| 3,852,293 A | 12/1974 | Ariyan et al. |
| 5,948,777 A | 9/1999 | Bender et al. |
| 6,323,227 B1 | 11/2001 | Klein et al. |
| 6,511,998 B2 | 1/2003 | Kordik et al. |
| 6,596,746 B1 | 7/2003 | Das et al. |
| 6,864,252 B2 | 3/2005 | Sakya et al. |
| 6,956,053 B2 | 10/2005 | McDonald et al. |
| 7,125,875 B2 | 10/2006 | Das et al. |
| 7,223,780 B2 | 5/2007 | Nazare et al. |
| 7,223,782 B2 | 5/2007 | Atkinson et al. |
| 7,235,549 B2 | 6/2007 | Duplantier et al. |
| 7,294,644 B2 | 11/2007 | Mayweg et al. |
| 7,491,821 B2 | 2/2009 | Brotherton-Pleiss et al. |
| 7,517,900 B2 | 4/2009 | Pendri et al. |
| 7,863,314 B2 | 1/2011 | Fryszman et al. |
| 8,501,746 B2 | 8/2013 | Dales et al. |

(Continued)

FOREIGN PATENT DOCUMENTS

| | | |
|---|---|---|
| AU | 2007/256708 A1 | 12/2007 |
| DE | 2221647 A1 | 11/1972 |

(Continued)

OTHER PUBLICATIONS

International Search Report and Written Opinion, issued Feb. 12, 2009 for International Application PCT/US2008/070613, filed Jul. 21, 2008.

(Continued)

*Primary Examiner* — Nyeemah A Grazier
(74) *Attorney, Agent, or Firm* — Mary Catherine Di Nunzio

(57) ABSTRACT

5-Membered heterocyclic amides and related compounds are provided, of the Formula: wherein variables are as described herein. Such compounds are ligands that may be used to modulate specific receptor activity in vivo or in vitro, and are particularly useful in the treatment of conditions associated with pathological receptor activation in humans, domesticated companion animals and livestock animals. Pharmaceutical compositions and methods for using such compounds to treat such disorders are provided, as are methods for using such ligands for receptor localization studies.

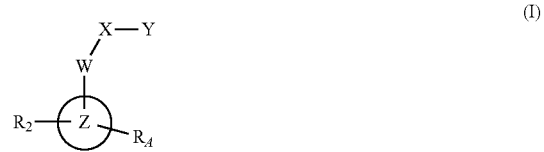

(I)

13 Claims, No Drawings

(56) References Cited

U.S. PATENT DOCUMENTS

| | | |
|---|---|---|
| 2004/0220170 A1 | 11/2004 | Atkinson et al. |
| 2004/0235926 A1 | 11/2004 | Sakya |
| 2005/0020564 A1 | 1/2005 | Atkinson et al. |
| 2005/0261290 A1 | 11/2005 | Cheng et al. |

FOREIGN PATENT DOCUMENTS

| | | |
|---|---|---|
| DE | 2331246 A1 | 1/1974 |
| DE | 102004051277 A1 | 4/2006 |
| WO | 97/005131 A1 | 2/1997 |
| WO | 99/29660 A1 | 6/1999 |
| WO | 99/29661 A1 | 6/1999 |
| WO | 03/037274 | 5/2003 |
| WO | 2004/041813 A1 | 5/2004 |
| WO | 2004/048334 A1 | 6/2004 |
| WO | 2004/099146 A1 | 11/2004 |
| WO | 2005/014529 A1 | 2/2005 |
| WO | 2005/035514 | 4/2005 |
| WO | 2005/049018 A1 | 6/2005 |
| WO | 2005/061462 A2 | 7/2005 |
| WO | 2005/075435 A1 | 8/2005 |
| WO | 2005/095386 A1 | 10/2005 |
| WO | 2006/045350 A1 | 5/2006 |
| WO | 2006/089076 A2 | 8/2006 |
| WO | 2007/020194 A1 | 2/2007 |
| WO | 2007/056046 A1 | 5/2007 |
| WO | 2007/056091 A1 | 5/2007 |
| WO | 2007/087283 A2 | 8/2007 |
| WO | 2008/011131 A2 | 1/2008 |
| WO | 2008/045484 A1 | 4/2008 |
| WO | 2008/073825 | 6/2008 |
| WO | 2008/117241 A2 | 10/2008 |
| WO | 2008/138876 A1 | 11/2008 |

OTHER PUBLICATIONS

Supplementary Search Report for corresponding European Application No. 08796352.6, issued Feb. 11, 2011.

Written Opinion for corresponding Singapore Application No. 200908543-2, issued Feb. 22, 2011.

Office Action for corresponding Eurasian Application No. 200971084, issued Jul. 21, 2011.

Office Action for corresponding Chinese Application No. 200880021346.2 issued Dec. 25, 2012.

Baraldi, P.G., et al., (Feb. 17, 2004), "Design Synthesis and Biological Evaluation of New 8-Heterocyclic Xanthine Derivatives as Highly Potent and Delective Human A2B Adenosine Receptor Antagonists", J.Med. Chem., vol. 47, No. 6, pp. 1434-1447, XP002619021.

Office Action for Japanese Application 2013-243253, issued Nov. 11, 2014.

5-MEMBERED HETEROCYCLIC AMIDES AND RELATED COMPOUNDS

CROSS-REFERENCE TO RELATE APPLICATIONS

The present application is a continuation of U.S. application Ser. No. 12/669,308 filed Aug. 4, 2010 which is a 371 of PCT International Application No. PCT/US2008/070613 filed Jul. 21, 2008, which claims priority of U.S. Provisional Application No. 60/950,625 filed Jul. 19, 2007. Each of these applications is hereby incorporated by reference in its entirety.

FIELD OF THE INVENTION

This invention relates generally to 5-membered heterocyclic amides and related compounds that have useful pharmacological properties. The invention further relates to the use of such compounds for treating conditions related to $P2X_7$ receptor activation, for identifying other agents that bind to $P2X_7$ receptor, and as probes for the detection and localization of $P2X_7$ receptors.

BACKGROUND OF THE INVENTION

Pain perception, or nociception, is mediated by the peripheral terminals of a group of specialized sensory neurons, termed "nociceptors." A wide variety of physical and chemical stimuli induce activation of such neurons in mammals, leading to recognition of a potentially harmful stimulus. Inappropriate or excessive activation of nociceptors, however, can result in debilitating acute or chronic pain.

Neuropathic pain, which typically results from damage to the nervous system, involves pain signal transmission in the absence of stimulus, pain from a normally innocuous stimulus (allodynia) and increased pain from a normally painful stimulus (hyperalgesia). In most instances, neuropathic pain is thought to occur because of sensitization in the peripheral and central nervous systems following initial damage to the peripheral system (e.g., via direct injury or systemic disease). Neuropathic pain is typically burning, shooting and unrelenting in its intensity and can sometimes be more debilitating than the initial injury or disease process that induced it.

Existing treatments for neuropathic pain are generally suboptimal. Opiates, such as morphine, are potent analgesics, but their usefulness is limited because of adverse side effects, such as physical addictiveness and withdrawal properties, as well as respiratory depression, mood changes, and decreased intestinal motility with concomitant constipation, nausea, vomiting, and alterations in the endocrine and autonomic nervous systems. In addition, neuropathic pain is frequently non-responsive or only partially responsive to conventional opioid analgesic regimens, or to treatment with other drugs, such as gabapentin. Treatments employing the N-methyl-D-aspartate antagonist ketamine or the alpha(2)-adrenergic agonist clonidine can reduce acute or chronic pain, and permit a reduction in opioid consumption, but these agents are often poorly tolerated due to side effects.

Another common condition for which existing therapies are insufficient or problematic is inflammation. Transient inflammation is a beneficial mechanism that protects mammals from invading pathogens. Uncontrolled inflammation, however, causes tissue damage and pain and is the underlying cause of many illnesses, including asthma, as well as other allergic, infectious, autoimmune, degenerative, and idiopathic diseases. Existing treatments often exhibit low, delayed or only temporary efficacy, undesirable side-effects and/or a lack of selectivity. There is a continuing need for new drugs that overcome one or more of the shortcomings of drugs currently used for immunosuppression or in the treatment or prevention of inflammatory disorders, including allergic disorders, autoimmune disorders, fibrogenic disorders, and neurodegenerative diseases, such as amyotrophic lateral sclerosis, Alzheimer's disease, and Huntington's disease.

The $P2X_7$ receptor is a ligand-gated ion channel that is activated by ATP and is present on a variety of cell types, including microglia in the central nervous system and cells involved in inflammation and immune system function, such as immune cells. In particular, $P2X_7$ is involved in activation of lymphocytes and monocyte/macrophages leading to the increased release of pro-inflammatory cytokines (e.g., TNFalpha and IL-1beta) from these cells. Recent studies indicate that inhibiting $P2X_7$ receptor activation in situations of inflammation (e.g., rheumatoid arthritis and other autoimmune diseases, osteoarthritis, uveitis, asthma, chronic obstructive pulmonary disease and inflammatory bowel disease) or interstitial fibrosis results in a therapeutic effect. These and other studies indicate that $P2X_7$ receptor antagonists may find use in the treatment and prophylaxis of pain, including acute, chronic and neuropathic pain, as well as a variety of other conditions including osteoarthritis, rheumatoid arthritis, arthrosclerosis, inflammatory bowel disease, Alzheimer's disease, traumatic brain injury, asthma, chronic obstructive pulmonary disease, and fibrosis of internal organs (e.g., interstitial fibrosis).

Small molecule $P2X_7$ receptor antagonists are desirable for such therapies. The present invention fulfills this need, and provides further related advantages.

SUMMARY OF THE INVENTION

The present invention provides 5-membered heterocyclic amides and related compounds of Formula A:

Formula A as well as pharmaceutically acceptable salts, solvates (e.g., hydrates), amides and esters of such compounds.
Within Formula A:

represents a 5-membered heteroaryl ring;
W is —C(=O)NR$_4$—, —NR$_4$C(=O)— or —NR$_4$—NR$_4$—C(=O)—;
X is absent or $C_1$-$C_6$alkylene that is optionally substituted and is preferably substituted with from 0 to 4 substituents independently chosen from: (i) hydroxy and —COOH; (ii) $C_1$-$C_8$alkyl, ($C_3$-$C_8$cycloalkyl)$C_0$-$C_4$alkyl, $C_1$-$C_6$aminoalkyl, $C_2$-$C_8$alkyl ether, mono- or di-($C_1$-$C_6$alkyl)amino$C_0$-$C_4$alkyl, (4- to 7-membered heterocycloalkyl)$C_0$-$C_4$alkyl and phenyl$C_0$-$C_2$alkyl; (iii) substituents that are taken together, with any intervening carbon atoms, to form a 3- to 7-membered cycloalkyl or a 4- to 7-membered heterocycloalkyl; and (iv) substituents that are taken together with $R_4$ and any intervening atoms to form a 4- to 7-membered heterocycloalkyl; each of which (ii), (iii) and (iv) is optionally substituted, and each of which (ii), (iii) and (iv) is preferably substituted with from 0 to 3 substituents independently chosen from hydroxy, halogen, amino, oxo, aminocarbonyl, aminosulfonyl, —COOH, $C_1$-$C_6$alkyl, $C_1$-$C_6$haloalkyl, $C_1$-$C_6$alkoxy, ($C_3$-$C_7$cycloalkyl)$C_0$-$C_4$alkyl, mono- or di-($C_1$-$C_6$alkyl)amino, mono- or di-($C_1$-$C_6$alkyl)aminocarbonyl, mono- or di-($C_1$-$C_6$alkyl)aminosulfonyl and 4- to 7-membered heterocycloalkyl;

Y is $C_1$-$C_8$alkyl, $C_3$-$C_{16}$cycloalkyl, 4- to 16-membered heterocycloalkyl, 6- to 16-membered aryl or (5- to 16-membered heteroaryl, each of which is optionally substituted and each of which is preferably substituted with from 0 to 6 substituents independently chosen from hydroxy, halogen, cyano, amino, nitro, oxo, aminocarbonyl, aminosulfonyl, —COOH, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$aminoalkyl, $C_1$-$C_6$alkoxy, $C_1$-$C_6$haloalkoxy, $C_2$-$C_6$alkyl ether, $C_1$-$C_6$alkanoyl, $C_1$-$C_6$alkylsulfonyl, ($C_3$-$C_7$cycloalkyl)$C_0$-$C_4$alkyl, mono- or di-($C_1$-$C_6$alkyl)amino, $C_1$-$C_6$alkanoylamino, mono- or di-($C_1$-$C_6$alkyl)aminocarbonyl, mono- or di-($C_1$-$C_6$alkyl)aminosulfonyl and ($C_1$-$C_6$alkyl)sulfonylamino;

$R_2$ represents from 0 to 2 substituents independently chosen from halogen, cyano, amino, nitro, aminocarbonyl, aminosulfonyl, —COOH, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$aminoalkyl, $C_1$-$C_6$alkoxy, $C_1$-$C_6$haloalkoxy, $C_1$-$C_6$alkanoyl, $C_2$-$C_6$alkyl ether, ($C_3$-$C_7$cycloalkyl)$C_0$-$C_4$alkyl, mono- or di-($C_1$-$C_6$alkyl)amino, $C_1$-$C_6$alkylsulfonyl, $C_1$-$C_6$alkanoylamino, mono- or di-($C_1$-$C_6$alkyl)aminocarbonyl, mono- or di-($C_1$-$C_6$alkyl)aminosulfonyl and ($C_1$-$C_6$alkyl)sulfonylamino;

each $R_4$ is independently hydrogen, $C_1$-$C_6$alkyl, ($C_3$-$C_8$cycloalkyl)$C_0$-$C_2$alkyl or taken together with a substituent of X to form a 4- to 7-membered heterocycloalkyl; and $R_A$ is a group of the formula -L-A-M, wherein:
L is absent or $C_1$-$C_6$alkylene that is optionally modified by the replacement of a carbon-carbon single bond with a double or triple carbon-carbon bond, which alkylene is optionally substituted with oxo, —COOH, —SO$_3$H, —SO$_2$NH$_2$, —PO$_3$H$_2$, tetrazole or oxadiazolone;
A is absent or CO, O, NR$_6$, S, SO, SO$_2$, CONR$_6$, NR$_6$CO, ($C_4$-$C_7$cycloalkyl)$C_0$-$C_2$alkyl, 4- to 7-membered heterocycloalkyl or 5- or 6-membered heteroaryl; wherein $R_6$ is hydrogen or $C_1$-$C_6$alkyl; and
M is:
(i) hydroxy, halogen, cyano, amino, aminocarbonyl, aminosulfonyl or —COOH; or
(ii) $C_1$-$C_6$alkyl, $C_1$-$C_6$halo alkyl, $C_1$-$C_6$alkoxy, (4- to 10-membered carbocycle)$C_0$-$C_4$alkyl, (4- to 10-membered heterocycle)$C_0$-$C_4$alkyl, $C_1$-$C_6$alkanoyloxy, $C_6$alkanoylamino, $C_1$-$C_6$alkylsulfonyl, $C_1$-$C_6$alkylsulfonylamino, $C_1$-$C_6$alkylsulfonyloxy, mono- or di-$C_1$-$C_6$alkylamino, mono- or di-($C_1$-$C_6$alkyl)aminosulfonyl, or mono- or di-($C_1$-$C_6$alkyl)aminocarbonyl; each of which is optionally substituted and each of which is preferably substituted with from 0 to 4 substituents independently chosen from oxo, amino, halogen, hydroxy, cyano, aminocarbonyl, aminosulfonyl, —COOH, $C_1$-$C_6$alkyl, $C_1$-$C_6$hydroxyalkyl, $C_1$-$C_6$haloalkyl, $C_1$-$C_6$alkoxy, $C_1$-$C_6$haloalkoxy, $C_2$-$C_6$alkyl ether, $C_1$-$C_6$alkanoylamino, mono- or di-($C_1$-$C_6$alkyl)amino, $C_1$-$C_6$alkylsulfonyl, $C_1$-$C_6$alkylsulfonylamino, mono- or di-($C_1$-$C_6$alkyl)aminosulfonyl, mono- or di-($C_1$-$C_6$alkylamino)carbonyl, and 4- to 7-membered heterocycle.

Within certain aspects, the present invention provides 5-membered heterocyclic amides and related compounds of Formula I:

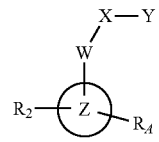

Formula I in which:
Y is $C_4$-$C_{12}$cycloalkyl that is substituted with from 0 to 6 substituents independently chosen from halogen, hydroxy, cyano, amino, nitro, oxo, aminocarbonyl, aminosulfonyl, —COOH, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, ($C_3$-$C_7$cycloalkyl)$C_0$-$C_4$alkyl, (4- to 7-membered heterocycloalkyl)$C_0$-$C_4$alkyl and mono- or di-($C_1$-$C_6$alkyl)amino$C_0$-$C_4$alkyl;

$R_2$ represents from 0 to 2 substituents independently chosen from halogen, cyano, amino, nitro, aminocarbonyl, aminosulfonyl, —COOH, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$aminoalkyl, $C_1$-$C_6$alkoxy, $C_1$-$C_6$haloalkoxy, $C_1$-$C_6$alkanoyl, $C_2$-$C_6$alkyl ether, ($C_3$-$C_7$cycloalkyl)$C_0$-$C_4$alkyl, mono- or di-($C_1$-$C_6$alkyl)amino, $C_1$-$C_6$alkylsulfonyl, $C_1$-$C_6$alkanoylamino, mono- or di-($C_1$-$C_6$alkyl)aminocarbonyl, mono- or di-($C_1$-$C_6$alkyl)aminosulfonyl and ($C_1$-$C_6$alkyl)sulfonylamino; such that $R_2$ is not an alkoxy or haloalkoxy group if

represents pyrazole or imidazole;
$R_A$ is a group of the formula -L-A-M, wherein L and A are as described above and M is:
(i) hydroxy, cyano, amino, aminocarbonyl, aminosulfonyl or —COOH; or
(ii) $C_3$-$C_6$alkyl, $C_1$-$C_6$haloalkyl, $C_1$-$C_6$alkoxy, (4- to 10-membered carbocycle)$C_0$-$C_4$alkyl, (4- to 7-membered heterocycle)$C_0$-$C_4$alkyl, $C_1$-$C_6$alkanoyloxy, $C_1$-$C_6$alkanoylamino, $C_1$-$C_6$alkylsulfonyl, $C_1$-$C_6$alkylsulfonylamino, $C_1$-$C_6$alkylsulfonyloxy, mono- or di-$C_1$-$C_6$alkylamino, mono- or di-($C_1$-$C_6$alkyl)aminosulfonyl, or mono- or di-($C_1$-$C_6$alkyl)aminocarbonyl; each of which is optionally substituted and each of which is preferably substituted with from 0 to 4 substituents independently chosen from oxo, amino, halogen, hydroxy, cyano, aminocarbonyl, aminosulfonyl, —COOH, $C_1$-$C_6$alkyl, $C_1$-$C_6$hydroxyalkyl, $C_1$-$C_6$haloalkyl, $C_1$-$C_6$alkoxy, $C_1$-$C_6$haloalkoxy, $C_2$-$C_6$alkyl ether, $C_1$-$C_6$alkanoylamino, mono- or di-($C_1$-$C_6$alkyl)amino, $C_1$-$C_6$alkylsulfonyl, $C_1$-$C_6$alkylsulfonylamino, mono- or di-($C_1$-$C_6$alkyl)aminosulfonyl, mono- or di-($C_1$-$C_6$alkylamino)carbonyl, and 4- to 7-membered heterocycle;

such that:

$R_4$ is not unsubstituted benzyl; and if

represents pyrazole or imidazole and L is absent, then:

(a) A is not O; and (b) if A is absent, then M is not unsubstituted or substituted $C_1$-$C_6$alkoxy;

and the remaining variables are as described for Formula A.

Within certain aspects, the present invention provides 5-membered heterocyclic amides and related compounds of Formula A that further satisfy Formula III:

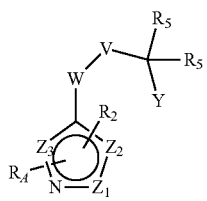

Formula III as well as pharmaceutically acceptable salts, solvates (e.g., hydrates), amides and esters of such compounds.

Within Formula III:

$Z_1$, $Z_2$ and $Z_3$ are independently N, NH, CH, S or O; such that no more than one of $Z_1$, $Z_2$ and $Z_3$ is chosen from O and S;

W, $R_2$ and $R_4$ are as described for Formula A;

V is $C_1$-$C_6$alkylene that is optionally substituted and is preferably substituted with from 0 to 4 substituents independently chosen from: (i) $C_1$-$C_4$alkyl, ($C_3$-$C_8$cycloalkyl)$C_0$-$C_2$alkyl and phenyl$C_0$-$C_2$alkyl; (ii) substituents that are taken together, with any intervening carbon atoms, to form a 3- to 7-membered cycloalkyl or a 4- to 7-membered heterocycloalkyl ring; and (iii) substituents that are taken together with $R_4$ and any intervening atoms to form a 4- to 7-membered heterocycloalkyl;

Y is $C_3$-$C_{16}$cycloalkyl, 6- to 16-membered aryl or 5- to 16-membered heteroaryl, each of which is optionally substituted and each of which is preferably substituted with from 0 to 6 substituents independently chosen from hydroxy, halogen, cyano, amino, nitro, oxo, aminocarbonyl, aminosulfonyl, —COOH, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$aminoalkyl, $C_1$-$C_6$alkoxy, $C_1$-$C_6$haloalkoxy, $C_2$-$C_6$alkyl ether, $C_1$-$C_6$alkanoyl, $C_1$-$C_6$alkylsulfonyl, ($C_3$-$C_7$cycloalkyl)$C_0$-$C_4$alkyl, mono- or di-($C_1$-$C_6$alkyl)amino, $C_1$-$C_6$alkanoylamino, mono- or di-($C_1$-$C_6$alkyl)aminocarbonyl, mono- or di-($C_1$-$C_6$alkyl)aminosulfonyl and ($C_1$-$C_6$alkyl)sulfonylamino;

Either:

(i) each $R_5$ is independently hydrogen, —COOH, $C_1$-$C_6$alkyl or ($C_3$-$C_7$cycloalkyl)$C_0$-$C_4$alkyl, such that at least one $R_5$ is not hydrogen; or (ii) both $R_5$ moieties are taken together, with the carbon atom to which they are bound, to form a $C_3$-$C_7$cycloalkyl; and $R_4$ is a group of the formula -L-A-M, wherein:

L is as described for Formula A;

A is absent or CO, O, $NR_6$, S, SO, $SO_2$, $CONR_6$, ($C_4$-$C_7$cycloalkyl)$C_0$-$C_2$alkyl, or 4- to 7-membered heterocycloalkyl; wherein $R_6$ is hydrogen or $C_1$-$C_6$alkyl; and M is a (5- to 10-membered heteroaryl)$C_0$-$C_4$alkyl that is optionally substituted and is preferably substituted with from 0 to 4 substituents independently chosen from oxo, amino, halogen, hydroxy, cyano, aminocarbonyl, aminosulfonyl, —COOH, $C_1$-$C_6$alkyl, $C_2$-$C_6$alkenyl, $C_1$-$C_6$hydroxyalkyl, $C_1$-$C_6$haloalkyl, $C_1$-$C_6$alkoxy, $C_1$-$C_6$haloalkoxy, $C_2$-$C_6$alkyl ether, $C_1$-$C_6$alkanoylamino, mono- or di-($C_1$-$C_6$alkyl)amino, $C_1$-$C_6$alkylsulfonyl, $C_1$-$C_6$alkylsulfonylamino, mono- or di-($C_1$-$C_6$alkyl)aminosulfonyl, mono- or di-($C_1$-$C_6$alkylamino)carbonyl, and 4- to 7-membered heterocycle;

such that $R_4$ is not pyrrole.

Within further aspects, the present invention provides 5-membered heterocyclic amides and related compounds of Formula A that further satisfy Formula IV or Formula V:

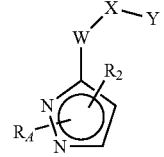

Formula IV

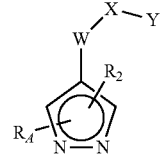

Formula V as well as pharmaceutically acceptable salts, solvates (e.g., hydrates), amides and esters of such compounds.

Within Formulas IV and V:

W is —C(=O)$NR_4$— or —$NR_4$C(=O)—;

X is $C_2$-$C_6$alkylene that is substituted with from 0 to 4 substituents independently chosen from:

(i) hydroxy and —COOH;

(ii) $C_1$-$C_8$alkyl, ($C_3$-$C_8$cycloalkyl)$C_0$-$C_4$alkyl, $C_1$-$C_6$aminoalkyl, $C_2$-$C_8$alkyl ether, mono- or di-($C_1$-$C_6$alkyl)amino$C_0$-$C_4$alkyl, (4- to 7-membered heterocycloalkyl)$C_0$-$C_4$alkyl and phenyl$C_0$-$C_2$alkyl;

(iii) substituents that are taken together, with any intervening carbon atoms, to form a 3- to 7-membered cycloalkyl or a 4- to 7-membered heterocycloalkyl; and (iv) substituents that are taken together with $R_4$ and any intervening atoms to form a 4- to 7-membered heterocycloalkyl;

each of which (ii), (iii) and (iv) is substituted with from 0 to 3 substituents independently chosen from hydroxy, halogen, amino, oxo, aminocarbonyl, aminosulfonyl, —COOH, $C_1$-$C_6$alkyl, $C_1$-$C_6$haloalkyl, $C_1$-$C_6$alkoxy, ($C_3$-$C_7$cycloalkyl)$C_0$-$C_4$alkyl, mono- or di-($C_1$-$C_6$alkyl)amino, mono- or di-($C_1$-$C_6$alkyl)aminocarbonyl, mono- or di-($C_1$-$C_6$alkyl)aminosulfonyl and 4- to 7-membered heterocycloalkyl;

$R_2$ and $R_4$ are as described for Formula A;

Y is $C_3$-$C_{16}$cycloalkyl, phenyl or 6- to 10-membered heterocycle, each of which is optionally substituted and each of which is preferably substituted with from 0 to 6 substituents independently chosen from hydroxy, halogen, cyano, amino, nitro, oxo, aminocarbonyl, aminosulfonyl, —COOH, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$aminoalkyl, $C_1$-$C_6$alkoxy, $C_1$-$C_6$haloalkoxy, $C_2$-$C_6$alkyl ether, $C_1$-$C_6$alkanoyl, $C_1$-$C_6$alkylsulfonyl, ($C_3$-$C_7$cycloalkyl)$C_0$-$C_4$alkyl, mono- or di-($C_1$-$C_6$alkyl)amino, $C_1$-$C_6$alkanoylamino, mono- or di-($C_1$-$C_6$alkyl)aminocarbonyl, mono- or di-($C_1$-$C_6$alkyl)aminosulfonyl and ($C_1$-$C_6$alkyl)sulfonylamino;

$R_4$ comprises a ring and has the formula -L-A-M, wherein:
L and A are as described for Formula A; and
M is:
(i) hydroxy, cyano, amino, halogen, aminocarbonyl, aminosulfonyl or —COOH; or
(ii) $C_1$-$C_6$alkyl, $C_1$-$C_6$haloalkyl, $C_1$-$C_6$alkoxy, (4- to 10-membered carbocycle)$C_0$-$C_4$alkyl, (4- to 7-membered heterocycle)$C_0$-$C_4$alkyl, $C_1$-$C_6$alkanoyloxy, $C_1$-$C_6$alkanoylamino, $C_1$-$C_6$alkylsulfonyl, $C_1$-$C_6$alkylsulfonylamino, $C_1$-$C_6$alkylsulfonyloxy, mono- or di-$C_1$-$C_6$alkylamino, mono- or di-($C_1$-$C_6$alkyl)aminosulfonyl, or mono- or di-($C_1$-$C_6$alkyl) aminocarbonyl; each of which is substituted with from 0 to 4 substituents independently chosen from:
(a) oxo, amino, halogen, hydroxy, cyano, aminocarbonyl, aminosulfonyl and —COOH; and
(b) $C_1$-$C_6$alkyl, $C_1$-$C_6$alkenyl, $C_1$-$C_6$hydroxyalkyl, $C_1$-$C_6$haloalkyl, $C_1$-$C_6$alkoxy, $C_1$-$C_6$haloalkoxy, $C_1$-$C_6$alkylthio, $C_2$-$C_6$alkyl ether, $C_1$-$C_6$alkanoylamino, mono- or di-($C_1$-$C_6$alkyl)amino, $C_1$-$C_6$alkylsulfonyl, $C_1$-$C_6$alkylsulfonylamino, mono- or di-($C_1$-$C_6$alkyl)aminosulfonyl, mono- or di-($C_1$-$C_6$alkylamino)carbonyl, mono- or di-($C_1$-$C_6$alkyl) amino$C_0$-$C_2$alkyl, phenyl$C_0$-$C_2$alkyl and (4- to 7-membered heterocycle)$C_0$-$C_4$alkyl; each of which is substituted with from 0 to 4 substituents independently chosen from oxo, amino, halogen, hydroxy, cyano, $C_1$-$C_4$alkyl, $C_1$-$C_4$alkenyl and $C_1$-$C_4$haloalkyl;
such that $R_4$ is not: (i) pyridazine that is substituted with $C_1$-$C_6$alkoxy, (ii) substituted or unsubstituted benzyl, (iii) unsubstituted phenyl or (iv) an O-linked moiety.

Within certain aspects, the present invention provides 5-membered heterocyclic amides and related compounds of Formula A that further satisfy Formula VI:

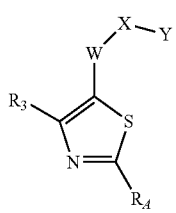

Formula VI as well as pharmaceutically acceptable salts, solvates (e.g., hydrates), amides and esters of such compounds.
Within Formula VI:
W and X and each $R_4$ are as described for Formula A;
Y is $C_3$-$C_{16}$cycloalkyl, 6- to 16-membered aryl or 5- to 16-membered heteroaryl, each of which is substituted with from 0 to 6 substituents independently chosen from hydroxy, halogen, cyano, amino, nitro, oxo, aminocarbonyl, aminosulfonyl, —COOH, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$aminoalkyl, $C_1$-$C_6$alkoxy, $C_1$-$C_6$haloalkoxy, $C_2$-$C_6$alkyl ether, $C_1$-$C_6$alkanoyl, $C_1$-$C_6$alkylsulfonyl, ($C_3$-$C_7$cycloalkyl)$C_0$-$C_4$alkyl, mono- or di-($C_1$-$C_6$alkyl)amino, $C_1$-$C_6$alkanoylamino, mono- or di-($C_1$-$C_6$alkyl)aminocarbonyl, mono- or di-($C_1$-$C_6$alkyl)aminosulfonyl and ($C_1$-$C_6$alkyl)sulfonylamino;

$R_3$ is hydrogen, halogen, cyano, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$aminoalkyl, $C_2$-$C_6$alkyl ether or ($C_3$-$C_7$cycloalkyl)$C_0$-$C_4$alkyl; and $R_4$ is phenyl$C_0$-$C_4$alkyl, (5- or 6-membered heterocycle)$C_0$-$C_4$alkyl, phenyl$C_0$-$C_2$alkyl-T- or (5- or 6-membered heterocycle)$C_0$-$C_4$alkyl-T-, wherein T is S or O; each of which is substituted with from 0 to 4 substituents independently chosen from:
(i) oxo, amino, halogen, hydroxy, cyano, aminocarbonyl, aminosulfonyl and —COOH; and
(ii) $C_1$-$C_6$alkyl, $C_2$-$C_6$alkenyl, $C_1$-$C_6$haloalkyl, $C_1$-$C_6$hydroxyalkyl, $C_1$-$C_6$alkoxy, $C_1$-$C_6$haloalkoxy, $C_1$-$C_6$alkylthio, $C_2$-$C_6$alkyl ether, $C_1$-$C_6$alkanoylamino, mono- or di-($C_1$-$C_6$alkyl)amino, $C_1$-$C_6$alkylsulfonyl, $C_1$-$C_6$alkylsulfonylamino, mono- or di-($C_1$-$C_6$alkyl) aminosulfonyl, mono- or di-($C_1$-$C_6$alkylamino)carbonyl and (4- to 7-membered heterocycle)$C_0$-$C_2$alkyl, each of which is substituted with from 0 to 4 substituents independently chosen from oxo, amino, halogen, hydroxy, cyano, $C_1$-$C_4$alkyl, $C_1$-$C_4$alkenyl and $C_1$-$C_4$haloalkyl.

Within certain aspects, the present invention provides 5-membered heterocyclic amides and related compounds of Formula A that further satisfy Formula VII:

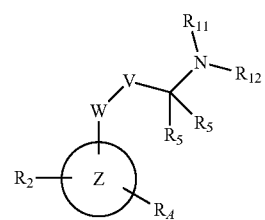

Formula VII or are a pharmaceutically acceptable salt or hydrate thereof, wherein:

represents a 5-membered heteroaryl ring; such that

is not furan, 1H-pyrrole or isoxazole;
W, $R_2$ and each $R_4$ are as described for Formula A;
V is absent or $C_1$-$C_5$alkylene that is substituted with from 0 to 4 substituents independently chosen from: (i) —COOH, $C_1$-$C_6$alkyl, ($C_3$-$C_8$cycloalkyl)$C_0$-$C_4$alkyl, $C_1$-$C_6$aminoalkyl, $C_2$-$C_6$alkyl ether, mono- or di-($C_1$-$C_6$alkyl)amino$C_0$-$C_4$alkyl, (4- to 7-membered heterocycloalkyl)$C_0$-$C_4$alkyl and phenyl$C_0$-$C_2$alkyl; (ii) substituents that are taken together, with any intervening carbon atoms, to form a 3- to 7-membered cycloalkyl or a 4- to 7-membered heterocycloalkyl; and (iii) substituents that are taken together with $R_4$ and any intervening atoms to form a 4- to 7-membered heterocycloalkyl;

each $R_5$ is independently (i) —COOH; (ii) ($C_3$-$C_8$cycloalkyl) $C_0$-$C_4$alkyl, $C_1$-$C_6$aminoalkyl, $C_2$-$C_6$alkyl ether, mono- or di-($C_1$-$C_6$alkyl)amino$C_0$-$C_4$alkyl, (4- to 7-membered heterocycloalkyl)$C_0$-$C_4$alkyl and phenyl$C_0$-$C_2$alkyl; or (iii) taken together with another $R_5$ moiety and the carbon atom to which they are bound to form a $C_3$-$C_8$cycloalkyl or 4- to 7-membered heterocycloalkyl; each of which (ii) or (iii) is substituted with from 0 to 3 substituents independently chose from hydroxy, halogen, amino, aminocarbonyl, $C_1$-$C_6$alkyl $C_1$-$C_6$alkoxy, mono- or di-($C_1$-$C_6$alkyl)amino, mono- or di-($C_1$-$C_6$alkyl)aminocarbonyl, and 4- to 7-membered heterocycloalkyl; such that at least one $R_5$ is not methyl; and $R_{11}$ and $R_{12}$ are (i) independently chosen from $C_1$-$C_6$alkyl, $C_2$-$C_6$alkenyl, $C_2$-$C_6$alkynyl and ($C_3$-$C_8$cycloalkyl)$C_0$-$C_2$alkyl; or (ii) taken together with the nitrogen atom to which they are bound to form a 4- to 7-membered heterocycloalkyl;

each of which (i) and (ii) is substituted with from 0 to 4 substituents independently chosen from hydroxy, halogen, cyano, amino, $C_1$-$C_6$alkyl, $C_1$-$C_6$hydroxyalkyl, $C_1$-$C_6$haloalkyl, $C_1$-$C_6$alkoxy, $C_1$-$C_6$haloalkoxy, $C_2$-$C_6$alkyl ether, $C_1$-$C_6$alkanoylamino, mono- or di-($C_1$-$C_6$alkyl)amino, $C_1$-$C_6$alkylsulfonyl, $C_1$-$C_6$alkylsulfonylamino, mono- or di-($C_1$-$C_6$alkyl)aminosulfonyl, mono- or di-($C_1$-$C_6$alkylamino)carbonyl, and 4- to 7-membered heterocycle; and $R_4$ is a group of the formula -L-A-M, wherein:

L and A are as described for Formula A; and

M is:

(i) hydroxy, cyano, amino, aminocarbonyl, aminosulfonyl or —COOH; or (ii) $C_1$-$C_6$alkyl, $C_1$-$C_6$haloalkyl, $C_1$-$C_6$alkoxy, (4- to 10-membered carbocycle)$C_0$-$C_4$alkyl, (4- to 10-membered heterocycle)$C_0$-$C_4$alkyl, $C_1$-$C_6$alkanoyloxy, $C_1$-$C_6$alkanoylamino, $C_1$-$C_6$alkylsulfonyl, $C_1$-$C_6$alkylsulfonyl amino, $C_1$-$C_6$alkylsulfonyloxy, mono- or di-$C_1$-$C_6$alkylamino, mono- or di-($C_1$-$C_6$alkyl)aminosulfonyl, or mono- or di-($C_1$-$C_6$alkyl)aminocarbonyl; each of which is substituted with from 0 to 4 substituents independently chosen from oxo, amino, halogen, hydroxy, cyano, aminocarbonyl, aminosulfonyl, —COOH, $C_1$-$C_6$alkyl, $C_1$-$C_6$hydroxyalkyl, $C_1$-$C_6$haloalkyl, $C_1$-$C_6$alkoxy, $C_1$-$C_6$haloalkoxy, $C_2$-$C_6$alkyl ether, $C_1$-$C_6$alkanoylamino, mono- or di-($C_1$-$C_6$alkyl)amino, $C_1$-$C_6$alkylsulfonyl, $C_1$-$C_6$alkylsulfonylamino, mono- or di-($C_1$-$C_6$alkyl)aminosulfonyl, mono- or di-($C_1$-$C_6$alkylamino)carbonyl, and 4- to 7-membered heterocycle;

such that (i) $R_4$ is not methyl, acetyl or trifluoroethanone; (ii) if

is thiophene, then $R_{11}$ and $R_{12}$ not taken together to form morpholinyl; (iii) if

is pyrazole, then $R_4$ is not benzyl or 4-methylbenzyl; and (iv) if

is thiazole, then $R_4$ is not unsubstituted phenyl, unsubstituted pyridin-2-yl, unsubstituted thiophen-2-yl, unsubstituted thiophen-3-yl, 4-methylphenyl, 4-ethylphenyl, 4-methoxyphenyl, 3,4-dimethoxyphenyl or 4-(p-tolyloxymethyl).

Within certain aspects, the present invention provides 5-membered heterocyclic amides and related compounds of Formula A that further satisfy Formula VIII:

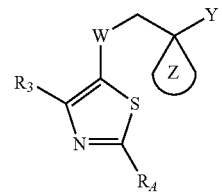

Formula VIII or are a pharmaceutically acceptable salt or hydrate thereof, wherein:

W and each $R_4$ are as described for Formula A;

is a 3- to 7-membered cycloalkyl or a 4- to 7-membered heterocycloalkyl;

Y is 5- to 7-membered heterocycloalkyl that is substituted with from 0 to 6 substituents independently chosen from hydroxy, halogen, cyano, amino, nitro, oxo, aminocarbonyl, aminosulfonyl, —COOH, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$aminoalkyl, $C_1$-$C_6$alkoxy, $C_1$-$C_6$haloalkoxy, $C_2$-$C_6$alkyl ether, $C_1$-$C_6$alkanoyl, $C_1$-$C_6$alkylsulfonyl, ($C_3$-$C_7$cycloalkyl)$C_0$-$C_4$alkyl, mono- or di-($C_1$-$C_6$alkyl) amino, $C_1$-$C_6$alkanoylamino, mono- or di-($C_1$-$C_6$alkyl) aminocarbonyl, mono- or di-($C_1$-$C_6$alkyl)aminosulfonyl and ($C_1$-$C_6$alkyl)sulfonylamino;

$R_3$ is halogen, cyano, $C_3$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$aminoalkyl, $C_2$-$C_6$alkyl ether, ($C_3$-$C_7$cycloalkyl)$C_0$-$C_4$alkyl, phenyl or 5- or 6-membered heteroaryl; and $R_4$ is phenyl$C_0$-$C_4$alkyl, (5- or 6-membered heterocycle)$C_0$-$C_4$alkyl, phenyl$C_0$-$C_2$alkyl-T- or (5- or 6-membered heterocycle)$C_0$-$C_4$alkyl-T-, wherein T is S or O; each of which is substituted with from 0 to 4 substituents independently chosen from:

(i) oxo, amino, halogen, hydroxy, cyano, aminocarbonyl, aminosulfonyl and —COOH; and (ii) $C_1$-$C_6$alkyl, $C_2$-$C_6$alkenyl, $C_1$-$C_6$haloalkyl, $C_1$-$C_6$hydroxyalkyl, $C_1$-$C_6$alkoxy, $C_1$-$C_6$haloalkoxy, $C_1$-$C_6$alkylthio, $C_2$-$C_6$alkyl ether, $C_1$-$C_6$alkanoylamino, mono- or di-($C_1$-$C_6$alkyl)amino, $C_1$-$C_6$alkylsulfonyl, $C_1$-$C_6$alkylsulfonylamino, mono- or di-($C_1$-$C_6$alkyl)aminosulfonyl, mono- or di-($C_1$-$C_6$alkylamino)carbonyl and (4- to 7-membered heterocycle)$C_0$-$C_2$alkyl, each of which is substituted with from 0 to 4 substituents independently chosen from oxo, amino, halogen, hydroxy, cyano, $C_1$-$C_4$alkyl, $C_2$-$C_4$alkenyl and $C_1$-$C_4$haloalkyl.

Within still further aspects, the present invention provides 5-membered heterocyclic amides and related compounds of Formula A that further satisfy Formula IX:

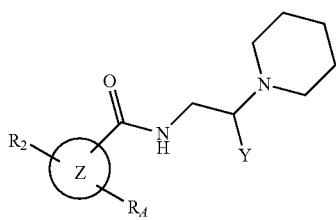

Formula IX or are a pharmaceutically acceptable salt or hydrate thereof, wherein:

represents a 5-membered heteroaryl ring; such that

is not furan or isoxazole;

Y is 6- to 16-membered aryl or 5- to 16-membered heteroaryl, each of which is optionally substituted and each of which is preferably substituted with from 0 to 6 substituents independently chosen from hydroxy, halogen, cyano, amino, nitro, oxo, aminocarbonyl, aminosulfonyl, —COOH, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$aminoalkyl, $C_1$-$C_6$alkoxy, $C_1$-$C_6$haloalkoxy, $C_2$-$C_6$alkyl ether, $C_1$-$C_6$alkanoyl, $C_1$-$C_6$alkylsulfonyl, ($C_3$-$C_7$cycloalkyl)$C_0$-$C_4$alkyl, mono- or di-($C_1$-$C_6$alkyl)amino, $C_1$-$C_6$alkanoylamino, mono- or di-($C_1$-$C_6$alkyl)aminocarbonyl, mono- or di-($C_1$-$C_6$alkyl)aminosulfonyl and ($C_1$-$C_6$alkyl)sulfonylamino;

$R_2$ is as described for Formula A;

$R_4$ is a group of the formula -L-A-M, wherein L, A and M are as described for Formula A; such that (i) $R_4$ is not methyl; and (ii) if

is thiazole, then $R_4$ is not unsubstituted phenyl or unsubstituted thiophen-3-yl.

Within certain aspects, 5-membered heterocyclic amides and related compounds of Formula A or I-LX, as well as other Formula(s) provided herein, are $P2X_7$ receptor antagonists and exhibit an $IC_{50}$ value of no greater than 20 micromolar, 10 micromolar, 5 micromolar, 1 micromolar, 500 nanomolar, or 100 nanomolar in an in vitro assay for determination of $P2X_7$ receptor antagonist activity. In certain embodiments, such $P2X_7$ receptor antagonists exhibit no detectable agonist activity in an in vitro assay of $P2X_7$ receptor activity (i.e., within an assay provided in Example 4, herein) at a concentration equal to the $IC_{50}$, 10 times the $IC_{50}$ or 100 times the $IC_{50}$ and/or at a concentration of 2,500 nM.

Within certain aspects, 5-membered heterocyclic amides and related compounds provided herein are labeled with a detectable marker (e.g., radiolabeled or fluorescein conjugated).

The present invention further provides, within other aspects, pharmaceutical compositions comprising at least one 5-membered heterocyclic amides or related compound provided herein in combination with a physiologically acceptable carrier or excipient.

Within further aspects, methods are provided for modulating (e.g., reducing) cellular $P2X_7$ receptor activation or activity, comprising contacting a cell (e.g., microglia, astrocyte or peripheral macrophage or monocyte) that expresses a $P2X_7$ receptor with at least one $P2X_7$ receptor modulator as described herein. Such contact may occur in vivo or in vitro and is generally performed using a concentration of $P2X_7$ receptor modulator that is sufficient to detectably alter $P2X_7$ receptor activity in vitro (as determined using an assay provided in Example 4).

The present invention further provides methods for treating a condition responsive to $P2X_7$ receptor modulation in a patient, comprising administering to the patient a therapeutically effective amount of at least one $P2X_7$ receptor antagonist as described herein.

Within other aspects, methods are provided for treating pain in a patient, comprising administering to a patient suffering from (or at risk for) pain a therapeutically effective amount of at least one $P2X_7$ receptor antagonist as described herein.

Within other aspects, methods are provided for treating inflammation in a patient, comprising administering to a patient suffering from (or at risk for) inflammation a therapeutically effective amount of at least one $P2X_7$ receptor antagonist as described herein.

Methods are further provided for treating neurological and/or neurodegenerative disorders, cardiovascular disorders, osteoarthritis, rheumatoid arthritis, arthrosclerosis, irritable bowel syndrome, inflammatory bowel disease, Alzheimer's disease, traumatic brain injury, asthma, chronic obstructive pulmonary disease, ocular conditions (e.g., glaucoma), cirrhosis, lupus, scleroderma, or fibrosis of internal organs (e.g., interstitial fibrosis) in a patient, comprising administering to a patient suffering from (or at risk for) one or more of the foregoing conditions a therapeutically effective amount of at least one $P2X_7$ receptor antagonist as described herein.

Within still further aspects, the present invention provides methods for inhibiting death of retinal ganglion cells in a patient, comprising administering to the patient a therapeutically effective amount of at least one $P2X_7$ receptor antagonist as described herein.

Also provided herein are methods for promoting weight loss in a patient, comprising administering to the patient a therapeutically effective amount of at least one $P2X_7$ receptor antagonist such as, but not limited to, a $P2X_7$ receptor antagonist as described herein.

Methods are further provided for identifying an agent that binds to $P2X_7$ receptor, comprising: (a) contacting $P2X_7$ receptor with a labeled compound that is a 5-membered heterocyclic amides or related compound as described herein under conditions that permit binding of the compound to $P2X_7$ receptor, thereby generating bound, labeled compound; (b) detecting a signal that corresponds to the amount of bound, labeled compound in the absence of test agent; (c) contacting the bound, labeled compound with a test agent; (d) detecting a signal that corresponds to the amount of bound labeled compound in the presence of test agent; and (e) detecting a decrease in signal detected in step (d), as compared to the signal detected in step (b).

Within further aspects, the present invention provides methods for determining the presence or absence of $P2X_7$ receptor in a sample, comprising: (a) contacting a sample with a compound as described herein under conditions that permit modulation by the compound of $P2X_7$ receptor activity; and (b) detecting a signal indicative of a level of the compound modulating $P2X_7$ receptor activity.

The present invention also provides packaged pharmaceutical preparations, comprising: (a) a pharmaceutical composition as described herein in a container; and (b) instructions for using the composition to treat one or more conditions responsive to $P2X_7$ receptor modulation, such as pain, inflammation, a neurological or neurodegenerative disorder, a cardiovascular disorder, an ocular disorder or an immune system disorder, osteoarthritis rheumatoid arthritis, arthrosclerosis, inflammatory bowel disease, Alzheimer's disease, traumatic brain injury, asthma, chronic obstructive pulmonary disease, and/or fibrosis of internal organs such as interstitial fibrosis.

In yet another aspect, the present invention provides methods for preparing the compounds disclosed herein, including the intermediates.

These and other aspects of the invention will become apparent upon reference to the following detailed description.

DETAILED DESCRIPTION

As noted above, the present invention provides 5-membered heterocyclic amides and related compounds. Such compounds may be used in vitro or in vivo, to modulate $P2X_7$ receptor activity in a variety of contexts.

TERMINOLOGY

Compounds are generally described herein using standard nomenclature. For compounds having asymmetric centers, it should be understood that (unless otherwise specified) all of the optical isomers and mixtures thereof are encompassed. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms. Certain compounds are described herein using a general formula that includes variables (e.g., $R_1$, A, X). Unless otherwise specified, each variable within such a formula is defined independently of any other variable, and any variable that occurs more than one time in a formula is defined independently at each occurrence.

The phrase "5-membered heterocyclic amides and related compounds," as used herein, encompasses all compounds of Formula A, I, II, III, IV, V, VI, VII, VIII and/or IX, as well as compounds of other Formulas provided herein (including any enantiomers, racemates and stereoisomers) and pharmaceutically acceptable salts, solvates, amides and esters of such compounds.

A "pharmaceutically acceptable salt" of a compound recited herein is an acid or base salt that is suitable for use in contact with the tissues of human beings or animals without excessive toxicity or carcinogenicity, and preferably without irritation, allergic response, or other problem or complication. Such salts include mineral and organic acid salts of basic residues such as amines, as well as alkali or organic salts of acidic residues such as carboxylic acids. Specific pharmaceutically acceptable anions for use in salt formation include, but are not limited to, acetate, 2-acetoxybenzoate, ascorbate, benzoate, bicarbonate, bromide, calcium edetate, carbonate, chloride, citrate, dihydrochloride, diphosphate, ditartrate, edetate, estolate (ethylsuccinate), formate, fumarate, gluceptate, gluconate, glutamate, glycolate, glycollylarsanilate, hexylresorcinate, hydrabamine, hydrobromide, hydrochloride, hydroiodide, hydroxymaleate, hydroxynaphthoate, iodide, isethionate, lactate, lactobionate, malate, maleate, mandelate, methylbromide, methylnitrate, methylsulfate, mucate, napsylate, nitrate, pamoate, pantothenate, phenylacetate, phosphate, polygalacturonate, propionate, salicylate, stearate, subacetate, succinate, sulfamate, sulfanilate, sulfate, sulfonates including besylate (benzenesulfonate), camsylate (camphorsulfonate), edisylate (ethane-1,2-disulfonate), esylate (ethanesulfonate) 2-hydroxyethylsulfonate, mesylate (methanesulfonate), triflate (trifluoromethanesulfonate) and tosylate (p-toluenesulfonate), tannate, tartrate, teoclate and triethiodide. Similarly, pharmaceutically acceptable cations for use in salt formation include, but are not limited to ammonium, benzathine, chloroprocaine, choline, diethanolamine, ethylenediamine, meglumine, procaine, and metals such as aluminum, calcium, lithium, magnesium, potassium, sodium and zinc. Those of ordinary skill in the art will recognize further pharmaceutically acceptable salts for the compounds provided herein. In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, the use of nonaqueous media, such as ether, ethyl acetate, ethanol, methanol, isopropanol or acetonitrile, is preferred.

It will be apparent that each compound provided herein may, but need not, be formulated as a solvate (e.g., hydrate) or non-covalent complex. In addition, the various crystal forms and polymorphs are within the scope of the present invention. Also provided herein are prodrugs of the compounds of the recited Formulas. A "prodrug" is a compound that may not fully satisfy the structural requirements of the compounds provided herein, but is modified in vivo, following administration to a patient, to produce a compound a formula provided herein. For example, a prodrug may be an acylated derivative of a compound as provided herein. Prodrugs include compounds wherein hydroxy, amine or sulthydryl groups are bonded to any group that, when administered to a mammalian subject, cleaves to form a free hydroxy, amino or sulfhydryl group, respectively. Examples of prodrugs include, but are not limited to, acetate, formate, benzoate and peptide derivatives of alcohol and amine functional groups within the compounds provided herein. Prodrugs of the compounds provided herein may be prepared by modifying functional groups present in the compounds in such a way that the modifications are cleaved in vivo to yield the parent compounds.

As used herein, the term "alkyl" refers to a straight or branched chain saturated aliphatic hydrocarbon. Alkyl groups include groups having from 1 to 8 carbon atoms ($C_1$-$C_8$alkyl), from 1 to 6 carbon atoms ($C_1$-$C_6$alkyl) and from 1 to 4 carbon atoms ($C_1$-$C_4$alkyl), such as methyl, ethyl, propyl, isopropyl, n-butyl, sec-butyl, tert-butyl, pentyl, 2-pentyl, isopentyl, neopentyl, hexyl, 2-hexyl, 3-hexyl and 3-methylpentyl. "$C_0$-$C_n$alkyl" refers to a single covalent bond ($C_0$) or an alkyl group having from 1 to n carbon atoms; for example "$C_0$-$C_4$alkyl" refers to a single covalent bond or a $C_1$-$C_4$alkyl group. In some instances, a substituent of an alkyl group is specifically indicated. For example, "hydroxyalkyl" refers to an alkyl group substituted with at least one —OH; "aminoalkyl" refers to an alkyl group substituted with at least one —$NH_2$.

"Alkenyl" refers to straight or branched chain alkene groups, which comprise at least one unsaturated carbon-carbon double bond. Alkenyl groups include $C_2$-$C_8$alkenyl, $C_2$-$C_6$alkenyl and $C_2$-$C_4$alkenyl groups, which have from 2 to 8, 2 to 6 or 2 to 4 carbon atoms, respectively, such as ethenyl, allyl or isopropenyl. "Alkynyl" refers to straight or branched chain alkyne groups, which have one or more unsaturated carbon-carbon bonds, at least one of which is a triple bond. Alkynyl groups include $C_2$-$C_8$alkynyl, $C_2$-$C_6$alkynyl and $C_2$-$C_4$alkynyl groups, which have from 2 to 8, 2 to 6 or 2 to 4 carbon atoms, respectively.

"Alkylene" refers to a divalent alkyl group, as defined above. $C_1$-$C_2$alkylene is methylene or ethylene; $C_0$-$C_4$alkylene is a single covalent bond or an alkylene group having 1, 2, 3 or carbon atoms; $C_0$-$C_2$alkylene is a single covalent bond, methylene or ethylene.

A "$C_1$-$C_6$alkylene that is optionally modified by the replacement of a carbon-carbon single bond with a double or triple carbon-carbon bond" is a $C_1$-$C_6$alkylene group as described above, or a divalent $C_2$-$C_6$alkene or $C_2$-$C_6$alkyne.

A "cycloalkyl" is a group that comprises one or more saturated and/or partially saturated rings in which all ring members are carbon, such as cyclopropyl, cyclobutyl, cyclopentyl, cyclohexyl, cycloheptyl, cyclooctyl, adamantyl, mertanyl, and partially saturated variants of the foregoing, such as cyclohexenyl. Cycloalkyl groups do not comprise an aromatic ring or a heterocyclic ring. Certain cycloalkyl groups are $C_3$-$C_7$cycloalkyl, in which the cycloalkyl group contains a single ring having from 3 to 7 ring members, all of which are carbon. A "($C_3$-$C_7$cycloalkyl)$C_0$-$C_4$alkyl" is a $C_3$-$C_7$cycloalkyl group linked via a single covalent bond or a $C_1$-$C_4$alkylene group.

Certain cycloalkyl groups are described herein as resulting from two substituents (e.g., $R_5$ moieties) being taken together, along with any intervening atoms. "Intervening atoms" in this context are any atoms that appear in the chain of covalently bonded atoms linking the two substituents. If the two substituents are attached to the same carbon atom, then the carbon atom to which they are attached is the only intervening atom. If the two substituents are attached to different atoms (typically carbon or nitrogen), then the atoms to which they are attached are intervening atoms, as are additional atoms (if any) that are needed to complete the chain of covalent linkages between the two substituents.

A "($C_4$-$C_7$cycloalkyl)$C_0$-$C_4$alkylene" is a divalent ($C_3$-$C_7$cycloalkyl)$C_0$-$C_4$alkyl group that is linked via two single covalent bonds to two specified moieties. In general, one such single covalent bond is located on the cyclic portion and the other is located on the alkylene portion, if present; alternatively, if no alkylene group is present, both such single covalent bonds are located on different ring members. For example, one a ($C_6$cycloalkyl)$C_2$alkylene moiety is:

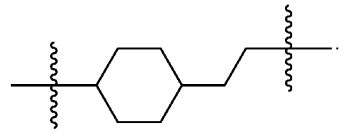 [SMILES: *CCC1CCC(*)CC1]

By "alkoxy," as used herein, is meant an alkyl group as described above attached via an oxygen bridge. Alkoxy groups include $C_1$-$C_6$alkoxy and $C_1$-$C_4$alkoxy groups, which have from 1 to 6 or from 1 to 4 carbon atoms, respectively. Methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy are representative alkoxy groups.

Similarly, "alkylthio" refers to an alkyl group as described above attached via a sulfur bridge, and "alkenylthio" refers to an alkenyl group as described above attached via a sulfur bridge.

The term "oxo" is used herein to refer to an oxygen substituent of a carbon atom that results in the formation of a carbonyl group (C=O). An oxo group that is a substituent of a nonaromatic carbon atom results in a conversion of —$CH_2$— to —C(=O)—. An oxo group that is a substituent of an aromatic carbon atom results in a conversion of —CH— to —C(=O)— and may result in a loss of aromaticity.

The term "alkanoyl" refers to an acyl group (e.g., —(C=O)-alkyl), in which carbon atoms are in a linear or branched alkyl arrangement and where attachment is through the carbon of the keto group. Alkanoyl groups have the indicated number of carbon atoms, with the carbon of the keto group being included in the numbered carbon atoms. For example a $C_2$alkanoyl group is an acetyl group having the formula —(C=O)$CH_3$. Alkanoyl groups include, for example, $C_1$-$C_8$alkanoyl, $C_1$-$C_6$alkanoyl and $C_1$-$C_4$alkanoyl groups, which have from 1 to 8, from 1 to 6 or from 1 to 4 carbon atoms, respectively. "$C_1$alkanoyl" refers to —(C=O)H.

"Alkyl ether" refers to a linear or branched ether substituent (i.e., an alkyl group that is substituted with an alkoxy group). Alkyl ether groups include $C_2$-$C_8$alkyl ether, $C_2$-$C_6$alkyl ether and $C_2$-$C_4$alkyl ether groups, which have 2 to 8, 6 or 4 carbon atoms, respectively. A $C_2$ alkyl ether has the structure —$CH_2$—O—$CH_3$.

The term "alkoxycarbonyl" refers to an alkoxy group attached through a keto (—(C=O)—) bridge (i.e., a group having the general structure —C(=O)—O-alkyl). Alkoxycarbonyl groups include $C_1$-$C_8$, $C_1$-$C_6$ and $C_1$-$C_4$alkoxycarbonyl groups, which have from 1 to 8, 6 or 4 carbon atoms, respectively, in the alkyl portion of the group (i.e., the carbon of the keto bridge is not included in the indicated number of carbon atoms). "$C_1$alkoxycarbonyl" refers to —C(=O)—O—$CH_3$; $C_3$alkoxycarbonyl indicates —C(=O)—O—($CH_2$)$_2$$CH_3$ or —C(=O)—O—(CH)($CH_3$)$_2$.

"Alkanoyloxy," as used herein, refers to an alkanoyl group linked via an oxygen bridge (i.e., a group having the general structure —O—C(=O)-alkyl). Alkanoyloxy groups include $C_1$-$C_8$, $C_1$-$C_6$ and $C_1$-$C_4$alkanoyloxy groups, which have from 1 to 8, 6 or 4 carbon atoms, respectively, in the alkyl portion of the group. For example, "$C_1$alkanoyloxy" refers to —O—C(=O)—CH$_3$.

Similarly, "alkanoylamino," as used herein, refers to an alkanoyl group linked via a nitrogen bridge (i.e., a group having the general structure —N(R)—C(=O)-alkyl), in which R is hydrogen or $C_1$-$C_6$alkyl. Alkanoylamino groups include $C_1$-$C_8$, $C_1$-$C_6$ and $C_1$-$C_4$alkanoylamino groups, which have from 1 to 8, 6 or 4 carbon atoms within the alkanoyl group, respectively, in the alkyl portion of the group.

"Alkylsulfonyl" refers to groups of the formula —(SO$_2$)-alkyl, in which the sulfur atom is the point of attachment. Alkylsulfonyl groups include $C_1$-$C_6$alkylsulfonyl and $C_1$-$C_4$alkylsulfonyl groups, which have from 1 to 6 or from 1 to 4 carbon atoms, respectively. Methylsulfonyl is one representative alkylsulfonyl group. "$C_1$-$C_6$alkylsulfonyl$C_0$-$C_4$alkyl" is a $C_1$-$C_6$alkylsulfonyl moiety that is linked via a single covalent bond or a $C_1$-$C_4$alkylne group. "$C_1$-$C_4$haloalkylsulfonyl" is an alkylsulfonyl group that has from 1 to 4 carbon atoms and is substituted with at least one halogen (e.g., trifluoromethylsulfonyl). "$C_1$-$C_6$alkylsulfonyloxy" refers to a $C_1$-$C_6$alkylsulfonyl moiety that is linked via an oxygen bridge.

"Alkylsulfonylamino" refers to groups of the formula —N(R)—(SO$_2$)-alkyl, in which R is hydrogen or $C_1$-$C_6$alkyl and the nitrogen atom is the point of attachment. Alkylsulfonylamino groups include $C_1$-$C_6$alkylsulfonylamino and $C_1$-$C_4$alkylsulfonylamino groups, which have from 1 to 6 or 1 to 4 carbon atoms, respectively. Methylsulfonylamino is a representative alkylsulfonylamino group. "$C_1$-$C_6$alkylsulfonylamino$C_0$-$C_4$alkyl" is a $C_1$-$C_6$alkylsulfonylamino moiety linked via a single covalent bond or a $C_1$-$C_4$alkylene group. "$C_1$-$C_6$haloalkylsulfonylamino" is an alkylsulfonylamino group that has from 1 to 6 carbon atoms and is substituted with at least one halogen (e.g., trifluoromethylsulfonylamino).

"Aminosulfonyl" refers to groups of the formula —(SO$_2$)—NH$_2$, in which the sulfur atom is the point of attachment. The term "mono- or di-($C_1$-$C_6$alkyl)aminosulfonyl" refers to groups that satisfy the formula —(SO$_2$)—NR$_2$, in which the sulfur atom is the point of attachment, and in which one R is $C_1$-$C_6$alkyl and the other R is hydrogen or an independently chosen $C_1$-$C_6$alkyl.

"Alkylaminoalkyl" refers to an alkylamino group linked via an alkylene group (i.e., a group having the general structure-alkylene-NH-alkyl or -alkylene-N(alkyl)(alkyl)) in which each alkyl is selected independently from alkyl, cycloalkyl and (cycloalkyl)alkyl groups. Alkylaminoalkyl groups include, for example, mono- and di-($C_1$-$C_8$alkyl)amino$C_1$-$C_8$alkyl, mono- and di-($C_1$-$C_6$alkyl)amino$C_1$-$C_6$alkyl and mono- and di-($C_1$-$C_6$alkyl)amino$C_1$-$C_4$alkyl. "Mono- or di-($C_1$-$C_6$alkyl)amino$C_0$-$C_6$alkyl" refers to a mono- or di-($C_1$-$C_6$alkyl)amino group linked via a single covalent bond or a $C_1$-$C_6$alkylene group. The following are representative alkylaminoalkyl groups:

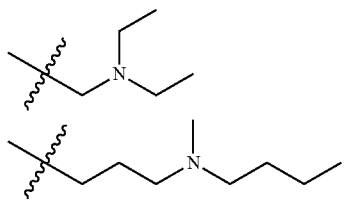
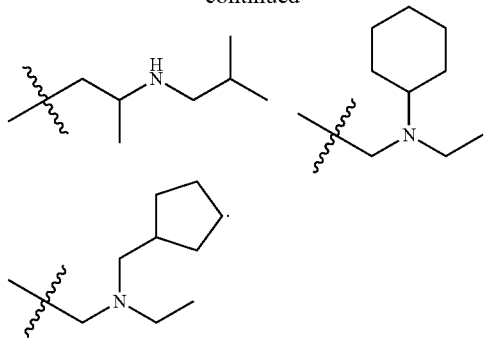

It will be apparent that the definition of "alkyl" as used in the terms "alkylamino" and "alkylaminoalkyl" differs from the definition of "alkyl" used for all other alkyl-containing groups, in the inclusion of cycloalkyl and (cycloalkyl)alkyl groups (e.g., ($C_3$-$C_7$cycloalkyl)$C_0$-$C_6$alkyl).

The term "aminocarbonyl" refers to an amide group (i.e., —(C=O)NH$_2$). "Mono- or di-($C_1$-$C_6$alkyl)aminocarbonyl" refers to groups of the formula —(C=O)—N(R)$_2$, in which the carbonyl is the point of attachment, one R is $C_1$-$C_6$alkyl and the other R is hydrogen or an independently chosen $C_1$-$C_6$alkyl.

"Mono- or di-($C_1$-$C_6$alkyl)aminocarbonyl$C_0$-$C_4$alkyl" is an aminocarbonyl group in which one or both of the hydrogen atoms is replaced with $C_1$-$C_6$alkyl, and which is linked via a single covalent bond (i.e., mono- or di-($C_1$-$C_6$alkyl)aminocarbonyl) or a $C_1$-$C_4$alkylene group (i.e., —($C_0$-$C_4$alkyl)-(C=O)N($C_1$-$C_6$alkyl)$_2$). If both hydrogen atoms are so replaced, the $C_1$-$C_6$alkyl groups may be the same or different.

The term "aminosulfonyl" refers to a sulfonamide group (i.e., —(SO$_2$)NH$_2$). "Mono- or di-($C_1$-$C_8$alkyl)aminosulfonyl" refers to groups of the formula —(SO$_2$)—N(R)$_2$, in which the sulfur atom is the point of attachment, one R is $C_1$-$C_8$alkyl and the other R is hydrogen or an independently chosen $C_1$-$C_8$alkyl.

"Mono- or di-($C_1$-$C_6$alkyl)aminosulfonyl$C_0$-$C_4$alkyl" is an aminosulfonyl group in which one or both of the hydrogen atoms is replaced with $C_1$-$C_6$alkyl, and which is linked via a single covalent bond (i.e., mono- or di-($C_1$-$C_6$alkyl)aminosulfonyl) or a $C_1$-$C_4$alkylene group (i.e., —($C_1$-$C_4$alkyl)-(SO$_2$)N($C_1$-$C_6$alkyl)$_2$). If both hydrogen atoms are so replaced, the $C_1$-$C_6$alkyl groups may be the same or different.

The term "halogen" refers to fluorine, chlorine, bromine or iodine.

A "haloalkyl" is an alkyl group that is substituted with 1 or more independently chosen halogens (e.g., "$C_1$-$C_6$haloalkyl" groups have from 1 to 6 carbon atoms). Examples of haloalkyl groups include, but are not limited to, mono-, di- or trifluoromethyl; mono-, di- or tri-chloromethyl; mono-, di-, tri-, tetra- or penta-fluoroethyl; mono-, di-, tri-, tetra- or penta-chloroethyl; and 1,2,2,2-tetrafluoro-1-trifluoromethyl-ethyl. Typical haloalkyl groups are trifluoromethyl and difluoromethyl. The term "haloalkoxy" refers to a haloalkyl group as defined above that is linked via an oxygen bridge.

A dash ("-") that is not between two letters or symbols is used to indicate a point of attachment for a substituent. For example, —CONH$_2$ is attached through the carbon atom.

A "carbocycle" or "carbocyclic group" comprises at least one ring formed entirely by carbon-carbon bonds (referred to herein as a carbocycle), and does not contain a heterocycle. Unless otherwise specified, each ring within a carbocycle may be independently saturated, partially saturated or aromatic, and is optionally substituted as indicated. A carbocycle generally has from 1 to 3 fused, pendant or Spiro rings and optionally further contains one or more alkylene bridges; carbocycles within certain embodiments have one ring or two fused rings. Typically, each ring contains from 3 to 8 ring members (i.e., $C_3$-$C_8$); $C_5$-$C_7$ rings are recited in certain embodiments. Carbocycles comprising fused, pendant or Spiro rings typically contain from 9 to 16 ring members. Certain representative carbocycles are cycloalkyl as described above (e.g., cyclohexyl, cycloheptyl or adamantly). Other carbocycles are aryl (i.e., contain at least one aromatic carbocyclic ring, with or without one or more additional aromatic and/or cycloalkyl rings). Such aryl carbocycles include, for example, phenyl, naphthyl (e.g., 1-naphthyl and 2-naphthyl), fluorenyl, indanyl and 1,2,3,4-tetrahydronaphthyl.

Certain carbocycles recited herein are phenyl groups linked via a single covalent bond or $C_1$-$C_2$alkylene group (e.g., benzyl, 1-phenyl-ethyl and 2-phenyl-ethyl), and are designated phenyl$C_0$-$C_2$alkyl.

A "heterocycle" or "heterocyclic group" has from 1 to 3 fused, pendant or spiro rings, at least one of which is a heterocyclic ring (i.e., one or more ring atoms is a heteroatom independently chosen from O, S and N, with the remaining ring atoms being carbon). Additional rings, if present, may be heterocyclic or carbocyclic. Typically, a heterocyclic ring comprises 1, 2, 3 or 4 heteroatoms; within certain embodiments each heterocycle has 1 or 2 heteroatoms per ring. Each heterocyclic ring generally contains from 3 to 8 ring members (rings having from 4 or 5 to 7 ring members are recited in certain embodiments) and heterocycles comprising fused, pendant or spiro rings typically contain from 9 to 14 ring members. Certain heterocycles comprise a sulfur atom as a ring member; in certain embodiments, the sulfur atom is oxidized to SO or $SO_2$. Unless otherwise specified, a heterocycle may be a heterocycloalkyl group (i.e., each ring is saturated or partially saturated), such as a 4- to 7-membered heterocycloalkyl, which generally comprises 1, 2, 3 or 4 ring atoms that are independently chosen from C, O, N and S; or a heteroaryl group (i.e., at least one ring within the group is aromatic), such as a 5- to 10-membered heteroaryl (which may be monocyclic or bicyclic) or a 6-membered heteroaryl (e.g., pyridyl or pyrimidyl). N-linked heterocyclic groups are linked via a component nitrogen atom.

A "heterocycle$C_0$-$C_4$alkyl" is a heterocyclic group linked via a single covalent bond or $C_1$-$C_4$alkylene group. A "(4- to 7-membered heterocycloalkyl)$C_1$-$C_4$alkyl" is a heterocycloalkyl ring with from 4 to 7 ring members that is linked via a $C_1$-$C_4$alkylene group.

A "(4- to 7-membered heterocycloalkyl)$C_0$-$C_4$alkylene" is a divalent (4- to 7-membered heterocycloalkyl)$C_0$-$C_4$alkyl group that is linked via two single covalent bonds to two specified moieties. In general, one such single covalent bond is located on the cyclic portion and the other is located on the alkylene portion, if present; alternatively, if no alkylene group is present, both such single covalent bonds are located on different ring members. For example, with respect to the group $R_4$, if L is a (piperidinyl)$C_2$alkylene, A is absent and M is —COOH, one $R_4$ moiety so formed is:

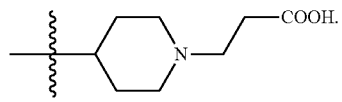

A "substituent," as used herein, refers to a molecular moiety that is covalently bonded to an atom within a molecule of interest. For example, a ring substituent may be a moiety such as a halogen, alkyl group, haloalkyl group or other group that is covalently bonded to an atom (preferably a carbon or nitrogen atom) that is a ring member. Substituents of aromatic groups are generally covalently bonded to a ring carbon atom. The term "substitution" refers to replacing a hydrogen atom in a molecular structure with a substituent, such that the valence on the designated atom is not exceeded, and such that a chemically stable compound (i.e., a compound that can be isolated, characterized, and tested for biological activity) results from the substitution.

Groups that are "optionally substituted" are unsubstituted or are substituted by other than hydrogen at one or more available positions, typically 1, 2, 3, 4 or 5 positions, by one or more suitable groups (which may be the same or different). Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substituents). Other optionally substituted groups are substituted with at least one substituent (e.g., substituted with from 1 to 2, 3 or 4 independently selected substituents).

The term "$P2X_7$ receptor" refers to any P2X7 receptor, preferably a mammalian receptor such as the human or rat P2X7 receptor disclosed in U.S. Pat. No. 6,133,434, as well as homologues thereof found in other species.

A "$P2X_7$ receptor modulator," also referred to herein as a "modulator," is a compound that modulates $P2X_7$ receptor activation and/or $P2X_7$ receptor-mediated activity (e.g., signal transduction). $P2X_7$ receptor modulators specifically provided herein are compounds of Formula A and pharmaceutically acceptable salts, hydrates and esters thereof. A modulator may be a $P2X_7$ receptor agonist or antagonist.

A modulator is considered an "antagonist" if it detectably inhibits $P2X_7$ receptor-mediated signal transduction (using, for example, a representative assay provided in Example 4); in general, such an antagonist inhibits $P2X_7$ receptor activation with a $IC_{50}$ value of less than 20 micromolar, preferably less than 10 micromolar, more preferably less than 5 micromolar, more preferably less than 1 micromolar, still more preferably less than 500 nanomolar, and most preferably less than 100 nanomolar within an assay provided in Example 4. $P2X_7$ receptor antagonists include neutral antagonists and inverse agonists.

An "inverse agonist" of $P2X_7$ receptor is a compound that reduces the activity of $P2X_7$ receptor below its basal activity level in the absence of added ligand. Inverse agonists of $P2X_7$ receptor may also inhibit the activity of ligand at $P2X_7$ receptor and/or binding of ligand to $P2X_7$ receptor. The basal activity of $P2X_7$ receptor, as well as a reduction in $P2X_7$ receptor activity due to the presence of $P2X_7$ receptor antagonist, may be determined from a calcium mobilization assay (e.g., the assay of Example 4).

A "neutral antagonist" of $P2X_7$ receptor is a compound that inhibits the activity of ligand at $P2X_7$ receptor, but does not significantly change the basal activity of the receptor (i.e., within a calcium mobilization assay as described in Example 4 performed in the absence of ligand, $P2X_7$ receptor activity is reduced by no more than 10%, preferably by no more than 5%, and more preferably by no more than 2%; most preferably, there is no detectable reduction in activity). Neutral antagonists of $P2X_7$ receptor may inhibit the binding of ligand to $P2X_7$ receptor.

As used herein a "P2X$_7$ receptor agonist" is a compound that elevates the activity of the P2X$_7$ receptor above the basal activity level of the receptor (i.e., enhances P2X$_7$ receptor activation and/or P2X$_7$ receptor-mediated activity, such as signal transduction). P2X$_7$ receptor agonist activity may be detected using the representative assay provided in Example 4. P2X$_7$ receptor agonists include ATP and 2'(3')-O-(4-benzoyl-benzoyl)adenosine 5'-triphosephate (BzATP).

A "therapeutically effective amount" (or dose) is an amount that, upon administration to a patient, results in a discernible patient benefit (e.g., provides detectable relief from at least one condition being treated). Such relief may be detected using any appropriate criteria, including alleviation of one or more symptoms such as pain. A therapeutically effective amount or dose generally results in a concentration of compound in a body fluid (such as blood, plasma, serum, CSF, synovial fluid, lymph, cellular interstitial fluid, tears or urine) that is sufficient to alter P2X$_7$ receptor-mediated signal transduction (using an assay provided in Example 4). It will be apparent that the discernible patient benefit may be apparent after administration of a single dose, or may become apparent following repeated administration of the therapeutically effective dose according to a predetermined regimen, depending upon the indication for which the compound is administered.

By "statistically significant," as used herein, is meant results varying from control at the p<0.1 level of significance as measured using a standard parametric assay of statistical significance such as a student's T test.

A "patient" is any individual treated with a compound provided herein. Patients include humans, as well as other animals such as companion animals (e.g., dogs and cats) and livestock. Patients may be experiencing one or more symptoms of a condition responsive to P2X$_7$ receptor modulation or may be free of such symptom(s) (i.e., treatment may be prophylactic in a patient considered at risk for the development of such symptoms).

5-Membered Heterocyclic Amides and Related Compounds

As noted above, the present invention provides 5-membered heterocyclic amides and related compounds of Formula A and other formulas recited herein. Within certain aspects, such compounds are modulators that may be used in a variety of contexts, including in the treatment of conditions responsive to P2X$_7$ receptor modulation, such as pain. Such modulators are also useful as probes for detection and localization of P2X$_7$ receptor and as standards in P2X$_7$ receptor-mediated signal transduction assays.

Within certain compounds of any of Formulas A, I, III, IV, V or VI:
Y is

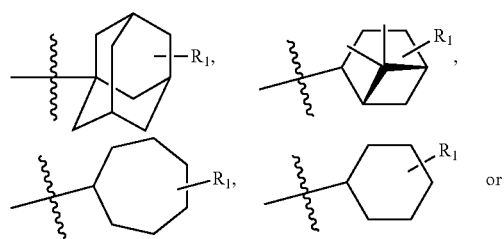

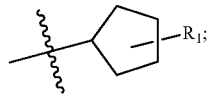

and
R$_1$ represents from 0 to 6 substituents independently chosen from halogen, hydroxy, cyano, amino, nitro, oxo, aminocarbonyl, aminosulfonyl, —COOH, C$_1$-C$_6$alkyl, C$_2$-C$_6$alkenyl, C$_2$-C$_6$alkynyl, C$_1$-C$_6$haloalkyl, C$_1$-C$_6$hydroxyalkyl, C$_1$-C$_6$alkoxy, C$_1$-C$_6$haloalkoxy, (C$_3$-C$_7$cycloalkyl)C$_0$-C$_4$alkyl, (4- to 7-membered heterocycloalkyl)C$_0$-C$_4$alkyl and mono- or di-(C$_1$-C$_6$alkyl)aminoC$_0$-C$_4$alkyl.

Certain such compounds of Formulas A or Formula I further satisfy Formula IIa, IIb or IIc:

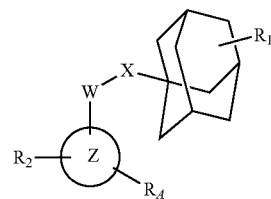

Formula IIa

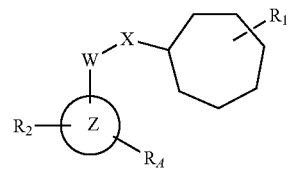

Formula IIb

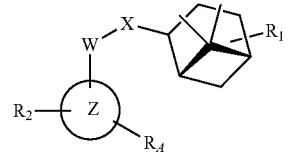

Formula IIc wherein variables are as described above. Within certain embodiments of Formulas A, 1 and IIa-c, X is not absent (e.g., C$_1$-C$_3$alkylene, optionally substituted as described above).

Within Formulas A, 1, IIa-c or VII, as noted above, the heteroaryl core:

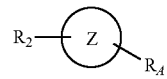

represents a 5-membered heteroaryl ring that is substituted with exactly one substituent R$_A$ and is optionally substituted with from 0 to 2 substituents represented by R$_2$. The 5-membered heteroaryl ring represented by

is, in certain embodiments, pyrazole, thiazole, imidazole, oxazole or thiophene. R$_2$, in certain embodiments, represents zero substituents or 1 or 2 substituents independently chosen from halogen, C$_1$-C$_6$alkyl and C$_1$-C$_6$haloalkyl.

Representative subformulas of Formulas A, I and IIa-c include, for example:

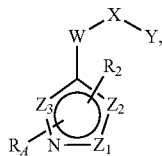

such as:

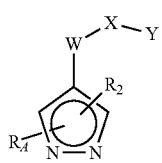 (e.g.,

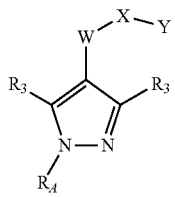),

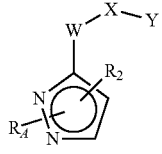 (e.g., 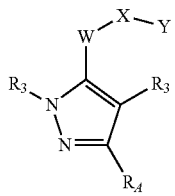,

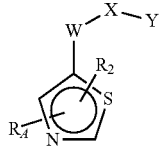), or

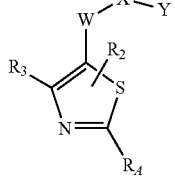 (e.g.,

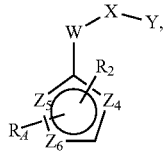 ); and

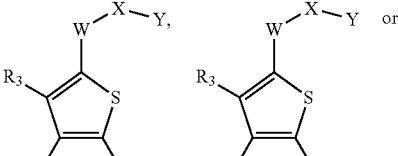 such as: 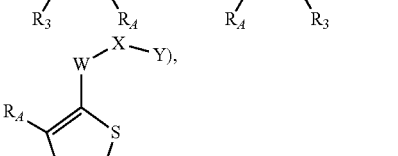 (e.g.,

in which each $R_3$ is independently hydrogen, halogen, cyano, amino, nitro, aminocarbonyl, aminosulfonyl, —COOH, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$aminoalkyl, $C_1$-$C_6$alkoxy, $C_1$-$C_6$haloalkoxy, $C_1$-$C_6$alkanoyl, $C_2$-$C_6$alkyl ether, ($C_3$-$C_7$cycloalkyl)$C_0$-$C_4$alkyl, mono- or di-($C_1$-$C_6$alkyl)amino, $C_1$-$C_6$alkylsulfonyl, $C_1$-$C_6$alkanoylamino, mono- or di-($C_1$-$C_6$alkyl)aminocarbonyl, mono- or di-($C_1$-$C_6$alkyl)aminosulfonyl or ($C_1$-$C_6$alkyl)sulfonylamino; $Z_1$, $Z_2$ and $Z_3$ are independently N, NH, CH, S or O; such that no more than one of $Z_1$, $Z_2$ and $Z_3$ is chosen from O and S; $Z_4$ and $Z_5$ are independently CH, N, NH, O or S; and $Z_6$ is CH, S or O, such that no more than one of $Z_4$, $Z_5$ and $Z_6$ is chosen from O and S. It will be apparent that, within these formulas and any others provided herein with such variables, any CH or NH moiety at $Z_1$, $Z_2$, $Z_3$, $Z_4$, $Z_5$ and/or $Z_6$ may be substituted with a substituent represented by $R_A$ or $R_2$, and that such substitution will result in the replacement of the hydrogen atom with a substituent represented by $R_A$ or $R_2$. In certain compounds in which the variable $R_3$ is present, each $R_3$ is independently hydrogen, halogen, $C_1$-$C_4$alkyl or $C_1$-$C_4$haloalkyl.

Within certain 5-membered heterocyclic amides and related compounds of Formula A, I, IIa-c, VII and other Formulas provided herein, $R_A$ is phenyl$C_0$-$C_2$alkyl, (5- or 6-membered heteroaryl)$C_0$-$C_4$alkyl, phenyl$C_0$-$C_2$alkyl-T- or (5- or 6-membered heteroaryl)$C_0$-$C_4$alkyl-T-, wherein T is S or O; each of which is substituted with from 0 to 4 substituents independently chosen from:
 (i) oxo, amino, halogen, hydroxy, cyano, aminocarbonyl, aminosulfonyl and —COOH; and
 (ii) $C_1$-$C_6$alkyl, $C_2$-$C_6$alkenyl, $C_1$-$C_6$hydroxyalkyl, $C_1$-$C_6$haloalkyl, $C_1$-$C_6$alkoxy, $C_1$-$C_6$haloalkoxy, $C_1$-$C_6$alkylthio, $C_2$-$C_6$alkenylthio, $C_2$-$C_6$alkyl ether, (mono- or di-$C_1$-$C_6$alkylamino)$C_0$-$C_4$alkyl, $C_1$-$C_6$alkylsulfonyl, $C_1$-$C_6$alkylsulfonylamino, mono- or di-($C_1$-$C_6$alkyl)aminosulfonyl, and (4- to 7-membered heterocycloalkyl)$C_0$-$C_4$alkyl; each of which is substituted with from 0 to 4 substituents independently chosen from halogen, hydroxy, amino, oxo, aminocarbonyl, aminosulfonyl, —COOH, $C_1$-$C_4$alkyl and $C_1$-$C_4$haloalkyl.

Within certain such compounds (e.g., compounds of Formula I or III-c in which

represents pyrazole or imidazole), T is not O and $R_A$ is not unsubstituted benzyl. Within further compounds, $R_A$ is phenyl$C_0$-$C_2$alkyl or (5- or 6-membered heteroaryl)$C_0$-$C_4$alkyl, optionally substituted as described above, such that $R_A$ is not unsubstituted benzyl. Such $R_A$ moieties include, for example, (5- or 6-membered heteroaryl)$C_0$-$C_4$alkyl that is substituted with from 0 to 4 substituents independently chosen from oxo, amino, halogen, hydroxy, cyano, aminocarbonyl, aminosulfonyl, —COOH, $C_1$-$C_6$alkyl, $C_1$-$C_6$haloalkyl, $C_1$-$C_6$hydroxyalkyl, $C_1$-$C_6$alkoxy, $C_1$-$C_6$haloalkoxy, $C_1$-$C_6$alkylthio, $C_2$-$C_6$alkyl ether, $C_1$-$C_6$alkanoylamino, mono- or di-($C_1$-$C_6$alkyl)amino, $C_1$-$C_6$alkylsulfonyl, $C_1$-$C_6$alkylsulfonylamino, mono- or di-($C_1$-$C_6$alkyl)aminosulfonyl, mono- or di-($C_1$-$C_6$alkylamino)carbonyl, and 4- to 7-membered heterocycle, wherein the 5- or 6-membered heteroaryl is pyridyl, pyrimidinyl, imidazolyl or chosen from

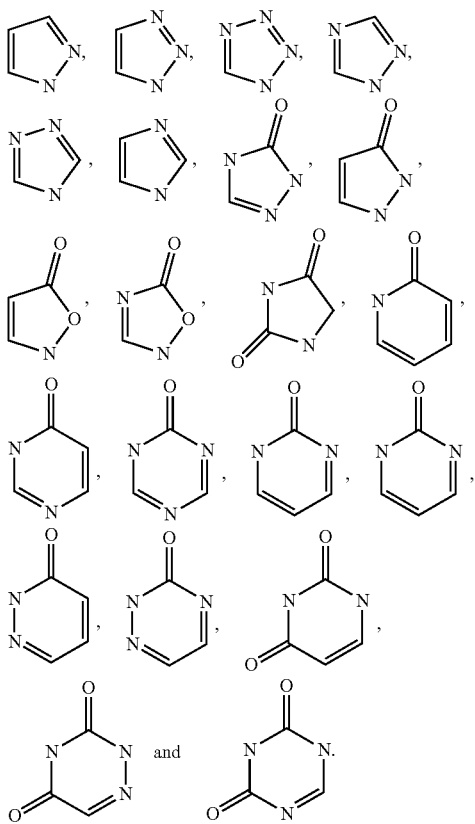

Within certain 5-membered heterocyclic amides and related compounds of Formulas A, I, IIa-IIc and other Formulas provided herein, $R_A$ is $C_3$-$C_6$alkyl, $C_2$-$C_6$alkenyl, $C_1$-$C_6$alkoxy, $C_1$-$C_6$alkylthio, $C_2$-$C_6$alkenylthio, $C_2$-$C_6$alkyl ether, $C_1$-$C_6$alkoxycarbonyl, $C_6$alkylsulfonyl, $C_1$-$C_6$alkylsulfonylamino, mono- or di-$C_1$-$C_6$alkylaminosulfonyl, mono- or di-($C_1$-$C_6$alkyl)amino$C_0$-$C_4$alkyl, (4- to 7-membered heterocycloalkyl)$C_0$-$C_4$alkyl or (4- to 7-membered heterocycloalkyl)$C_0$-$C_4$alkyl-T- wherein T is S or O; each of which is substituted with from 0 to 4 substituents independently chosen from:
  (i) oxo, amino, halogen, hydroxy, aminocarbonyl, aminosulfonyl and —COOH; and
  (ii) $C_1$-$C_6$alkyl, $C_1$-$C_6$hydroxyalkyl, $C_1$-$C_6$haloalkyl, $C_1$-$C_6$alkoxy, $C_1$-$C_6$alkylthio, $C_2$-$C_6$alkyl ether, $C_1$-$C_6$alkanoylamino, mono- or di-($C_1$-$C_6$alkyl)amino, $C_1$-$C_6$alkylsulfonyl, $C_1$-$C_6$alkylsulfonylamino, mono- or di-$C_1$-$C_6$alkylaminocarbonyl, mono- or di-$C_1$-$C_6$alkylaminosulfonyl and 4- to 7-membered heterocycle; each of which is substituted with from 0 to 4 substituents independently chosen from halogen, hydroxy, amino, oxo, aminocarbonyl, aminosulfonyl, —COOH, $C_1$-$C_4$alkyl and $C_1$-$C_4$haloalkyl.

Within certain such compounds (e.g., those in which

represents pyrazole or imidazole), $R_A$ is not optionally substituted alkoxy. Within further such compounds, $R_A$ is $C_3$-$C_6$alkyl, $C_2$-$C_6$alkyl ether, $C_1$-$C_4$alkoxycarbonyl, mono- or di-($C_1$-$C_6$alkyl)amino$C_0$-$C_4$alkyl, or (4- to 7-membered heterocycloalkyl)$C_0$-$C_4$alkyl; each of which is substituted with from 0 to 4 substituents independently chosen from amino, hydroxy, oxo, aminocarbonyl, aminosulfonyl, C, $C_6$alkyl, $C_1$-$C_6$hydroxyalkyl, $C_2$-$C_6$alkyl ether, mono- or di-($C_1$-$C_6$alkyl)amino, mono- or di-($C_1$-$C_6$alkyl)aminocarbonyl, $C_1$-$C_6$alkylsulfonyl, $C_1$-$C_6$alkylsulfonylamino, 4- to 7-membered heterocycloalkyl, and 5- or 6-membered heteroaryl. Representative such $R_A$ moieties include, for example, $C_3$-$C_6$alkyl, $C_2$-$C_6$alkyl ether, and mono- or di-($C_1$-$C_6$alkyl)amino$C_0$-$C_4$alkyl, each of which is substituted with from 1 to 4 substituents independently chosen from halogen, hydroxy, amino, oxo, aminocarbonyl, aminosulfonyl, —COOH, $C_1$-$C_6$alkoxy, mono- or di-($C_1$-$C_6$alkyl)amino, $C_1$-$C_6$alkanoylamino, $C_1$-$C_6$alkylsulfonyl, $C_1$-$C_6$alkylsulfonyloxy, $C_1$-$C_6$alkylsulfonylamino, and 4- to 7-membered heterocycle. Within certain such compounds, $R_A$ is: (i) $C_3$-$C_6$alkyl that is substituted with amino, hydroxy or —COOH; or (ii) mono- or di-($C_1$-$C_6$alkyl)amino$C_0$-$C_2$alkyl that is substituted with from 0 to 2 substituents independently chosen from hydroxy, oxo, amino, —COOH and $C_1$-$C_4$alkylsulfonylamino.

Within further compounds of Formulas A, I, IIa-c, VII and other Formulas provided herein, $R_A$ is a group of the formula:

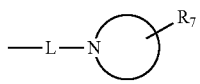

wherein:
L is absent or $C_1$-$C_6$alkylene that is optionally substituted with oxo;

represents a 4- to 7-membered heterocycloalkyl that is optionally fused to phenyl or to a 6-membered heteroaryl; and $R_7$ represents from 0 to 4 substituents independently chosen from:
  (i) hydroxy, amino, oxo, aminocarbonyl, aminosulfonyl and —COOH;
  (ii) $C_1$-$C_6$alkyl, mono- or di-($C_1$-$C_6$alkyl)amino$C_0$-$C_4$alkyl, $C_1$-$C_6$alkylsulfonyl$C_0$-$C_4$alkyl, $C_1$-$C_6$alkylsulfonylamino$C_0$-$C_4$alkyl, and 4- to 7-membered heterocycle; each of which is substituted with from 0 to 4 substituents independently chosen from halogen, hydroxy, amino, oxo, aminocarbonyl, aminosulfonyl, —COOH, $C_1$-$C_6$alkyl, $C_1$-$C_6$alkoxy, mono- or di-($C_1$-$C_6$alkyl)amino, and $C_1$-$C_6$alkylsulfonylamino; and (iii) substituents that are taken together to form a bridge of the Formula —$(CH_2)_q$—P—$(CH_2)_r$—, wherein q and r are independently 0 or 1 and P is $CH_2$, O, NH or S.

Certain such $R_A$ moieties satisfy the formula:

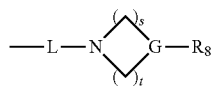

wherein:
G is CH or N; s and t are independently 0, 1, 2, 3 or 4, such that the sum of s and t ranges from 2 to 5; and $R_8$ is: (i) hydrogen, aminocarbonyl, aminosulfonyl or —COOH; or (ii) $C_1$-$C_6$alkyl, mono- or di-($C_1$-$C_6$alkyl)amino$C_0$-$C_4$alkyl, $C_1$-$C_6$alkylsulfonyl$C_0$-$C_4$alkyl, $C_1$-$C_6$alkylsulfonylamino$C_0$-$C_4$alkyl, or 4- to 7-membered heterocycle; each of which is substituted with from 0 to 4 substituents independently chosen from halogen, hydroxy, amino, oxo, aminocarbonyl, aminosulfonyl, —COOH, $C_1$-$C_6$alkyl, $C_1$-$C_6$alkoxy, mono- or di-($C_1$-$C_6$alkyl)amino, and $C_1$-$C_6$alkylsulfonylamino. Other such $R_A$ moieties include:

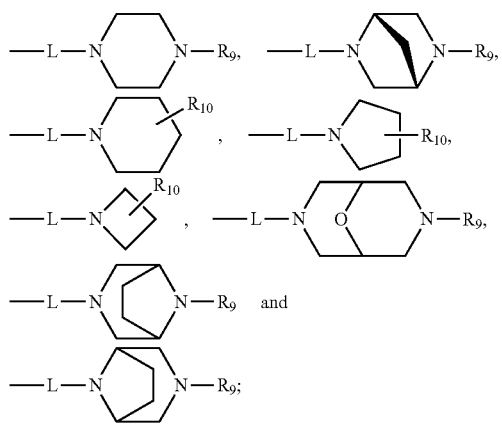

wherein:
$R_9$ is: (i) $C_1$-$C_6$alkyl that is substituted with —COOH; or (ii) a 5- or 6-membered heteroaryl that is unsubstituted or substituted with 1 or 2 oxo; and $R_{10}$ represents one substituent chosen from: (i) —COOH; (ii) $C_1$-$C_6$alkyl that is substituted with —COOH; (iii) mono- or di-($C_1$-$C_6$alkyl)amino$C_0$-$C_2$alkyl, $C_1$-$C_6$alkylsulfonyl and $C_1$-$C_6$alkylsulfonylamino; each of which is substituted with from 0 to 3 substituents independently chosen from hydroxy, oxo and —COOH; and (iv) $C_1$-$C_6$haloalkylsulfonylamino.

Within certain 5-membered heterocyclic amides and related compounds of Formulas A, I, IIa-IIc and other Formulas provided herein, one or more of the following conditions applies:
(a) $R_2$ represents from 0 to 2 substituents independently chosen from halogen, $C_1$-$C_6$alkyl and $C_1$-$C_6$haloalkyl;
(b) X is methylene or ethylene, each of which is substituted with from 0 to 4 substituents independently chosen from $C_1$-$C_4$alkyl, ($C_3$-$C_8$cycloalkyl)$C_0$-$C_2$alkyl, phenyl$C_0$-$C_2$alkyl and substituents that are taken together, with the carbon atom or carbon atoms to which they are bound, to form a 3- to 7-membered cycloalkyl or a 4- to 7-membered heterocycloalkyl ring;
(c) Y is substituted with from 0 to 4 substituents independently chosen from halogen, hydroxy, cyano, amino, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, and mono- or di-($C_1$-$C_6$alkyl)amino; and/or
(d) —W—X—Y is:

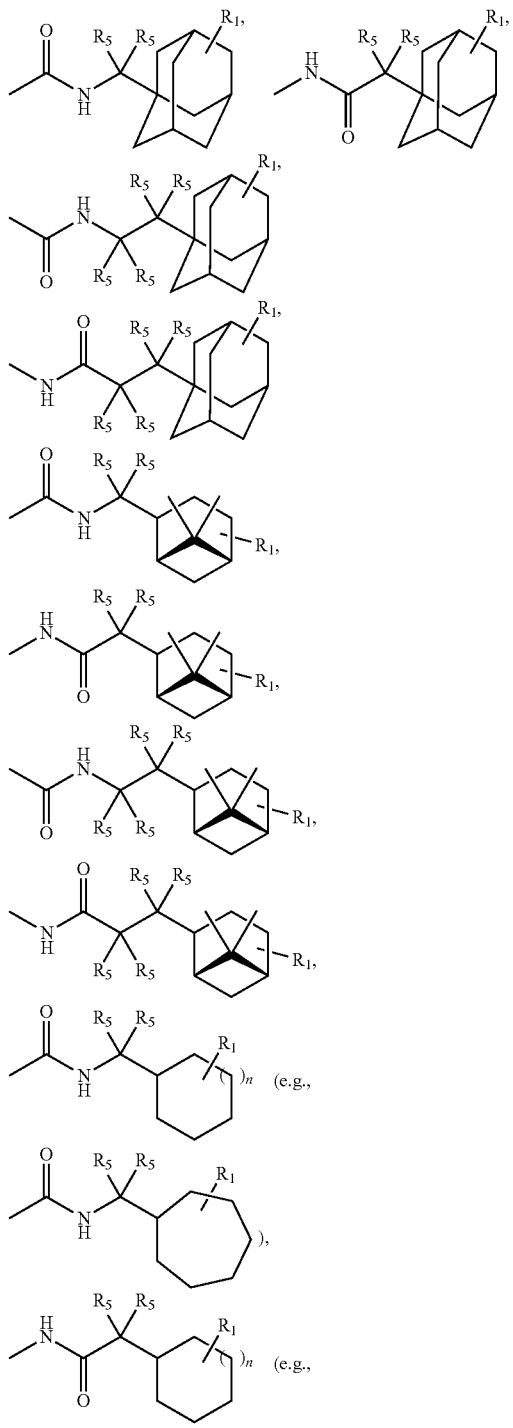

-continued

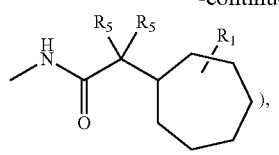

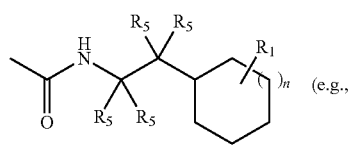 (e.g.,

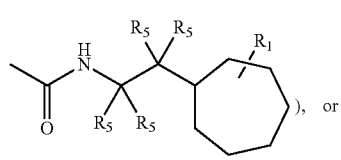), or

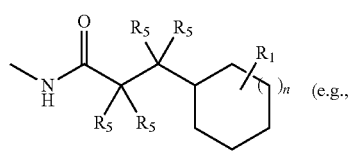 (e.g.,

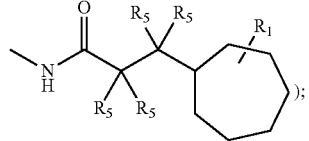);

wherein:

$R_1$ represents from 0 to 2 substituents independently chosen from halogen, hydroxy, cyano, amino, nitro, aminocarbonyl, aminosulfonyl, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, ($C_3$-$C_7$cycloalkyl)$C_0$-$C_4$alkyl, and mono- or di-($C_1$-$C_6$alkyl)amino; and each $R_5$ is independently hydrogen, $C_1$-$C_6$alkyl, $C_3$-$C_7$cycloalkyl or phenyl; or two $R_5$ are taken together with the carbon atom or carbon atoms to which they are bound to form a $C_3$-$C_8$cycloalkyl.

Certain representative such compounds satisfy one of the following subformulas:

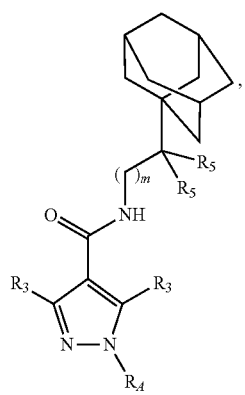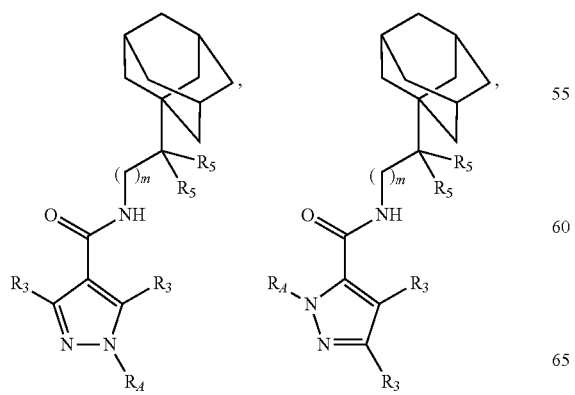

-continued

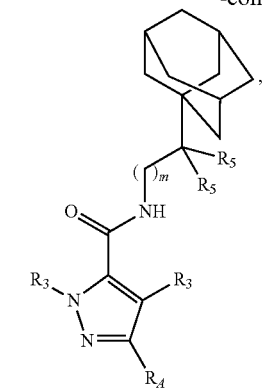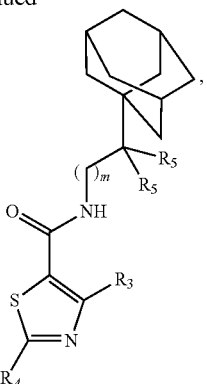

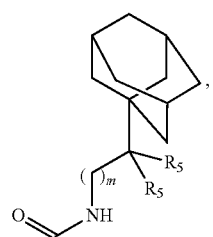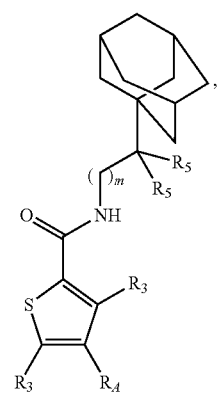

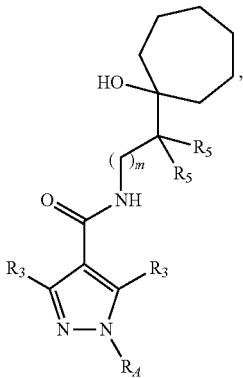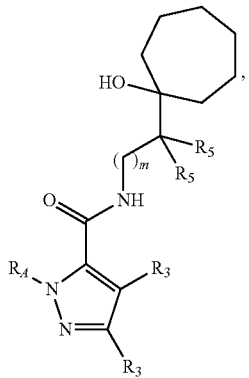

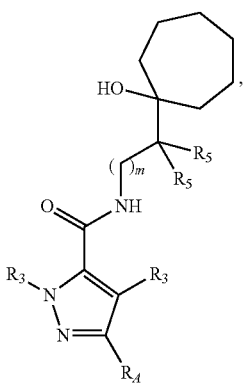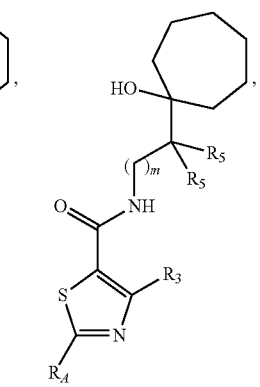

-continued
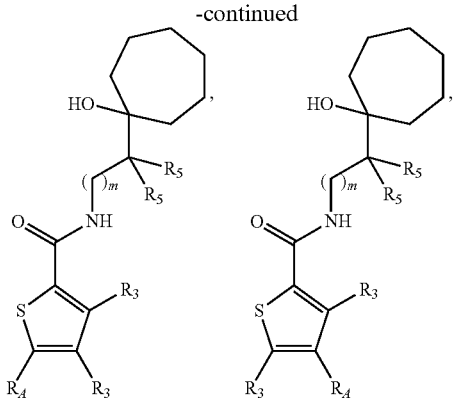
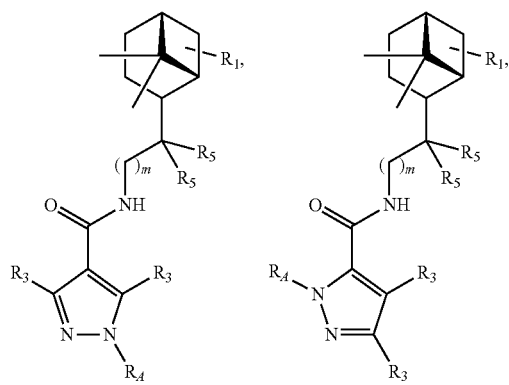
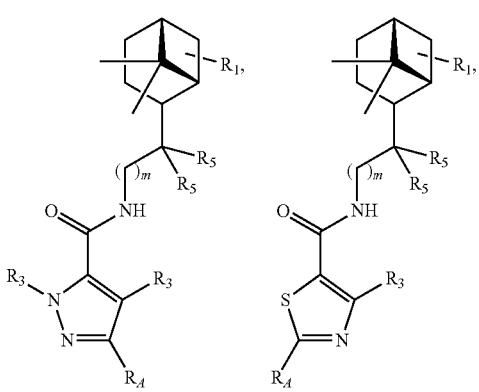
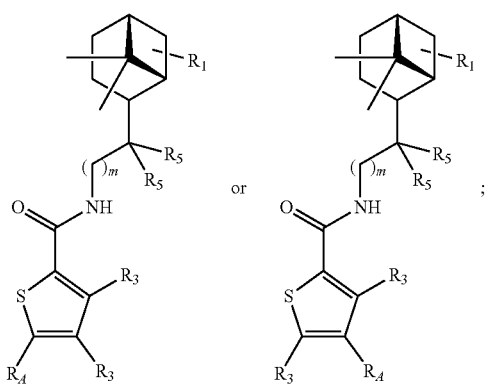
wherein in is 0 or 1, and each R₃ is as described above.
Representative subformulas of Formula III include, for example:
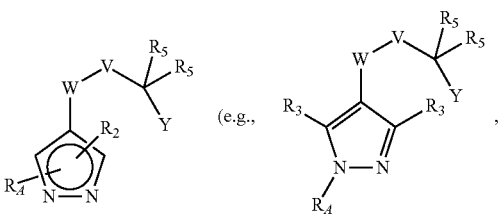 (e.g.,
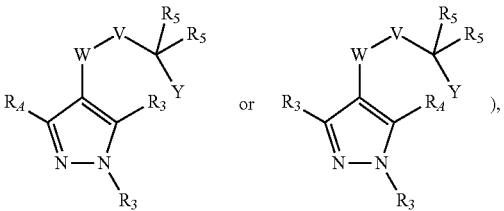 or
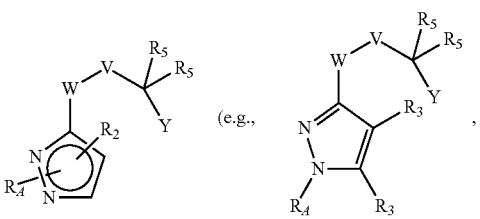 (e.g.,
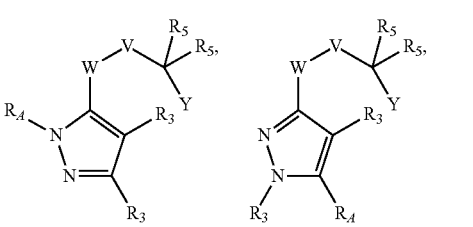
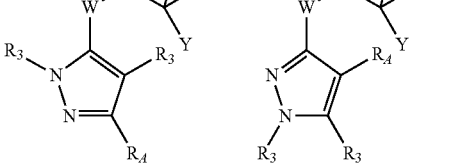 or
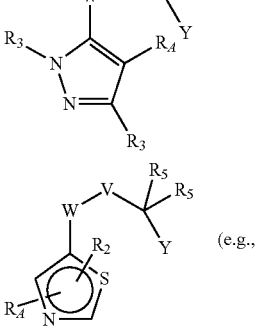), and
(e.g.,

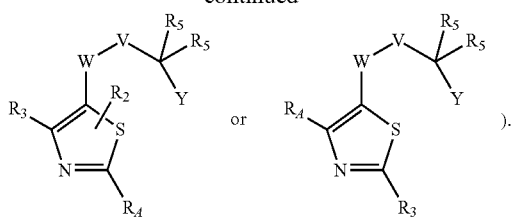

in which each $R_3$ is independently hydrogen, halogen, cyano, amino, nitro, aminocarbonyl, aminosulfonyl, —COOH, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$aminoalkyl, $C_1$-$C_6$alkoxy, $C_1$-$C_6$haloalkoxy, $C_1$-$C_6$alkanoyl, $C_2$-$C_6$alkyl ether, ($C_3$-$C_7$cycloalkyl)$C_0$-$C_4$alkyl, mono- or di-($C_1$-$C_6$alkyl)amino, $C_1$-$C_6$alkylsulfonyl, $C_1$-$C_6$alkanoylamino, mono- or di-($C_1$-$C_6$alkyl)aminocarbonyl, mono- or di-($C_1$-$C_6$alkyl)aminosulfonyl or ($C_1$-$C_6$alkyl)sulfonylamino; $Z_1$, $Z_2$ and $Z_3$ are as described for Formula III; $Z_4$ and $Z_5$ are independently CH, N, NH, O or S; and $Z_6$ is CH, S or O, such that no more than one of $Z_4$, $Z_5$ and $Z_6$ is chosen from O and S. It will be apparent that any CH or NH at $Z_1$, $Z_2$, $Z_3$, $Z_4$, $Z_5$ and/or $Z_6$ may be substituted with a substituent represented by $R_A$ or $R_2$, and that such substitution with result in the replacement of the hydrogen atom with a substituent represented by $R_A$ or $R_2$. In certain compounds in which the variable $R_3$ is present, each $R_3$ is independently hydrogen, halogen, $C_1$-$C_4$alkyl or $C_1$-$C_4$haloalkyl.

Within certain compounds of Formulas A and III, $R_A$ is (5- or 6-membered heteroaryl)$C_0$-$C_4$alkyl or (5- or 6-membered heteroaryl)$C_0$-$C_4$alkyl-T-, wherein T is S or O; each of which is substituted with from 0 to 4 substituents independently chosen from: (i) oxo, amino, halogen, hydroxy, cyano, aminocarbonyl, aminosulfonyl and —COOH; and (ii) $C_1$-$C_6$alkyl, $C_2$-$C_6$alkenyl, $C_1$-$C_6$hydroxyalkyl, $C_1$-$C_6$haloalkyl, $C_1$-$C_6$alkoxy, $C_1$-$C_6$haloalkoxy, $C_1$-$C_6$alkylthio, $C_2$-$C_6$alkenylthio, $C_2$-$C_6$alkyl ether, (mono- or di-$C_1$-$C_6$alkylamino)$C_0$-$C_4$alkyl, $C_1$-$C_6$alkylsulfonyl, $C_1$-$C_6$alkylsulfonylamino, mono- or di-($C_1$-$C_6$alkyl)aminosulfonyl, phenyl$C_0$-$C_4$alkyl and (4- to 7-membered heterocycle)$C_0$-$C_4$alkyl; each of which is substituted with from 0 to 4 substituents independently chosen from halogen, hydroxy, amino, oxo, aminocarbonyl, aminosulfonyl, —COOH, $C_1$-$C_4$alkyl and $C_1$-$C_4$haloalkyl. Representative such $R_A$ groups include (5- or 6-membered heteroaryl)$C_0$-$C_4$alkyl that is substituted with from 0 to 4 substituents independently chosen from oxo, amino, halogen, hydroxy, cyano, aminocarbonyl, aminosulfonyl, —COOH, $C_1$-$C_6$alkyl, $C_2$-$C_6$alkenyl, $C_1$-$C_6$haloalkyl, $C_1$-$C_6$hydroxyalkyl, $C_1$-$C_6$alkoxy, $C_1$-$C_6$haloalkoxy, $C_1$-$C_6$alkylthio, $C_2$-$C_6$alkyl ether, $C_1$-$C_6$alkanoylamino, mono- or di-($C_1$-$C_6$alkyl)amino, $C_1$-$C_6$alkylsulfonyl, $C_1$-$C_6$alkylsulfonylamino, mono- or di-($C_1$-$C_6$alkyl)aminosulfonyl, mono- or di-($C_1$-$C_6$alkylamino)carbonyl, and 4- to 7-membered heterocycle, wherein the 5- or 6-membered heteroaryl is pyridyl, pyrimidinyl, imidazolyl or chosen from

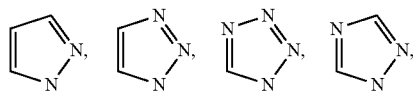

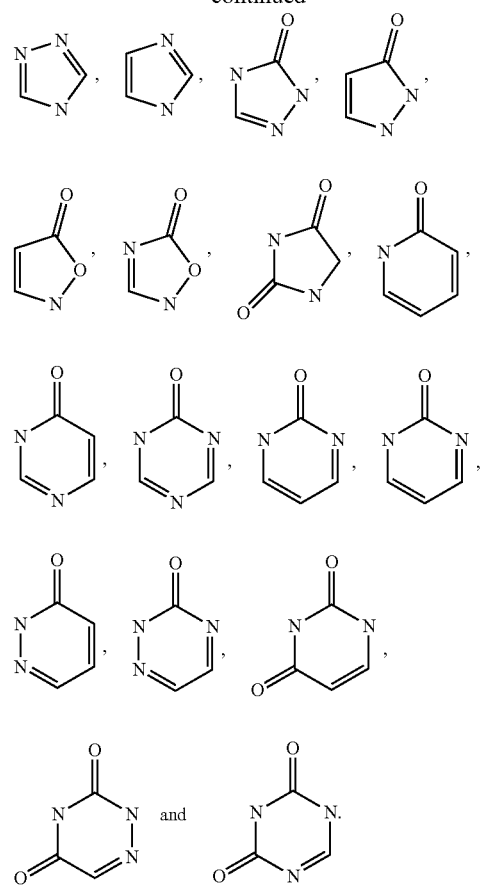

Within certain compounds of Formula III (or the subformulas thereof), one or more of the following conditions applies:

(a) $R_2$ represents from 0 to 2 substituents independently chosen from halogen, $C_1$-$C_6$alkyl and $C_1$-$C_6$haloalkyl;

(b) V is methylene or ethylene, each of which is substituted with from 0 to 4 substituents independently chosen from $C_1$-$C_4$alkyl, ($C_3$-$C_8$cycloalkyl)$C_0$-$C_2$alkyl, phenyl$C_0$-$C_2$alkyl and substituents that are taken together, with the carbon atom or carbon atoms to which they are bound, to form a 3- to 7-membered cycloalkyl ring or a 4- to 7-membered heterocycloalkyl ring;

(c) V is methylene;

(d) Y is $C_3$-$C_{16}$cycloalkyl, 6- to 10-membered aryl or 5- to 10-membered heteroaryl, each of which substituted with from 0 to 4 substituents independently chosen from halogen, hydroxy, cyano, amino, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, and mono- or di-($C_1$-$C_6$alkyl)amino;

(e) Y is phenyl or a 5- or 6-membered heteroaryl; each of which is optionally fused to a 5- to 7-membered carbocycle or to a 5- to 7-membered heterocycle; each of which phenyl, heteroaryl, carbocycle and heterocycle is substituted with from 0 to 4 substituents independently chosen from halogen, hydroxy, cyano, amino, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, and mono- or di-($C_1$-$C_6$alkyl)amino; and/or (f) —W—V—C(R$_5$)(R$_5$)—Y is:

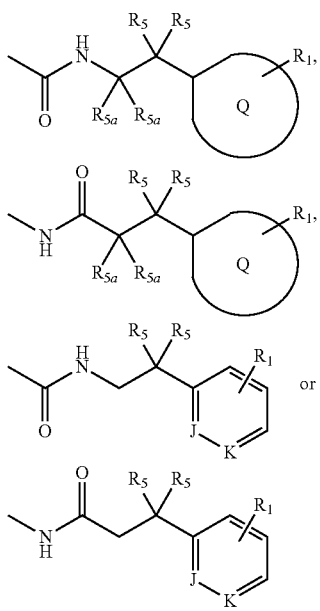

wherein:

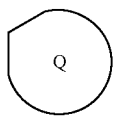

is phenyl or a 5- or 6-membered heteroaryl (e.g., pyridyl, pyrazolyl or pyrimidinyl);

J and K are independently CH or N;

R$_1$ represents from 0 to 2 substituents independently chosen from halogen, hydroxy, cyano, amino, nitro, aminocarbonyl, aminosulfonyl, C$_1$-C$_6$alkyl, C$_2$-C$_6$alkenyl, C$_2$-C$_6$alkynyl, C$_1$-C$_6$haloalkyl, C$_1$-C$_6$hydroxyalkyl, C$_1$-C$_6$alkoxy, C$_1$-C$_6$haloalkoxy, (C$_3$-C$_7$cycloalkyl)C$_0$-C$_4$alkyl, and mono- or di-(C$_1$-C$_6$alkyl)amino; or two substituents represented by R$_1$ are taken together, with any intervening ring atoms, to form a fused 4- to 7-membered carbocycle or a fused 4- to 7-membered heterocycle;

Each R$_5$ is independently hydrogen, C$_1$-C$_6$alkyl, C$_3$-C$_7$cycloalkyl or phenyl; or both R$_5$ are taken together with the carbon atom to which they are bound to form a C$_3$-C$_8$cycloalkyl; and Each R$_{5a}$ is independently hydrogen, C$_1$-C$_6$alkyl, C$_3$-C$_7$cycloalkyl or phenyl; or both R$_{5a}$ are taken together with the carbon atom to which they are bound to form a C$_3$-C$_8$cycloalkyl.

Within these formulas and others in which the variables J and K appear, if J or K is CH, the carbon atom at that ring position may optionally be substituted with a substituent represented by R$_1$. For example, if both J and K are CH, substituents represented by R$_1$ may be present at any of positions 2-6 of the resulting phenyl moiety (with position 1 being the point of attachment to C(R$_5$)(R$_5$)).

Representative subformulas of Formula III include, for example:

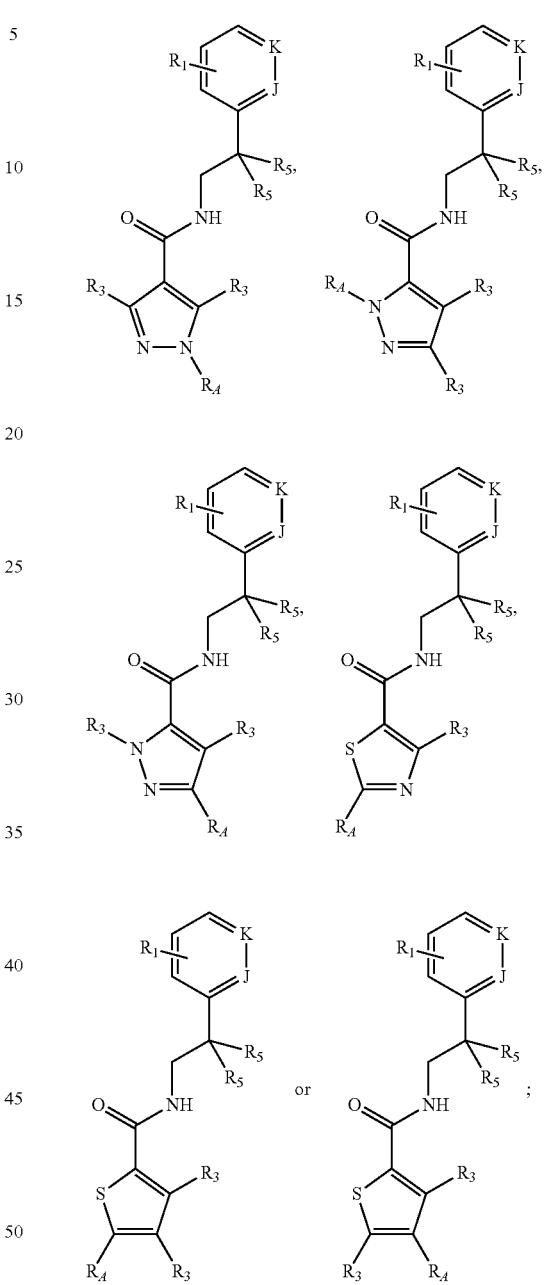

wherein R$_3$ is as described above.

Within certain such compounds, each R$_3$ is independently hydrogen, halogen, cyano, amino, nitro, aminocarbonyl, aminosulfonyl, —COOH, C$_1$-C$_6$alkyl, C$_2$-C$_6$alkenyl, C$_2$-C$_6$alkynyl, C$_1$-C$_6$haloalkyl, C$_1$-C$_6$hydroxyalkyl, C$_1$-C$_6$aminoalkyl, C$_1$-C$_6$alkoxy, C$_1$-C$_6$haloalkoxy, C$_1$-C$_6$alkanoyl, C$_2$-C$_6$alkyl ether, (C$_3$-C$_7$cycloalkyl)C$_0$-C$_4$alkyl, or mono- or di-(C$_1$-C$_6$alkyl)amino. Within further such compounds, each R$_3$ is independently hydrogen, halogen, C$_1$-C$_4$alkyl or C$_1$-C$_4$haloalkyl.

Representative subformulas of Formulas IV and V include, for example:

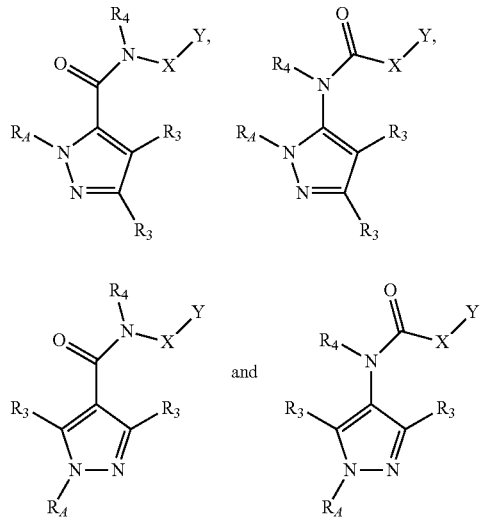

and wherein each $R_3$ is as described above. Within certain such compounds, each $R_3$ is independently hydrogen, halogen, cyano, amino, nitro, aminocarbonyl, aminosulfonyl, —COOH, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$aminoalkyl, $C_1$-$C_6$alkoxy, $C_1$-$C_6$haloalkoxy, $C_1$-$C_6$alkanoyl, $C_2$-$C_6$alkyl ether, ($C_3$-$C_7$cycloalkyl)$C_0$-$C_4$alkyl, or mono- or di-($C_1$-$C_6$alkyl)amino. Within further such compounds, each $R_3$ is independently hydrogen, halogen, $C_1$-$C_4$alkyl or $C_1$-$C_4$haloalkyl.

Within certain compounds of Formulas IV and V, and subformulas thereof, $R_4$ is (5- or 6-membered heteroaryl)$C_0$-$C_4$alkyl that is substituted with from 0 to 4 substituents independently chosen from: (i) oxo, amino, halogen, hydroxy, cyano, aminocarbonyl, aminosulfonyl and —COOH; and (ii) $C_1$-$C_6$alkyl, $C_2$-$C_6$alkenyl, $C_1$-$C_6$haloalkyl, $C_1$-$C_6$hydroxyalkyl, $C_1$-$C_6$alkoxy, $C_1$-$C_6$haloalkoxy, $C_1$-$C_6$alkylthio, $C_2$-$C_6$alkyl ether, $C_1$-$C_6$alkanoylamino, mono- or di-($C_1$-$C_6$alkyl)amino, $C_1$-$C_6$alkylsulfonyl, $C_1$-$C_6$alkylsulfonylamino, mono- or di-($C_1$-$C_6$alkyl)aminosulfonyl, mono- or di-($C_1$-$C_6$alkylamino)carbonyl and (4- to 7-membered heterocycle)$C_0$-$C_2$alkyl, each of which is substituted with from 0 to 4 substituents independently chosen from oxo, amino, halogen, hydroxy, cyano, $C_1$-$C_4$alkyl, $C_2$-$C_4$alkenyl and $C_1$-$C_4$haloalkyl. In certain such compounds, the (5- or 6-membered heteroaryl)$C_0$-$C_4$alkyl (which is unsubstituted or substituted as described above) is thiazolyl, pyrazolyl, pyridinyl, pyrimidinyl or pyridazinyl.

Within certain compounds of Formulas IV and V, and subformulas thereof, Y is phenyl or a 6-membered heteroaryl, each of which is substituted with from 0 to 3 substituents independently chosen from hydroxy, halogen, cyano, amino, nitro, oxo, aminocarbonyl, aminosulfonyl, —COOH, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$aminoalkyl, $C_1$-$C_6$alkoxy, $C_1$-$C_6$haloalkoxy, $C_2$-$C_6$alkyl ether, $C_1$-$C_6$alkanoyl, $C_1$-$C_6$alkyl sulfonyl, ($C_3$-$C_7$cycloalkyl)$C_0$-$C_4$alkyl, mono- or di-($C_1$-$C_6$alkyl)amino; and $R_4$ is hydrogen or $C_1$-$C_4$alkyl. In certain such compounds, —X—Y is:

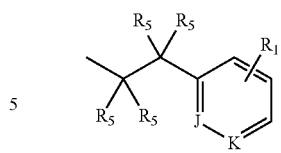

wherein J and K are independently CH or N; $R_1$ represents from 0 to 3 substituents independently chosen from halogen, hydroxy, cyano, amino, nitro, aminocarbonyl, aminosulfonyl, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, ($C_3$-$C_7$cycloalkyl)$C_0$-$C_4$alkyl, and mono- or di-($C_1$-$C_6$alkyl)amino; and each $R_5$ is independently hydrogen, $C_1$-$C_6$alkyl, $C_3$-$C_7$cycloalkyl, phenyl, or taken together with another $R_5$ attached to the same carbon atom, and the carbon atom to which they are bound, to form a $C_3$-$C_8$cycloalkyl.

Certain compounds of Formula V further satisfy the formula:

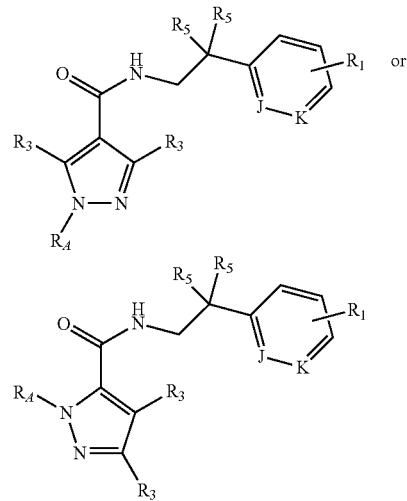

wherein $R_4$ is (5- or 6-membered heteroaryl)$C_0$-$C_4$alkyl that is substituted with from 0 to 4 substituents independently chosen from: (i) oxo, amino, halogen, hydroxy, cyano, aminocarbonyl, aminosulfonyl and —COOH; and (ii) $C_1$-$C_6$alkyl, $C_2$-$C_6$alkenyl, $C_1$-$C_6$haloalkyl, $C_1$-$C_6$hydroxyalkyl, $C_1$-$C_6$alkoxy, $C_1$-$C_6$haloalkoxy, $C_1$-$C_6$alkylthio, $C_2$-$C_6$alkyl ether, $C_1$-$C_6$alkanoylamino, mono- or di-($C_1$-$C_6$alkyl)amino, $C_1$-$C_6$alkylsulfonyl, $C_1$-$C_6$alkylsulfonylamino, mono- or di-($C_1$-$C_6$alkyl)aminosulfonyl, mono- or di-($C_1$-$C_6$alkylamino)carbonyl and (4- to 7-membered heterocycle)$C_0$-$C_2$alkyl, each of which is substituted with from 0 to 4 substituents independently chosen from oxo, amino, halogen, hydroxy, cyano, $C_1$-$C_4$alkyl, $C_2$-$C_4$alkenyl and $C_1$-$C_4$haloalkyl; J and K are independently CH or N; $R_1$ represents from 0 to 3 substituents chosen from halogen, hydroxy, cyano, amino, nitro, aminocarbonyl, aminosulfonyl, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, ($C_3$-$C_7$cycloalkyl)$C_0$-$C_4$alkyl, and mono- or di-($C_1$-$C_6$alkyl)amino; each $R_3$ is independently hydrogen, halogen, $C_1$-$C_4$alkyl or $C_1$-$C_4$haloalkyl; and each $R_5$ is independently hydrogen, $C_1$-$C_6$alkyl, $C_3$-$C_7$cycloalkyl or phenyl; or two $R_5$ are taken together with the carbon atom to which they are bound to form a $C_3$-$C_8$cycloalkyl.

Within certain compounds of Formula IV, V or VI, and subformulas thereof, at least one R₅ is not hydrogen (e.g., both R₅ are taken together with the carbon atom to which they are bound to form a C₃-C₈cycloalkyl).

Within certain compounds of Formula VI, R₃ is hydrogen, halogen, C₁-C₄alkyl or C₁-C₄halo alkyl.

Within further compounds of Formula VI, —W—X—Y is:

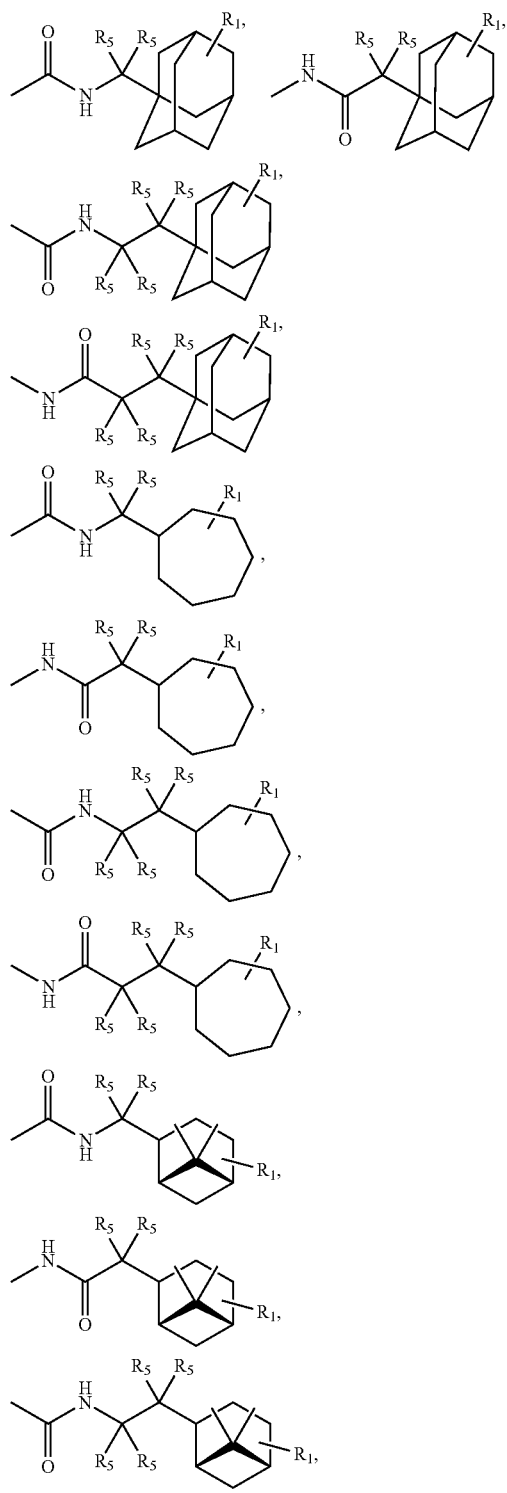

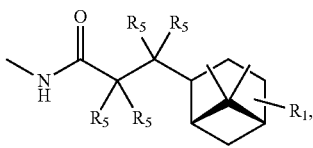

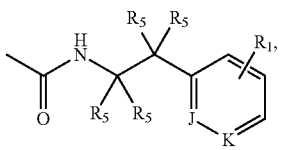

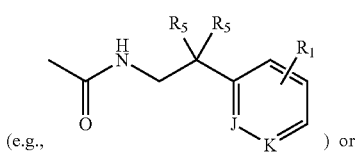

(e.g., 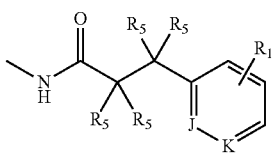 ) or

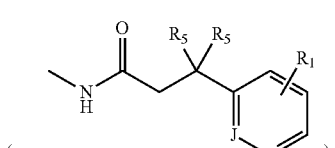

(e.g., ... );

wherein J and K are independently CH or N; R₁ represents from 0 to 3 substituents independently chosen from halogen, hydroxy, cyano, amino, nitro, aminocarbonyl, aminosulfonyl, C₁-C₆alkyl, C₂-C₆alkenyl, C₂-C₆alkynyl, C₁-C₆haloalkyl, C₁-C₆hydroxyalkyl, C₁-C₆alkoxy, C₁-C₆haloalkoxy, (C₃-C₇cycloalkyl)C₀-C₄ alkyl, and mono- or di-(C₁-C₆alkyl)amino; and each R₅ is independently hydrogen, C₁-C₆alkyl, C₃-C₇cycloalkyl or phenyl; or taken together with another R₅ moiety and the carbon atom to which they are bound to form a C₃-C₈cycloalkyl.

Certain compounds of Formulas III-VI further satisfy the formula:

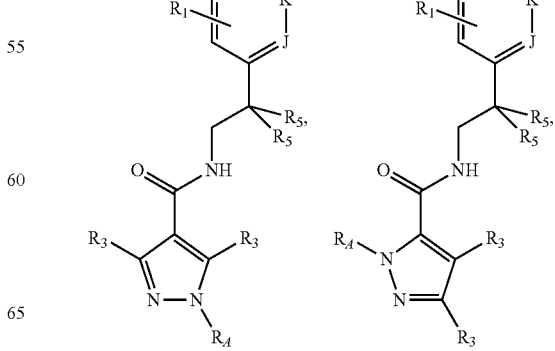

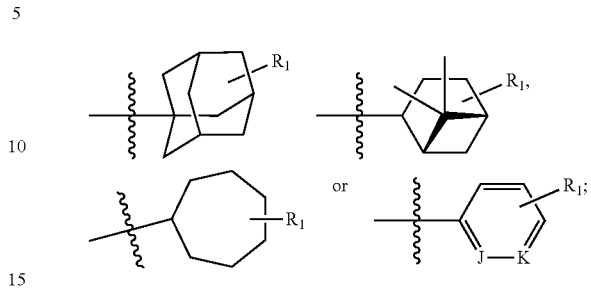

-continued

Within certain compounds of Formula VI, $R_A$ is phenyl or 5- or 6-membered heteroaryl, each of which is substituted with from 0 to 4 substituents independently chosen from: (i) oxo, amino and halogen; and (ii) $C_1$-$C_6$alkyl, $C_2$-$C_6$alkenyl, $C_1$-$C_6$haloalkyl, $C_1$-$C_6$hydroxyalkyl, $C_1$-$C_6$alkoxy, $C_1$-$C_6$haloalkoxy, $C_2$-$C_6$alkyl ether, mono- or di-($C_1$-$C_6$alkyl)amino, and (4- to 7-membered heterocycle)$C_0$-$C_2$alkyl, each of which is substituted with from 0 to 4 substituents independently chosen from oxo, amino, halogen, hydroxy, cyano, $C_1$-$C_4$alkyl, $C_2$-$C_4$alkenyl and $C_1$-$C_4$haloalkyl.

Within other compounds of Formula VI, $R_A$ is 5- to 7-membered heterocycloalkyl that is substituted with from 0 to 4 substituents independently chosen from: (i) oxo, amino and halogen; and (ii) $C_1$-$C_6$alkyl, $C_2$-$C_6$alkenyl, $C_1$-$C_6$haloalkyl, $C_1$-$C_6$hydroxyalkyl, $C_1$-$C_6$alkoxy, $C_1$-$C_6$haloalkoxy, $C_2$-$C_6$alkyl ether, mono- or di-($C_1$-$C_6$alkyl)amino, and (4- to 7-membered heterocycle)$C_0$-$C_2$alkyl, each of which is substituted with from 0 to 4 substituents independently chosen from oxo, amino, halogen, hydroxy, cyano, $C_1$-$C_4$alkyl, $C_2$-$C_4$alkenyl and $C_1$-$C_4$haloalkyl.

Certain compounds of Formula VI further satisfy the formula:

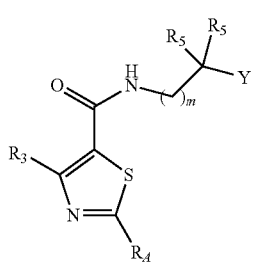

wherein:

m is 0 or 1;

Y is:

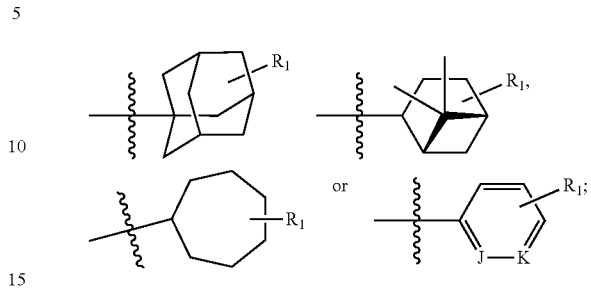

J and K are independently CH or N;

$R_1$ represents from 0 to 3 substituents independently chosen from halogen, hydroxy, cyano, amino, nitro, aminocarbonyl, aminosulfonyl, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, ($C_3$-$C_7$cycloalkyl)$C_0$-$C_4$alkyl, and mono- or di-($C_1$-$C_6$alkyl)amino;

$R_3$ is hydrogen, halogen, $C_1$-$C_4$alkyl or $C_1$-$C_4$haloalkyl;

Each $R_5$ is independently (i) hydrogen; (ii) $C_1$-$C_6$alkyl, $C_3$-$C_7$cycloalkyl, 4- to 7-membered heterocycloalkyl or phenyl; or (iii) taken together with another $R_5$ moiety and the carbon atom to which they are bound to form a $C_3$-$C_8$cycloalkyl or 4- to 7-membered heterocycloalkyl; each of which (ii) or (iii) is substituted with from 0 to 3 substituents independently chose from hydroxy, halogen, amino, aminocarbonyl, $C_1$-$C_6$alkyl $C_1$-$C_6$alkoxy, mono- or di-($C_1$-$C_6$alkyl)amino, mono- or di-($C_1$-$C_6$alkyl)aminocarbonyl, and 4- to 7-membered heterocycloalkyl; and $R_A$ is 5- to 7-membered heterocycloalkyl, phenyl or 5- or 6-membered heteroaryl, each of which is substituted with from 0 to 4 substituents independently chosen from:

(i) oxo, amino and halogen; and (ii) $C_1$-$C_6$alkyl, $C_2$-$C_6$alkenyl, $C_1$-$C_6$haloalkyl, $C_1$-$C_6$hydroxyalkyl, $C_1$-$C_6$alkoxy, $C_1$-$C_6$haloalkoxy, $C_2$-$C_6$alkyl ether, mono- or di-($C_1$-$C_6$alkyl)amino, and (4- to 7-membered heterocycle)$C_0$-$C_2$alkyl, each of which is substituted with from 0 to 4 substituents independently chosen from oxo, amino, halogen, hydroxy, cyano, $C_1$-$C_4$alkyl, $C_2$-$C_4$alkenyl and $C_1$-$C_4$haloalkyl.

Within certain compounds, one $R_5$ moiety is a N-linked 5- or 6-membered heterocycloalkyl group (e.g., piperazinyl, morpholinyl, thiomorpholinyl, piperidinyl or pyrrolidinyl), each of which is unsubstituted or substituted with one substituent such as hydroxy, halogen, aminocarbonyl, $C_1$-$C_4$alkoxy, mono- or di-($C_1$-$C_4$alkyl)amino or 4- to 7-membered heterocycloalkyl.

Within certain compounds of Formula VII, V is absent or methylene. Within further compounds of Formula VII, represents pyrazole, thiazole, imidazole, oxazole or thiophene.

Certain compounds of Formula VII further satisfy the formula:

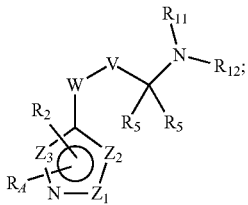

wherein $Z_1$, $Z_2$ and $Z_3$ are independently N, NH, CH, S or O; such that no more than one of $Z_1$, $Z_2$ and $Z_3$ is chosen from O and S. Certain such compounds satisfy one or more of the following formulas:

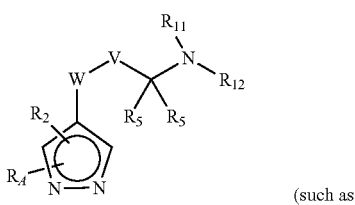

(such as

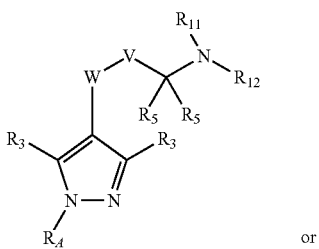

or

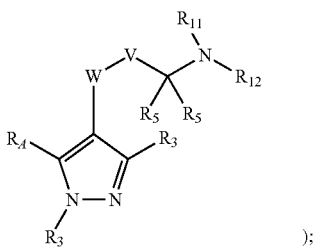

);

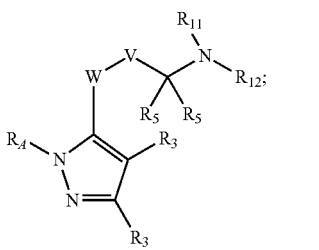

or

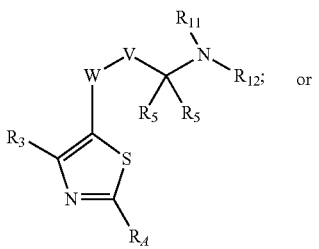

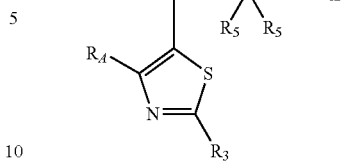

wherein each $R_3$ is independently hydrogen, halogen, cyano, amino, nitro, aminocarbonyl, aminosulfonyl, —COOH, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$aminoalkyl, $C_1$-$C_6$alkoxy, $C_1$-$C_6$haloalkoxy, $C_1$-$C_6$alkanoyl, $C_2$-$C_6$alkyl ether, ($C_3$-$C_7$cycloalkyl)$C_0$-$C_4$alkyl, mono- or di-($C_1$-$C_6$alkyl)amino, $C_1$-$C_6$alkylsulfonyl, $C_1$-$C_6$alkanoylamino, mono- or di-($C_1$-$C_6$alkyl)aminocarbonyl, mono- or di-($C_1$-$C_6$alkyl)aminosulfonyl or ($C_1$-$C_6$alkyl)sulfonylamino.

Other compounds of Formula VII further satisfy the formula:

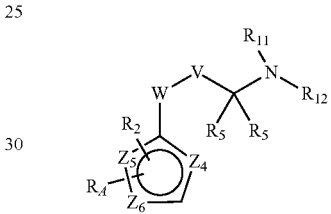

wherein $Z_4$ and $Z_5$ are independently CH, N, NH, O or S; and $Z_6$ is CH, S or O; such that no more than one of $Z_4$, $Z_5$ and $Z_6$ is chosen from 0 and S. Certain such compounds further satisfy the formula:

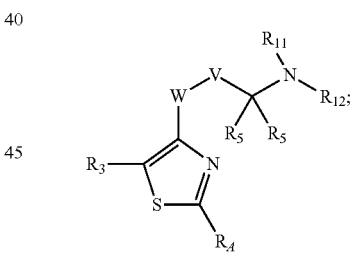

wherein $R_3$ is as described above.

Within certain embodiments of the above subformulas of Formula VII, each $R_3$ is independently hydrogen, halogen, $C_1$-$C_4$alkyl or $C_1$-$C_4$haloalkyl. Within further such subformulas, and within Formula VII, $R_A$ is as described above, or $R_A$ is $C_1$-$C_6$alkyl, $C_2$-$C_6$alkenyl, $C_1$-$C_6$alkoxy, $C_1$-$C_6$alkylthio, $C_2$-$C_6$alkenylthio, $C_2$-$C_6$alkyl ether, $C_1$-$C_6$alkoxycarbonyl, $C_1$-$C_6$alkylsulfonyl, $C_1$-$C_6$alkylsulfonylamino, mono- or di-$C_1$-$C_6$alkylaminosulfonyl, mono- or di-($C_1$-$C_6$alkyl)amino$C_0$-$C_4$alkyl, (4- to 7-membered heterocycloalkyl)$C_0$-$C_4$alkyl or (4- to 7-membered heterocycloalkyl)$C_0$-$C_4$alkyl-T-, wherein T is S or O; each of which is substituted with from 0 to 4 substituents independently chosen from: (i) oxo, amino, halogen, hydroxy, aminocarbonyl, aminosulfonyl and —COOH; and (ii) $C_1$-$C_6$alkyl, $C_1$-$C_6$hydroxyalkyl, $C_1$-$C_6$haloalkyl, $C_1$-$C_6$alkoxy, $C_1$-$C_6$alkylthio, $C_2$-$C_6$alkyl ether, $C_1$-$C_6$alkanoylamino, mono- or di-($C_1$-$C_6$alkyl)amino, $C_1$-$C_6$alkylsulfonyl, $C_1$-$C_6$alkylsulfonylamino, mono- or di-$C_1$-$C_6$alkylaminocarbonyl, mono- or di-$C_1$-$C_6$alkylaminosulfonyl and 4- to 7-membered heterocycle; each of which is substituted with from 0 to 4 substituents independently chosen from halogen, hydroxy, amino, oxo, aminocarbonyl, aminosulfonyl, —COOH, $C_1$-$C_4$alkyl and $C_1$-$C_4$haloalkyl, such that if

represents pyrazole or imidazole, then $R_A$ is not optionally substituted $C_1$-$C_6$alkoxy. Within certain such compounds, $R_A$ is $C_1$-$C_6$alkyl, $C_2$-$C_6$alkyl ether, $C_1$-$C_4$alkoxycarbonyl, mono- or di-($C_1$-$C_6$alkyl)amino$C_0$-$C_4$alkyl, or (4- to 7-membered heterocycloalkyl)$C_0$-$C_4$alkyl; each of which is substituted with from 0 to 4 substituents independently chosen from amino, hydroxy, oxo, aminocarbonyl, aminosulfonyl, $C_1$-$C_6$alkyl, $C_1$-$C_6$hydroxyalkyl, $C_2$-$C_6$alkyl ether, mono- or di-($C_1$-$C_6$alkyl)amino, mono- or di-($C_1$-$C_6$alkyl)aminocarbonyl, $C_1$-$C_6$alkylsulfonyl, $C_1$-$C_6$alkylsulfonylamino, 4- to 7-membered heterocycloalkyl, and 5- or 6-membered heteroaryl.

Within certain compounds of Formula VII and the subformulas thereof,

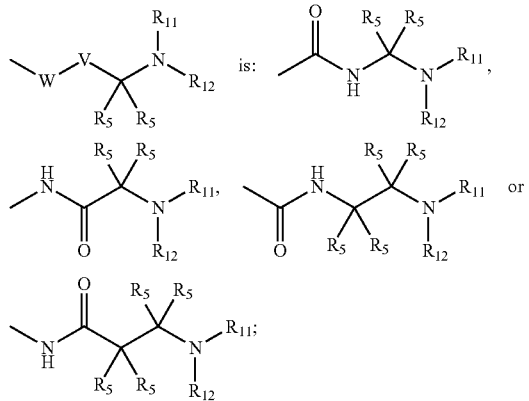

wherein:

$R_{11}$ and $R_{12}$ are taken together, with the nitrogen atom to which they are bound, to form a 4- to 7-membered heterocycloalkyl that is substituted with from 0 to 4 substituents independently chosen from hydroxy, halogen, cyano, amino, $C_1$-$C_6$alkyl, $C_1$-$C_6$hydroxyalkyl, $C_1$-$C_6$haloalkyl, $C_1$-$C_6$alkoxy, $C_1$-$C_6$haloalkoxy, $C_2$-$C_6$alkyl ether, $C_1$-$C_6$alkanoylamino, mono- or di-($C_1$-$C_6$alkyl)amino, $C_1$-$C_6$alkylsulfonyl, $C_1$-$C_6$alkylsulfonylamino, mono- or di-($C_1$-$C_6$alkyl)aminosulfonyl, mono- or di-($C_1$-$C_6$alkylamino) carbonyl, and 4- to 7-membered heterocycle; and each $R_5$ is independently hydrogen, $C_1$-$C_6$alkyl, $C_3$-$C_7$cycloalkyl or phenyl; or taken together with another $R_5$ moiety and the carbon atom to which they are bound to form a $C_3$-$C_8$cycloalkyl or 4- to 7-membered heterocycloalkyl. Certain such compounds further satisfy one of the following formulas:

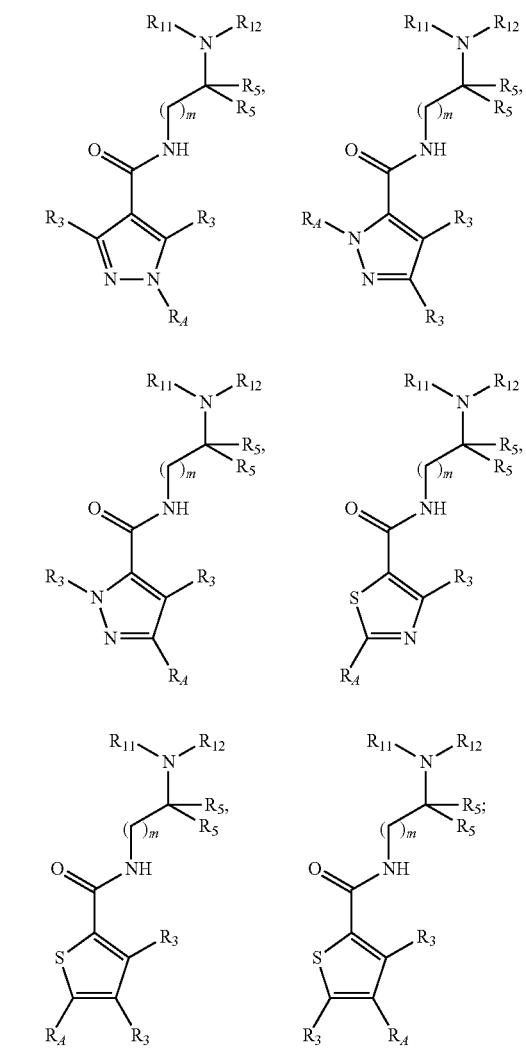

wherein m is 0 or 1. Within certain such compounds, the $R_5$ moieties are taken together, with the carbon atom to which they are bound, to form a $C_3$-$C_8$cycloalkyl.

Within certain compounds of Formula VIII, $R_3$ is halogen, cyano, $C_1$-$C_4$haloalkyl, phenyl or 5- or 6-membered heteroaryl; and/or Y is piperidinyl, piperazinyl, morpholinyl or thiomorpholinyl, each of which is substituted with from 0 to 2 substituents independently chosen from $C_1$-$C_6$alkyl. In further such compounds,

is a group of the formula

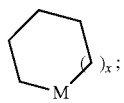

wherein x is 0, 1 or 2; and M is CH$_2$, NH, S or O. Representative such compounds have the formula:

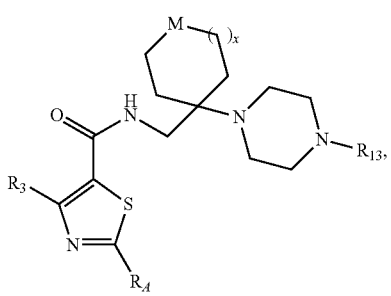

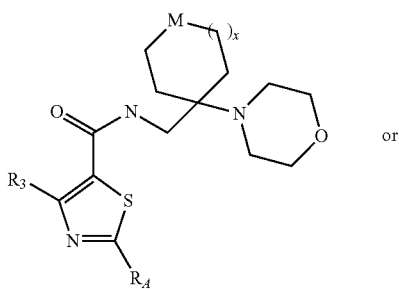

or

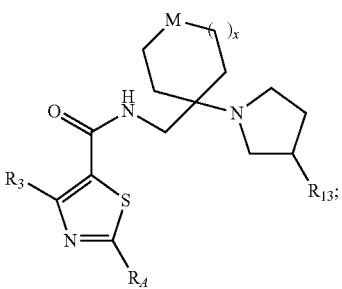

wherein R$_{13}$ is hydrogen or C$_1$-C$_4$alkyl.

Within further compounds of Formula VIII, R$_A$ is phenyl or 5- or 6-membered heteroaryl, each of which is substituted with from 0 to 4 substituents independently chosen from: (i) oxo, amino, and halogen; and (ii) C$_1$-C$_6$alkyl, C$_2$-C$_6$alkenyl, C$_1$-C$_6$haloalkyl, C$_1$-C$_6$hydroxyalkyl, C$_1$-C$_6$alkoxy, C$_1$-C$_6$haloalkoxy, C$_2$-C$_6$alkyl ether, mono- or di-(C$_1$-C$_6$alkyl)amino, and (4- to 7-membered heterocycle)C$_0$-C$_2$alkyl, each of which is substituted with from 0 to 4 substituents independently chosen from oxo, amino, halogen, hydroxy, cyano, C$_1$-C$_4$alkyl, C$_2$-C$_4$alkenyl and C$_1$-C$_4$haloalkyl. Within other such compounds, R$_A$ is 5- to 7-membered heterocycloalkyl that is substituted with from 0 to 4 substituents independently chosen from: (i) oxo, amino, and halogen; and (ii) C$_1$-C$_6$alkyl, C$_2$-C$_6$alkenyl, C$_1$-C$_6$haloalkyl, C$_1$-C$_6$hydroxyalkyl, C$_1$-C$_6$alkoxy, C$_1$-C$_6$haloalkoxy, C$_2$-C$_6$alkyl ether, mono- or di-(C$_1$-C$_6$alkyl)amino, and (4- to 7-membered heterocycle)C$_0$-C$_2$alkyl, each of which is substituted with from 0 to 4 substituents independently chosen from oxo, amino, halogen, hydroxy, cyano, C$_1$-C$_4$alkyl, C$_2$-C$_4$alkenyl and C$_1$-C$_4$haloalkyl.

Within certain compounds of Formula IX,

is pyrazole, thiazole, imidazole, oxazole or thiophene. Representative such compounds further satisfy the formula:

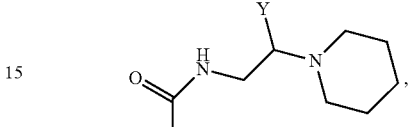

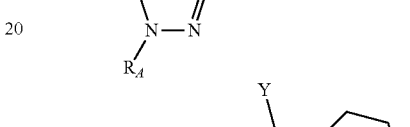

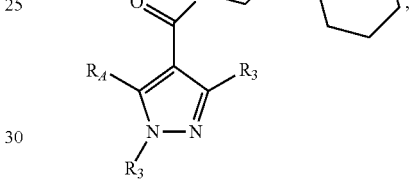

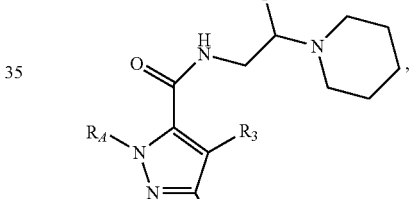

or

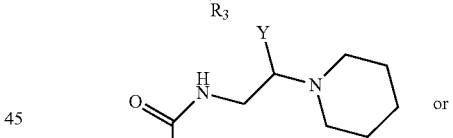

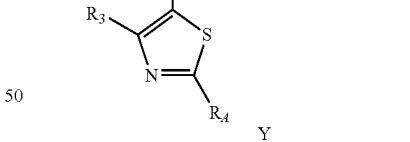

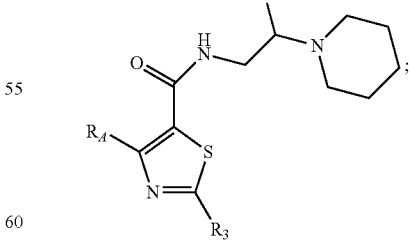

wherein each R$_3$ is independently hydrogen, halogen, cyano, amino, nitro, aminocarbonyl, aminosulfonyl, —COOH, C$_1$-C$_6$alkyl, C$_2$-C$_6$alkenyl, C$_2$-C$_6$alkynyl, C$_1$-C$_6$haloalkyl, C$_1$-C$_6$hydroxyalkyl, C$_1$-C$_6$aminoalkyl, C$_1$-C$_6$alkoxy, C$_1$-C$_6$haloalkoxy, C$_1$-C$_6$alkanoyl, C$_2$-C$_6$alkyl ether, (C$_3$-

$C_7$cycloalkyl)$C_0$-$C_4$alkyl, mono- or di-($C_1$-$C_6$alkyl)amino, $C_1$-$C_6$alkylsulfonyl, $C_1$-$C_6$alkanoylamino, mono- or di-($C_1$-$C_6$alkyl)aminocarbonyl, mono- or di-($C_1$-$C_6$alkyl)aminosulfonyl or ($C_1$-$C_6$alkyl)sulfonylamino; within certain such compounds each $R_3$ is independently hydrogen, halogen, $C_1$-$C_4$alkyl or $C_1$-$C_4$haloalkyl. Representative $R_4$ moieties include, for example, phenyl$C_0$-$C_2$alkyl, (5- or 6-membered heteroaryl)$C_0$-$C_4$alkyl, phenyl$C_0$-$C_2$alkyl-T- or (5- or 6-membered heteroaryl)$C_0$-$C_4$alkyl-T-, wherein T is S or O; each of which is substituted with from 0 to 4 substituents independently chosen from: (i) oxo, amino, halogen, hydroxy, cyano, aminocarbonyl, aminosulfonyl and —COOH; and (ii) $C_1$-$C_6$alkyl, $C_2$-$C_6$alkenyl, $C_1$-$C_6$hydroxyalkyl, $C_1$-$C_6$haloalkyl, $C_1$-$C_6$alkoxy, $C_1$-$C_6$haloalkoxy, $C_1$-$C_6$alkylthio, $C_2$-$C_6$alkenylthio, $C_2$-$C_6$alkyl ether, (mono- or di-$C_1$-$C_6$alkylamino)$C_0$-$C_4$alkyl, $C_1$-$C_6$alkylsulfonyl, $C_1$-$C_6$alkylsulfonylamino, mono- or di-($C_1$-$C_6$alkyl)aminosulfonyl, and (4- to 7-membered heterocycloalkyl)$C_0$-$C_4$alkyl; each of which is substituted with from 0 to 4 substituents independently chosen from halogen, hydroxy, amino, oxo, aminocarbonyl, aminosulfonyl, —COOH, $C_1$-$C_4$alkyl and $C_1$-$C_4$haloalkyl. Representative Y groups include, for example,

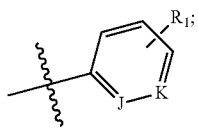

in which J and K are independently CH or N; and $R_1$ represents from 0 to 3 substituents independently chosen from halogen, hydroxy, cyano, amino, nitro, aminocarbonyl, aminosulfonyl, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, ($C_3$-$C_7$cycloalkyl)$C_0$-$C_4$alkyl, and mono- or di-($C_1$-$C_6$alkyl)amino.

Representative 5-membered heterocyclic amides and related compounds provided herein include, but are not limited to, those specifically described in Examples 1-3. It will be apparent that the specific compounds recited herein are representative only, and are not intended to limit the scope of the present invention. Further, as noted above, all compounds of the present invention may be present as a free acid or base, or as a pharmaceutically acceptable salt. In addition, other forms such as hydrates and prodrugs of such compounds are specifically contemplated by the present invention.

Within certain aspects of the present invention, 5-membered heterocyclic amides and related compounds provided herein detectably alter (modulate) $P2X_7$ receptor activity, as determined using an assay such as an assay recited in Example 4, herein. Additional assays that may be used for this purpose include assays that measure IL-1β release; assays that measure uptake of a membrane-impermeant fluorescent dye such as YO-PRO1; assays that measure lucifer yellow uptake; assays that measure ethidium bromide uptake; and assays that use calcium imaging to detect $P2X_7$ activity; all of which assays are well known in the art. Certain modulators provided herein detectably modulate $P2X_7$ receptor activity at micromolar concentrations, at nanomolar concentrations, or at subnanomolar concentrations.

As noted above, compounds that are $P2X_7$ receptor antagonists are preferred within certain embodiments. $IC_{50}$ values for such compounds may be determined using a standard in vitro $P2X_7$ receptor-mediated calcium mobilization assay, as provided in Example 4. Briefly, cells expressing $P2X_7$ receptor are contacted with a compound of interest and with an indicator of intracellular calcium concentration (e.g., a membrane permeable calcium sensitivity dye such as Fluo-3, Fluo-4 or Fura-2 (Invitrogen, Carlsbad, Calif.), each of which produce a fluorescent signal when bound to $Ca^{++}$). Such contact is preferably carried out by one or more incubations of the cells in buffer or culture medium comprising either or both of the compound and the indicator in solution. Contact is maintained for an amount of time sufficient to allow the dye to enter the cells (e.g., 1-2 hours). Cells are washed or filtered to remove excess dye and are then contacted with a $P2X_7$ receptor agonist (e.g., ATP or 2'(3')-O-(4-benzoyl-benzoyl)adenosine 5'-triphosephate at, for example, a concentration equal to the $EC_{50}$ concentration), and a fluorescence response is measured. When agonist-contacted cells are contacted with a compound that is a $P2X_7$ receptor antagonist, the fluorescence response is generally reduced by at least 20%, preferably at least 50% and more preferably at least 80%, as compared to cells that are contacted with the agonist in the absence of test compound. In certain embodiments, $P2X_7$ receptor antagonists provided herein exhibit no detectable agonist activity an in vitro assay of $P2X_7$ receptor agonism at a concentration of compound equal to the $IC_{50}$. Certain such antagonists exhibit no detectable agonist activity an in vitro assay of $P2X_7$ receptor agonism at a concentration of compound that is 100-fold higher than the $IC_{50}$.

$P2X_7$ receptor modulating activity may also, or alternatively, be assessed using an in vivo pain relief assay as provided in Example 5. Modulators provided herein preferably have a statistically significant specific effect on $P2X_7$ receptor activity within such a functional assay.

In certain embodiments, preferred modulators are non-sedating. In other words, a dose of modulator that is twice the minimum dose sufficient to provide analgesia in an animal model for determining pain relief (such as a model provided in Example 5, herein) causes only transient (i.e., lasting for no more than ½ the time that pain relief lasts) or preferably no statistically significant sedation in an animal model assay of sedation (using the method described by Fitzgerald et al. (1988) *Toxicology* 49(2-3):433-9). Preferably, a dose that is five times the minimum dose sufficient to provide analgesia does not produce statistically significant sedation. More preferably, a modulator provided herein does not produce sedation at intravenous doses of less than 25 mg/kg (preferably less than 10 mg/kg) or at oral doses of less than 140 mg/kg (preferably less than 50 mg/kg, more preferably less than 30 mg/kg).

If desired, compounds provided herein may be evaluated for certain pharmacological properties including, but not limited to, oral bioavailability (preferred compounds are orally bioavailable to an extent allowing for therapeutically effective concentrations of the compound to be achieved at oral doses of less than 140 mg/kg, preferably less than 50 mg/kg, more preferably less than 30 mg/kg, even more preferably less than 10 mg/kg, still more preferably less than 1 mg/kg and most preferably less than 0.1 mg/kg), toxicity (a preferred compound is nontoxic when a therapeutically effective amount is administered to a subject), side effects (a preferred compound produces side effects comparable to placebo when a therapeutically effective amount of the compound is administered to a subject), serum protein binding and in vitro and in vivo half-life (a preferred compound exhibits an in vivo half-life allowing for Q.I.D. dosing, preferably T.I.D. dosing, more preferably B.I.D. dosing, and most preferably once-a-day dosing). In addition, differential penetration of the blood brain barrier may be desirable for modulators used to treat pain or neurodegenerative disease by modulating CNS P2X$_7$ receptor activity such that total daily oral doses as described above provide such modulation to a therapeutically effective extent, while low brain levels of modulators used to treat peripheral nerve mediated pain or certain inflammatory diseases (e.g. rheumatoid arthritis) may be preferred (i.e., such doses do not provide brain (e.g., CSF) levels of the compound sufficient to significantly modulate P2X$_7$ receptor activity). Routine assays that are well known in the art may be used to assess these properties, and identify superior compounds for a particular use. For example, assays used to predict bioavailability include transport across human intestinal cell monolayers, including Caco-2 cell monolayers. Penetration of the blood brain barrier of a compound in humans may be predicted from the brain levels of the compound in laboratory animals given the compound (e.g., intravenously). Serum protein binding may be predicted from albumin binding assays. Compound half-life is inversely proportional to the frequency of dosage of a compound. In vitro half-lives of compounds may be predicted from assays of microsomal half-life as described, for example, within Example 7 of U.S. Patent Application Publication Number 2005/0070547.

As noted above, preferred compounds provided herein are nontoxic. In general, the term "nontoxic" shall be understood in a relative sense and is intended to refer to any substance that has been approved by the United States Food and Drug Administration ("FDA") for administration to mammals (preferably humans) or, in keeping with established criteria, is susceptible to approval by the FDA for administration to mammals (preferably humans). In addition, a highly preferred nontoxic compound generally satisfies one or more of the following criteria: (1) does not substantially inhibit cellular ATP production; (2) does not significantly prolong heart QT intervals; (3) does not cause substantial liver enlargement, or (4) does not cause substantial release of liver enzymes.

As used herein, a compound that does not substantially inhibit cellular ATP production is a compound that satisfies the criteria set forth in Example 8 of U.S. Patent Application Publication Number 2005/0070547. In other words, cells treated as described therein with 100 μM of such a compound exhibit ATP levels that are at least 50% of the ATP levels detected in untreated cells. In more highly preferred embodiments, such cells exhibit ATP levels that are at least 80% of the ATP levels detected in untreated cells.

A compound that does not significantly prolong heart QT intervals is a compound that does not result in a statistically significant prolongation of heart QT intervals (as determined by electrocardiography) in guinea pigs, minipigs or dogs upon administration of a dose that yields a serum concentration equal to the EC$_{50}$ or IC$_{50}$ for the compound. In certain preferred embodiments, a dose of 0.01, 0.05, 0.1, 0.5, 1, 5, 10, 40 or 50 mg/kg administered parenterally or orally does not result in a statistically significant prolongation of heart QT intervals.

A compound does not cause substantial liver enlargement if daily treatment of laboratory rodents (e.g., mice or rats) for 5-10 days with a dose that yields a serum concentration equal to the EC$_{50}$ or IC$_{50}$ for the compound results in an increase in liver to body weight ratio that is no more than 100% over matched controls. In more highly preferred embodiments, such doses do not cause liver enlargement of more than 75% or 50% over matched controls. If non-rodent mammals (e.g., dogs) are used, such doses should not result in an increase of liver to body weight ratio of more than 50%, preferably not more than 25%, and more preferably not more than 10% over matched untreated controls. Preferred doses within such assays include 0.01, 0.05, 0.1, 0.5, 1, 5, 10, 40 or 50 mg/kg administered parenterally or orally.

Similarly, a compound does not promote substantial release of liver enzymes if administration of twice the minimum dose that yields a serum concentration equal to the EC$_{50}$ or IC$_{50}$ at P2X$_7$ receptor for the compound does not elevate serum levels of ALT, LDH or AST in laboratory animals (e.g., rodents) by more than 100% over matched mock-treated controls. In more highly preferred embodiments, such doses do not elevate such serum levels by more than 75% or 50% over matched controls. Alternatively, a compound does not promote substantial release of liver enzymes if, in an in vitro hepatocyte assay, concentrations (in culture media or other such solutions that are contacted and incubated with hepatocytes in vitro) that are equal to the EC$_{50}$ or IC$_{50}$ for the compound do not cause detectable release of any of such liver enzymes into culture medium above baseline levels seen in media from matched mock-treated control cells. In more highly preferred embodiments, there is no detectable release of any of such liver enzymes into culture medium above baseline levels when such compound concentrations are five-fold, and preferably ten-fold the EC$_{50}$ or IC$_{50}$ for the compound.

In other embodiments, certain preferred compounds do not inhibit or induce microsomal cytochrome P450 enzyme activities, such as CYP1A2 activity, CYP2A6 activity, CYP2C9 activity, CYP2C19 activity, CYP2D6 activity, CYP2E1 activity or CYP3A4 activity at a concentration equal to the EC$_{50}$ or IC$_{50}$ at P2X$_7$ receptor for the compound.

Certain preferred compounds are not clastogenic (e.g., as determined using a mouse erythrocyte precursor cell micronucleus assay, an Ames micronucleus assay, a spiral micronucleus assay or the like) at a concentration equal the EC$_{50}$ or IC$_{50}$ for the compound. In other embodiments, certain preferred compounds do not induce sister chromatid exchange (e.g., in Chinese hamster ovary cells) at such concentrations.

For detection purposes, as discussed in more detail below, modulators provided herein may be isotopically-labeled or radiolabeled. For example, compounds may have one or more atoms replaced by an atom of the same element having an atomic mass or mass number different from the atomic mass or mass number usually found in nature. Examples of isotopes that can be present in the compounds provided herein include isotopes of hydrogen, carbon, nitrogen, oxygen, phosphorous, fluorine and chlorine, such as $^2$H, $^3$H, $^{11}$C, $^{13}$C, $^{14}$C $^{15}$N, $^{18}$O, $^{17}$O, $^{31}$P, $^{32}$P, $^{35}$S, $^{18}$F and $^{36}$Cl. In addition, substitution with heavy isotopes such as deuterium (i.e., $^2$H) can afford certain therapeutic advantages resulting from greater metabolic stability, for example increased in vivo half-life or reduced dosage requirements and, hence, may be preferred in some circumstances.

Preparation of 5-Membered Heterocyclic Amides and Related Compounds 5-membered heterocyclic amides and related compounds may generally be prepared using standard synthetic methods. Starting materials are commercially available from suppliers such as Sigma-Aldrich Corp. (St. Louis, Mo.), or may be synthesized from commercially available precursors using established protocols. By way of example, a synthetic route similar to that shown in any of the following Schemes may be used, together with synthetic methods known in the art of synthetic organic chemistry. In some cases, protecting groups may be required during preparation. Such protecting groups can be removed by methods well known to those of ordinary skill in the art, such as methods described in Greene and Wuts, "Protective Groups in Organic Synthesis" (2nd Edition, John Wiley & Sons, 1991). In some cases, further organic transformations may be performed using methods well known to those of ordinary skill in the art, such as methods described in Richard C. Larock, "Comprehensive Organic Transformation," (VCH Publisher, Inc. 1989). Each variable in the following Schemes refers to any group consistent with the description of the compounds provided herein. In schemes with more than one $R_3$ variable, it will be apparent that (as in the Formulas provided elsewhere herein) each $R_3$ is independently chosen.

Certain abbreviations used in the following Schemes and elsewhere herein include:
Ac acetyl
ACN acetonitrile
BOP benzotriazol-1-yloxytris(dimethylamino)phosphonium hexafluorophosphate
δ chemical shift
DCM dichloromethane
DIEA diisopropylethylamine
DMC 2-chloro-1,3-dimethyl-4,5-dihydro-3H-imidazolium chloride
DMF dimethylformamide
DMSO dimethylsulfoxide
Et ethyl
EtOAc ethyl acetate
EtOH ethanol
h hour(s)
$^1$H NMR proton nuclear magnetic resonance
HOBt hydroxybenzotriazole
Hz hertz
LAH lithium aluminum hydride
LC/MS liquid chromatography/mass spectrometry
MeOH methanol
min minute(s)
(M+1) mass+1
NMP n-methylpyrrolidone
Pd(PPh$_3$)$_4$ tetrakis(triphenylphosphine)palladium(0)
PTLC preparative thin layer chromatography
RT room temperature
TEA triethylamine
TFA trifluoroacetic acid
THF tetrahydrofuran
TMS trimethylsilyl
xantphos 9,9-dimethyl-4,5-bis(diphenylphosphino)xanthene Scheme 1

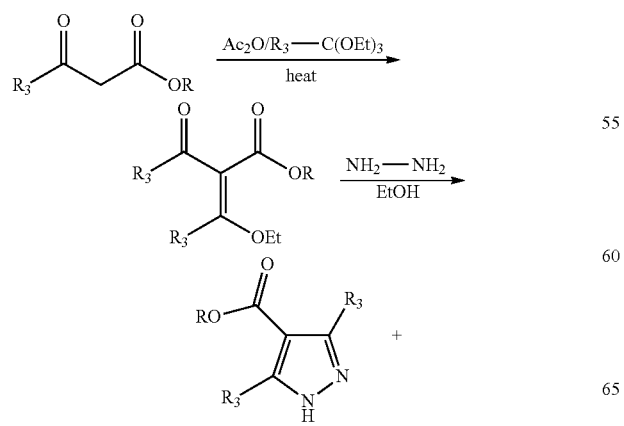

Scheme 2

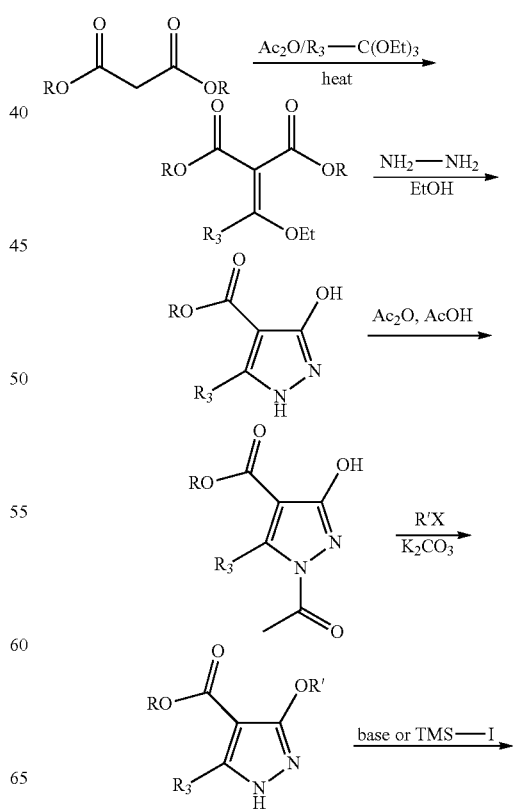

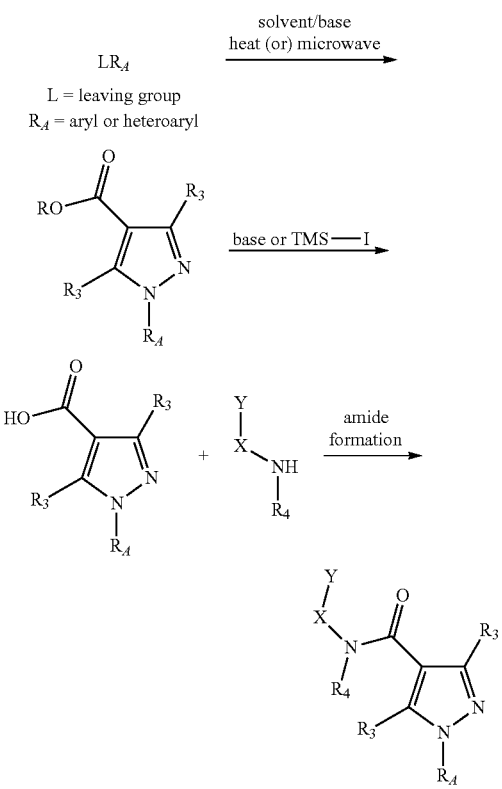

55
-continued
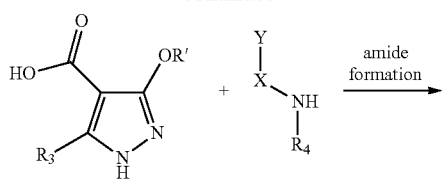
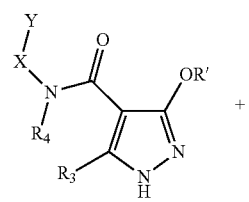
L = leaving group
R$_A$ = aryl or heteroaryl
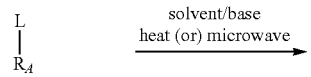
Scheme 3
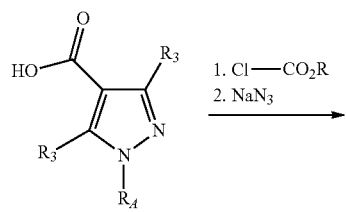
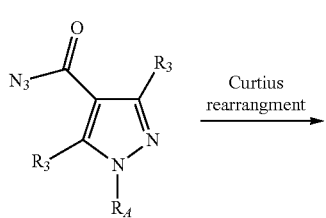
Curtius rearrangment
56
-continued
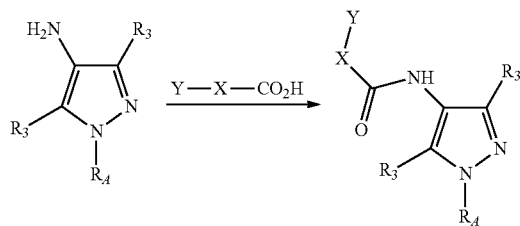
Scheme 4
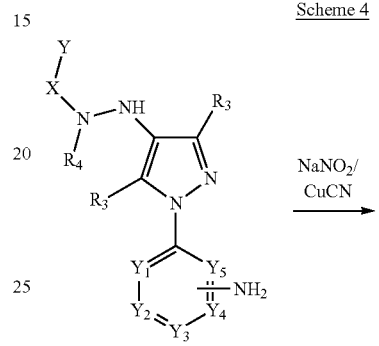
NaNO$_2$/
CuCN
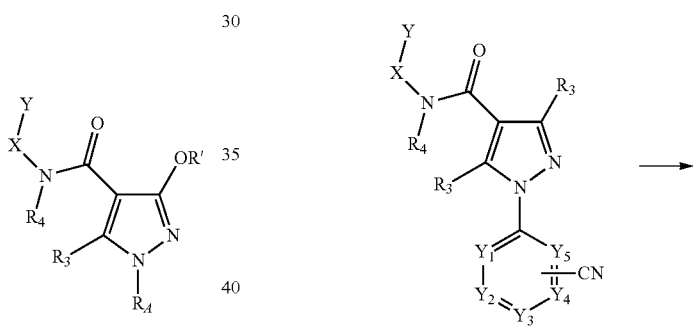
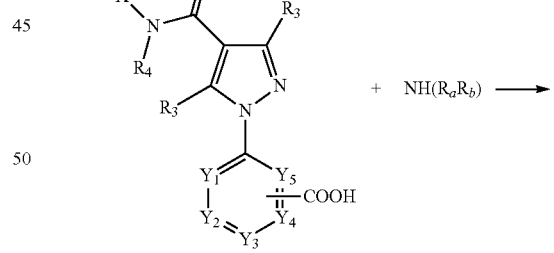
+ NH(R$_a$R$_b$) →
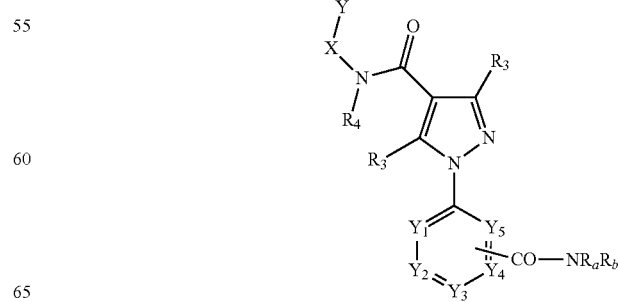

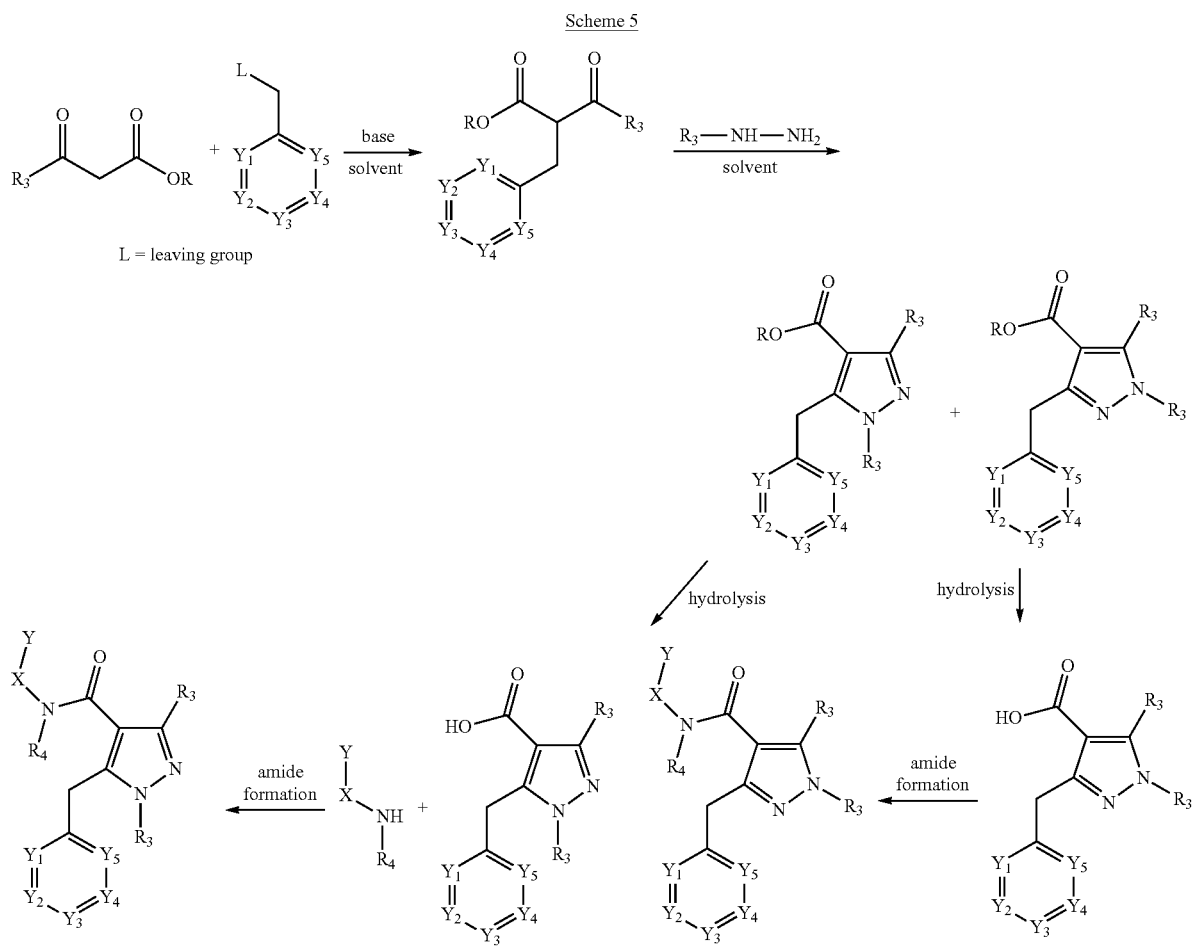
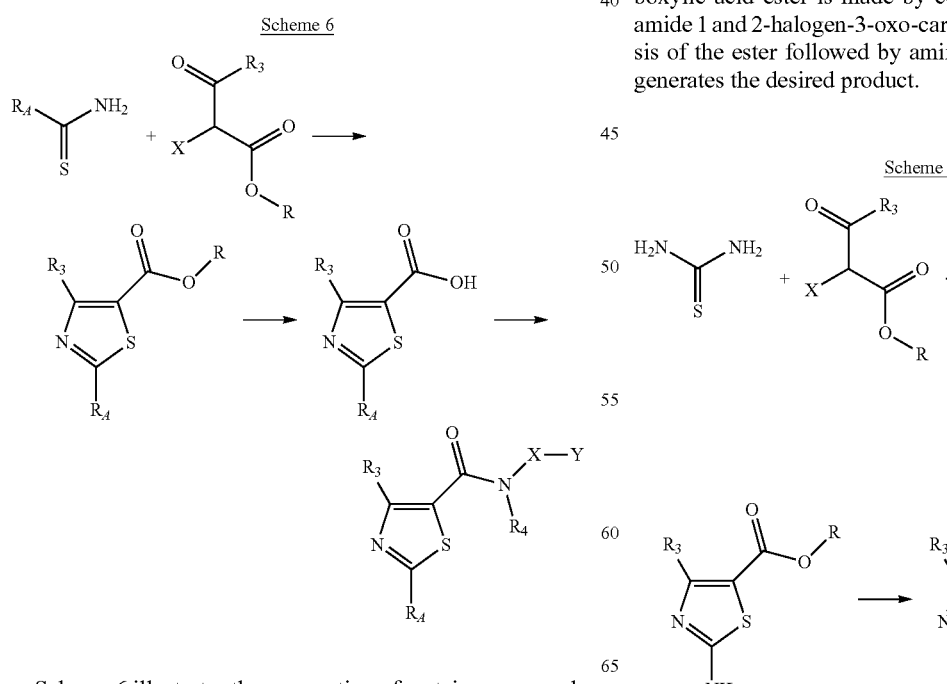
boxylic acid ester is made by condensing carbothioic acid amide 1 and 2-halogen-3-oxo-carboxylic acid ester. Hydrolysis of the ester followed by amination of the resulting acid generates the desired product.
Scheme 6 illustrates the preparation of certain compounds provided herein that have a thiazole core. Thiazole 5-car-

59
-continued

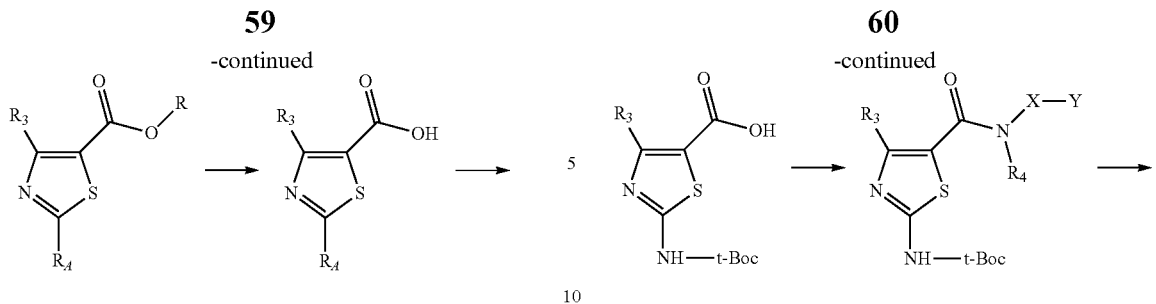

60
-continued

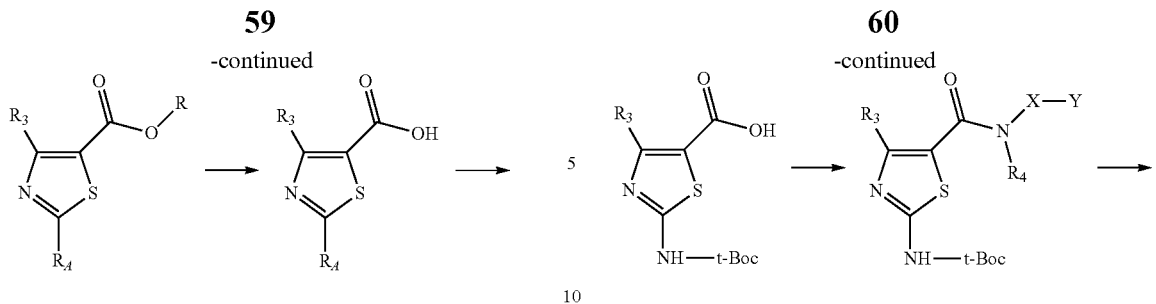

Scheme 7 illustrates a general route for the preparation of certain compounds provided herein that have a thiazole core. Condensation of thiourea and the 2-halogen-3-oxo-carboxylic acid ester generates the 2-aminothiazole, which is converted to the bromothiazole via Sandermyer reaction. The bromothiazole can be either coupled to an organometallic compound under transition metal catalyzed reaction conditions, such as a boronic acid under Suzuki condition or an organostannane under Stille reaction condition, or condensed directly with a heterocycle to give the thiazole ester. Hydrolysis of the thiazole ester followed by amination of the resulting acid generates the desired product.

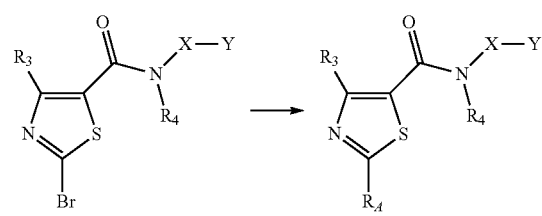

Scheme 8 illustrates a general method for preparing certain compounds provided herein that have a thiazole core. Protection of the 2-aminothiazole 5-carboxylic acid ester by t-Boc, followed by hydrolysis, amination, deprotection, and Sandermyer reaction generates the bromothiazole. The desired product is prepared by coupling the bromothiazole with an organometallic compound under transition metal catalyzed reaction conditions or by condensing the bromothiazole directly with a heterocycle.

Scheme 8

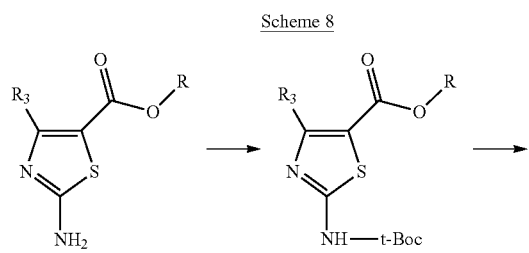

Scheme 9

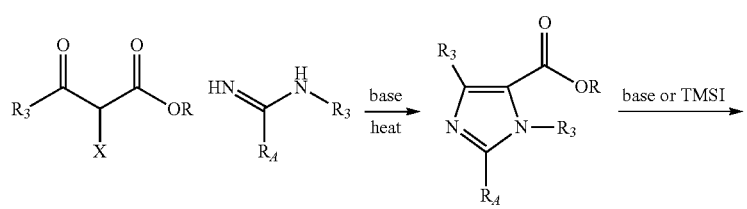

-continued
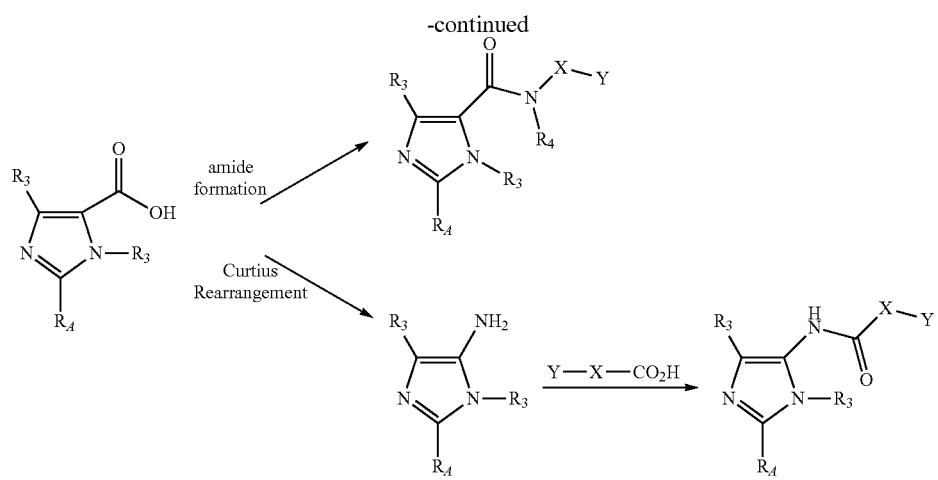
Scheme 10
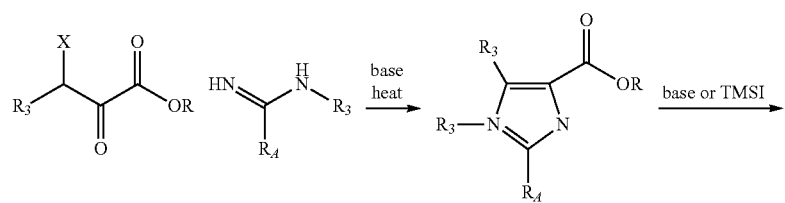
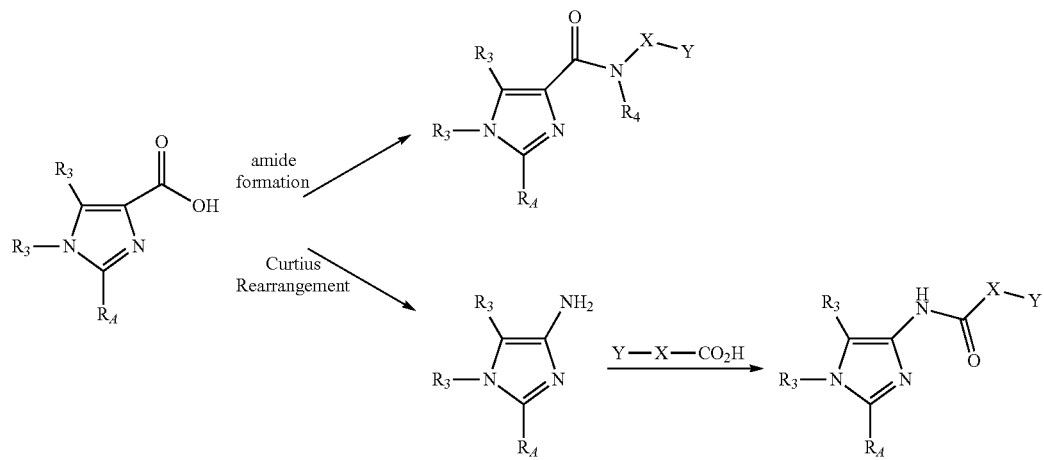
Scheme 11
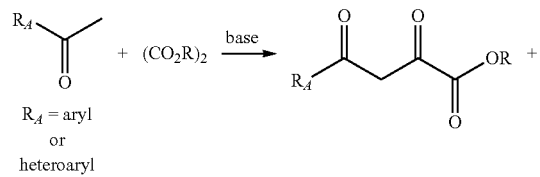

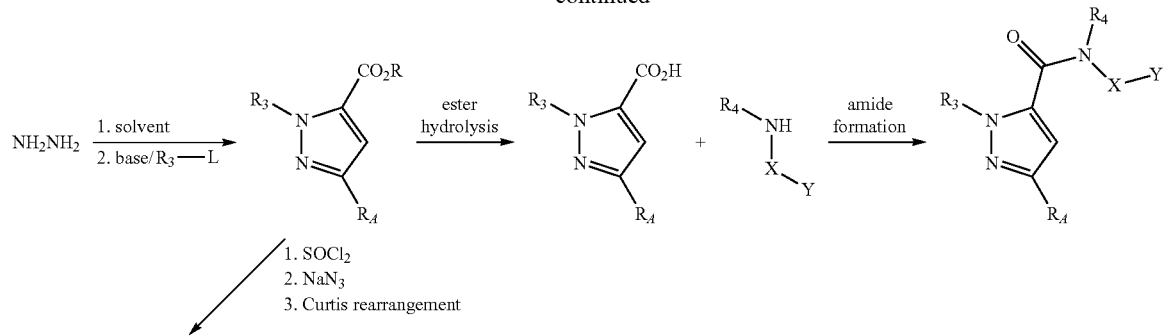
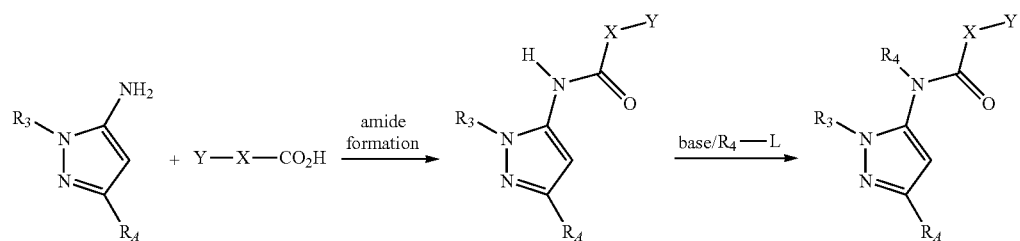
Scheme 12
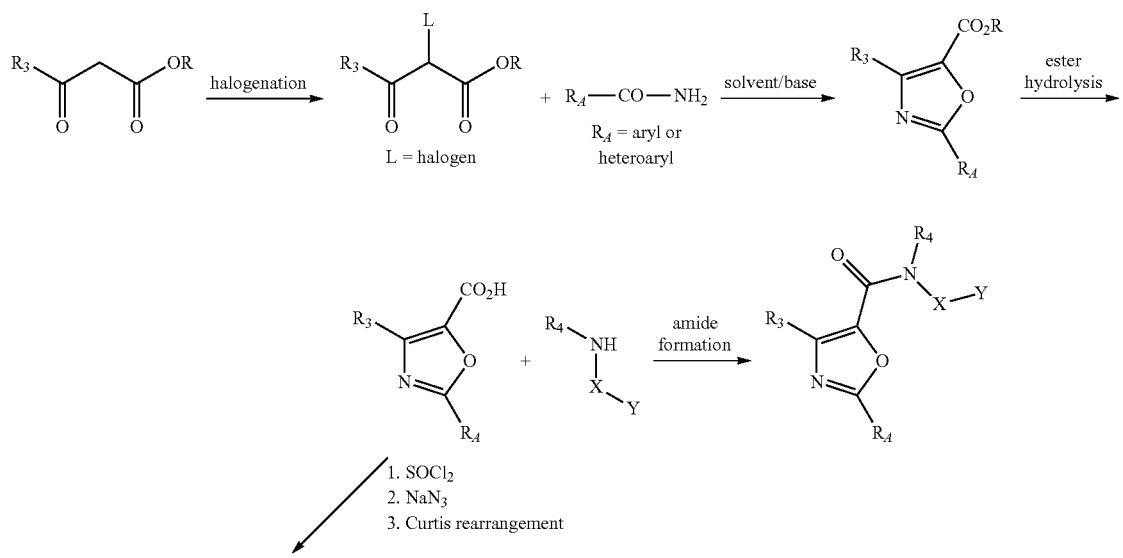
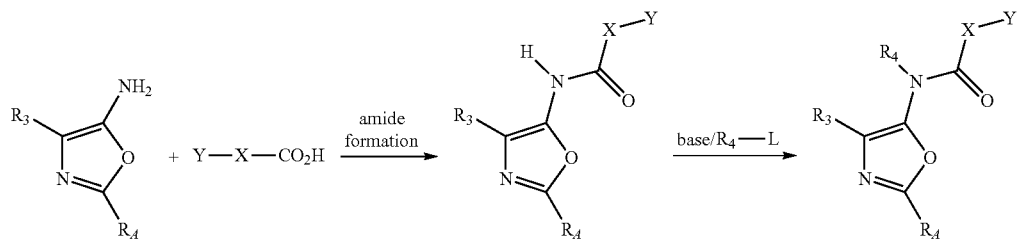

Scheme 13

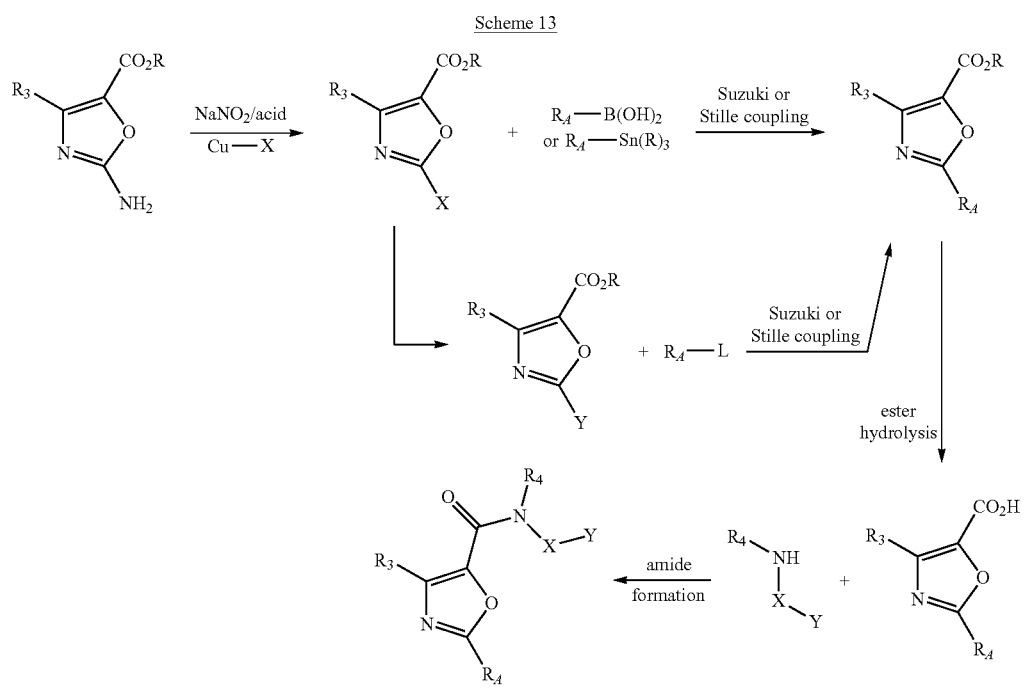

X = halogen
R$_A$ = aryl or heteroaryl
Y = B(OH)$_2$ or Sn(R)$_3$

Scheme 14

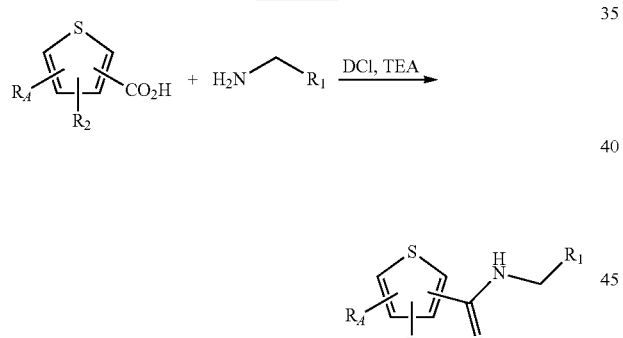

In Scheme 14, a thiophene carboxylic acid is reacted with an amine in the presence of a base such as TEA and a dehydrating agent such as 2-chloro-1,3-dimethylimidazolinium chloride in a solvent such as dimethylacetamide.

Scheme 15

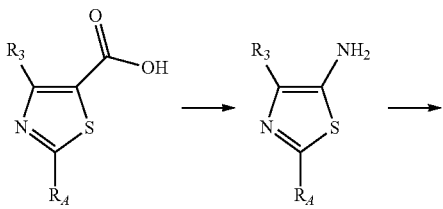

-continued

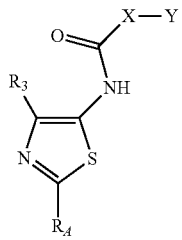

Scheme 15 illustrates a general method for preparing compounds of Formula X. Curtius rearrangement of the acid generates the amino intermediate, which provides the compound of Formula X upon amination.

Scheme 16

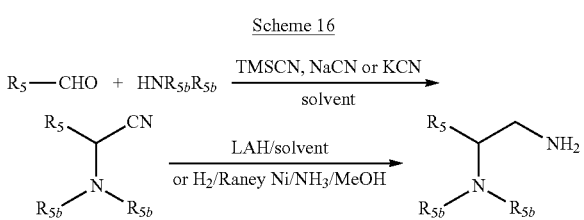

Scheme 16 illustrates a general method of preparing certain intermediates NH$_2$—CH$_2$—CHR$_5$—Y of Formula X wherein R$_5$ is substituted phenyl or heteroaryl and Y=N—R$_{5b}$R$_{5b}$, wherein R$_{5b}$ is independently hydrogen, C$_1$-C$_6$alkyl, or C$_3$-C$_7$cycloalkyl; or both R$_{5b}$ are taken together to form a heterocycle. Strecker condensation of the aryl carboxaldehyde and amine either with TMSCN in a solvent such as acetonitrile, or with NaCN or KCN in a solvent such MeOH-water or water at pH 3-4 (adjusted by hydrogen chloride) gives the aminonitrile, which is reduced by LAH in a solvent such as THF or by hydrogenation with Raney Nickel as a catalyst in a solvent such as 7N ammonia in methanol to give the amine intermediate $NH_2$—$CH_2$—$CHR_5$—Y.

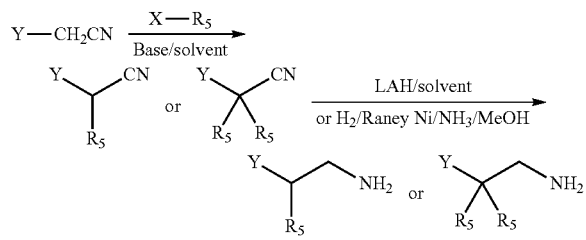

Scheme 17

Scheme 17 illustrates a general method of preparing certain intermediates $NH_2$—$CH_2$—$CHR_5$—Y or $NH_2$—$CH_2$—$CR_5R_5$—Y of Formula X wherein Y is substituted phenyl or heteroaryl. Alkylation of the starting acetonitrile with one equivalent of X—$R_5$ (X=Br or I), with base such as sodium hydride in a solvent such as THF-DMSO gives intermediate Y—X($R_5$)—CN. Alkylation of the starting acetonitrile with two equivalents of X—$R_5$ (X=Br or I) or one equivalent of dibromo or diiodo (when $R_5$ and $R_5$ are taken together to form a ring) with base such as sodium hydride in a solvent such as THF-DMSO gives intermediate Y—X($R_5$)($R_5$)—CN. Reduction of either product by LAH in a solvent such as THF or by hydrogenation with Raney Nickel as a catalyst in a solvent such as 7N ammonia in methanol provides $NH_2$—$CH_2$—$CHR_5$—Y or $NH_2$—$CH_2$—$CR_5R_5$—Y.

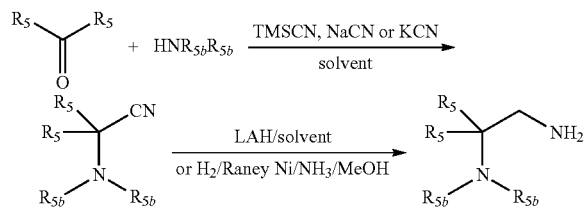

Scheme 18

Scheme 18 illustrates a general method of preparing certain intermediates $NH_2$—$CH_2$—$CR_5R_5$—Y of Formula X wherein $R_5$ is independently hydrogen, $C_1$-$C_6$alkyl, $C_3$-$C_7$cycloalkyl or phenyl; or both $R_5$ are taken together to form a $C_3$-$C_8$cycloalkyl or heterocycle, and Y=N—$R_{5b}R_{5b}$ wherein $R_{5b}$ is $C_1$-$C_6$ alkyl, optionally substituted with halogen, hydroxyl, $C_1$-$C_4$ alkyl, $C_1$-$C_4$ alkoxy or $CO_2H$, or both $R_{5b}$ are taken together to form a 5- to 7-membered heterocycle. Strecker condensation of the ketone and amine either with TMSCN in a solvent such methanol with a catalyst such as $ZnI_2$, or with NaCN or KCN in a solvent such MeOH-water or water at pH 3-4 (adjusted by hydrogen chloride) gives the aminonitrile. Reduction of the aminonitrile by LAH in a solvent such as THF or by hydrogenation with Raney Nickel as a catalyst in a solvent such as 7N ammonia in methanol gives $NH_2$—$CH_2$—$CR_5R_5$—Y.

In certain embodiments, a compound provided herein may contain one or more asymmetric carbon atoms, so that the compound can exist in different stereoisomeric forms. Such forms can be, for example, racemates or optically active forms. As noted above, all stereoisomers are encompassed by the present invention. Nonetheless, it may be desirable to obtain single enantiomers (i.e., optically active forms). Standard methods for preparing single enantiomers include asymmetric synthesis and resolution of the racemates. Resolution of the racemates can be accomplished, for example, by conventional methods such as crystallization in the presence of a resolving agent, or chromatography using, for example a chiral HPLC column.

Compounds may be radiolabeled by carrying out their synthesis using precursors comprising at least one atom that is a radioisotope. Each radioisotope is preferably carbon (e.g., $^{14}C$), hydrogen (e.g., $^3H$), sulfur (e.g., $^{35}S$) or iodine (e.g., $^{125}I$). Tritium labeled compounds may also be prepared catalytically via platinum-catalyzed exchange in tritiated acetic acid, acid-catalyzed exchange in tritiated trifluoroacetic acid, or heterogeneous-catalyzed exchange with tritium gas using the compound as substrate. In addition, certain precursors may be subjected to tritium-halogen exchange with tritium gas, tritium gas reduction of unsaturated bonds, or reduction using sodium borotritide, as appropriate. Preparation of radiolabeled compounds may be conveniently performed by a radioisotope supplier specializing in custom synthesis of radiolabeled probe compounds.

Pharmaceutical Compositions

The present invention also provides pharmaceutical compositions comprising one or more compounds provided herein, together with at least one physiologically acceptable carrier or excipient. Pharmaceutical compositions may comprise, for example, one or more of water, buffers (e.g., sodium bicarbonate, neutral buffered saline or phosphate buffered saline), ethanol, mineral oil, vegetable oil, dimethylsulfoxide, carbohydrates (e.g., glucose, mannose, sucrose, starch, mannitol or dextrans), proteins, adjuvants, polypeptides or amino acids such as glycine, antioxidants, chelating agents such as EDTA or glutathione and/or preservatives. In addition, other active ingredients may (but need not) be included in the pharmaceutical compositions provided herein.

Pharmaceutical compositions may be formulated for any appropriate manner of administration, including, for example, topical, oral, nasal, rectal or parenteral administration. The term parenteral as used herein includes subcutaneous, intradermal, intravascular (e.g., intravenous), intramuscular, spinal, intracranial, intrathecal and intraperitoneal injection, as well as any similar injection or infusion technique. In certain embodiments, compositions suitable for oral use are preferred. Such compositions include, for example, tablets, troches, lozenges, aqueous or oily suspensions, dispersible powders or granules, emulsion, hard or soft capsules, or syrups or elixirs. Within yet other embodiments, pharmaceutical compositions may be formulated as a lyophilizate. Formulation for topical administration may be preferred for certain conditions (e.g., in the treatment of skin conditions such as burns or itch). Formulation for direct administration into the bladder (intravesicular administration) may be preferred for treatment of urinary incontinence and overactive bladder.

Compositions intended for oral use may further comprise one or more components such as sweetening agents, flavoring agents, coloring agents and/or preserving agents in order to provide appealing and palatable preparations. Tablets contain the active ingredient in admixture with physiologically acceptable excipients that are suitable for the manufacture of tablets. Such excipients include, for example, inert diluents (e.g., calcium carbonate, sodium carbonate, lactose, calcium phosphate or sodium phosphate), granulating and disintegrating agents (e.g., corn starch or alginic acid), binding agents (e.g., starch, gelatin or acacia) and lubricating agents (e.g., magnesium stearate, stearic acid or talc). Tablets may be formed using standard techniques, including dry granulation, direct compression and wet granulation. The tablets may be uncoated or they may be coated by known techniques.

Formulations for oral use may also be presented as hard gelatin capsules wherein the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oil).

Aqueous suspensions contain the active material(s) in admixture with suitable excipients, such as suspending agents (e.g., sodium carboxymethylcellulose, methylcellulose, hydropropylmethylcellulose, sodium alginate, polyvinylpyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also comprise one or more preservatives, such as ethyl or n-propyl p-hydroxybenzoate, one or more coloring agents, one or more flavoring agents, and/or one or more sweetening agents, such as sucrose or saccharin.

Oily suspensions may be formulated by suspending the active ingredient(s) in a vegetable oil (e.g., arachis oil, olive oil, sesame oil or coconut oil) or in a mineral oil such as liquid paraffin. The oily suspensions may contain a thickening agent such as beeswax, hard paraffin or cetyl alcohol. Sweetening agents such as those set forth above, and/or flavoring agents may be added to provide palatable oral preparations. Such suspensions may be preserved by the addition of an antioxidant such as ascorbic acid.

Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, such as sweetening, flavoring and coloring agents, may also be present.

Pharmaceutical compositions may also be formulated as oil-in-water emulsions. The oily phase may be a vegetable oil (e.g., olive oil or arachis oil), a mineral oil (e.g., liquid paraffin) or a mixture thereof. Suitable emulsifying agents include naturally-occurring gums (e.g., gum acacia or gum tragacanth), naturally-occurring phosphatides (e.g., soy bean lecithin, and esters or partial esters derived from fatty acids and hexitol), anhydrides (e.g., sorbitan monoleate) and condensation products of partial esters derived from fatty acids and hexitol with ethylene oxide (e.g., polyoxyethylene sorbitan monooleate). An emulsion may also comprise one or more sweetening and/or flavoring agents.

Syrups and elixirs may be formulated with sweetening agents, such as glycerol, propylene glycol, sorbitol or sucrose. Such formulations may also comprise one or more demulcents, preservatives, flavoring agents and/or coloring agents.

Formulations for topical administration typically comprise a topical vehicle combined with active agent(s), with or without additional optional components. Suitable topical vehicles and additional components are well known in the art, and it will be apparent that the choice of a vehicle will depend on the particular physical form and mode of delivery. Topical vehicles include water; organic solvents such as alcohols (e.g., ethanol or isopropyl alcohol) or glycerin; glycols (e.g., butylene, isoprene or propylene glycol); aliphatic alcohols (e.g., lanolin); mixtures of water and organic solvents and mixtures of organic solvents such as alcohol and glycerin; lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile); and hydrocarbon-based materials such as microsponges and polymer matrices. A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (Pharmaceutical Press, London 1993) and *Remington: The Science and Practice of Pharmacy*, $21^{st}$ ed., Lippincott Williams & Wilkins, Philadelphia, Pa. (2005). Formulations may comprise microcapsules, such as hydroxymethylcellulose or gelatin-microcapsules, liposomes, albumin microspheres, microemulsions, nanoparticles or nanocapsules.

A topical formulation may be prepared in any of a variety of physical forms including, for example, solids, pastes, creams, foams, lotions, gels, powders, aqueous liquids and emulsions. The physical appearance and viscosity of such pharmaceutically acceptable forms can be governed by the presence and amount of emulsifier(s) and viscosity adjuster(s) present in the formulation. Solids are generally firm and non-pourable and commonly are formulated as bars or sticks, or in particulate form; solids can be opaque or transparent, and optionally can contain solvents, emulsifiers, moisturizers, emollients, fragrances, dyes/colorants, preservatives and other active ingredients that increase or enhance the efficacy of the final product. Creams and lotions are often similar to one another, differing mainly in their viscosity; both lotions and creams may be opaque, translucent or clear and often contain emulsifiers, solvents, and viscosity adjusting agents, as well as moisturizers, emollients, fragrances, dyes/colorants, preservatives and other active ingredients that increase or enhance the efficacy of the final product. Gels can be prepared with a range of viscosities, from thick or high viscosity to thin or low viscosity. These formulations, like those of lotions and creams, may also contain solvents, emulsifiers, moisturizers, emollients, fragrances, dyes/colorants, preservatives and other active ingredients that increase or enhance the efficacy of the final product. Liquids are thinner than creams, lotions, or gels and often do not contain emulsifiers. Liquid topical products often contain solvents, emulsifiers, moisturizers, emollients, fragrances, dyes/colorants, preservatives and other active ingredients that increase or enhance the efficacy of the final product.

Suitable emulsifiers for use in topical formulations include, but are not limited to, ionic emulsifiers, cetearyl alcohol, non-ionic emulsifiers like polyoxyethylene oleyl ether, PEG-40 stearate, ceteareth-12, ceteareth-20, ceteareth-30, ceteareth alcohol, PEG-100 stearate and glyceryl stearate. Suitable viscosity adjusting agents include, but are not limited to, protective colloids or non-ionic gums such as hydroxyethylcellulose, xanthan gum, magnesium aluminum silicate, silica, microcrystalline wax, beeswax, paraffin, and cetyl palmitate. A gel composition may be formed by the addition of a gelling agent such as chitosan, methyl cellulose, ethyl cellulose, polyvinyl alcohol, polyquaterniums, hydroxyethylcellulose, hydroxypropylcellulose, hydroxypropylmethylcellulose, carbomer or ammoniated glycyrrhizinate. Suitable surfactants include, but are not limited to, nonionic, amphoteric, ionic and anionic surfactants. For example, one or more of dimethicone copolyol, polysorbate 20, polysorbate 40, polysorbate 60, polysorbate 80, lauramide DEA, cocamide DEA, and cocamide MEA, oleyl betaine, cocamidopropyl phosphatidyl PG-dimonium chloride, and ammonium laureth sulfate may be used within topical formulations. Suitable preservatives include, but are not limited to, antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. Suitable moisturizers include, but are not limited to, lactic acid and other hydroxy acids and their salts, glycerin, propylene glycol, and butylene glycol. Suitable emollients include lanolin alcohol, lanolin, lanolin derivatives, cholesterol, petrolatum, isostearyl neopentanoate and mineral oils. Suitable fragrances and colors include, but are not limited to, FD&C Red No. 40 and FD&C Yellow No. 5. Other suitable additional ingredients that may be included a topical formulation include, but are not limited to, abrasives, absorbents, anti-caking agents, anti-foaming agents, anti-static agents, astringents (e.g., witch hazel, alcohol and herbal extracts such as chamomile extract), binders/excipients, buffering agents, chelating agents, film forming agents, conditioning agents, propellants, opacifying agents, pH adjusters and protectants.

An example of a suitable topical vehicle for formulation of a gel is: hydroxypropylcellulose (2.1%); 70/30 isopropyl alcohol/water (90.9%); propylene glycol (5.1%); and Polysorbate 80 (1.9%). An example of a suitable topical vehicle for formulation as a foam is: cetyl alcohol (1.1%); stearyl alcohol (0.5%; Quaternium 52 (1.0%); propylene glycol (2.0%); Ethanol 95 PGF3 (61.05%); deionized water (30.05%), P75 hydrocarbon propellant (4.30%). All percents are by weight.

Typical modes of delivery for topical compositions include application using the fingers; application using a physical applicator such as a cloth, tissue, swab, stick or brush; spraying (including mist, aerosol or foam spraying); dropper application; sprinkling; soaking; and rinsing.

A pharmaceutical composition may be prepared as a sterile injectable aqueous or oleaginous suspension. The compound(s) provided herein, depending on the vehicle and concentration used, can either be suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid find use in the preparation of injectable compositions, and adjuvants such as local anesthetics, preservatives and/or buffering agents can be dissolved in the vehicle.

Pharmaceutical compositions may also be formulated as suppositories (e.g., for rectal administration). Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

Compositions for inhalation typically can be provided in the form of a solution, suspension or emulsion that can be administered as a dry powder or in the form of an aerosol using a conventional propellant (e.g., dichlorodifluoromethane or trichlorofluoromethane).

Pharmaceutical compositions may be formulated for release at a pre-determined rate. Instantaneous release may be achieved, for example, via sublingual administration (i.e., administration by mouth in such a way that the active ingredient(s) are rapidly absorbed via the blood vessels under the tongue rather than via the digestive tract). Controlled release formulations (i.e., formulations such as a capsule, tablet or coated tablet that slows and/or delays release of active ingredient(s) following administration) may be administered by, for example, oral, rectal or subcutaneous implantation, or by implantation at a target site. In general, a controlled release formulation comprises a matrix and/or coating that delays disintegration and absorption in the gastrointestinal tract (or implantation site) and thereby provides a delayed action or a sustained action over a longer period. One type of controlled-release formulation is a sustained-release formulation, in which at least one active ingredient is continuously released over a period of time at a constant rate. Preferably, the therapeutic agent is released at such a rate that blood (e.g., plasma) concentrations are maintained within the therapeutic range, but below toxic levels, over a period of time that is at least 4 hours, preferably at least 8 hours, and more preferably at least 12 hours. Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of modulator release. The amount of modulator contained within a sustained release formulation depends upon, for example, the site of implantation, the rate and expected duration of release and the nature of the condition to be treated or prevented.

Controlled release may be achieved by combining the active ingredient(s) with a matrix material that itself alters release rate and/or through the use of a controlled-release coating. The release rate can be varied using methods well known in the art, including (a) varying the thickness or composition of coating, (b) altering the amount or manner of addition of plasticizer in a coating, (c) including additional ingredients, such as release-modifying agents, (d) altering the composition, particle size or particle shape of the matrix, and (e) providing one or more passageways through the coating. The amount of modulator contained within a sustained release formulation depends upon, for example, the method of administration (e.g., the site of implantation), the rate and expected duration of release and the nature of the condition to be treated or prevented.

The matrix material, which itself may or may not serve a controlled-release function, is generally any material that supports the active ingredient(s). For example, a time delay material such as glyceryl monosterate or glyceryl distearate may be employed. Active ingredient(s) may be combined with matrix material prior to formation of the dosage form (e.g., a tablet). Alternatively, or in addition, active ingredient(s) may be coated on the surface of a particle, granule, sphere, microsphere, bead or pellet that comprises the matrix material. Such coating may be achieved by conventional means, such as by dissolving the active ingredient(s) in water or other suitable solvent and spraying.

Optionally, additional ingredients are added prior to coating (e.g., to assist binding of the active ingredient(s) to the matrix material or to color the solution). The matrix may then be coated with a barrier agent prior to application of controlled-release coating. Multiple coated matrix units may, if desired, be encapsulated to generate the final dosage form.

In certain embodiments, a controlled release is achieved through the use of a controlled release coating (i.e., a coating that permits release of active ingredient(s) at a controlled rate in aqueous medium). The controlled release coating should be a strong, continuous film that is smooth, capable of supporting pigments and other additives, non-toxic, inert and tack-free. Coatings that regulate release of the modulator include pH-independent coatings, pH-dependent coatings (which may be used to release modulator in the stomach) and enteric coatings (which allow the formulation to pass intact through the stomach and into the small intestine, where the coating dissolves and the contents are absorbed by the body). It will be apparent that multiple coatings may be employed (e.g., to allow release of a portion of the dose in the stomach and a portion further along the gastrointestinal tract). For example, a portion of active ingredient(s) may be coated over an enteric coating, and thereby released in the stomach, while the remainder of active ingredient(s) in the matrix core is protected by the enteric coating and released further down the GI tract. pH dependent coatings include, for example, shellac, cellulose acetate phthalate, polyvinyl acetate phthalate, hydroxypropylmethylcellulose phthalate, methacrylic acid ester copolymers and zein.

In certain embodiments, the coating is a hydrophobic material, preferably used in an amount effective to slow the hydration of the gelling agent following administration. Suitable hydrophobic materials include alkyl celluloses (e.g., ethylcellulose or carboxymethylcellulose), cellulose ethers, cellulose esters, acrylic polymers (e.g., poly(acrylic acid), poly (methacrylic acid), acrylic acid and methacrylic acid copolymers, methyl methacrylate copolymers, ethoxy ethyl methacrylates, cyanoethyl methacrylate, methacrylic acid alkamide copolymer, poly(methyl methacrylate), polyacrylamide, ammonio methacrylate copolymers, aminoalkyl methacrylate copolymer, poly(methacrylic acid anhydride) and glycidyl methacrylate copolymers) and mixtures of the foregoing. Representative aqueous dispersions of ethylcellulose include, for example, AQUACOAT® (FMC Corp., Philadelphia, Pa.) and SURELEASE® (Colorcon, Inc., West Point, Pa.), both of which can be applied to the substrate according to the manufacturer's instructions. Representative acrylic polymers include, for example, the various EUDRAGIT® (Rohm America, Piscataway, N.J.) polymers, which may be used singly or in combination depending on the desired release profile, according to the manufacturer's instructions.

The physical properties of coatings that comprise an aqueous dispersion of a hydrophobic material may be improved by the addition or one or more plasticizers. Suitable plasticizers for alkyl celluloses include, for example, dibutyl sebacate, diethyl phthalate, triethyl citrate, tributyl citrate and triacetin. Suitable plasticizers for acrylic polymers include, for example, citric acid esters such as triethyl citrate and tributyl citrate, dibutyl phthalate, polyethylene glycols, propylene glycol, diethyl phthalate, castor oil and triacetin.

Controlled-release coatings are generally applied using conventional techniques, such as by spraying in the form of an aqueous dispersion. If desired, the coating may comprise pores or channels to facilitate release of active ingredient. Pores and channels may be generated by well known methods, including the addition of organic or inorganic material that is dissolved, extracted or leached from the coating in the environment of use. Certain such pore-forming materials include hydrophilic polymers, such as hydroxyalkylcelluloses (e.g., hydroxypropylmethylcellulose), cellulose ethers, synthetic water-soluble polymers (e.g., polyvinylpyrrolidone, cross-linked polyvinylpyrrolidone and polyethylene oxide), water-soluble polydextrose, saccharides and polysaccharides and alkali metal salts. Alternatively, or in addition, a controlled release coating may include one or more orifices, which may be formed my methods such as those described in U.S. Pat. Nos. 3,845,770; 4,034,758; 4,077,407; 4,088,864; 4,783,337 and 5,071,607. Controlled-release may also be achieved through the use of transdermal patches, using conventional technology (see, e.g., U.S. Pat. No. 4,668,232).

Further examples of controlled release formulations, and components thereof, may be found, for example, in U.S. Pat. Nos. 4,572,833; 4,587,117; 4,606,909; 4,610,870; 4,684,516; 4,777,049; 4,994,276; 4,996,058; 5,128,143; 5,202,128; 5,376,384; 5,384,133; 5,445,829; 5,510,119; 5,618,560; 5,643,604; 5,891,474; 5,958,456; 6,039,980; 6,143,353; 6,126,969; 6,156,342; 6,197,347; 6,387,394; 6,399,096; 6,437,000; 6,447,796; 6,475,493; 6,491,950; 6,524,615; 6,838,094; 6,905,709; 6,923,984; 6,923,988; and 6,911,217; each of which is hereby incorporated by reference for its teaching of the preparation of controlled release dosage forms.

In addition to or together with the above modes of administration, a compound provided herein may be conveniently added to food or drinking water (e.g., for administration to non-human animals including companion animals (such as dogs and cats) and livestock). Animal feed and drinking water compositions may be formulated so that the animal takes in an appropriate quantity of the composition along with its diet. It may also be convenient to present the composition as a premix for addition to feed or drinking water.

Compounds are generally administered in a therapeutically effective amount. Preferred systemic doses are no higher than 50 mg per kilogram of body weight per day (e.g., ranging from about 0.001 mg to about 50 mg per kilogram of body weight per day), with oral doses generally being about 5-20 fold higher than intravenous doses (e.g., ranging from 0.01 to 40 mg per kilogram of body weight per day).

The amount of active ingredient that may be combined with the carrier materials to produce a single dosage unit will vary depending, for example, upon the patient being treated, the particular mode of administration and any other co-administered drugs. Dosage units generally contain between from about 10 µg to about 500 mg of active ingredient. Optimal dosages may be established using routine testing, and procedures that are well known in the art.

Pharmaceutical compositions may be packaged for treating conditions responsive to $P2X_7$ receptor modulation (e.g., pain, inflammation, neurodegeneration or other condition described herein). Packaged pharmaceutical compositions generally include (i) a container holding a pharmaceutical composition that comprises at least one modulator as described herein and (ii) instructions (e.g., labeling or a package insert) indicating that the contained composition is to be used for treating a condition responsive to $P2X_7$ receptor modulation in the patient.

Methods of Use $P2X_7$ receptor modulators provided herein may be used to alter activity and/or activation of $P2X_7$ receptors in a variety of contexts, both in vitro and in vivo. Within certain aspects, $P2X_7$ receptor antagonists may be used to inhibit the binding of ligand agonist to $P2X_7$ receptor in vitro or in vivo. In general, such methods comprise the step of contacting a $P2X_7$ receptor with one or more $P2X_7$ receptor modulators provided herein, in the presence of ligand in aqueous solution and under conditions otherwise suitable for binding of the ligand to $P2X_7$ receptor. The modulator(s) are generally present at a concentration that is sufficient to alter $P2X_7$ receptor-mediated signal transduction (using an assay provided in Example 4). The $P2X_7$ receptor may be present in solution or suspension (e.g., in an isolated membrane or cell preparation), or in a cultured or isolated cell. Within certain embodiments, the $P2X_7$ receptor is expressed by a cell that is present in a patient, and the aqueous solution is a body fluid. Preferably, one or more modulators are administered to an animal in an amount such that the modulator is present in at least one body fluid of the animal at a therapeutically effective concentration that is 20 micromolar or less, 10 micromolar or less, 5 micromolar or less, or 1 micromolar or less. For example, such compounds may be administered at a therapeutically effective dose that is less than 20 mg/kg body weight, preferably less than 5 mg/kg and, in some instances, less than 1 mg/kg.

Also provided herein are methods for modulating, preferably reducing, cellular $P2X_7$ receptor activation and/or activity, such as signal-transducing activity (e.g., calcium conductance). Such modulation may be achieved by contacting a $P2X_7$ receptor (either in vitro or in vivo) with one or more modulators provided herein under conditions suitable for binding of the modulator(s) to the receptor. The modulator(s) are generally present at a concentration that is sufficient to alter $P2X_7$ receptor-mediated signal transduction as described herein. The receptor may be present in solution or suspension, in a cultured or isolated cell preparation or in a cell within a patient. For example, the cell may be contacted in vivo in an animal. Modulation of signal tranducing activity may be assessed by detecting an effect on calcium ion conductance (also referred to as calcium mobilization or flux). Modulation of signal transducing activity may alternatively be assessed by detecting an alteration of a symptom (e.g., pain or inflammation) of a patient being treated with one or more modulators provided herein.

$P2X_7$ receptor modulator(s) provided herein are preferably administered to a patient (e.g., a human) orally or topically, and are present within at least one body fluid of the animal while modulating $P2X_7$ receptor signal-transducing activity.

The present invention further provides methods for treating conditions responsive to $P2X_7$ receptor modulation. Within the context of the present invention, the term "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms). A condition is "responsive to $P2X_7$ receptor modulation" if it is characterized by inappropriate activity of a $P2X_7$ receptor, regardless of the amount of $P2X_7$ agonist present locally, and/or if modulation of $P2X_7$ receptor activity results in alleviation of the condition or a symptom thereof. Such conditions include, for example, pain, inflammation, cardiovascular disorders, neurodegenerative disorders and respiratory disorders (such as cough, asthma, chronic obstructive pulmonary disease, chronic bronchitis, cystic fibrosis and rhinitis, including allergic rhinitis, such as seasonal an perennial rhinitis, and non-allergic rhinitis), fibrosis as well as other conditions described in more detail below. Such conditions may be diagnosed and monitored using criteria that have been established in the art. Patients may include humans, domesticated companion animals and livestock, with dosages as described above.

Treatment regimens may vary depending on the compound used and the particular condition to be treated; however, for treatment of most disorders, a frequency of administration of 4 times daily or less is preferred. In general, a dosage regimen of 2 times daily is more preferred, with once a day dosing particularly preferred. For the treatment of acute pain, a single dose that rapidly reaches effective concentrations is desirable. It will be understood, however, that the specific dose level and treatment regimen for any particular patient will depend upon a variety of factors including the activity of the specific compound employed, the age, body weight, general health, sex, diet, time of administration, route of administration, and rate of excretion, drug combination and the severity of the particular disease undergoing therapy. In general, the use of the minimum dose sufficient to provide effective therapy is preferred. Patients may generally be monitored for therapeutic effectiveness using medical or veterinary criteria suitable for the condition being treated or prevented.

Pain that may be treated using the modulators provided herein includes, for example, acute, chronic, inflammatory, and neuropathic pain. Specific pain indications that may be treated as described herein include, but are not limited to, pain associated with osteoarthritis or rheumatoid arthritis; various neuropathic pain syndromes (such as post-herpetic neuralgia, trigeminal neuralgia, reflex sympathetic dystrophy, diabetic neuropathy, Guillian Barre syndrome, fibromyalgia, oral neuropathic pain, phantom limb pain, post-mastectomy pain, peripheral neuropathy, myofascial pain syndromes, MS-related neuropathy, HIV or AIDS-related neuropathy, and chemotherapy-induced and other iatrogenic neuropathies); visceral pain, (such as that associated with gastroesophageal reflux disease (GERD), irritable bowel syndrome, inflammatory bowel disease, pancreatitis, intestinal gas, gynecological disorders (e.g., menstrual pain, dysmenorrhoea, pain associated with cystitis, labor pain, chronic pelvic pain, chronic prostitis, endometriosis, heart pain and abdominal pain), and urological disorders); dental pain (e.g., toothache, denture pain, nerve root pain, pain resulting from periodontal disease, and pain due to dental surgery including operative and postoperative pain); headache (e.g., headaches involving peripheral nerve activity, sinus headache, cluster headache (i.e., migranous neuralgia) tension headache, migraine, temporomandibular pain and maxillary sinus pain); stump pain; meralgia paresthetica; burning-mouth syndrome; pain associated with nerve and root damage, including as pain associated with peripheral nerve disorders (e.g., nerve entrapment and brachial plexus avulsions, amputation, peripheral neuropathies including bilateral peripheral neuropathy, tic douloureux, atypical facial pain, nerve root damage, and arachnoiditis), causalgia, neuritis (including, for example, sciatic neuritis, peripheral neuritis, polyneuritis, optic neuritis, postfebrile neuritis, migrating neuritis, segmental neuritis and Gombault's neuritis), neuronitis, neuralgias (e.g., those mentioned above, cervicobrachial neuralgia, cranial neuralgia, geniculate neuralgia, glossopharyngial neuralgia, migranous neuralgia, idiopathic neuralgia, intercostals neuralgia, mammary neuralgia, mandibular joint neuralgia, Morton's neuralgia, nasociliary neuralgia, occipital neuralgia, red neuralgia, Sluder's neuralgia, splenopalatine neuralgia, supraorbital neuralgia and vidian neuralgia); surgery-related pain; musculoskeletal pain; central nervous system pain (e.g., pain due to brain stem damage, sciatica, and ankylosing spondylitis); and spinal pain, including spinal cord injury-related pain.

Further pain conditions that can be treated as described herein include Charcot's pains, ear pain, muscle pain, eye pain, orofacial pain (e.g., odontalgia), carpel tunnel syndrome, acute and chronic back pain (e.g., lower back pain), gout, scar pain, hemorrhoidal pain, dyspeptic pains, angina, nerve root pain, "non-painful" neuropathies, complex regional pain syndrome, homotopic pain and heterotopic pain—including pain associated with carcinoma, often referred to as cancer-associated pain (e.g., in patients with bone cancer), pain (and inflammation) associated with venom exposure (e.g., due to snake bite, spider bite, or insect sting) and trauma-associated pain (e.g., post-surgical pain, episiotomy pain, pain from cuts, musculoskeletal pain, bruises and broken bones, and burn pain, especially primary hyperalgesia associated therewith). Additional pain conditions that may be treated as described herein include pain associated with autoimmune diseases or immunodeficiency disorders, hot flashes, burns, sunburn, and pain that results from exposure to heat, cold or external chemical stimuli.

Conditions associated with inflammation and/or immune system disorders that may be treated using the modulators provided herein include, but are not limited to, arthritis (including osteoarthritis, rheumatoid arthritis, psoriatic arthritis, Reiter's syndrome, gout, traumatic arthritis, rubella arthritis, rheumatoid spondylitis, gouty arthritis and juvenile arthritis); cystic fibrosis; uveitis; systemic lupus erythematosus (and associated glomerulonephritis); spondyloarthropathies; psoriasis; scleritis; allergic conditions (including allergic reactions, allergic rhinitis, allergic contact hypersensitivity, allergic dermatitis, eczema and contact dermatitis), reperfusion injury (e.g., cardiac and renal reperfusion injury), respiratory system disorders (including hyper-responsiveness of the airway, cough, asthma (e.g., to prevent or decrease the severity of both acute early phase asthma attack and the late phase reactions that follow such an asthma attack; including bronchial, allergic, intrinsic, extrinsic, exercise-induced, drug-induced (e.g., aspirin or NSAID-induced) and dust-induced asthma), reactive airway disease, emphysema, acute (adult) respiratory distress syndrome (ARDS), bronchitis (e.g., infectious and eosinophilic bronchitis), bronchiectasis, chronic pulmonary obstructive disorder (COPD), chronic pulmonary inflammatory disease, silicosis, pulmonary sarcoidosis, farmer's lung, hypersensitivity pneumonitis and lung fibrosis), viral infection, fungal infection, bacterial infection, Crohn's disease, glomerulornephritis, HIV infection and AIDS, irritable bowel syndrome, inflammatory bowel disease, dermatomyositis, multiple sclerosis, pemphigus, pemphigoid, scleroderma, myasthenia gravis, autoimmune hemolytic and thrombocytopenic states, Goodpasture's syndrome (and associated glomerulonephritis and pulmonary hemorrhage), tissue graft rejection, hyperacute rejection of transplanted organs, allograft rejection, organ transplant toxicity, neutropenia, sepsis, septic shock, endotoxic shock, conjunctivitis shock, toxic shock syndrome, Alzheimer's disease, inflammation associated with severe burns, lung injury, systemic inflammatory response syndrome (SIRS), neonatal-onset multisystem inflammatory disease (NOMID), Hashimoto's thyroiditis, Grave's disease, Addison's disease, idiopathic thrombocytopaenic purprua, eosinophilic fascitis, hyper-IgE syndrome, antiphospholipid syndrome, leprosy, Sezary syndrome, paraneoplastic syndromes, Muckle-Wells syndrome, lichen planus, familial cold autoinflammatory syndrome (FCAS), colitis, ruptured abdominal aortic aneurysm and multiple organ dysfunction syndrome (MODS). Also included are pathologic sequellae associated with insulin-dependent diabetes mellitus (including diabetic retinopathy), lupus nephropathy, Heyman nephritis, membranous nephritis and other forms of glomerulonephritis, macular degeneration, contact sensitivity responses, and inflammation resulting from contact of blood with artificial surfaces as occurs, for example, during extracorporeal circulation of blood (e.g., during hemodialysis or via a heart-lung machine, for example, in association with vascular surgery such as coronary artery bypass grafting or heart valve replacement) such as extracorporeal post-dialysis syndrome, or in association with contact with other artificial vessel or container surfaces (e.g., ventricular assist devices, artificial heart machines, transfusion tubing, blood storage bags, plasmapheresis, plateletpheresis, and the like).

Still further conditions that may be treated using the modulators provided herein include:

Cardiovascular disorders, such as cardiovascular disease, stroke, cerebral ischemia, myocardial infarction, atherosclerosis, ischemic heart disease, ischemia-reperfusion injury, aortic aneurysm, and congestive heart failure;

Neurological disorders (e.g., neurodegeneration), such as neurodegenerative conditions associated with progressive CNS disorders, including, but not limited to, Alzheimer's disease, Parkinson's disease, amyotrophic lateral sclerosis, Huntington's disease, Creutzfeldt-Jakob disease, dementia with Lewy bodies, traumatic brain injury, spinal cord injury, neurotrauma, cerebral amyloid angiopathy, and encephalitis; epilepsy and seizure disorders; multiple sclerosis and other demyelinating syndromes; cerebral atherosclerosis; vasculitis; temporal arteritis; myasthenia gravis; neurosarcoidosis; and central and peripheral nervous system complications of malignant, infectious or autoimmune processes; the modulators provided herein may also be used to promote neuroregeneration;

Centrally-mediated neuropsychiatric disorders, such as depression, depression mania, bipolar disease, anxiety, schizophrenia, eating disorders, sleep disorders and cognition disorders;

Obesity (e.g., the modulator may be used to promote weight loss in an obese patient); and Other disorders, such as cirrhosis, interstitial fibrosis, prostate, bladder and bowel dysfunction (e.g., urinary incontinence, urinary hesitancy, rectal hypersensitivity, fecal incontinence and benign prostatic hypertrophy); itch/pruritus; obesity; lipid disorders; cancer; hypertension; renal disorders; abnormal wound healing; myoblastic leukemia; diabetes; meningitis; varicose veins; muscle degeneration; cachexia; restenosis; thrombosis; cerebral malaria; disorders of bones and joints (e.g., osteoporosis, bone resorption disease, loosening of artificial joint implants, and others listed above); epidermolysis bullosa; ocular angiogenesis; corneal injury; corneal scarring; and tissue ulceration.

Within other aspects, modulators provided herein may be used within combination therapy for the treatment of conditions responsive to $P2X_7$ receptor modulation (e.g., conditions involving pain and/or inflammatory components). Such conditions include, for example, autoimmune disorders and pathologic autoimmune responses known to have an inflammatory component including, but not limited to, arthritis (especially rheumatoid arthritis), psoriasis, Crohn's disease, lupus erythematosus, irritable bowel syndrome, tissue graft rejection, and hyperacute rejection of transplanted organs. Other such conditions include trauma (e.g., injury to the head or spinal cord), cardio- and cerebro-vascular disease and certain infectious diseases.

Within such combination therapy, a modulator is administered to a patient along with a second therapeutic agent (e.g., an analgesic and/or anti-inflammatory agent). The modulator and second therapeutic agent may be present in the same pharmaceutical composition, or may be administered separately in either order. Anti-inflammatory agents include, for example, non-steroidal anti-inflammatory drugs (NSAIDs), non-specific and cyclooxygenase-2 (COX-2) specific cyclooxgenase enzyme inhibitors, gold compounds, corticosteroids, methotrexate, leflunomide, cyclosporine A, IM gold, minocycline, azathioprine, tumor necrosis factor (TNF) receptor antagonists, soluble TNF alpha receptor (etanercept), anti-TNF alpha antibodies (e.g., infliximab and adalimumab), anti-C5 antibodies, interleukin-1 (IL-1) receptor antagonists (e.g., anakinra or IL-1 trap), IL-18 binding protein, CTLA4-Ig (e.g., abatacept), anti-human IL-6 receptor monoclonal antibody (e.g., tocilizumab), LFA-3-Ig fusion proteins (e.g., alefacept), LFA-1 antagonists, anti-VLA4 monoantibody (e.g., natalizumab), anti-CD11a monoclonal antibody, anti-CD20 monoclonal antibody (e.g., rituximab), anti-IL-12 monoclonal antibody, anti-IL-15 monoclonal antibody, CDP 484, CDP 870, chemokine receptor antagonists, selective iNOS inhibitors, p38 kinase inhibitors, integrin antagonists, angiogenesis inhibitors, and TMI-1 dual inhibitors. Further anti-inflammatory agents include meloxicam, rofecoxib, celecoxib, etoricoxib, parecoxib, valdecoxib and tilicoxib.

NSAIDs include, but are not limited to, ibuprofen, flurbiprofen, naproxen or naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. One class of NSAIDs consists of compounds that inhibit cyclooxygenase (COX) enzymes; such compounds include celecoxib and rofecoxib. NSATDs further include salicylates such as acetylsalicylic acid or aspirin, sodium salicylate, choline and magnesium salicylates, and salsalate, as well as corticosteroids such as cortisone, dexamethasone, methylprednisolone, prednisolone, prednisolone sodium phosphate, and prednisone.

Suitable dosages for $P2X_7$ receptor modulator within such combination therapy are generally as described above. Dosages and methods of administration of anti-inflammatory agents can be found, for example, in the manufacturer's instructions in the *Physician's Desk Reference*. In certain embodiments, the combination administration of a modulator with an anti-inflammatory agent results in a reduction of the dosage of the anti-inflammatory agent required to produce a therapeutic effect (i.e., a decrease in the minimum therapeutically effective amount). Thus, preferably, the dosage of anti-inflammatory agent in a combination or combination treatment method is less than the maximum dose advised by the manufacturer for administration of the anti-inflammatory agent without combination administration of a modulator. More preferably this dosage is less than ¾, even more preferably less than ½, and highly preferably, less than ¼ of the maximum dose, while most preferably the dose is less than 10% of the maximum dose advised by the manufacturer for administration of the anti-inflammatory agent(s) when administered without combination administration of a modulator. It will be apparent that the dosage amount of modulator component of the combination needed to achieve the desired effect may similarly be reduced by the co-administraction of the anti-inflammatory agent.

In certain preferred embodiments, the combination administration of a modulator with an anti-inflammatory agent is accomplished by packaging one or more modulators and one or more anti-inflammatory agents in the same package, either in separate containers within the package or in the same contained as a mixture of one or more modulators and one or more anti-inflammatory agents. Preferred mixtures are formulated for oral administration (e.g., as pills, capsules, tablets or the like). In certain embodiments, the package comprises a label hearing indicia indicating that the one or more modulators and one or more anti-inflammatory agents are to be taken together for the treatment of an inflammatory pain condition.

Within further aspects, modulators provided herein may be used in combination with one or more additional pain relief medications. Certain such medications are also anti-inflammatory agents, and are listed above. Other such medications are analgesic agents, including narcotic agents which typically act at one or more opioid receptor subtypes (e.g., μ, κ and/or δ), preferably as agonists or partial agonists. Such agents include opiates, opiate derivatives and opioids, as well as pharmaceutically acceptable salts and hydrates thereof. Specific examples of narcotic analgesics include, within preferred embodiments, alfentanil, alphaprodine, anileridine, bezitramide, buprenorphine, butorphanol, codeine, diacetyldihydromorphine, diacetylmorphine, dihydrocodeine, diphenoxylate, ethylmorphine, fentanyl, heroin, hydrocodone, hydromorphone, isomethadone, levomethorphan, levorphane, levorphanol, meperidine, metazocine, methadone, methorphan, metopon, morphine, nalbuphine, opium extracts, opium fluid extracts, powdered opium, granulated opium, raw opium, tincture of opium, oxycodone, oxymorphone, paregoric, pentazocine, pethidine, phenazocine, piminodine, propoxyphene, racemethorphan, racemorphan, sulfentanyl, thebaine and pharmaceutically acceptable salts and hydrates of the foregoing agents.

Other examples of narcotic analgesic agents include acetorphine, acetyldihydrocodeine, acetylmethadol, allylprodine, alphracetylmethadol, alphameprodine, alphamethadol, benzethidine, benzylmorphine, betacetylmethadol, betameprodine, betamethadol, betaprodine, clonitazene, codeine methylbromide, codeine-N-oxide, cyprenorphine, desomorphine, dextromoramide, diampromide, diethylthiambutene, dihydromorphine, dimenoxadol, dimepheptanol, dimethylthiamubutene, dioxaphetyl butyrate, dipipanone, drotebanol, ethanol, ethylmethylthiambutene, etonitazene, etorphine, etoxeridine, furethidine, hydromorphinol, hydroxypethidine, ketobemidone, levomoramide, levophenacylmorphan, methyldesorphine, methyldihydromorphine, morpheridine, morphine, methylpromide, morphine methylsulfonate, morphine-N-oxide, myrophin, naloxone, naltyhexone, nicocodeine, nicomorphine, noracymethadol, norlevorphanol, normethadone, normorphine, norpipanone, pentazocaine, phenadoxone, phenampromide, phenomorphan, phenoperidine, piritramide, pholcodine, proheptazoine, properidine, propiran, racemoramide, thebacon, trimeperidine and the pharmaceutically acceptable salts and hydrates thereof.

Further specific representative analgesic agents include, for example acetaminophen (paracetamol); aspirin and other NSAIDs described above; NR2B antagonists; bradykinin antagonists; anti-migraine agents; anticonvulsants such as oxcarbazepine and carbamazepine; antidepressants (such as TCAs, SSRIs, SNRIs, substance P antagonists, etc.); spinal blocks; pentazocine/naloxone; meperidine; levorphanol; buprenorphine; hydromorphone; fentanyl; sufentanyl; oxycodone; oxycodone/acetaminophen, nalbuphine and oxymorphone. Still further analgesic agents include CB2-receptor agonists, such as AM1241, capsaicin receptor antagonists and compounds that bind to the α2δ subunit of voltage-gated calcium channels, such as gabapentin and pregabalin.

Representative anti-migraine agents for use in combination with a modulator provided herein include CGRP antagonists, capsaicin receptor antagonists, ergotamines and $5-HT_1$ agonists, such as sumatripan, naratriptan, zolmatriptan and rizatriptan.

Within still further aspects, modulators provided herein may be used, for example, in the treatment of pulmonary disorders such as asthma, in combination with one or more beta(2)-adrenergic receptor agonists or leukotriene receptor antagonists (e.g., agents that inhibits the cysteinyl leukotriene CysLT$_1$ receptor). CysLT$_1$ antagonists include montelukast, zafirlukast, and pranlukast.

Suitable dosages for P2X$_7$ receptor modulator within such combination therapy are generally as described above. Dosages and methods of administration of other pain relief medications can be found, for example, in the manufacturer's instructions in the *Physician's Desk Reference*. In certain embodiments, the combination administration of a modulator with one or more additional pain medications results in a reduction of the dosage of each therapeutic agent required to produce a therapeutic effect (e.g., the dosage or one or both agent may less than ¼, less than ½, less than ¼ or less than 10% of the maximum dose listed above or advised by the manufacturer).

For use in combination therapy, pharmaceutical compositions as described above may further comprise one or more additional medications as described above. In certain such compositions, the additional medication is an analgesic. Also provided herein are packaged pharmaceutical preparations comprising one or more modulators and one or more additional medications (e.g., analgesics) in the same package. Such packaged pharmaceutical preparations generally include (i) a container holding a pharmaceutical composition that comprises at least one modulator as described herein; (ii) a container holding a pharmaceutical composition that comprises at least one additional medication (such as a pain relief and/or anti-inflammatory medication) as described above and (iii) instructions (e.g., labeling or a package insert) indicating that the compositions are to be used simultaneously, separately or sequentially for treating or preventing a condition responsive to P2X$_7$ receptor modulation in the patient (such as a condition in which pain and/or inflammation predominates).

Within separate aspects, the present invention provides a variety of non-pharmaceutical in vitro and in vivo uses for the modulator compounds provided herein. For example, such compounds may be labeled and used as probes for the detection and localization of P2X$_7$ receptor (in samples such as cell preparations or tissue sections, preparations or fractions thereof). In addition, modulators provided herein that comprise a suitable reactive group (such as an aryl carbonyl, nitro or azide group) may be used in photoaffinity labeling studies of receptor binding sites. In addition, modulators provided herein may be used as positive controls in assays for receptor activity or as radiotracers (e.g., in receptor mapping procedures). For example, a modulator compound may be labeled using any of a variety of well known techniques (e.g., radio-labeled with a radionuclide such as tritium, as described herein), and used as a probe for receptor autoradiography (receptor mapping) of P2X$_7$ receptor in cultured cells or tissue samples, which may be performed as described by Kuhar in sections 8.1.1 to 8.1.9 of Current Protocols in Pharmacology (1998) John Wiley & Sons, New York, which sections are incorporated herein by reference. Such receptor mapping procedures also include methods that can be used to characterize P2X$_7$ receptor in living subjects, such as positron emission tomography (PET) imaging or single photon emission computerized tomography (SPECT).

The following Examples are offered by way of illustration and not by way of limitation. Unless otherwise specified all reagents and solvent are of standard commercial grade and are used without further purification. Using routine modifications, the starting materials may be varied and additional steps employed to produce other compounds provided herein.

EXAMPLES

Mass spectroscopy data provided herein is Electrospray MS, obtained in positive ion mode. Unless otherwise specified, such data is obtained using a Micromass Time-of-Flight LCT (Waters Corp.; Milford, Mass.), equipped with a Waters 600 pump (Waters Corp.), Waters 996 photodiode array detector (Waters Corp.), and a Gilson 215 autosampler (Gilson, Inc.; Middleton, Wis.). MassLynx™ (Waters Corp.) version 4.0 software with OpenLynx Global Server™, OpenLynx™ and AutoLynx™ processing is used for data collection and analysis. MS conditions are as follows: capillary voltage=3.5 kV; cone voltage=30 V, desolvation and source temperature=350° C. and 120° C., respectively; mass range=181-750 with a scan time of 0.22 seconds and an interscan delay of 0.05 seconds.

Sample volume of 1 microliter is injected onto a 50×4 6 mm Chromolith SpeedROD RP-18e column (Merck KGaA, Darmstadt, Germany), and eluted using a 2-phase linear gradient at a flow rate of 6 mL/min. Sample is detected using total absorbance count over the 220-340 nm UV range. The elution conditions are: Mobile Phase A—95% water, 5% MeOH with 0.05% TFA; Mobile Phase B—5% water, 95% MeOH with 0.025% TFA. The following gradient is used: 0-0.5 min 10-100% B, hold at 100% B to 1.2 min, return to 10% B at 1.21 min Inject to inject cycle is 2.15 min.

Where indicated, retention times (R$_T$) are provided in minutes.

Example 1

Preparation of Representative 5-Membered Heterocyclic Amides and Related Compounds This Example illustrates the preparation of representative 5-membered heterocyclic amides and related compounds, as well as certain intermediates useful in the preparation of such compounds. Mass spectroscopy characterization data is obtained as described above. A "*IC$_{50}$" after the mass spectroscopy data provided for a compound indicates that the IC$_{50}$ determined as described in Example 4A is 2 micromolar or less (i.e., the concentration of the compound that is required to provide a 50% decrease in the fluorescence response of cells exposed to 80 µM of (2'(3')-O-(4-benzoyl-benzoyl)adenosine 5'-triphosephate is 2 micromolar or less).

A. N-(Adamantan-1-ylmethyl)-1-(4-amino-5-fluoro-pyrimidin-2-yl)-3-(trifluoromethyl)-1H-pyrazole-4-carboxamide (Compound 1)

Step 1. Trifluoromethyl-1H-pyrazole-4-carboxylic acid

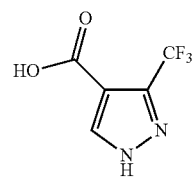

NaOH (3 mL, 10 N) is added to a solution of 3-trifluoromethyl-1H-pyrazole-4-carboxylic acid ethyl ester (5.0 g, 24 mmol) in MeOH (25 mL) at RT. The mixture is heated to 40° C. for 3 h. The solvent is removed to dryness. H₂O is added. The solution is acidified with 2N HCl to pH=6 to afford the title compound as an off-white solid.

Step 2. 3-Trifluoromethyl-1H-pyrazole-4-carboxylic acid (adamantan-1-ylmethyl)-amide

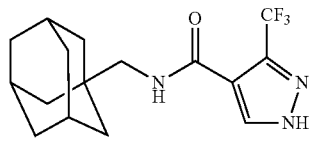 [SMILES: O=C(NCC12CC3CC(CC(C3)C1)C2)c1c[nH]nc1C(F)(F)F]

BOP (2.6 g, 5.8 mmol) is added to a solution of 3-trifluoromethyl-1H-pyrazole-4-carboxylic acid (1.0 g, 5.55 mmol), admantan-1-yl-methylamine (959 mg, 5.8 mmol), HOBt (200 mg, 1.4 mmol) and DIEA (1.1 mL, 6.5 mmol) in DMF (25 mL) at RT. The mixture is stirred for 14 h. The mixture is poured into a sat. NH₄Cl (450 mL) and filtered to afford the title compound as a white solid.

Step 3. 1-(4-Amino-5-fluoro-pyrimidin-2-yl)-3-trifluoromethyl-1H-pyrazole-4-carboxylic acid (adamantan-1-ylmethyl)-amide

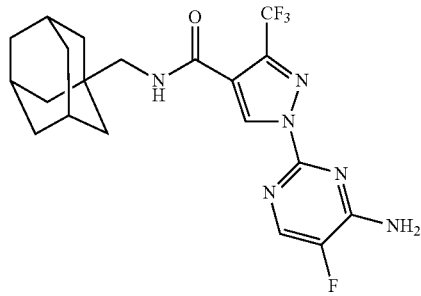 [SMILES: Nc1nc(-n2cc(C(=O)NCC34CC5CC(CC(C5)C3)C4)c(C(F)(F)F)n2)ncc1F]

A solution of 3-trifluoromethyl-1H-pyrazole-4-carboxylic acid (adamantan-1-ylmethyl)-amide (100 mg, 0.306 mmol), 2-chloro-5-fluoro-pyrimidin-4-ylamine (52 mg, 0.35 mmol) and Cs₂CO₃ (130 mg, 0.4 mmol) in NMP (1.0 mL) is heated in a microwave reactor at 150° C. for 1 h. The mixture is poured into H₂O. The crude product is filtered out, dissolved in 10% MeOH in DCM, and dried over anhydrous Na₂SO₄. The title compound is purified by PTLC (eluted with 5% MeOH in DCM). ¹H NMR (CD₃OD): 8.96 (s, 1H), 8.11 (s, 1H), 3.0 (s, 2H), 1.98 (m, 3H), 1.78-1.68 (m, 6H), 1.58 (s, 6H). MS (M+1)=439.29; R$_T$=1.34 min. *IC₅₀.

B. 1-(4-Amino-5-fluoropyrimidin-2-yl)-N-((1-(pyridin-3-yl)cyclohexyl)methyl)-3-(trifluoromethyl)-1H-pyrazole-4-carboxamide (Compound 2)

Step 1. Ethyl 1-(4-amino-5-fluoropyrimidin-2-yl)-3-(trifluoromethyl)-1H-pyrazole-4-carboxylate

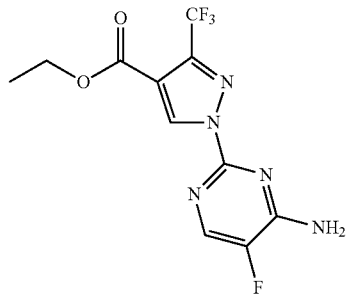 [SMILES: CCOC(=O)c1cn(-c2ncc(F)c(N)n2)nc1C(F)(F)F]

A solution of ethyl 3-trifluoromethyl-1H-pyrazole-4-carboxylic acid (150 mg, 0.72 mmol), 2-chloro-5-fluoro-pyrimidin-4-ylamine (102 mg, 0.79 mmol) and Cs₂CO₃ (325 mg, 1 mmol) in NMP (1.0 mL) is heated in a microwave reactor at 150° C. for 1 h. The mixture is poured into H₂O. The crude product is filtered out, dissolved in 10% MeOH in DCM, and dried over anhydrous Na₂SO₄. The title compound is purified by PTLC (eluted with 5% MeOH in DCM).

Step 2. 1-(4-Amino-5-fluoropyrimidin-2-yl)-3-(trifluoromethyl)-1H-pyrazole-4-carboxylic acid

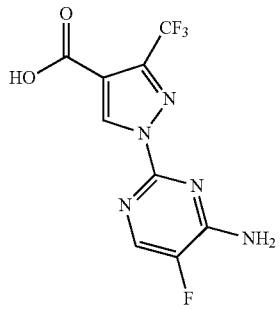 [SMILES: Nc1nc(-n2cc(C(=O)O)c(C(F)(F)F)n2)ncc1F]

A solution of ethyl 1-(4-amino-5-fluoropyrimidin-2-yl)-3-(trifluoromethyl)-1H-pyrazole-4-carboxylate (269 mg, 0.84 mmol) and NaOH (2 mL, 10N) in MeOH is heated to 45° C. for 2 h. The solvent is removed to dryness. H₂O is added. The solution is acidified with 2N HCl to pH=5, to afford the title compound as an off-white solid.

Step 3. 1-(4-amino-5-fluoropyrimidin-2-yl)-N4(1-(pyridin-3-yl)cyclohexyl)methyl)-3-(trifluoromethyl)-1H-pyrazole-4-carboxamide

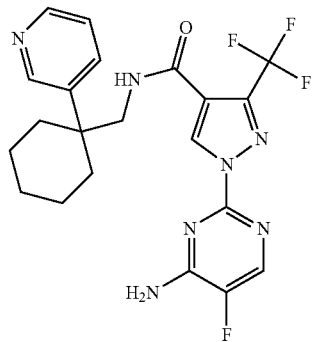 [SMILES: Nc1nc(-n2cc(C(=O)NCC3(c4cccnc4)CCCCC3)c(C(F)(F)F)n2)ncc1F]

BOP (18 mg, 0.04 mmol) is added to a solution of 1-(4-amino-5-fluoro-pyrimidin-2-yl)-3-trifluoromethyl-1H-pyrazole-4-carboxylic acid (10 mg, 0.03 mmol), (1-pyridin-3-yl-cyclohexyl)-methylamine (8 mg, 0.04 mmol), HOBt (2 mg, 0.01 mmol) and DIEA (1.7 µL, 0.1 mmol) in DMF (0.2 mL) at rt. The mixture is stirred for 4 h. $H_2O$ is added. The mixture is extracted with 5% MeOH in DCM and dried over $Na_2SO_4$. The crude product is purified by PTLC (eluted with 5% MeOH in DCM) to give the title compound. $^1$H NMR ($CD_3OD$): 8.81 (s, 1H), 8.59 (b, 1H), 8.38 (b, 1H), 8.10 (m, 1H), 7.94-7.92 (d, 1H), 7.43 (b, 1H), 2.31-2.28 (b, 2H), 1.76-1.55 (m, 4H), 1.45-1.28 (m, 6H). MS (M+1)=464.27; $R_T$=1.11 min. *$IC_{50}$.

C. 3-(Difluoromethyl)-1-(5-fluoro-pyrimidin-2-yl)-1H-pyrazole-4-carboxylic acid (adamantan-1-ylmethyl)-amide (Compound 3)

Step 1. Ethyl 3-(difluoromethyl)-1H-pyrazole-4-carboxylate

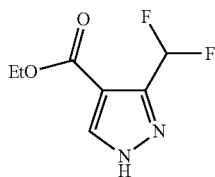

A mixture of ethyl 4,4-difluoro-3-oxobutanoate (4.65 g, 0.028 moles), acetic anhydride (8.0 g, 0.078 moles) and triethylorthoformate (7.3 g, 0.049 moles) is heated at 110° C. for 4 h. The mixture is concentrated under vacuum to afford (Z)-ethyl 2-(ethoxymethylene)-4,4-difluoro-3-oxobutanoate as yellow oil. The oil is dissolved in EtOH (25 mL) and cooled in an ice bath. To this cooled stirred mixture is added anhydrous hydrazine (0.7 mL, 0.022 mole) and the mixture is allowed to warm gradually to RT overnight. The mixture is concentrated under vacuum and the crude product is purified by silica gel column chromatography using 1-2% MeOH/$CH_2Cl_2$ to afford the title compound as a yellow solid.

Step 2. Ethyl 3-(difluoromethyl)-1-(5-fluoropyrimidin-2-yl)-1H-pyrazole-4-carboxylate

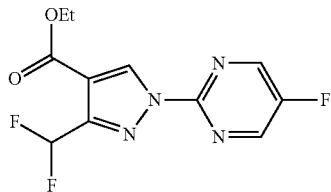 [SMILES: O=C(O)c1cn(-c2ncc(F)cn2)nc1C(F)F]

A solution of ethyl 3-(difluoromethyl)-1H-pyrazole-4-carboxylic acid (190 mg, 1.0 mmol), 2-chloro-5-fluoro-pyrimidine (132 mg, 1.0 mmol) and $K_2CO_3$ (276 mg, 2.0 mmol) in NMP (2.0 mL) is heated in a microwave reactor at 150° C. for 1 h. The mixture is poured into $H_2O$, extracted with EtOAc (3×25 mL) and dried over anhydrous $MgSO_4$. The crude product is purified by silica gel column chromatography using 15-25% EtOAc/hexane to afford the title compound as a white solid.

Step 3. 3-(Difluoromethyl)-1-(5-fluoropyrimidin-2-yl)-1H-pyrazole-4-carboxylic acid

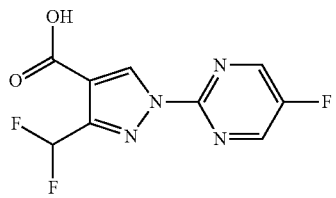

A mixture of ethyl 3-(difluoromethyl)-1-(5-fluoropyrimidin-2-yl)-1H-pyrazole-4-carboxylate (50 mg) and iodotrimethylsilane (1.0 mL) is heated at 90° C. for 4 h. The mixture is concentrated under vacuum, quenched with ice, and sodium metabisulfite is added until the aqueous solution becomes colorless. The mixture is then extracted with EtOAc (3×10 mL) and dried over anhydrous $MgSO_4$. The dried extract is filtered and concentrated under vacuum to afford the title compound as white solid.

Step 4. 3-(Difluoromethyl)-1-(5-fluoro-pyrimidin-2-yl)-1H-pyrazole-4-carboxylic acid (adamantan-1-ylmethyl)-amide

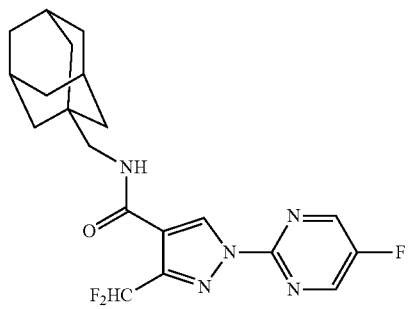 [SMILES: O=C(NCC12CC3CC(CC(C3)C1)C2)c1cn(-c2ncc(F)cn2)nc1C(F)F]

BOP (98 mg, 0.22 mmol) is added to a solution of 3-(difluoromethyl)-1-(5-fluoropyrimidin-2-yl)-1H-pyrazole-4-carboxylic acid (38 mg, 0.147 mmol), admantan-1-yl-methylamine (24 mg, 0.147 mmol) and DMA (0.052 mL) in DMF (1.0 mL) at rt. The mixture is stirred for 20 h. The mixture is poured into ice water (5 mL), extracted with EtOAc (3×20 mL) and dried over anhydrous $MgSO_4$. The crude product is purified by silica gel column chromatography using 30% EtOAc/hexane to afford the title compound as a white solid. $^1$H NMR (DMSO-$D_6$): 9.45 (s, 1H), 9.05 (s, 2H), 8.35 (m, 1H), 7.29-7.36 (t, 1H), 2.93 (d, 2H), 1.91 (m, 3H), 1.47-1.65 (m, 12H). MS (M+1)=406.28; $R_T$=1.34 min *$IC_{50}$.

D. N-(Adamantan-1-ylmethyl)-3-methyl-1-[5-methyl-4-(morpholin-4-ylcarbonyl)pyrimidin-2-yl]-1H-pyrazole-4-carboxamide (Compound 4)

Step 1. 3-Methyl-1H-pyrazole-4-carboxylic acid (adamantan-1-ylmethyl)-amide

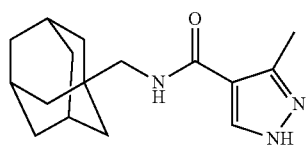 [SMILES: Cc1n[nH]cc1C(=O)NCC12CC3CC(CC(C3)C1)C2]

BOP (3.53 g, 8 mmol) is added to a solution of adamantan-1-yl-methylamine (1.32 g, 8 mmol), 3-methyl-1H-pyrazole-4-carboxylic acid (1 g, 7 mmol) and DIEA (2.6 g, 20 mmol) in DCM (25 mL). The solution is stirred overnight and evaporated, and then partitioned between EtOAc and saturated aqueous sodium bicarbonate. The organic layer is washed with brine, dried and evaporated. The residue is triturated with DCM and air-dried to give the title compound.

Step 2. 1-(4-Amino-5-methyl-pyrimidin-2-yl)-3-methyl-1H-pyrazole-4-carboxylic acid (adamantan-1-ylmethyl)-amide

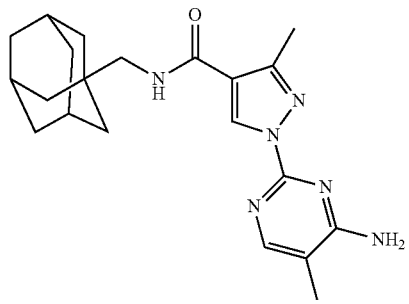 [SMILES: Cc1cnc(-n2cc(C(=O)NCC34CC5CC(CC(C5)C3)C4)c(C)n2)nc1N]

A mixture of 3-methyl-1H-pyrazole-4-carboxylic acid (adamantan-1-ylmethyl)-amide (1.6 g, 5.85 mmol), 4-amino-2-chloro-5-methylpyrimidine (924 mg, 6.4 mmol) and potassium carbonate (1.6 g, 11.7 mmol) in DMSO (10 mL) is heated at 165° C. for 14 h. The mixture is cooled to RT and partitioned between EtOAc and water and separate the layers. The aqueous layer is extracted twice with further EtOAc. The extracts are combined, dried and evaporated. Purification by flash chromatography eluting with a mixture of 7% MeOH and 1% TEA in DCM affords the title compound.

Step 3. 1-(4-Bromo-5-methyl-pyrimidin-2-yl)-3-methyl-1H-pyrazole-4-carboxylic acid (adamantan-1-ylmethyl)-amide

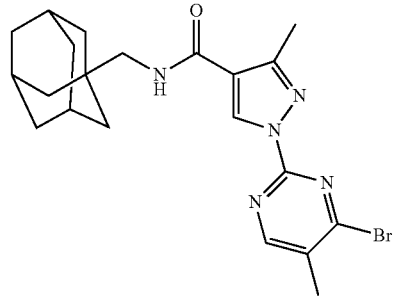 [SMILES: Cc1cnc(-n2cc(C(=O)NCC34CC5CC(CC(C5)C3)C4)c(C)n2)nc1Br]

A mixture of tert-butyl nitrite (182 mg, 1.75 mmol) and copper(II)bromide (388 mg, 1.75 mmol) in ACN is heated to 60° C. and 1-(4-amino-5-methyl-pyrimidin-2-yl)-3-methyl-1H-pyrazole-4-carboxylic acid (adamantan-1-ylmethyl)-amide (336 mg, 0.875 mmol) is added in portions. After heating for an additional 2 h, the mixture is cooled and partitioned between EtOAc and 10% aqueous ammonium hydroxide. The aqueous layer is extracted twice with further EtOAc. The extracts are combined, dried and evaporated. Purification by flash chromatography, eluting with a mixture of 5% MeOH and 1% TEA in DCM, affords the title compound.

Step 4. 1-(4-Cyano-5-methyl-pyrimidin-2-yl)-3-methyl-1H-pyrazole-4-carboxylic acid (adamantan-1-ylmethyl)-amide

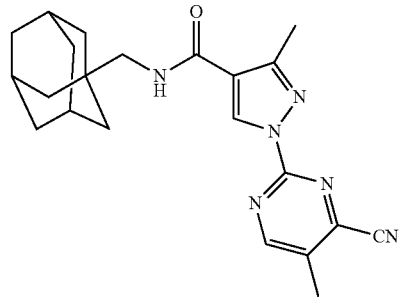 [SMILES: Cc1cnc(-n2cc(C(=O)NCC34CC5CC(CC(C5)C3)C4)c(C)n2)nc1C#N]

A solution of 1-(4-bromo-5-methyl-pyrimidin-2-yl)-3-methyl-1H-pyrazole-4-carboxylic acid (adamantan-1-ylmethyl)-amide (1.05 g, 2.4 mmol), zinc cyanide (328 mg, 2.8 mmol) and Pd(PPh$_3$)$_4$ (240 mg) in DMF (12 mL) is heated at 90° C. for 12 h. The mixture is cooled to RT and EtOAc and brine are added. The mixture is filtered through Celite, and the organic layer is separated, washed with brine, dried and evaporated. Purification by flash chromatography, eluting with a mixture of 5% MeOH and 1% TEA in DCM, affords the title compound. MS (M+1)=391.27; $R_T$=1.34 min. *$IC_{50}$.

Step 5. 2-{4[(Adamantan-1-ylmethyl)-carbamoyl]-3-methyl-pyrazol-1-yl}-5-methyl-pyrimidine-4-carboxylic acid

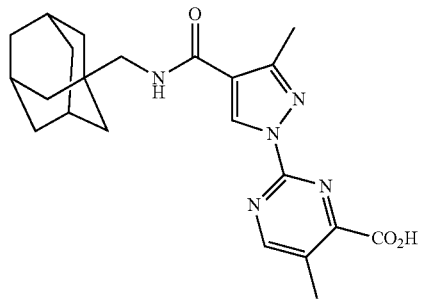 [SMILES: Cc1cnc(-n2cc(C(=O)NCC34CC5CC(CC(C5)C3)C4)c(C)n2)nc1C(=O)O]

A solution of 1-(4-cyano-5-methyl-pyrimidin-2-yl)-3-methyl-1H-pyrazole-4-carboxylic acid (adamantan-1-ylmethyl)-amide (150 mg, 0.38 mmol) in concentrated hydrochloric acid (1 mL) is heated at 80° C. overnight. The mixture is cooled to RT, water (3 mL) is added, and solid title compound is obtained by filtration and air-dried.

Step 6. N-(Adamantan-1-ylmethyl)-3-methyl-1-[5-methyl-4-(morpholin-4-ylcarbonyl) pyrimidin-2-yl]-1H-pyrazole-4-carboxamide

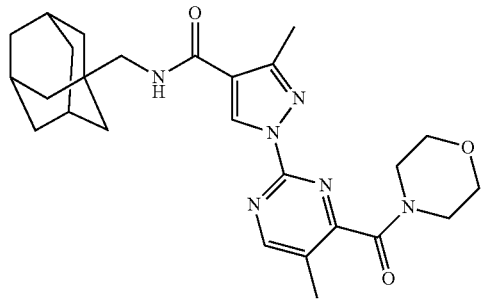 [SMILES: Cc1cnc(-n2cc(C(=O)NCC34CC5CC(CC(C5)C3)C4)c(C)n2)nc1C(=O)N1CCOCC1]

BOP (88 mg, 8 mmol) is added to a solution of 2-{4-[(adamantan-1-ylmethyl)-carbamoyl]-3-methyl-pyrazol-1-yl}-5-methyl-pyrimidine-4-carboxylic acid (41 mg, 0.1 mmol), morpholine (13 mg, 0.15 mmol) and DIEA (39 mg, 0.3 mmol) in DCM (3 mL). The solution is stirred overnight, evaporated and partitioned between EtOAc and saturated aqueous sodium bicarbonate. The organic layer is washed with brine, dried and evaporated. Purification by PTLC, eluting with a mixture of 5% MeOH and 1% TEA in DCM, affords the title compound. $^1$H NMR (CDCl$_3$): 8.80 (s, 1H), 8.65 (s, 1H), 5.93 (s, 1H), 3.81 (s, 4H), 3.63-3.66 (m, 1H), 3.46 (s, 1H), 3.29 (t, 1H), 3.10-3.15 (m, 2H), 2.85-2.90 (m, 1H), 2.58 (s, 3H), 2.31 (s, 3H), 1.99 (s, 3H), 1.53-1.73 (m, 12H). MS (M+1)=479.37; R$_T$=1.30 min. *IC$_{50}$.

E. N-(Adamantan-1-ylmethyl)-3-methoxy-1-pyrimidin-2-yl-1H-pyrazole-4-carboxamide (Compound 5)

Step 1. Ethyl 3-hydroxy-1H-pyrazole-4-carboxylate

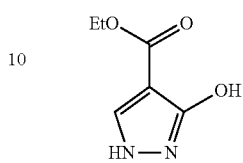

A solution of diethyl (ethoxymethylene)malonate (20 g, 92.5 mmol) in 200 mL of EtOH is treated with hydrazine (2.9 mL, 92.5 mmol) by dropwise addition. After 10 min, 100 mL of 1 N NaOH is added (slightly exothermic), and the reaction mixture is stirred for a further 30 min. The EtOH is removed in vacuo, and the aqueous solution is diluted with a little more water and extracted with EtOAc. The aqueous phase is cooled to 0° C. and acidified to pH=5 with conc. HCl. The resulting precipitate is collected by vacuum filtration and dried in vacuo to give the title compound as an off-white solid.

Step 2. Ethyl 1-acetyl-3-hydroxy-1H-pyrazole-4-carboxylate

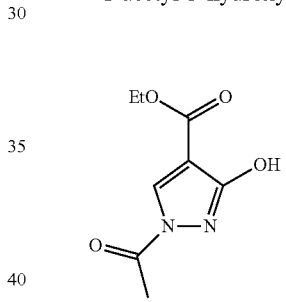

Acetic anhydride (1.2 mL, 12.8 mmol) is added to a suspension of ethyl 3-hydroxy-1H-pyrazole-4-carboxylate (2.0 g, 12.8 mmol) in 30 mL of acetic acid. The reaction mixture is stirred at RT for 2 h. The solvent is removed in vacuo, and the remaining solid is washed with water, collected by vacuum filtration, and dried in vacuo to give the title compound as a white solid. $^1$H NMR (400 MHz, CDCl$_3$) δ 8.45 (1H, s), 8.27 (1H, bs), 4.38 (2H, q), 2.64 (3H, s), 1.38 (3H, t).

Step 3. Ethyl 3-methoxy-1H-pyrazole-4-carboxylate

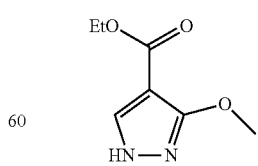

A mixture of ethyl 1-acetyl-3-hydroxy-1H-pyrazole-4-carboxylate (2.1 g, 10.6 mmol) and potassium carbonate (1.5 g, 10.6 mmol) in 45 mL of DMF is stirred at RT for 30 minutes. Dimethyl sulfate (1.0 mL, 10.6 mmol) in 25 mL of DMF is then added dropwise over 10 min, and the resulting reaction mixture is heated to 70° C. for 4 h. The solvent is evaporated in vacuo, and the residue is dissolved in water and extracted with CH₂Cl₂ (2×30 mL). The combined organic extracts are dried (Na₂SO₄), filtered, and evaporated in vacuo to give a yellow/brown oil. Purification by silica gel column chromatography (gradient from 50% EtOAc/hexane to 80% EtOAc/hexane) affords the title compound as a clear, viscous oil which slowly solidifies on standing.

Step 4. Ethyl 3-methoxy-1-pyrimidin-2-yl-1H-pyrazole-4-carboxylate

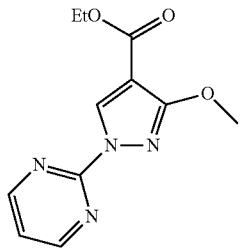 [SMILES: CCOC(=O)c1cn(-c2ncccn2)nc1OC]

Sodium hydride (60% in mineral oil, 528 mg, 13.2 mmol) is added portion wise to a solution of ethyl 3-methoxy-1H-pyrazole-4-carboxylate (1.5 g, 8.81 mmol) in 40 mL of THF at RT. Evolution of H₂ (g) is observed. After about 5-10 min, 2-chloropyrimidine (1.0 g, 8.81 mmol) is added, and the resulting reaction mixture is stirred at reflux for 15 h. After cooling to RT, the reaction is quenched with 10 mL of sat. NH₄Cl and 10 mL of water and extracted with CH₂Cl₂ (2×40 mL). The combined organic extracts are dried (Na₂SO₄), filtered, and evaporated in vacuo to give a brown solid. Purification by silica gel column chromatography (gradient from 50% EtOAc/hexane to EtOAc) affords the title compound as a fluffy white solid.

Step 5. 3-Methoxy-1-pyrimidin-2-yl-1H-pyrazole-4-carboxylic acid

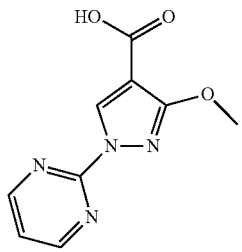 [SMILES: COc1nn(-c2ncccn2)cc1C(=O)O]

A 1 N aqueous sodium hydroxide solution (10 mL) is added to a slurry of ethyl 3-methoxy-1-pyrimidin-2-yl-1H-pyrazole-4-carboxylate (1.1 mg, 4.43 mmol) in 30 mL of EtOH. The reaction mixture becomes homogeneous and is stirred for 2 h at RT. Water (2-3 mL) is added, and the solution is cooled to 0° C. and acidified to pH=2-3 with conc. HCl. Most of the EtOH is removed in vacuo, and the resultant mixture is filtered. The collected solid is dried in vacuo to give the title compound as a white solid.

Step 6. N-(Adamantan-1-ylmethyl)-3-methoxy-1-pyrimidin-2-yl-1H-pyrazole-4-carboxamide

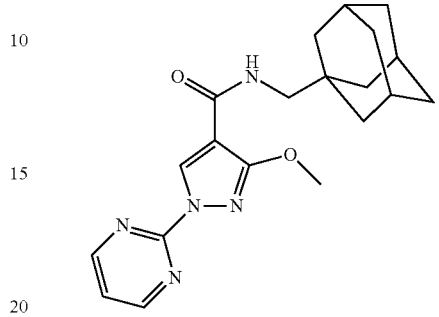

To a mixture of 3-methoxy-1-pyrimidin-2-yl-1H-pyrazole-4-carboxylic acid (40 mg, 0.18 mmol) in 1.0 mL of DMF is added sequentially DIEA (0.063 mL, 0.36 mmol), 1-adamantan-1-ylmethan-amine (30 mg, 0.18 mmol) and BOP (97 mg, 0.22 mmol). The resulting mixture is stirred at RT for 18 h. Water (3 mL) is added, and the mixture is extracted with EtOAc (5 mL). The EtOAc layer is dried (Na₂SO₄), filtered, and evaporated in vacuo to give a brown solid. Purification by column chromatography (gradient from 80% EtOAc/Hex to EtOAc) affords the title compound as a pale brown solid. ¹H NMR (400 MHz, CDCl₃) δ 9.02 (1H, s), 8.74 (2H, d, J 4.8), 7.19 (1H, t, J 4.8), 6.88 (1H, bs), 4.24 (3H, s), 3.12 (2H, d, J 6.4), 2.00 (3H, bs), 1.60 (12H, m). MS (M+1)=368.07; R$_T$=1.65 min. *IC$_{50}$.

F. N-(Adamantan-1-ylmethyl)-3-amino-1-pyrimidin-2-yl-1H-pyrazole-4-carboxamide (Compound 6)

Step 1. Ethyl 3-amino-1-pyrimidin-2-yl-1H-pyrazole-4-carboxylate

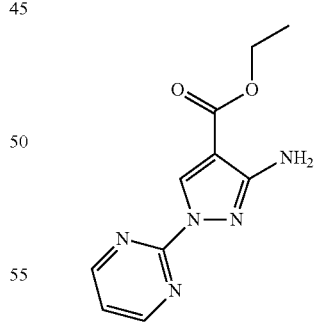

Potassium tert-butoxide (2.4 g, 21.23 mmol) is added to a mixture of ethyl 3-amino-1H-pyrazole-4-carboxylate (3.0 g, 19.3 mmol) and 2-chloropyrimidine (2.2 g, 19.3 mmol) in 50 mL of anhydrous dioxane. The reaction mixture is heated to 100° C. and stirred for 2 h. The solvent is removed in vacuo, and the residue is partitioned between EtOAc and water (50 mL each). The aqueous layer is extracted two more times with EtOAc (40 mL each), and the combined organic extracts are dried (Na₂SO₄), filtered, and evaporated in vacuo to give a yellow/brown oily solid. This crude product is triturated with EtOAc to give the title compound as a white solid.

Step 2.
3-Amino-1-pyrimidin-2-yl-1H-pyrazole-4-carboxylic acid

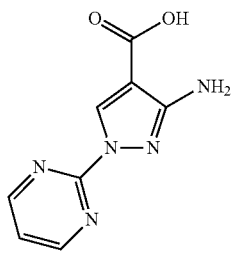 [SMILES: Nc1nn(-c2ncccn2)cc1C(=O)O]

A 1 N aqueous sodium hydroxide solution (3.0 mL) is added to a suspension of ethyl 3-amino-1-pyrimidin-2-yl-1H-pyrazole-4-carboxylate (500 mg, 2.14 mmol) in 6.0 mL of EtOH. The reaction mixture is heated to 50° C. for 16 h. After cooling to RT, water is added, and the mixture is extracted with EtOAc (3×20 mL). The aqueous layer is cooled to 0° C. and acidified to pH=2 with conc. HCl. The precipitated solid is collected by vacuum filtration and dried in vacuo to give the title compound as an off-white solid.

Step 3. N-(Adamantan-1-ylmethyl)-3-amino-1-pyrimidin-2-yl-1H-pyrazole-4-carboxamide

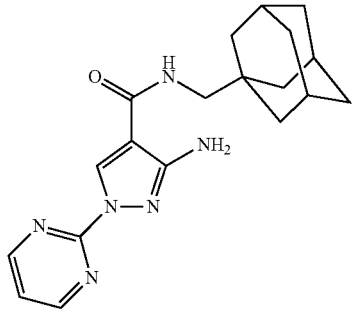 [SMILES: Nc1nn(-c2ncccn2)cc1C(=O)NCC12CC3CC(CC(C3)C1)C2]

To a mixture of 3-amino-1-pyrimidin-2-yl-1H-pyrazole-4-carboxylic acid (50 mg, 0.24 mmol) in 1.0 mL of DMF is added sequentially DIEA (0.08 mL, 0.48 mmol), 1-adamantan-1-ylmethan-amine (40 mg, 0.24 mmol), and BOP (128 mg, 0.29 mmol). The resulting mixture is stirred at RT for 18 h. Water (3 mL) is added, and the mixture is filtered. The solid is washed well with water and dried in vacuo to give the title compound as an off-white solid. $^1$H NMR (400 MHz, DMSO-$d_6$) δ 9.22 (1H, s), 8.75 (2H, s), 8.07 (1H, s), 7.33 (1H, s), 5.85 (2H, s), 2.90 (2H, d, J 5.2), 1.91 (3H, s), 1.61 (6H, m), 1.46 (6H, s). MS (M+1)=353.23; $R_T$=1.31 min *$IC_{50}$.

G. N-(Adamantan-1-ylmethyl)-3-chloro-1-pyrimidin-2-yl-1H-pyrazole-4-carboxamide (Compound 7)

Step 1. Ethyl 3-chloro-1-pyrimidin-2-yl-1H-pyrazole-4-carboxylate and ethyl 5-chloro-1-pyrimidin-2-yl-1H-pyrazole-4-carboxylate

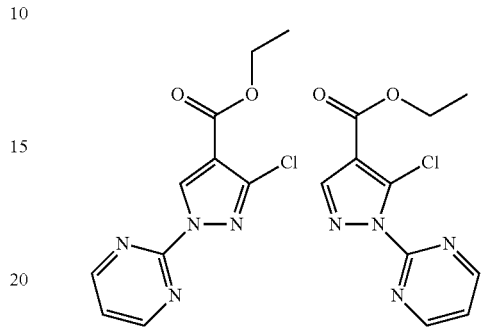

A solution of sodium nitrite (1.0 g, 15.1 mmol) in 5.0 mL of water is added dropwise to a solution of ethyl 3-amino-1-pyrimidin-2-yl-1H-pyrazole-4-carboxylate (2.7 g, 11.6 mmol) in 18 mL of conc. HCl at −5° C. with stirring. After 1 h at 0° C., the reaction mixture is added dropwise to a suspension of copper (I) chloride (1.8 g, 18.6 mmol) in 18 mL of CHCl$_3$ at RT. After 1 h at RT, water (40 mL) and CHCl$_3$ (40 mL) are added, and the layers are separated. The organic layer is washed once more with water (40 mL), dried (Na$_2$SO$_4$), filtered, and evaporated in vacuo to give a greenish/yellow solid. TLC analysis (70% EtOAc/CH$_2$Cl$_2$) of this crude solid reveals 2 products, which are separated by column chromatography (10% EtOAc/CH$_2$Cl$_2$) to afford ethyl 3-chloro-1-pyrimidin-2-yl-1H-pyrazole-4-carboxylate ($R_f$≈0.7) as a white solid. The minor, more polar compound ethyl 5-chloro-1-pyrimidin-2-yl-1H-pyrazole-4-carboxylate, $R_f$≈0.5) is also isolated as a white solid.

Step 2. 3-Chloro-1-pyrimidin-2-yl-1H-pyrazole-4-carboxylic acid

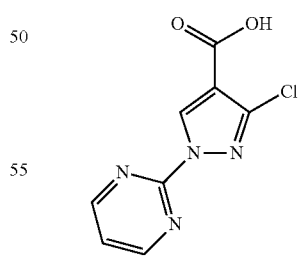

A 1 N aqueous sodium hydroxide solution (5.0 mL) is added to a suspension of ethyl 3-chloro-1-pyrimidin-2-yl-1H-pyrazole-4-carboxylate (850 mg, 3.36 mmol) in 10.0 mL of EtOH. The reaction mixture is stirred at RT for 1 h. Most of the EtOH is removed in vacuo, and the aqueous solution is diluted with water, extracted with EtOAc (3×), cooled to 0° C., and acidified to pH=2-3 with conc. HCl. The precipitated solid is collected by vacuum filtration and dried in vacuo to give the title compound as a white solid.

Step 3. N-(Adamantan-1-ylmethyl)-3-chloro-1-pyrimidin-2-yl-1H-pyrazole-4-carboxamide

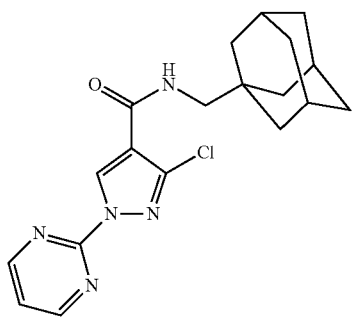 [SMILES: O=C(NCC12CC3CC(CC(C3)C1)C2)c1cn(-c2ncccn2)nc1Cl]

To a mixture of 3-chloro-1-pyrimidin-2-yl-1H-pyrazole-4-carboxylic acid (50 mg, 0.22 mmol) in 1.0 mL of DMF is added sequentially DIEA (0.08 mL, 0.44 mmol), 1-adamantan-1-ylmethan-amine (36 mg, 0.22 mmol), and BOP (115 mg, 0.26 mmol) The resulting mixture is stirred at RT for 20 h. Water (3 mL) is added, and the mixture is extracted with $CH_2Cl_2$ (5 mL). The $CH_2Cl_2$ layer is dried ($Na_2SO_4$), filtered, and evaporated in vacuo. The residue is purified by silica gel column chromatography (gradient from 30% EtOAc/hexane to 60% EtOAc/hexane) to give the title compound as a white solid. $^1$H NMR (400 MHz, DMSO-$d_6$) δ 9.31 (1H, s), 8.91 (2H, d, J 4.8), 8.18 (1H, bs), 7.56 (1H, t, J 4.8), 2.92 (2H, d, J 5.6), 1.92 (3H, s), 1.60 (6H, m), 1.47 (6H, s). MS (M+1)=372.18; $R_T$=1.35 min. *$IC_{50}$.

H. N-(Adamantan-1-ylmethyl)-5-chloro-1-pyridimin-2-yl-1H-pyrazole-4-carboxamide (Compound 8)

Step 1. 5-Chloro-1-pyrimidin-2-yl-1H-pyrazole-4-carboxylic acid

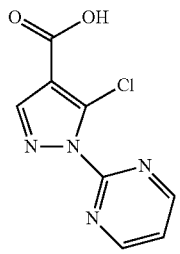 [SMILES: O=C(O)c1cnn(-c2ncccn2)c1Cl]

A 1 N aqueous sodium hydroxide solution (2.0 mL) is added to a suspension of ethyl 5-chloro-1-pyrimidin-2-yl-1H-pyrazole-4-carboxylate (250 mg, 1.11 mmol) in 5.0 mL of EtOH. The reaction mixture is stirred at RT for 1 h. Water is added, and the solution is washed with EtOAc. The aqueous layer is cooled to 0° C. and acidified to pH=2-3 with conc. HCl. The precipitated solid is collected by vacuum filtration and dried in vacuo to give the title compound as a white solid.

Step 2. N-(Adamantan-1-ylmethyl)-5-chloro-1-pyrimidin-2-yl-1H-pyrazole-4-carboxamide

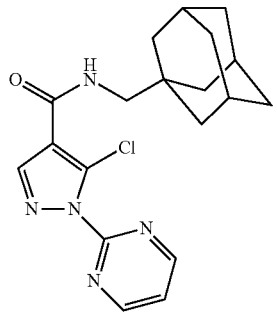 [SMILES: O=C(NCC12CC3CC(CC(C3)C1)C2)c1cnn(-c2ncccn2)c1Cl]

To a mixture of 5-chloro-1-pyrimidin-2-yl-1H-pyrazole-4-carboxylic acid (50 mg, 0.22 mmol) in 1.0 mL of DMF is added sequentially DIEA (0.08 mL, 0.44 mmol), 1-adamantan-1-ylmethan-amine (36 mg, 0.22 mmol), and BOP (115 mg, 0.26 mmol). The resulting mixture is stirred at RT for 18 h. Water (3 mL) is added, and the mixture is extracted with EtOAc (5 mL). The EtOAc layer is dried ($Na_2SO_4$), filtered, and evaporated in vacuo to give a reddish/brown oil. Purification by silica gel column chromatography (gradient from 90% EtOAc/hexane to EtOAc) affords the title compound as a light reddish/brown solid. $^1$H NMR (400 MHz, $CDCl_3$) δ 8.89 (2H, d, J 4.8), 8.28 (1H, s), 7.41 (1H, t, J 4.8), 6.47 (1H, bs), 3.18 (2H, d, J 6), 2.01 (3H, s), 1.69 (6H, m), 1.58 (6H, s). MS (M+1)=372.19; $R_T$=1.31 min. *$IC_{50}$.

I. 3-Chloro-N-{4-methyl-2-[4-(trifluoromethyl)phenyl]pentyl}-1-pyrimidin-2-yl-1H-pyrazole-4-carboxamide (Compound 9)

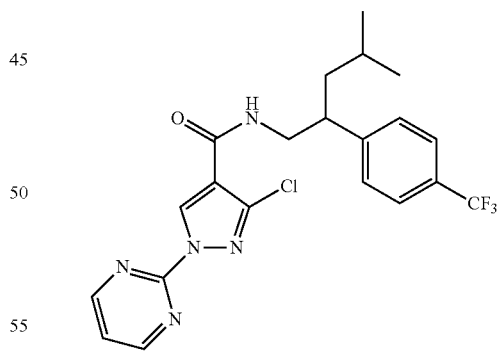

To a mixture of 3-chloro-1-pyrimidin-2-yl-1H-pyrazole-4-carboxylic acid (50 mg, 0.22 mmol) in 1.0 mL of DMF is added sequentially DIEA (0.08 mL, 0.44 mmol), 4-methyl-2-[4-(trifluoro-methyl)phenyl]pentan-1-amine (54 mg, 0.22 mmol), and BOP (115 mg, 0.26 mmol). The resulting mixture is stirred at RT for 20 h. Water (3 mL) is added, and the mixture is extracted with $CH_2Cl_2$ (5 mL). The $CH_2Cl_2$ layer is dried ($Na_2SO_4$), filtered, and evaporated in vacuo. The residue is purified by silica gel column chromatography (gradient from 20% EtOAc/Hex to 60% EtOAc/Hex) to give the title compound as a white solid. ¹H NMR (400 MHz, DMSO-d₆) δ 9.14 (1H, s), 8.89 (2H, d, J 4.8), 8.33 (1H, bs), 7.64 (2H, d, J 8), 7.55 (1H, t, J 4.8), 7.46 (2H, d, J 7.6), 3.44 (1H, m), 3.33 (1H, m), 3.07 (1H, m), 1.57 (1H, m), 1.51 (1H, m), 1.26 (1H, m), 0.81 (6H, d, J 6.4). MS (M+1)=452.14; R$_T$=1.36 min. *IC$_{50}$.

J. 3-Chloro-1-pyrimidin-2-yl-N-({1-[4-(trifluoromethyl)phenyl]cyclohexyl}methyl)-1H-pyrazole-4-carboxamide (Compound 10)

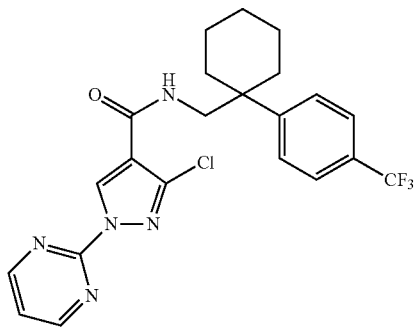 [SMILES: O=C(NCC1(c2ccc(C(F)(F)F)cc2)CCCCC1)c1cn(-c2ncccn2)nc1Cl]

To a mixture of 3-chloro-1-pyrimidin-2-yl-1H-pyrazole-4-carboxylic acid (50 mg, 0.22 mmol) in 1.0 mL of DMF is added sequentially DIEA (0.08 mL, 0.44 mmol), 1-{1-[4-(trifluoromethyl)-phenyl]cyclohexyl}methanamine (57 mg, 0.22 mmol), and BOP (115 mg, 0.26 mmol). The resulting mixture is stirred at RT for 20 h. Water (3 mL) is added, and the mixture is filtered. The solid is washed well with water and dried in vacuo to give the title compound as a white solid. ¹H NMR (400 MHz, CDCl₃) δ 9.09 (1H, s), 8.78 (2H, d, J 4.8), 7.65 (2H, d, J 8.4), 7.55 (2H, d, J 8.4), 7.31 (1H, t, J 4.8), 6.27 (1H, bs), 3.63 (2H, d, J 6), 2.17 (2H, m), 1.77 (2H, m), 1.66 (2H, m), 1.42 (4H, m). MS (M+1)=464.14; R$_T$=1.37 min. *IC$_{50}$.

K. 3-Chloro-N-[(1-pyridin-3-ylcyclohexyl)methyl]-1-pyrimidin-2-yl-1H-pyrazole-4-carboxamide (Compound 11)

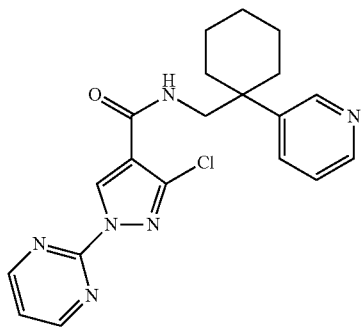 [SMILES: O=C(NCC1(c2cccnc2)CCCCC1)c1cn(-c2ncccn2)nc1Cl]

To a mixture of 3-chloro-1-pyrimidin-2-yl-1H-pyrazole-4-carboxylic acid (75 mg, 0.33 mmol) in 1.0 mL of DMF is added sequentially DIEA (0.11 mL, 0.66 mmol), 1-(1-pyridin-3-ylcyclohexyl)-methanamine (63 mg, 0.33 mmol), and BOP (177 mg, 0.40 mmol). The resulting mixture is stirred at RT for 20 h. Water (3 mL) is added, and the mixture is extracted with EtOAc (5 mL). The EtOAc layer is dried (Na₂SO₄), filtered, and evaporated in vacuo. The residue is purified by preparative chromatography (5% MeOH/CH₂Cl₂) to give the title compound as a white solid. ¹H NMR (400 MHz, DMSO-d₆) δ 9.17 (1H, s), 8.90 (2H, d, J 4.8), 8.58 (1H, s), 8.37 (1H, d, J 3.6), 8.05 (1H, s), 7.76 (1H, d, J 8.4), 7.56 (1H, t, J 4.8), 7.31 (1H, m), 2.16 (2H, m), 1.60 (4H, m), 1.43 (1H, m), 1.21 (5H, m). MS (M+1)=397.16; R$_T$=1.07 min. *IC$_{50}$.

L. 3-Chloro-N-{[1-(6-methylpyridin-3-yl)cyclohexyl]methyl}-1-pyrimidin-2-yl-1H-pyrazole-4-carboxamide (Compound 12)

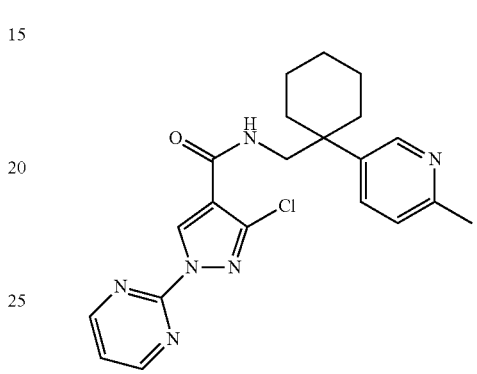

To a mixture of 3-chloro-1-pyrimidin-2-yl-1H-pyrazole-4-carboxylic acid (75 mg, 0.33 mmol) in 1.0 mL of DMF is added sequentially DIEA (0.11 mL, 0.66 mmol), 1-[1-(6-methylpyridin-3-yl)-cyclohexyl]methanamine (67 mg, 0.33 mmol), and BOP (177 mg, 0.40 mmol). The resulting mixture is stirred at RT for 20 h. Water (3 mL) is added, and the mixture is extracted with EtOAc (5 mL). The EtOAc layer is dried (Na₂SO₄), filtered, and evaporated in vacuo. The residue is purified by preparative chromatography (2% MeOH/CH₂Cl₂) to give the title compound as a white solid. ¹H NMR (400 MHz, DMSO-d₆) δ 9.18 (1H, s), 8.90 (2H, d, J 4), 8.43 (1H, s), 8.03 (1H, s), 7.64 (1H, d, J 8), 7.56 (1H, s), 7.18 (1H, d, J 7.6), 2.41 (3H, s), 2.13 (2H, m), 1.56 (5H, m), 1.22 (5H, m). MS (M+1)=411.18; R$_T$=1.08 min. *IC$_{50}$.

M. 3-Chloro-N-(4-methyl-ylpentyl)-1-pyrimidin-2-yl-1H-pyrazole-4-carboxamide (Compound 13)

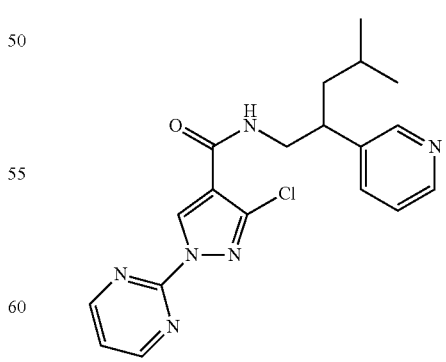

To a mixture of 3-chloro-1-pyrimidin-2-yl-1H-pyrazole-4-carboxylic acid (75 mg, 0.33 mmol) in 1.0 mL of DMF is added sequentially DIEA (0.11 mL, 0.66 mmol), 4-methyl-2-pyridin-3-yl-pentan-1-amine (59 mg, 0.33 mmol), and BOP (177 mg, 0.40 mmol). The resulting mixture is stirred at RT for 20 h. Water (3 mL) is added, and the mixture is extracted with EtOAc (5 mL). The EtOAc layer is dried (Na$_2$SO$_4$), filtered, and evaporated in vacuo. The residue is purified by preparative chromatography (2% MeOH/CH$_2$Cl$_2$) to give the title compound as a white solid. $^1$H NMR (400 MHz, DMSO-d$_6$) δ 9.13 (1H, s), 8.89 (2H, d, J 4.8), 8.39 (3H, m), 7.67 (1H, d, J 7.6), 7.55 (1H, t, J 4.4), 7.32 (1H, m), 3.43 (1H, m), 3.32 (1H, m), 2.99 (1H, bs), 1.58 (1H, m), 1.50 (1H, m), 1.25 (1H, m), 0.81 (6H, d, J 6). MS (M+1)=385.09; R$_T$=1.25 min.

N. 1-Imidazo[1,2-a]pyrazin-8-yl-3-trifluoromethyl-1H-pyrazole-4-carboxylic acid (1-pyridin-3-yl-cyclohexylmethyl)-amide (Compound 14)

Step 1. 8-Chloro-imidazol[1,2-a]pyrazine

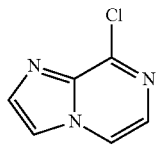

HBr (48% in H$_2$O) is added to a solution of 2-amino-3-chloropyrazine (1.2 g, 9.26 mmol) and BrCH$_2$CH(OEt)$_2$ (1.6 mL, 10 mmol) in MeOH and H$_2$O (5 mL and 10 mL) at RT. The mixture is stirred for 24 h at RT and then heated to 40° C. for 48 h. The pH is adjusted to 7 with sat. Na$_2$CO$_3$. The mixture is extracted with CH$_2$Cl$_2$. The organic phase is dried over anhydrous Na$_2$SO$_4$. The product is purified by silica gel column chromatography (4% MeOH in CH$_2$Cl$_2$) to give the title compound as an off white solid.

Step 2. 1-Imidazo[1,2-a]pyrazin-8-yl-3-trifluoromethyl-1H-pyrazole-4-carboxylic acid (1-pyridin-3-yl-cyclohexylmethyl)-amide

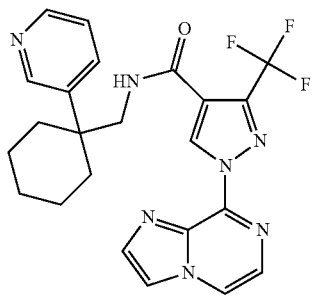 [SMILES: O=C(NCC1(c2cccnc2)CCCCC1)c1cn(-c2nccn3ccnc23)nc1C(F)(F)F]

Cs$_2$CO$_3$ is added to a solution of 8-chloro-imidazol[1,2-a]pyrazine (23 mg, 0.15 mmol) and 3-trifluoromethyl-1H-pyrazole-4-carboxylic acid (1-pyridin-3-yl-cyclohexymethyl)-amide (40 mg, 0.11 mmol) in NMP. The mixture is heated in a microwave reactor at 160° C. for 3 h. The mixture is poured into H$_2$O. The crude product is filtered out, dissolved in 10% MeOH in CH$_2$Cl$_2$, and dried over anhydrous Na$_2$SO$_4$. The crude material is purified by PTLC (eluted with 4% MeOH in DCM) to afford the title compound. $^1$H NMR (CD$_3$OD): 9.6 (s, 1H), 8.6 (m, 2H), 8.39-8.28 (m, 1H), 8.24 (s, 1H), 7.97-7.84 (m, 2H), 7.80-7.75 (m, 2H), 3.52 (s, 2H), 2.34-2.31 (m, 2H), 1.79-1.28 (m, 8H). MS (M+1)=470.11; R$_T$=1.09 min. *IC$_{50}$.

O. 1-Imidazo[1,2-A]pyrazin-8-yl-3-trifluoromethyl-1H-pyrazole-4-carboxylic acid (1-pyridin-3-yl-cyclohexylmethyl)-amide (Compound 15)

Step 1. 1-Pyrimidin-2-yl-3-trifluoromethyl-1H-pyrazol-4-carbonyl azide

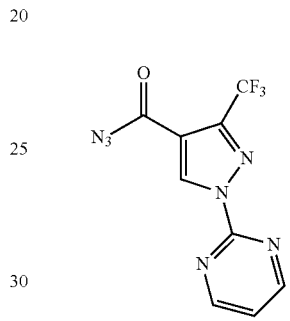

ClCOOMe (0.19 mL, 2.4 mmol) is added dropwise to a solution of acid (545 mg, 2.1 mmol) in acetone at −10° C. The mixture is stirred for 1 h. A solution of NaN$_3$ in H$_2$O is added to the mixture and warmed to RT and stirred for 2 h. The solvent is removed to dryness. H$_2$O is added and the solid is filtered out and washed with H$_2$O, and then dried to give crude product, which is used without purification in the next step.

Step 2. 1-Pyrimidin-2-yl-3-trifluoromethyl-1H-pyrazol-4-ylamine

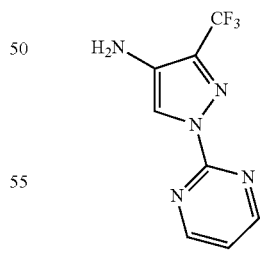

A solution of 1-pyrimidin-2-yl-3-trifluoromethyl-1H-pyrazole-4-carbonyl azide (564 mg, 1.99 mmol) in toluene (5 mL) is heated to 100° C. for 1 h. Conc. HCl is added and heated to 110° C. for 3 h. The mixture is cooled to RT. TEA (1.2 mL) and CH$_2$Cl$_2$ (10 mL) is added to the mixture. The organic phase is washed with brine and dried. The crude material is purified by PTLC (eluted with 2% MeOH in CH$_2$Cl$_2$) to afford the title compound.

Step 3. 2-Adamantan-1-yl-N-(1-pyrimidin-2-yl-3-trifluoromethyl-1H-pyrazol-4-yl)-acetamide

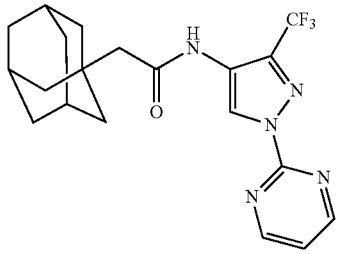 [SMILES: O=C(CC12CC3CC(CC(C3)C1)C2)Nc1cn(-c2ncccn2)nc1C(F)(F)F]

BOP (35 mg, 0.08 mmol) is added to a solution of 1-pyrimidin-2-yl-3-trifluoromethyl-1H-pyrazol-4-ylamine (15 mg, 0.065 mmol), HOBt (5 mg), 1-adamantaneacetic acid (16 mg, 0.08 mmol) and DIEA (17 μL, 0.1 mmol) in DMF (0.5 mL) at RT. The mixture is stirred for 6 h. $H_2O$ is added to the mixture and is extracted with EtOAc (3×10 mL). The organic phase is dried. The crude material is purified by PTLC using 4% MeOH in $CH_2Cl_2$ to afford the title compound. $^1$H NMR ($CDCl_3$): 9.38 (s, 1H), 8.6-81 (m, 2H), 7.30 (m, 1H), 2.16 (s, 2H), 2.01-1.97 (m, 3H), 1.80-1.50 (m, 12H). MS (M+1)=406.11; $R_T$=1.4 min. *$IC_{50}$.

P. 5-Benzyl-1,3-dimethyl-1H-pyrazole-4-carboxylic acid (adamantan-1-ylmethyl)-amide (Compound 16)

Step 1. 2-Acetyl-3-oxo-4-phenyl-butyric acid methyl ester

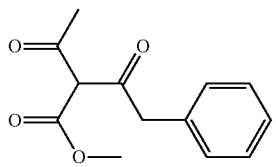 [SMILES: COC(=O)C(C(C)=O)C(=O)Cc1ccccc1]

NaOH (10 N, 4.4 mL, 44 mmol) in $H_2O$ is added to a solution of MeCOCH$_2$COOMe (5 g, 43.1 mmol) in THF at RT. PhCH$_2$COCl is added dropwise to the mixture and the mixture is stirred for 14 h. The mixture is extracted with EtOAc (2×30 mL). The organic phase is dried. The product is purified by silica gel column chromatography using 3-5% EtOAc in hexane to afford the title compound.

Step 2. 5-Benzyl-1,3-dimethyl-1H-pyrazole-4-carboxylic acid methyl ester and 3-Benzyl-1,5-dimethyl-1H-pyrazole-4-carboxylic acid methyl ester

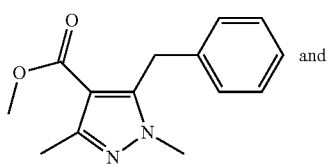

and

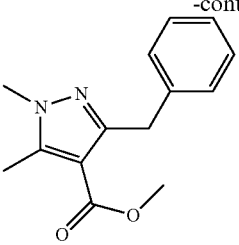

MeNHNH$_2$ (0.42 mL. 7.9 mmol) is added to a solution of 2-acetyl-3-oxo-4-phenyl-butyric acid methyl ester (1.84 g, 7.85 mmol) in EtOH (15 mL) at RT. The mixture is stirred for 14 h at RT. The solvent is removed and crude material is purified by column chromatography using 10-25% EtOAc in hexane to afford 5-benzyl-1,3-dimethyl-1H-pyrazole-4-carboxylic acid methyl ester (less polar) and 3-benzyl-1,5-dimethyl-1H-pyrazole-4-carboxylic acid methyl ester (more polar).

Step 3. 5-Benzyl-1,3-dimethyl-1H-pyrazole-4-carboxylic acid

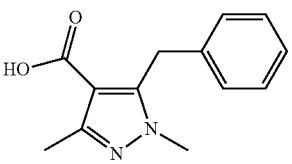 [SMILES: Cc1nn(C)c(Cc2ccccc2)c1C(=O)O]

NaOH (10 N, 7 mL) is added to a solution of 5-benzyl-1,3-dimethyl-1H-pyrazole-4-carboxylic acid methyl ester (680 mg, 2.78 mmol) in MeOH (10 mL) at RT. The mixture is heated to 50° C. for 4 h. The solvent is removed to dryness. $H_2O$ is added and pH is adjusted to 5 using aq. HCl. The solid is filtered and dried to give the title compound.

Step 4. 5-Benzyl-1,3-dimethyl-1H-pyrazole-4-carboxylic acid (adamantan-1-ylmethyl)-amide

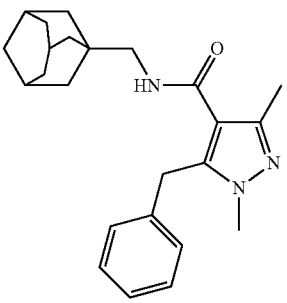 [SMILES: Cc1nn(C)c(Cc2ccccc2)c1C(=O)NCC12CC3CC(CC(C3)C1)C2]

BOP (44 mg, 0.1 mmol) is added to a solution of 5-benzyl-1,3-dimethyl-1H pyrazole-4-carboxylic acid (20 mg, 0.087 mmol), admantan-1-yl-methylamine (15 mg, 0.09 mmol), HOBt (5 mg) and DIEA (17 μL, 0.1 mmol) in DMF (0.5 mL) at it. The mixture is stirred for 14 h. $H_2O$ is added, and the mixture is extracted with EtOAc (3×10 mL). The organic phase is dried. The title compound is obtained by PTLC using 20% EtOAc in hexane. $^1$H NMR ($CDCl_3$): 7.29-7.21 (m, 3H), 7.12-7.11 (m, 2H), 5.39 (m, 1H), 4.33 (s, 2H), 3.65 (s, 3H), 3.07 (m, 2H), 2.46 (s, 3H), 1.94 (m, 3H), 1.70-1.56 (m, 12H). MS (M+1)=378.22; $R_T$=1.67 min. *$IC_{50}$.

Q. N-(Adamantan-1-ylmethyl)-1-benzyl-1H-pyrazole-5-carboxamide and N-(adamantan-1-ylmethyl)-1-benzyl-1H-pyrazole-3-carboxamide (Compounds 17 and 18)

Step 1. N-(1-adamantylmethyl)-1H-pyrazole-3-carboxamide

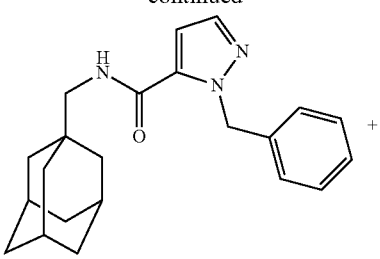

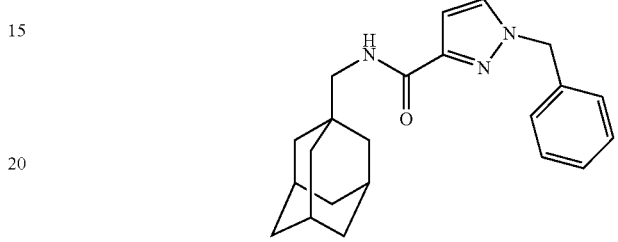

To a solution of 1H-pyrazole-3-carboxylic acid (594 mg, 5.3 mmol) in 20 mL ACN is added 2.3 mL of DIEA (13.25 mmol), followed by 1.28 g of adamantylmethylamine hydrochloride salt (6.36 mmol). The resulting mixture is stirred for 5 min at RT. 2.81 g of BOP (6.36 mmol) is added. The reaction mixture is stirred for 30 min at RT. The mixture is diluted with EtOAc and water. The organic layer is separated, and the aqueous layer is back extracted with EtOAc. The combined organic layers are washed with brine, dried over sodium sulfate and concentrated. The residue is triturated with DCM and air-dried to give the title compound.

Step 2. N-(adamantan-1-ylmethyl)-1-benzyl-1H-pyrazole-5-carboxamide and N-(adamantan-1-ylmethyl)-1-benzyl-1H-pyrazole-3-carboxamide

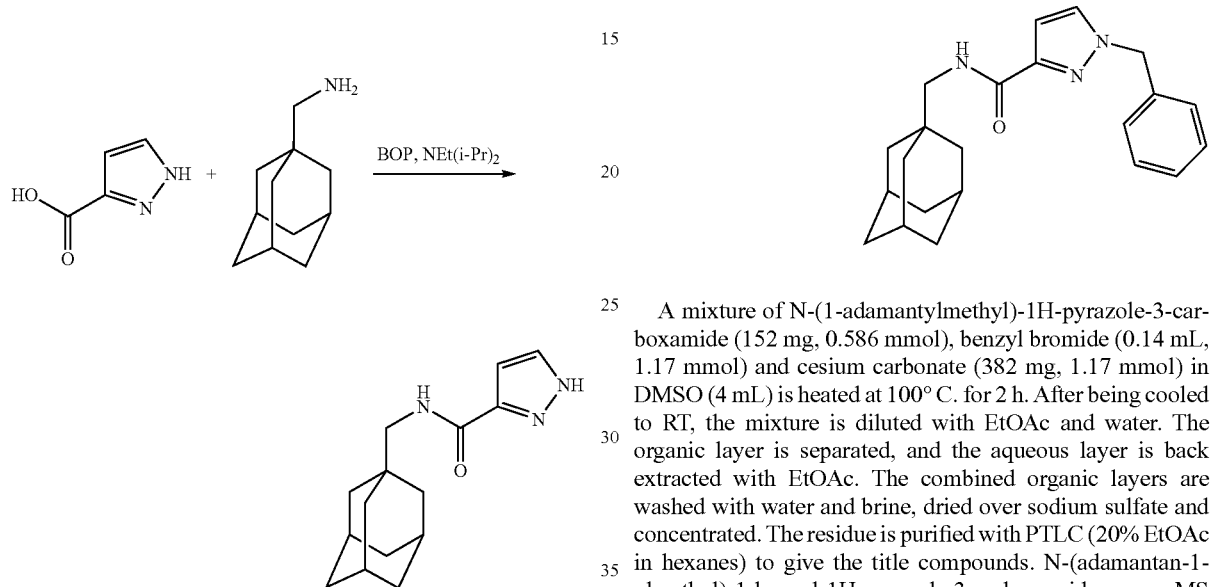

A mixture of N-(1-adamantylmethyl)-1H-pyrazole-3-carboxamide (152 mg, 0.586 mmol), benzyl bromide (0.14 mL, 1.17 mmol) and cesium carbonate (382 mg, 1.17 mmol) in DMSO (4 mL) is heated at 100° C. for 2 h. After being cooled to RT, the mixture is diluted with EtOAc and water. The organic layer is separated, and the aqueous layer is back extracted with EtOAc. The combined organic layers are washed with water and brine, dried over sodium sulfate and concentrated. The residue is purified with PTLC (20% EtOAc in hexanes) to give the title compounds. N-(adamantan-1-ylmethyl)-1-benzyl-1H-pyrazole-3-carboxamide: MS (M+1)=350.26; $R_T$=1.4 min. $^1$H-NMR (δ, ppm, CDCl$_3$ as internal standard): 7.51 (d, J=1.8 Hz, 1H), 7.38-7.21 (m, 5H), 6.51 (d, J=2.1 Hz, 1H), 5.94 (m, br, 1H), 5.77 (s, 2H), 3.05 (d, J=6.6 Hz, 2H), 1.96 (m, 3H), 1.72-1.57 (m, 6H), 1.44 (m, 6H). N-(adamantan-1-ylmethyl)-1-benzyl-1H-pyrazole-5-carboxamide: MS (M+1)=350.26; $R_T$=1.39 min. $^1$H-NMR (δ, ppm, CDCl$_3$ as internal standard): 7.40-7.31 (m, 4H), 7.22-7.19 (m, 2H), 6.96 (m, br, 1H), 6.82 (d, J=2.7 Hz, 1H), 5.32 (s, 2H), 3.11 (d, J=6.9 Hz, 2H), 1.99 (m, 3H), 1.73-1.56 (m, 12H). *$IC_{50}$ (for N-(adamantan-1-ylmethyl)-1-benzyl-1H-pyrazole-5-carboxamide).

R. 1-Methyl-3-phenyl-N-[(1-pyridin-3-ylcyclohexyl)methyl]-1H-pyrazole-5-carboxamide (Compound 19)

Step 1. 2-Methyl-5-phenyl-2H-pyrazole-3-carboxylic acid

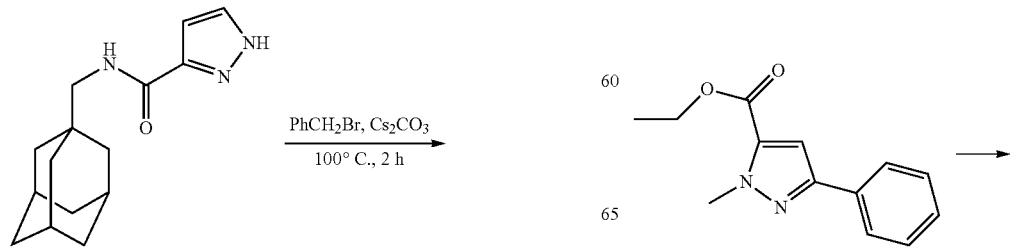

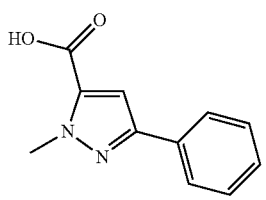

To a solution of 2-methyl-5-phenyl-2H-pyrazole-3-carboxylic acid ethyl ester (2.3 g, 10 mmol) in MeOH (30 mL) is added 1 N NaOH (12 mL) in one portion at RT. The mixture is stirred at RT for 1 h. Most of the MeOH is removed with a rotary evaporator, and the remaining aqueous solution is diluted with water (12 mL) and neutralized with 1 N HCl to pH=5. The precipitate is collected by filtration, washed with water and dried to give the title compound. $^1$H NMR (CDCl): 7.26-7.82 (m, 6H), 4.26 (s, 3H); LC/MS (M+1)=203.29; $R_T$=1.54 min Step 2. 1-Methyl-3-phenyl-N-[(1-pyridin-3-ylcyclohexyl)methyl]-1H-pyrazole-5-carboxamide

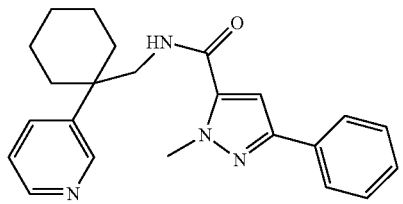 [SMILES: Cn1nc(-c2ccccc2)cc1C(=O)NCC1(c2cccnc2)CCCCC1]

A solution of DMC in DCM (1.2 mL, 0.1 M, 1.2 eq.) is added to a solution of 2-methyl-5-phenyl-2H-pyrazole-3-carboxylic acid (20 mg, 0.1 mmol, 1.0 equ.), (1-pyridin-3-ylcyclohexyl)-methylamine (19 mg, 0.1 mmol, 1.0 eq.) and TEA (33 µL, 0.24 mmol, 2. 4 eq.) in DCM (1.0 mL) at RT. After standing overnight at RT, the reaction mixture is purified by PTLC (EtOAc/Hexanes/TEA 50/50/1) to give the title compound. LC/MS (M+1)=375.16; $R_T$=1.38 min. *IC$_{50}$.

S. 1-Methyl-3-phenyl-N-{[1-(methylpyridin-3-yl)cyclohexyl]methyl}-1H-pyrazole-5-carboxamide (Compound 20)

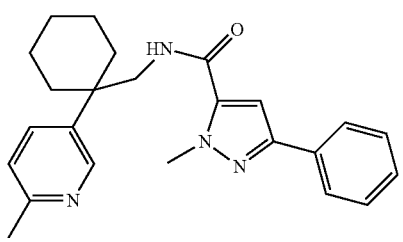 [SMILES: Cc1ccc(C2(CNC(=O)c3cc(-c4ccccc4)nn3C)CCCCC2)cn1]

This compound is prepared essentially as described in Example 1R, with readily apparent modification of starting material. LC/MS: (M+1)=389.18; $R_T$=1.37 min *IC$_{50}$.

T. 1-Methyl-3-phenyl-N-[1-(4-chlorophenyl)cyclohexyl]methyl-1H-pyrazole-5-carboxamide (Compound 21)

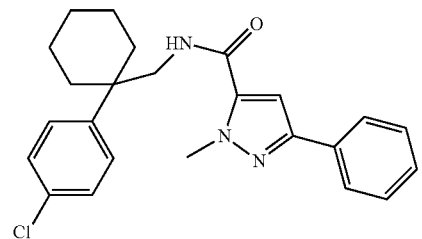 [SMILES: Cn1nc(-c2ccccc2)cc1C(=O)NCC1(c2ccc(Cl)cc2)CCCCC1]

This compound is prepared essentially as described in Example 1R, with readily apparent modification of starting material, and with PTLC using EtOAc/TEA 100:1. LC/MS (M+1)=408.13; $R_T$=1.75 min. *IC$_{50}$.

Example 2

Synthesis of Additional Representative 5-Membered Heterocyclic Amides and Related Compounds This Example illustrates the synthesis of additional representative 5-membered heterocyclic amides and related compounds provided herein, as well as certain intermediates useful in the preparation of such compounds.

A. 2-pyrimidin-2-yl-4-trifluoromethyl-thiazole-5-carboxylic acid ethyl ester

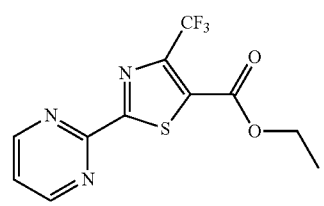 [SMILES: CCOC(=O)c1sc(-c2ncccn2)nc1C(F)(F)F]

Method A

Step 1. 2-Pyrimidinecarbothioamide

A mixture of 2-cyanopyrimidine (15 g) and thioacetamide (20 g) in 100 mL of 10% concentrated HCl in Miff is heated with stirring at 90° C. for three hours and cooled. The solid is collected by filtration, washed with water and dried to afford the title compound.

Step 2. 2-Pyrimidin-2-yl-4-trifluoromethyl-thiazole-5-carboxylic acid ethyl ester A mixture of 2-pyrimidinecarbothioamide (2 g) and 2-chloro-4,4,4-trifluoro-3-oxo-butyric acid ethyl ester (3.2 g) in 10 mL of DMF is heated at 110° C. with stirring overnight.

The mixture is concentrated under vacuum, and purified on silica gel column to afford the title compound.

Method B

Step 1.
2-Amino-4-trifluoromethyl-thiazole-5-carboxylic acid ethyl ester

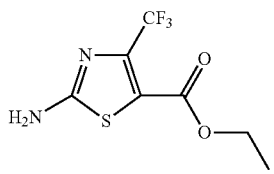

A mixture of thiourea (8.7 g) and 2-chloro-4,4,4-trifluoro-3-oxo-butyric acid ethyl ester (25 g) in 200 mL of EtOH is heated with stirring for 3 h. The solvent is evaporated and water is added to the residue, and basified with $NaHCO_3$. The solid is collected with filtration, washed with water and hexane, and dried to afford the title compound.

Step 2.
2-Bromo-4-trifluoromethyl-thiazole-5-carboxylic acid ethyl ester

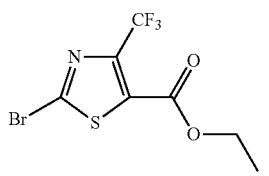

To a solution of 2-amino-4-trifluoromethyl-thiazole-5-carboxylic acid ethyl ester (10 g) in 48% HBr (75 mL) at 0° C. is added a solution of sodium nitrite (4.25 g) in water (50 mL) dropwise over 1 h. The mixture is stirred at the same temperature for an additional 30 min, then a solution of CuBr (6 g) in 48% HBr (50 mL) is added dropwise over 30 min. The reaction mixture is stirred for additional 30 min at 0° C. and for 2 h at RT. The mixture is extracted three times with methylene chloride. The combined organic extracts are dried over magnesium sulfate and concentrated in vacuo. The residue is purified by chromatography (silica gel, hexane to 3% EtOAc/Hexane) to yield the title compound.

Step 3. 2-pyrimidin-2-yl-4-trifluoromethyl-thiazole-5-carboxylic acid ethyl ester A mixture of 2-bromo-4-trifluoromethyl-thiazole-5-carboxylic acid ethyl ester (303 mg), 2-tributylstannanyl-pyrimidine (553 mg) and dichlorobis(triphenylphosphine)-palladium (II) (70 mg) in dioxane (5 mL) is heated at 110° C. in a sealed tube overnight. After the reaction mixture is cooled, a potassium fluoride solution and EtOAc are added and the mixture is stirred for 1 h and filtered. The organic layer is separated and aqueous layer is extracted with EtOAc once. The combined extracts are concentrated and the residue is purified by chromatography (silica gel, 4:1 Hexane and EtOAc) to give the title compound.

B. 2-Pyrimidin-2-yl-4-trifluoromethyl-thiazole-5-carboxylic acid

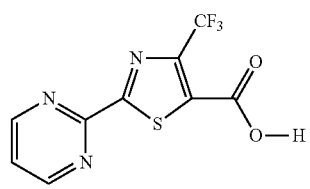 [SMILES: O=C(O)c1sc(-c2ncccn2)nc1C(F)(F)F]

A mixture of 2-pyrimidin-2-yl-4-trifluoromethyl-thiazole-5-carboxylic acid ethyl ester (1.6 g) and sodium hydroxide (1.2 g) in MeOH (10 mL) and water (3 mL) is heated at 50° C. with stirring for 30 min, cooled and evaporated. The residue is acidified with citric acid solution and extracted with EtOAc six times. The combined extracts are washed once with brine, dried over $Na_2SO_4$ and concentrated to give the title compound as a solid.

C. 4-Ethyl-2-pyrimidin-2-yl-thiazole-5-carboxylic acid

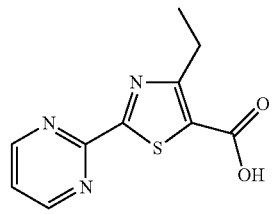 [SMILES: CCc1nc(-c2ncccn2)sc1C(=O)O]

This compound is prepared essentially as described for 2-pyrimidin-2-yl-4-trifluoromethyl-thiazole-5-carboxylic acid, with readily apparent starting material modification.

D. 4-Methyl-2-pyrimidin-2-yl-thiazole-5-carboxylic acid

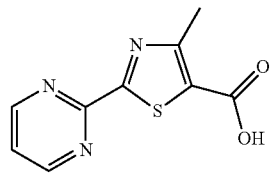

This compound is prepared essentially as described for 2-pyrimidin-2-yl-4-trifluoromethyl-thiazole-5-carboxylic acid, with readily apparent starting material modification.

E. 4-trifluoromethyl-2-pyrimidin-2-yl-thiazole-5-carboxylic acid[2-(4-chloro-phenyl)-4-methyl-pentyl]-amide (Compound 22)

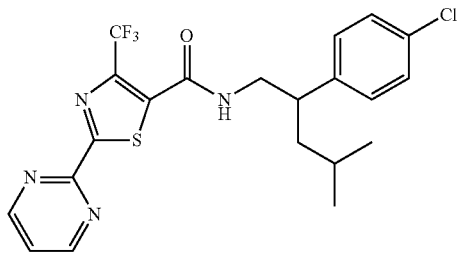 [SMILES: CC(C)CC(CNC(=O)c1sc(-c2ncccn2)nc1C(F)(F)F)c1ccc(Cl)cc1]

Step 1. 2-(4-Chloro-phenyl)-4-methyl-pentylamine

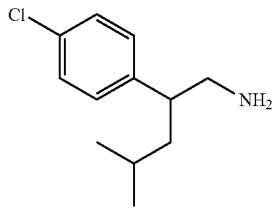

To a mixture of (4-chloro-phenyl)-acetonitrile (20 g) and 1-iodo-3-methyl-butane (24.3 g) in THF (100 mL) and DMSO (100 mL) is added NaH (60% in mineral oil, 5.28 g) portionwise at 0° C. over one hour. The mixture is allowed to warm to RT and stirred overnight. The reaction mixture is poured into water and extracted twice with EtOAc. The extract is concentrated and the residue is purified by silica gel chromatography to give 1-pyridin-3-yl-cyclohexanecarbonitrile.

To a solution of the above product (15 g) in 40 mL of 7.0 N $NH_3$ in MeOH is added carefully slurry of Raney Nickel (30 g). The mixture is hydrogenated at 50 psi overnight. The mixture is filtered through Celite and concentrated in vacuo to give the title compound.

Step 2. 4-trifluoromethyl-2-pyrimidin-2-yl-thiazole-5-carboxylic acid [2-(4-chloro-phenyl)-4-methyl-pentyl]amide A mixture of 2-pyrimidin-2-yl-4-trifluoromethyl-thiazole-5-carboxylic acid (15 mg), 2-(4-chloro-phenyl)-4-methyl-pentylamine hydrochloride (14 mg), BOP (25 mg) and TEA (20 mg) in ACN (1 mL) is stirred at RT overnight. EtOAc and water added to the mixture and the organic layer is separated, washed twice with water and concentrated in vacuo. The residue is purified by PTLC (1:1 EtOAc/Hexane) to give the title compound. MS (M+1)=469.11; $R_T$=1.36 min. *$IC_{50}$.

F. N-[2-(4-chlorophenyl)-2-piperidin-1-ylethyl]-2-pyrimidin-2-yl-4-(trifluoromethyl)-1,3-thiazole-5-carboxamide (Compound 23)

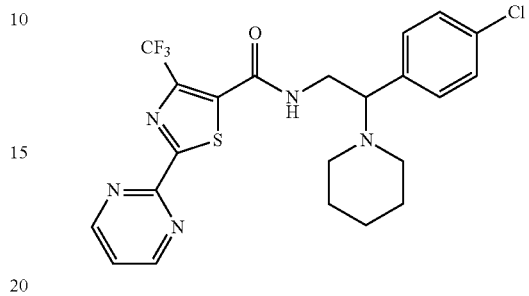

A mixture of 2-pyrimidin-2-yl-4-trifluoromethyl-thiazole-5-carboxylic acid (60 mg), 2-(4-chloro-phenyl)-2-piperidin-1-yl-ethylamine (60 mg), BOP (100 mg) and TEA (40 mg) in ACN (1 mL) is stirred at RT overnight. EtOAc and water added to the mixture and the organic layer is separated, washed twice with water and concentrated in vacuo. The residue is purified by PTLC (10% MeOH in methylene chloride) to give the title compound. MS (M+1)=496.09; $R_T$=1.14 min. *$IC_{50}$.

G. N-{[1-(4-methylpiperazin-1-yl)cycloheptyl]methyl}-2-pyrimidin-2-yl-4-(trifluoromethyl)-1,3-thiazole-5-carboxamide (Compound 24)

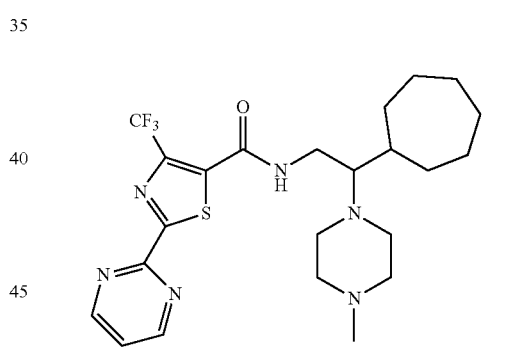

Step 1.
4-(1-cyano-cycloheptyl)-piperazine-1-carboxylic acid tert-butyl ester

To a solution of cycloheptanone (1 g) and trimethylsilyl cyanide (0.85 g) in ether (1 mL) is added zinc iodide (2 mg) at 0° C. and the solution is stirred at the same temperature for 15 min. To the solution is added dropwise a solution of t-Boc-piperazine (1.6 g) in 10 mL of MeOH at RT. The resultant reaction mixture is heated at reflux for 3 h and stirred at RT overnight. The mixture is then concentrated to dryness to give the title compound.

Step 2. [1-(4-methyl-piperazin-1-yl)-cycloheptyl]-methylamine

To solution of LAH in THF (1M, 27 mL) is added a solution of 4-(1-cyano-cycloheptyl)-piperazine-1-carboxylic acid tert-butyl ester (1 g) in THF (1 mL). The reaction mixture is stirred at RT overnight. Water is added to quench excess LAH and the mixture is treated with $Na_2SO_4$ and filtered through Celite. EtOAc is used to wash the Celite pad thoroughly and the filtrate is concentrated in vacuo to give the title compound.

Step 3. N-{[1-(4-methylpiperazin-1-yl)cycloheptyl]methyl}-2-pyrimidin-2-yl-4-(trifluoromethyl)-1,3-thiazole-5-carboxamide A mixture of 2-pyrimidin-2-yl-4-trifluoromethyl-thiazole-5-carboxylic acid (15 mg), 2-(4-chloro-phenyl)-2-piperidin-1-yl-ethylamine (15 mg), BOP (25 mg) and TEA (10 mg) in ACN (1 mL) is stirred at RT overnight. EtOAc and water are added to the mixture and the organic layer is separated, washed twice with water and concentrated in vacuo. The residue is purified by PTLC (10% MeOH in methylene chloride) to give the title compound. MS (M+1)=483.21; $R_T$=1.15 min. *$IC_{50}$.

H. 2-bromo-4-trifluoromethyl-thiazole-5-carboxylic acid (1-pyridin-3-yl-cyclohexylmethyl)-amide (Compound 25)

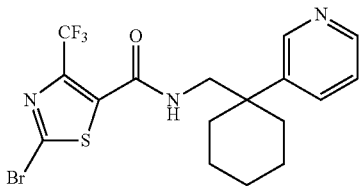 [SMILES: O=C(NCC1(c2cccnc2)CCCCC1)c1sc(Br)nc1C(F)(F)F]

Step 1. (1-Pyridin-3-yl-cyclohexyl)-methylamine

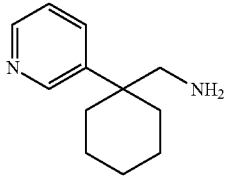 [SMILES: NCC1(c2cccnc2)CCCCC1]

To a mixture of pyridin-3-yl-acetonitrile (14.65 g) and 1,5-dibromo-pentane (28.52 g) in THF (450 mL) and DMSO (450 mL) is added NaH (60% in mineral oil, 10.42 g) portionwise at 0° C. over 1 h. The mixture is allowed to warm to RT and stirred overnight. The reaction mixture is poured into water and extracted twice with EtOAc. The extract is concentrated and the residue is purified by silica gel chromatography to give 1-pyridin-3-yl-cyclohexanecarbonitrile.

To a solution of the above product (18.5 g) in 140 mL of 7.0 N $NH_3$ in MeOH is added carefully slurry of Raney Nickel (16 g). The mixture is hydrogenated at 50 psi overnight. The mixture is filtered through Celite and concentrated in vacuo to give the title compound.

Step 2. 2-tert-butoxycarbonylamino-4-methyl-thiazole-5-carboxylic acid ethyl ester A mixture of 2-amino-4-trifluoromethyl-thiazole-5-carboxylic acid ethyl ester (9.69 g), di-tert-butyl dicarbonate (10.6 g) and 4-dimethylaminopyridine (500 mg) in THF (100 mL) is heated at reflux overnight. The mixture is concentrated in vacuo and purified by chromatography (silica gel, 5-10% EtOAc in Hexane) to yield the title compound.

Step 3. 2-tert-Butoxycarbonylamino-4-methyl-thiazole-5-carboxylic acid

A mixture of 2-tert-butoxycarbonylamino-4-methyl-thiazole-5-carboxylic acid ethyl ester (4.3 g) and sodium hydroxide (10 N, 2.5 mL) in MeOH (80 mL) is heated at 50° C. overnight. The mixture is cooled, concentrated in vacuo, diluted with water and acidified to pH 4-5 with 2 N HCl. The solid is collected by filtration and dried to give the title compound.

Step 4. 2-tert-Butoxycarbonylamino-4-trifluoromethyl-thiazole-5-carboxylic acid (1-pyridin-3-yl-cyclohexylmethyl)-amide A mixture of 2-tert-butoxycarbonylamino-4-methyl-thiazole-5-carboxylic acid (1.56 g), (1-pyridin-3-yl-cyclohexyl)-methylamine (1 g), BOP (2.66 g) and TEA (0.84 mL) in DMF (30 mL) is stirred at RT for 30 min and poured into ice water. The solid is collected by filtration and dried to give the title compound. MS (M+1)=485.21; $R_T$=1.18 min.

Step 5. 2-Amino-4-trifluoromethyl-thiazole-5-carboxylic acid (1-pyridin-3-yl-cyclohexylmethyl)-amide A mixture of 2-tert-butoxycarbonylamino-4-methyl-thiazole-5-carboxylic acid (1-pyridin-3-yl-cyclohexylmethyl)-amide (2.45 g) and TFA (10 mL) in methylene chloride (10 mL) is stirred at RT for 2 h and concentrated in vacuo. Water is added to the residue and the mixture is basified with $Na_2CO_3$ solution and extracted with EtOAc. The extract is washed with brine, dried and concentrated in vacuo to afford the title compound.

Step 6. 2-Bromo-4-trifluoromethyl-thiazole-5-carboxylic acid (1-pyridin-3-yl-cyclohexylmethyl)-amide To a stirred mixture of $CuBr_2$ (746 mg) in 40 mL of ACN is added tert-butyl nitrite (0.63 mL), followed by 2-amino-4-trifluoromethyl-thiazole-5-carboxylic acid (1-pyridin-3-yl-cyclohexylmethyl)-amide (1.36 g). The reaction mixture is stirred at RT for 30 min and EtOAc and water are added. The organic layer is separated, washed with diluted ammonium hydroxide solution and brine, and concentrated in vacuo. The

I. 2-(1,1-Dioxido-1,2-thiazinan-2-yl)-N-[(1-pyridin-3-ylcyclohexyl)methyl]-4-(trifluoromethyl)-1,3-thiazole-5-carboxamide (Compound 26)

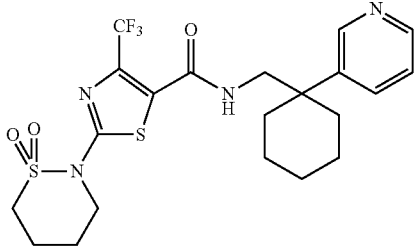 [SMILES: O=C(NCC1(c2cccnc2)CCCCC1)c1sc(N2CCCCS2(=O)=O)nc1C(F)(F)F]

A mixture of 2-bromo-4-trifluoromethyl-thiazole-5-carboxylic acid (1-pyridin-3-yl-cyclohexylmethyl)-amide (44.8 mg) 1,4-butanesultam (17.6 mg), palladium acetate (2.2 mg), xantphos (8.7 mg) and cesium carbonate (49 mg) in toluene (1 mL) is heated at 100° C. for 2 h. The mixture is cooled, poured into water and extracted with EtOAc. The extract is concentrated in vacuo and the residue is purified by PTLC (silica gel, 5% MeOH in methylene chloride) to give the title compound. MS (M+1)=503.16; $R_T$=1.14 min. *$IC_{50}$.

J. 2-((R)-3-Dimethylamino-pyrrolidin-1-yl)-4-trifluoromethyl-thiazole-5-carboxylic acid (1-pyridin-3-yl-cyclohexylmethyl)-amide (Compound 27)

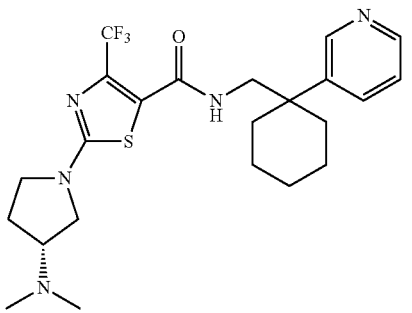 [SMILES: CN(C)[C@@H]1CCN(c2nc(C(F)(F)F)c(C(=O)NCC3(c4cccnc4)CCCCC3)s2)C1]

A mixture of 2-bromo-4-trifluoromethyl-thiazole-5-carboxylic acid (1-pyridin-3-yl-cyclohexylmethyl)-amide (44.8 mg), dimethyl-(R)-pyrrolidin-3-yl-amine (12.6 mg), and potassium carbonate (15.2 mg) in ACN (1 mL) is heated at 80° C. for 1 h. The mixture is cooled, poured into water and extracted with EtOAc. The extract is concentrated in vacuo and the residue is purified by PTLC (silica gel, 5% MeOH in methylene chloride) to give the title compound. MS (M+1)=482.24; $R_T$=1.03 min. *$IC_{50}$.

K. 2-(6-methoxy-pyridin-3-yl)-4-trifluoromethyl-thiazole-5-carboxylic acid (1-pyridin-3-yl-cyclohexylmethyl)-amide (Compound 28)

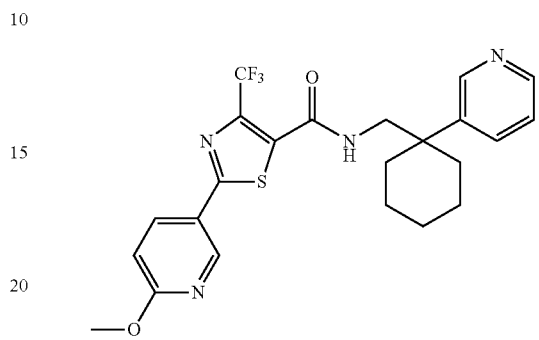

A mixture of 2-bromo-4-trifluoromethyl-thiazole-5-carboxylic acid (1-pyridin-3-yl-cyclohexylmethyl)-amide (44.8 mg), 2-methoxy-5-pyridineboronic acid (30.6 mg), Pd(PPh$_3$)$_4$ (5.8 mg) and Na$_2$CO$_3$ (42.4 mg) in dioxane (2 mL) and water (0.8 mL) is heated at 110° C. in an argon purged sealed vial for 2 h. The mixture is poured into water and extracted with EtOAc. The extract is concentrated and the residue is purified by PTLC (silica gel, 5% MeOH in methylene chloride) to give the title compound. MS (M+1)=477.19; $R_T$=1.19 min. *$IC_{50}$.

L. N-{[1-(4-Chlorophenyl)cyclohexyl]methyl}-4-methyl-2-pyridin-3-yl-1,3-thiazole-5-carboxamide (Compound 29)

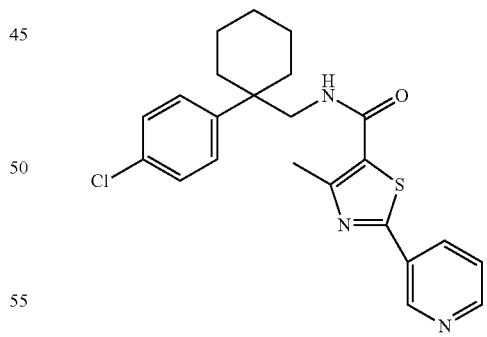

A solution of DMC in DCM (1.2 mL, 0.1 M, 1.2 eq.) is added to a solution of 2-(3-pyridyl)-4-methylthiazole-5-carboxylic acid (21 mg, 0.1 mmol, 1.0 eq.), [1-(4-chlorophenyl)cyclohexyl]-methylamine (22 mg, 0.1 mmol, 1.0 eq.) and TEA (33 µL, 0.24 mmol, 2. 4 eq.) in DCM (1.0 mL) at RT. After standing overnight at RT, the reaction mixture is purified by PTLC (EtOAc/MeOH/TEA 100/5/3) to give the title compound. LC/MS (M+1)=426.25; $R_T$=1.36 min. *$IC_{50}$.

M. N-{4-methyl-2-[4-trifluoromethyl)phenyl]pentyl}-4-methyl-2-pyridin-3-yl-1,3-thiazole-5-carboxamide (Compound 30)

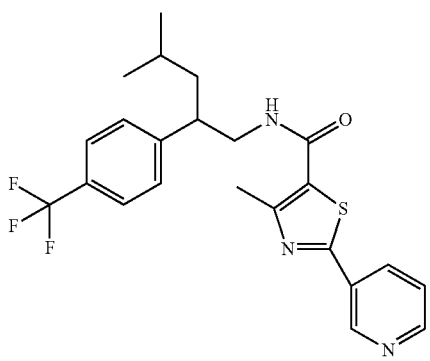 [SMILES: Cc1nc(-c2cccnc2)sc1C(=O)NCC(CC(C)C)c1ccc(C(F)(F)F)cc1]

This compound is prepared essentially as described in Example 2L, with readily apparent modification of starting material. LC/MS: (M+1)=448.26; $R_T$=1.36 min *IC$_{50}$.

N. N-[2-(4-Chlorophenyl)-4-methylpentyl}-4-methyl-2-pyridin-3-yl-1,3-thiazole-5-carboxamide (Compound 31)

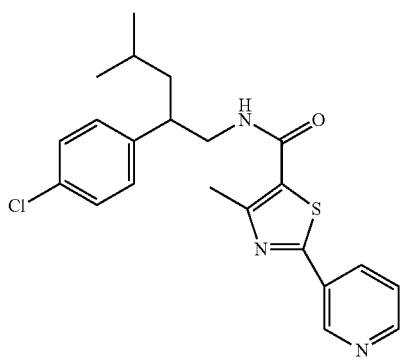 [SMILES: Cc1nc(-c2cccnc2)sc1C(=O)NCC(CC(C)C)c1ccc(Cl)cc1]

This compound is prepared essentially as described in Example 2L, with readily apparent modification of starting material. LC/MS: (M+1)=414.23; $R_T$=1.36 min. *IC$_{50}$.

O. N-({1-[4-(trifluoromethyl)phenyl]cyclohexyl}methyl)-4-methyl-2-pyridin-3-yl-1-,3-thiazole-5-carboxamide (Compound 32)

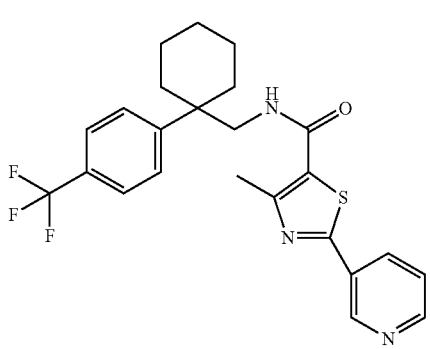 [SMILES: Cc1nc(-c2cccnc2)sc1C(=O)NCC1(c2ccc(C(F)(F)F)cc2)CCCCC1]

This compound is prepared essentially as described in Example 2L, with readily apparent modification of starting material. LC/MS: (M+1)=460.26; $R_T$=1.37 min *IC$_{50}$.

P. N-[4-methyl-2-(4-methylphenyl)pentyl}-4-methyl-2-pyridin-3-yl-1,3-thiazole-5-carboxamide (Compound 33)

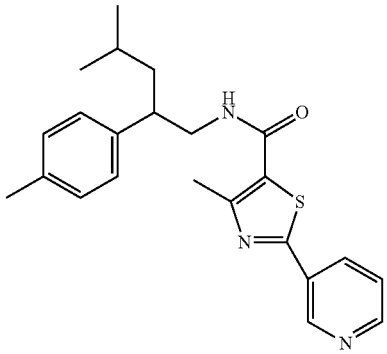 [SMILES: Cc1ccc(C(CNC(=O)c2sc(-c3cccnc3)nc2C)CC(C)C)cc1]

This compound is prepared essentially as described in Example 2L, with readily apparent modification of starting material. LC/MS: (M+1)=394.28; $R_T$=1.3 min. *IC$_{50}$.

Q. N{-[1-(4-fluorophenyl)cyclohexyl]methyl}}-4-methyl-2-pyridin-3-yl-1,3-thiazole-5-carboxamide (Compound 34)

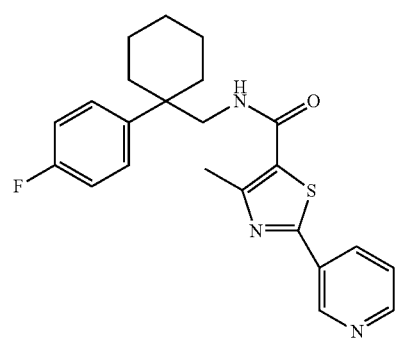

This compound is prepared essentially as described in Example 2L, with readily apparent modification of starting material. LC/MS: (M+1)=410.21; $R_T$=1.28 min *IC$_{50}$.

R. N-[2-(4-chlorophenyl)pentyl}-4-methyl-2-pyridin-3-yl-1,3-thiazole-5-carboxamide (Compound 35)

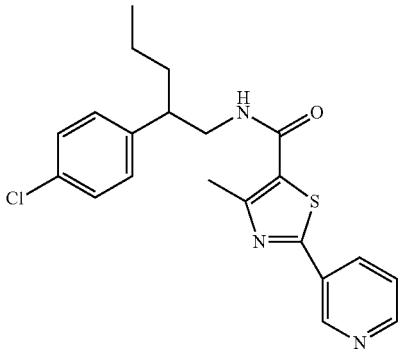 [SMILES: CCCC(CNC(=O)c1sc(-c2cccnc2)nc1C)c1ccc(Cl)cc1]

This compound is prepared essentially as described in Example 2L, with readily apparent modification of starting material. LC/MS: (M+1)=400.17; $R_T$=1.29 min. *IC$_{50}$.

S. N-{[1-(4-methoxyphenyl)cyclohexyl]methyl}-4-methyl-2-pyridin-3-yl-1,3-thiazole-5-carboxamide (Compound 36)

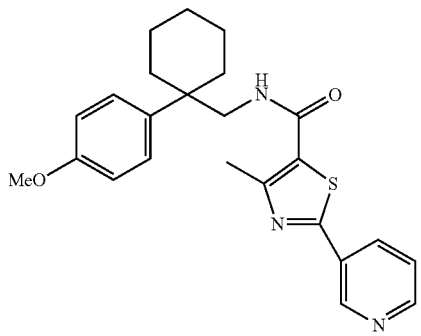 [SMILES: COc1ccc(C2(CNC(=O)c3sc(-c4cccnc4)nc3C)CCCCC2)cc1]

This compound is prepared essentially as described in Example 2L, with readily apparent modification of starting material. LC/MS: (M+1)=422.27; $R_T$=1.29 min. *IC$_{50}$.

T. N-{[4-(4-Chlorophenyl)tetrahydro-2H-pyran-4-yl]methyl}-4-methyl-2-pyridin-3-yl-1,3-thiazole-5-carboxamide (Compound 37)

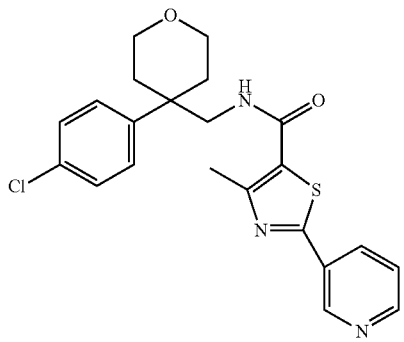 [SMILES: Cc1nc(-c2cccnc2)sc1C(=O)NCC1(c2ccc(Cl)cc2)CCOCC1]

This compound is prepared essentially as described in Example 2L, with readily apparent modification of starting material. LC/MS: (M+1)=428.17; $R_T$=1.2 min. *IC$_{50}$.

U. N-{[1-(4-methylphenyl)cyclohexyl]methyl}-4-methyl-2-pyridin-3-yl-1,3-thiazole-5-carboxamide (Compound 38)

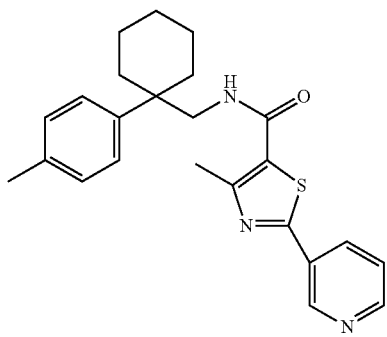 [SMILES: Cc1ccc(C2(CNC(=O)c3sc(-c4cccnc4)nc3C)CCCCC2)cc1]

This compound is prepared essentially as described in Example 2L, with readily apparent modification of starting material. LC/MS: (M+1)=406.24; $R_T$=1.33 min *IC$_{50}$.

V. N-{[1-(4-chloro-3-fluorophenyl)cyclohexyl]methyl}-4-methyl-2-pyridin-3-yl-1-,3-thiazole-5-carboxamide (Compound 39)

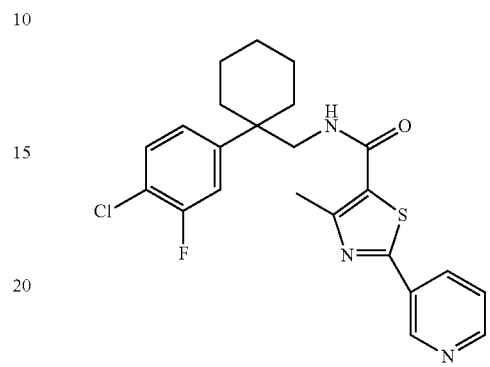

This compound is prepared essentially as described in Example 2L, with readily apparent modification of starting material. LC/MS: (M+1)=444.15; $R_T$=1.33 min. *IC$_{50}$.

W. N-{[1-(6-methylpyridin-3-yl)cyclohexyl]methyl}-4-methyl-2-pyridin-3-yl-1-,3-thiazole-5-carboxamide (Compound 40)

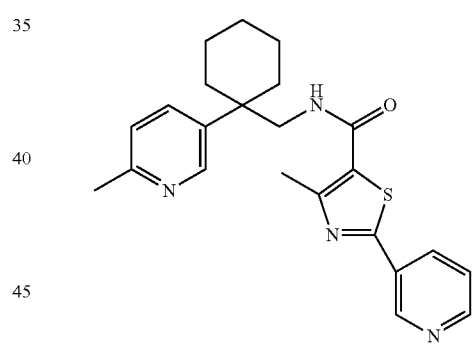

This compound is prepared essentially as described in Example 2L, with readily apparent modification of starting material. LC/MS: (M+1)=407.21; $R_T$=1.03 min. *IC$_{50}$.

X. N-(Adamantan-1-ylmethyl)-5-methylthiophene-2-carboxamide (Compound 41)

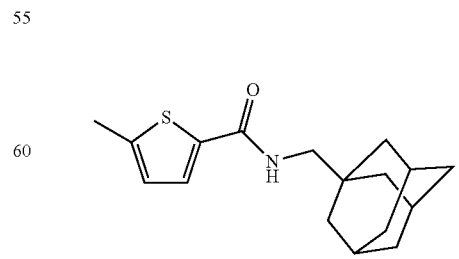

To a 2 mL reaction vial is added adamantylmethylamine (0.15 mL, 0.2M in toluene), 5-methylthiophene-2-carboxylic acid (0.15 mL, 0.2M in dimethylacetamide), 2-chloro-1,3-dimethylimidazolinium chloride (0.20 mL, 0.2M in ACN), and TEA (0.20 mL, 0.2M in toluene). The mixture is placed on a shaker and heated to 50° C. for 16 h. The mixture is cooled to RT and diluted with 1M aqueous sodium hydroxide (0.5 mL). The resulting mixture is extracted with 50% EtOAc-hexane (3×0.5 mL) and purified over benzenesulfonic acid ion exchange resin (eluted with 50% EtOAc-hexane) to afford the title compound. LC/MS: (M+1)=290.19; $R_T$=1.33 min.

Example 3

Synthesis of Additional Representative 5-Membered Heterocyclic Amides and Related Compounds Additional 5-membered heterocyclic amides and related compounds are synthesized by DMC (2 eq) coupling of carboxylic acid (1.2 eq) and amine (1.0 eq):

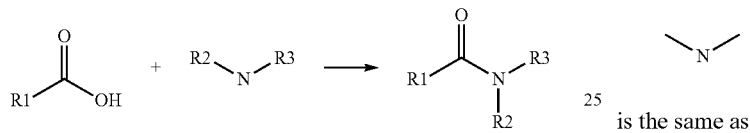

The amine (0.2 M in toluene; 0.10 mL) and acid (0.2 M in DMA; 0.12 mL) are added to a vial along with DMC 3 (0.2 M in ACN, freshly prepared; 0.2 mL) and TEA (0.3 M in toluene; 0.10 mL) are added to a vial and incubated at RT for 16 h. The reaction mixture is then extracted with 1 N NaOH (0.5 mL) and EtOAc (0.5 mL). The upper organic layer is removed and concentrated to dryness. The residue is purified via solid phase extraction chromatography eluting with 25% MeOH/EtOAc (4.0 mL) to afford the title compound.

Using routine modifications, the starting materials may be varied and additional steps employed to produce other compounds provided herein. Compounds listed in Table I are prepared using such methods. In the column of Table I labeled "$IC_{50}$," a "*" indicates that the $IC_{50}$ determined as described in Example 4A is 2 micromolar or less (i.e., the concentration of such compounds that is required to provide a 50% decrease in the fluorescence response of cells exposed to 80 μM of (2'(3')-O-(4-benzoyl-benzoyl)adenosine 5'-triphosephate is 2 micromolar or less). Mass spectroscopy data is provided as (M+1) in the column headed "MS." The retention time, in minutes, is provided in the column headed $R_T$. It will be apparent that, within Table I and elsewhere herein, an amine designated

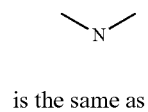

is the same as

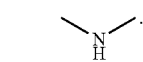

TABLE I

Representative 5-Membered Heterocyclic Amides and Related Compounds

| | Compound | Name | MS | RT | $IC_{50}$ |
|---|---|---|---|---|---|
| 42 | (structure) | N-(adamantan-1-ylmethyl)-1-(3-methoxypyrazin-2-yl)-3-methyl-1H-pyrazole-4-carboxamide | 382.23 | 1.35 | * |
| 43 | (structure) | N-(adamantan-1-ylmethyl)-1-(6-aminopyrazin-2-yl)-3-methyl-1H-pyrazole-4-carboxamide | 367.45 | 1.33 | * |

TABLE I-continued

Representative 5-Membered Heterocyclic Amides and Related Compounds

| | Compound | Name | MS | RT | IC$_{50}$ |
|---|---|---|---|---|---|
| 44 | 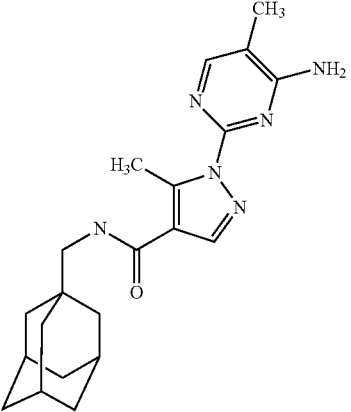 [SMILES: Cc1cnc(-n2ncc(C(=O)NCC34CC5CC(CC(C5)C3)C4)c2C)nc1N] | N-(adamantan-1-ylmethyl)-1-(4-amino-5-methylpyrimidin-2-yl)-5-methyl-1H-pyrazole-4-carboxamide | 381.30 | 1.33 | |
| 45 | 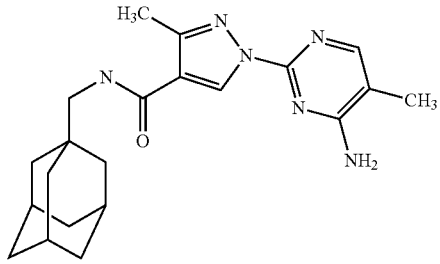 [SMILES: Cc1cnc(-n2cc(C(=O)NCC34CC5CC(CC(C5)C3)C4)c(C)n2)nc1N] | N-(adamantan-1-ylmethyl)-1-(4-amino-5-methylpyrimidin-2-yl)-3-methyl-1H-pyrazole-4-carboxamide | 381.29 | 1.29 | * |
| 46 | 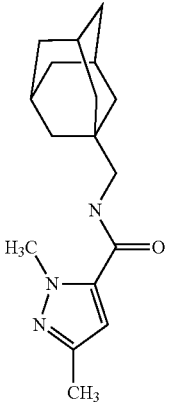 | N-(adamantan-1-ylmethyl)-1,3-dimethyl-1H-pyrazole-5-carboxamide | 288.27 | 1.35 | * |
| 47 | 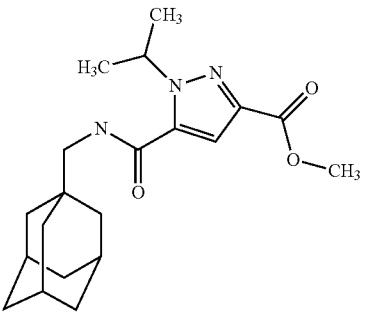 [SMILES: COC(=O)c1cc(C(=O)NCC23CC4CC(CC(C4)C2)C3)n(C(C)C)n1] | methyl 5-[(adamantan-1-ylmethyl)carbamoyl]-1-isopropyl-1H-pyrazole-3-carboxylate | 360.30 | 1.38 | * |

TABLE I-continued

Representative 5-Membered Heterocyclic Amides and Related Compounds

| | Compound | Name | MS | RT | IC$_{50}$ |
|---|---|---|---|---|---|
| 48 | | N-(adamantan-1-ylmethyl)-3-(hydroxymethyl)-1-isopropyl-1H-pyrazole-5-carboxamide | 332.20 | 1.26 | |
| 49 | | 4-bromo-1-ethyl-3-methyl-N-(4-methyl-2-phenylpentyl)-1H-pyrazole-5-carboxamide | 392.14 | 1.32 | * |
| 50 | | 4-bromo-N-(2,2-diphenylethyl)-1-ethyl-3-methyl-1H-pyrazole-5-carboxamide | 412.11 | 1.28 | * |
| 51 | | N-(adamantan-1-ylmethyl)-3-{[2-(2-hydroxyethyl)piperidin-1-yl]methyl}-1-isopropyl-1H-pyrazole-5-carboxamide | 443.30 | 1.19 | |

TABLE I-continued

Representative 5-Membered Heterocyclic Amides and Related Compounds

| | Compound | Name | MS | RT | IC$_{50}$ |
|---|---|---|---|---|---|
| 52 | 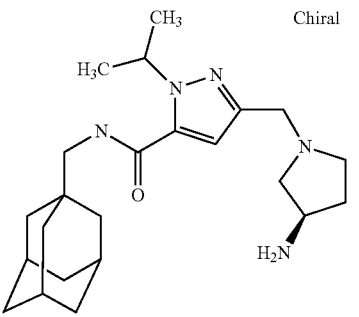 [SMILES: CC(C)n1nc(CN2CC[C@@H](N)C2)cc1C(=O)NCC12CC3CC(CC(C3)C1)C2] Chiral | N-(adamantan-1-ylmethyl)-3-{[(3R)-3-aminopyrrolidin-1-yl]methyl}-1-isopropyl-1H-pyrazole-5-carboxamide | 400.28 | 1.14 | |
| 53 | 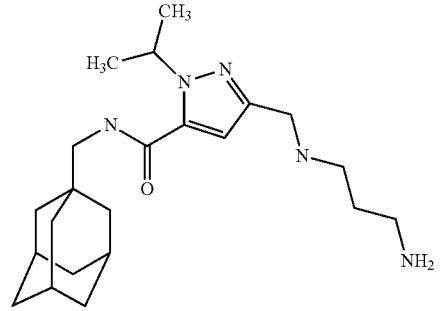 [SMILES: CC(C)n1nc(CNCCCN)cc1C(=O)NCC12CC3CC(CC(C3)C1)C2] | N-(adamantan-1-ylmethyl)-3-{[(3-aminopropyl)amino]methyl}-1-isopropyl-1H-pyrazole-5-carboxamide | 388.29 | 1.13 | |
| 54 | 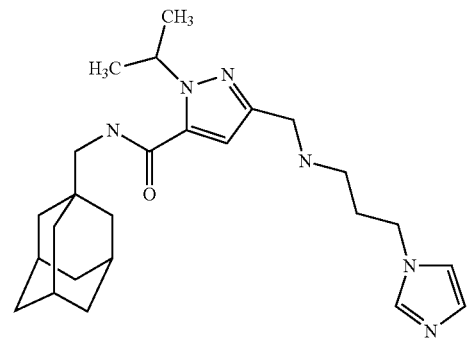 [SMILES: CC(C)n1nc(CNCCCn2ccnc2)cc1C(=O)NCC12CC3CC(CC(C3)C1)C2] | N-(adamantan-1-ylmethyl)-3-({[3-(1H-imidazol-1-yl)propyl]amino}methyl)-1-isopropyl-1H-pyrazole-5-carboxamide | 439.27 | 1.2 | |
| 55 | 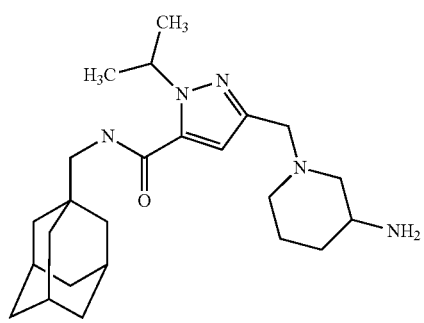 [SMILES: CC(C)n1nc(CN2CCCC(N)C2)cc1C(=O)NCC12CC3CC(CC(C3)C1)C2] | N-(adamantan-1-ylmethyl)-3-[(3-aminopiperidin-1-yl)methyl]-1-isopropyl-1H-pyrazole-5-carboxamide | 414.27 | 1.21 | * |

TABLE I-continued

Representative 5-Membered Heterocyclic Amides and Related Compounds

| | Compound | Name | MS | RT | IC$_{50}$ |
|---|---|---|---|---|---|
| 56 | | N-(adamantan-1-ylmethyl)-1-{4-[(2-hydroxyethyl)amino]-5-methylpyrimidin-2-yl}-3-methyl-1H-pyrazole-4-carboxamide | 425.20 | 1.29 | * |
| 57 | | N-(adamantan-1-ylmethyl)-1-{6-[(2-hydroxyethyl)amino]pyrazin-2-yl}-3-methyl-1H-pyrazole-4-carboxamide | 411.20 | 1.35 | |
| 58 | | N-(adamantan-1-ylmethyl)-1-(3-aminopyrazin-2-yl)-3-methyl-1H-pyrazole-4-carboxamide | 367.21 | 1.38 | * |
| 59 | | N-(adamantan-1-ylmethyl)-1-(6-aminopyridin-2-yl)-3-methyl-1H-pyrazole-4-carboxamide | 366.22 | 1.34 | * |
| 60 | | N-(adamantan-1-ylmethyl)-3-methyl-1-(6-piperazin-1-ylpyrazin-2-yl)-1H-pyrazole-4-carboxamide | 436.22 | 1.26 | |

TABLE I-continued

Representative 5-Membered Heterocyclic Amides and Related Compounds

| | Compound | Name | MS | RT | IC$_{50}$ |
|---|---|---|---|---|---|
| 61 | | N-(adamantan-1-ylmethyl)-1-(5-aminopyrazin-2-yl)-3-methyl-1H-pyrazole-4-carboxamide | 367.21 | 1.33 | * |
| 62 | | N-(adamantan-1-ylmethyl)-4-bromo-1,3-dimethyl-1H-pyrazole-5-carboxamide | 366.10 | 1.42 | * |
| 63 | | N-(adamantan-1-ylmethyl)-4-bromo-1-ethyl-3-methyl-1H-pyrazole-5-carboxamide | 380.11 | 1.43 | * |
| 64 | | N-(adamantan-1-ylmethyl)-1-(2-amino-6-methylpyrimidin-4-yl)-3-methyl-1H-pyrazole-4-carboxamide | 381.22 | 1.29 | * |
| 65 | | N-(adamantan-1-ylmethyl)-4-chloro-2-[2-(trifluoromethyl)phenyl]-1,3-thiazole-5-carboxamide | 455.05 | 1.46 | * |

TABLE I-continued

Representative 5-Membered Heterocyclic Amides and Related Compounds

| Compound | | Name | MS | RT | IC$_{50}$ |
|---|---|---|---|---|---|
| 66 | | N-(adamantan-1-ylmethyl)-2-[2-(2-hydroxyethyl)piperidin-1-yl]-1,3-thiazole-5-carboxamide | 404.21 | 1.28 | |
| 67 | | N-(adamantan-1-ylmethyl)-2-[2-(trifluoromethyl)phenyl]-1,3-thiazole-5-carboxamide | 421.15 | 1.34 | * |
| 68 | | 3-{4-[(adamantan-1-ylmethyl)carbamoyl]-5-isopropyl-1,3-thiazol-2-yl}benzoic acid | 439.20 | 1.48 | |
| 69 | | N-(adamantan-1-ylmethyl)-2-methyl-4-[(1-methyl-1H-imidazol-2-yl)thio]-1,3-thiazole-5-carboxamide | 403.20 | 1.23 | * |

TABLE I-continued

Representative 5-Membered Heterocyclic Amides and Related Compounds

| | Compound | Name | MS | RT | IC$_{50}$ |
|---|---|---|---|---|---|
| 70 | | N-(adamantan-1-ylmethyl)-4-methyl-2-(piperidin-4-yloxy)-1,3-thiazole-5-carboxamide | 390.27 | 1.26 | * |
| 71 | | N-(adamantan-1-ylmethyl)-2-[4-(2-hydroxyethyl)piperazin-1-yl]-4-methyl-1,3-thiazole-5-carboxamide | 419.46 | 1.23 | |
| 72 | | N-(adamantan-1-ylmethyl)-4-methyl-2-piperazin-1-yl-1,3-thiazole-5-carboxamide | 375.25 | 1.22 | * |
| 73 | | N-(1-adamantylmethyl)-3-methylthiophene-2-carboxamide | 290.19 | 1.33 | * |
| 74 | | N-(1-adamantylmethyl)-3-chlorothiophene-2-carboxamide | 310.14 | 1.37 | |

TABLE I-continued

Representative 5-Membered Heterocyclic Amides and Related Compounds

| | Compound | Name | MS | RT | $IC_{50}$ |
|---|---|---|---|---|---|
| 75 | | N-(1-adamantylmethyl)-5-(methylthio)thiophene-2-carboxamide | 322.16 | 1.35 | * |
| 76 | | N-(1-adamantylmethyl)-5-bromothiophene-2-carboxamide | 356.09 | 1.37 | * |
| 77 | | N-(1-adamantylmethyl)-3-bromothiophene-2-carboxamide | 356.08 | 1.37 | |
| 78 | | N-(1-adamantylmethyl)-5-propylthiophene-2-carboxamide | 318.22 | 1.39 | * |

TABLE I-continued

Representative 5-Membered Heterocyclic Amides and Related Compounds

| Compound | Name | MS | RT | IC$_{50}$ |
|---|---|---|---|---|
| 79 | N-(1-adamantylmethyl)-5-chlorothiophene-2-carboxamide | 310.15 | 1.36 | |
| 80 | N-(1-adamantylmethyl)-5-[1-methyl-3-(trifluoromethyl)-1H-pyrazol-5-yl]thiophene-2-carboxamide | 424.17 | 1.39 | * |
| 81 | N-[2-(1-adamantyl)ethyl]thiophene-2-carboxamide | 290.19 | 1.34 | |
| 82 | N-[2-(1-adamantyl)ethyl]-3-methylthiophene-2-carboxamide | 304.20 | 1.36 | |
| 83 | N-[2-(1-adamantyl)ethyl]-5-methylthiophene-2-carboxamide | 304.20 | 1.37 | |

TABLE I-continued

Representative 5-Membered Heterocyclic Amides and Related Compounds

| Compound | Name | MS | RT | IC$_{50}$ |
|---|---|---|---|---|
| 84 | N-[2-(1-adamantyl)ethyl]-5-(methylthio)thiophene-2-carboxamide | 336.18 | 1.39 | |
| 85 | N-[2-(1-adamantyl)ethyl]-5-[1-methyl-3-(trifluoromethyl)-1H-pyrazol-5-yl]thiophene-2-carboxamide | 438.20 | 1.43 | * |
| 86 | N-[2-(1-adamantyl)ethyl]thiophene-3-carboxamide | 290.20 | 1.34 | |
| 87 | N-(adamantan-1-ylmethyl)-3-chloro-4-methylthiophene-2-carboxamide | 324.12 | 1.45 | * |
| 88 | 3-chloro-N-[(1-hydroxycycloheptyl)methyl]-4-methylthiophene-2-carboxamide | 302.09 | 1.32 | |

TABLE I-continued

Representative 5-Membered Heterocyclic Amides and Related Compounds

| Compound | Name | MS | RT | IC$_{50}$ |
|---|---|---|---|---|
| 89 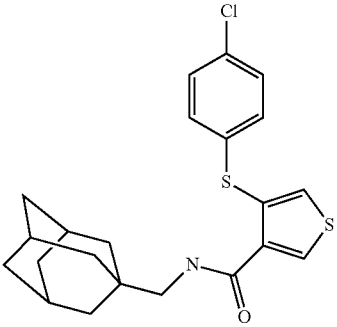 [SMILES: O=C(NCC12CC3CC(CC(C3)C1)C2)c1cscc1Sc1ccc(Cl)cc1] | N-(adamantan-1-ylmethyl)-4-[(4-chlorophenyl)thio]thiophene-3-carboxamide | 418.06 | 1.48 | |
| 90 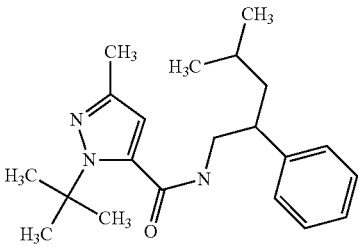 [SMILES: Cc1cc(C(=O)NCC(CC(C)C)c2ccccc2)n(C(C)(C)C)n1] | 1-tert-butyl-3-methyl-N-(4-methyl-2-phenylpentyl)-1H-pyrazole-5-carboxamide | 342.21 | 1.3 | |
| 91 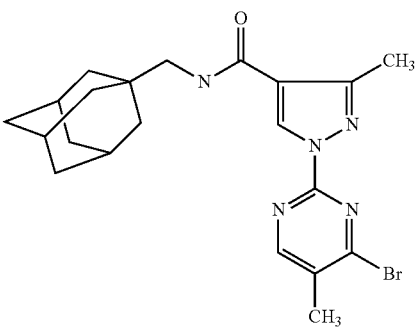 [SMILES: Cc1cnc(-n2cc(C(=O)NCC34CC5CC(CC(C5)C3)C4)c(C)n2)nc1Br] | N-(adamantan-1-ylmethyl)-1-(4-bromo-5-methylpyrimidin-2-yl)-3-methyl-1H-pyrazole-4-carboxamide | 444.10 | 1.33 | * |
| 92 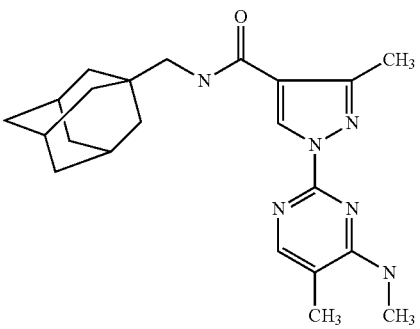 [SMILES: CNc1nc(-n2cc(C(=O)NCC34CC5CC(CC(C5)C3)C4)c(C)n2)ncc1C] | N-(adamantan-1-ylmethyl)-3-methyl-1-[5-methyl-4-(methylamino)pyrimidin-2-yl]-1H-pyrazole-4-carboxamide | 395.20 | 1.21 | * |

TABLE I-continued

Representative 5-Membered Heterocyclic Amides and Related Compounds

| Compound | Name | MS | RT | IC$_{50}$ |
|---|---|---|---|---|
| 93 | N-(adamantan-1-ylmethyl)-3-methyl-1-(5-methyl-4-phenylpyrimidin-2-yl)-1H-pyrazole-4-carboxamide | 442.32 | 1.41 | * |
| 94 | N-(adamantan-1-ylmethyl)-3-methyl-1-(5-methylpyrimidin-2-yl)-1H-pyrazole-4-carboxamide | 366.28 | 1.34 | * |
| 95 | N-(adamantan-1-ylmethyl)-3-methyl-1-(5-methyl-4-pyridin-3-ylpyrimidin-2-yl)-1H-pyrazole-4-carboxamide | 443.28 | 1.32 | * |
| 96 | 2-{4-[(adamantan-1-ylmethyl)carbamoyl]-3-methyl-1H-pyrazol-1-yl}-5-methylpyrimidine-4-carboxamide | 409.32 | 1.32 | * |

TABLE I-continued

Representative 5-Membered Heterocyclic Amides and Related Compounds

| Compound | | Name | MS | RT | IC$_{50}$ |
|---|---|---|---|---|---|
| 97 | | N-(adamantan-1-ylmethyl)-3-methyl-1-(5-methylpyridin-2-yl)-1H-pyrazole-4-carboxamide | 365.28 | 1.38 | * |
| 98 | | (N-(adamantan-1-ylmethyl)-3-methyl-1-pyridin-2-yl-1H-pyrazole-4-carboxamide | 351.26 | 1.36 | * |
| 99 | | N-(adamantan-1-ylmethyl)-1-(4-aminopyrimidin-2-yl)-3-methyl-1H-pyrazole-4-carboxamide | 367.29 | 1.26 | * |
| 100 | | N-(adamantan-1-ylmethyl)-1-(4-amino-5-methylpyrimidin-2-yl)-3-isopropyl-1H-pyrazole-4-carboxamide | 409.35 | 1.30 | * |
| 101 | | N-(adamantan-1-ylmethyl)-3-methyl-1-pyridin-4-yl-1H-pyrazole-4-carboxamide | 351.29 | 1.25 | * |

TABLE I-continued

Representative 5-Membered Heterocyclic Amides and Related Compounds

| | Compound | Name | MS | RT | IC$_{50}$ |
|---|---|---|---|---|---|
| 102 | | N-(adamantan-1-ylmethyl)-1-(5-ethylpyrimidin-2-yl)-3-methyl-1H-pyrazole-4-carboxamide | 380.32 | 1.35 | * |
| 103 | | N-(adamantan-1-ylmethyl)-3-methyl-1-(5-methyl-4-vinylpyrimidin-2-yl)-1H-pyrazole-4-carboxamide | 392.33 | 1.37 | * |
| 104 | | N-(adamantan-1 ylmethyl)-3-methyl-1-[5-methyl-4-(pyrrolidin-1-ylcarbonyl)pyrimidin-2-yl]-1H-pyrazole-4-carboxamide | 463.38 | 1.32 | * |
| 105 | Chiral | N-(adamantan-1-ylmethyl)-1-(4-{[(3R)-3-aminopiperidin-1-yl]carbonyl}-5-methylpyrimidin-2-yl)-3-methyl-1H-pyrazole-4-carboxamide | 492.41 | 1.23 | * |

TABLE I-continued

Representative 5-Membered Heterocyclic Amides and Related Compounds

| Compound | | Name | MS | RT | IC$_{50}$ |
|---|---|---|---|---|---|
| 106 | | N-(adamantan-1-ylmethyl)-1-(4-ethyl-5-methylpyrimidin-2-yl)-3-methyl-1H-pyrazole-4-carboxamide | 394.34 | 1.38 | * |
| 107 | | 2-{4-[(adamantan-1-ylmethyl)carbamoyl]-3-methyl-1H-pyrazol-1-yl}-N-ethyl-5-methylpyrimidine-4-carboxamide | 437.36 | 1.37 | * |
| 108 | | 2-{4-[(adamantan-1-ylmethyl)carbamoyl]-3-methyl-1H-pyrazol-1-yl}-5-methyl-N-propylpyrimidine-4-carboxamide | 451.37 | 1.41 | * |
| 109 | | 1-(4-amino-5-methylpyrimidin-2-yl)-N-[2-(4-chlorophenyl)-4-methylpentyl]-3-methyl-1H-pyrazole-4-carboxamide | 427.31 | 1.31 | * |

TABLE I-continued

Representative 5-Membered Heterocyclic Amides and Related Compounds

| Compound | | Name | MS | RT | IC$_{50}$ |
|---|---|---|---|---|---|
| 110 | | N-(adamantan-1-ylmethyl)-1-(4-amino-5-fluoropyrimidin-2-yl)-3-methyl-1H-pyrazole-4-carboxamide | 385.33 | 1.31 | * |
| 111 | | N-(adamantan-1-ylmethyl)-3-methyl-1-[4-(trifluoromethyl)pyrimidin-2-yl]-1H-pyrazole-4-carboxamide | 420.30 | 1.38 | * |
| 112 | | N-(adamantan-1-ylmethyl)-1-(5-fluoropyrimidin-2-yl)-3-methyl-1H-pyrazole-4-carboxamide | 370.30 | 1.32 | * |
| 113 | | 1-(4-amino-5-fluoropyrimidin-2-yl)-N-[2-(4-chlorophenyl)-4-methylpentyl]-3-methyl-1H-pyrazole-4-carboxamide | 431.27 | 1.34 | * |

TABLE I-continued

Representative 5-Membered Heterocyclic Amides and Related Compounds

| | Compound | Name | MS | RT | IC$_{50}$ |
|---|---|---|---|---|---|
| 114 | | N-[2-(4-chlorophenyl)-4-methylpentyl]-1-(5-fluoropyrimidin-2-yl)-3-methyl-1H-pyrazole-4-carboxamide | 416.27 | 1.35 | * |
| 115 | | 1-(4-amino-5-methylpyrimidin-2-yl)-3-methyl-N-{4-methyl-2-[4-(trifluoromethyl)phenyl]pentyl}-1H-pyrazole-4-carboxamide | 461.33 | 1.32 | * |
| 116 | | 1-(4-amino-5-fluoropyrimidin-2-yl)-3-methyl-N-{4-methyl-2-[4-(trifluoromethyl)phenyl]pentyl}-1H-pyrazole-4-carboxamide | 465.30 | 1.34 | * |
| 117 | | 1-(5-fluoropyrimidin-2-yl)-3-methyl-N-{4-methyl-2-[4-(trifluoromethyl)phenyl]pentyl}-1H-pyrazole-4-carboxamide | 450.28 | 1.35 | * |

TABLE I-continued

Representative 5-Membered Heterocyclic Amides and Related Compounds

| | Compound | Name | MS | RT | IC$_{50}$ |
|---|---|---|---|---|---|
| 118 | | N-(adamantan-1-ylmethyl)-1-(5-fluoropyrimidin-2-yl)-3-(trifluoromethyl)-1H-pyrazole-4-carboxamide | 424.28 | 1.34 | * |
| 119 | | N-(adamantan-1-ylmethyl)-3-methyl-1-(5-methyl-4-pyridin-4-ylpyrimidin-2-yl)-1H-pyrazole-4-carboxamide | 443.36 | 1.31 | * |
| 120 | | N-(adamantan-1-ylmethyl)-3-methyl-1-(5-methyl-4,5'-bipyrimidin-2-yl)-1H-pyrazole-4-carboxamide | 444.35 | 1.35 | * |
| 121 | | N-(adamantan-1-ylmethyl)-3-methyl-1-(5-methyl-4-pyridin-2-ylpyrimidin-2-yl)-1H-pyrazole-4-carboxamide | 443.35 | 1.39 | * |

TABLE I-continued

Representative 5-Membered Heterocyclic Amides and Related Compounds

| Compound | | Name | MS | RT | IC$_{50}$ |
|---|---|---|---|---|---|
| 122 | | N-(adamantan-1-ylmethyl)-3-methyl-1-(5'-methyl-2,4'-bipyrimidin-2'-yl)-1H-pyrazole-4-carboxamide | 444.35 | 1.35 | * |
| 123 | | N-(adamantan-1-ylmethyl)-1-(4-amino-5-methylpyrimidin-2-yl)-3-(trifluoromethyl)-1H-pyrazole-4-carboxamide | 435.30 | 1.35 | * |
| 124 | | N-(adamantan-1-ylmethyl)-1-(5-methylpyridin-2-yl)-3-(trifluoromethyl)-1H-pyrazole-4-carboxamide | 419.29 | 1.43 | * |
| 125 | | N-(adamantan-1-ylmethyl)-1-(5-bromopyrimidin-2-yl)-3-methyl-1H-pyrazole-4-carboxamide | 430.22 | 1.38 | * |

TABLE I-continued

Representative 5-Membered Heterocyclic Amides and Related Compounds

| | Compound | Name | MS | RT | IC$_{50}$ |
|---|---|---|---|---|---|
| 126 | | N-(adamantan-1-ylmethyl)-1-(4-amino-5-fluoropyrimidin-2-yl)-3-isopropyl-1H-pyrazole-4-carboxamide | 413.35 | 1.36 | * |
| 127 | | N-(adamantan-1-ylmethyl)-1-(5-fluoropyrimidin-2-yl)-3-isopropyl-1H-pyrazole-4-carboxamide | 398.32 | 1.38 | * |
| 128 | | N-(adamantan-1-ylmethyl)-1-(6-amino-5-methylpyrimidin-4-yl)-3-(trifluoromethyl)-1H-pyrazole-4-carboxamide | 435.27 | 1.37 | * |
| 129 | | N-(adamantan-1-ylmethyl)-1-pyrimidin-2-yl-3-(trifluoromethyl)-1H-pyrazole-4-carboxamide | 406.24 | 1.34 | * |
| 130 | | N-(adamantan-1-ylmethyl)-1-(4-aminopyrimidin-2-yl)-3-(trifluoromethyl)-1H-pyrazole-4-carboxamide | 421.24 | 1.33 | * |

TABLE I-continued

Representative 5-Membered Heterocyclic Amides and Related Compounds

| | Compound | Name | MS | RT | IC$_{50}$ |
|---|---|---|---|---|---|
| 131 | | N-(adamantan-1-ylmethyl)-1-(3-aminopyridin-2-yl)-3-(trifluoromethyl)-1H-pyrazole-4-carboxamide | 420.25 | 1.37 | * |
| 132 | | N-(adamantan-1-ylmethyl)-1-(3-methylpyridin-2-yl)-3-(trifluoromethyl)-1H-pyrazole-4-carboxamide | 419.26 | 1.38 | * |
| 133 | | N-(adamantan-1-ylmethyl)-3-isopropyl-1-(1,3-thiazol-2-yl)-1H-pyrazole-4-carboxamide | 385.30 | 1.43 | * |
| 134 | | N-(adamantan-1-ylmethyl)-3-(trifluoromethyl)-1H-pyrazole-4-carboxamide | 328.26 | 1.32 | * |
| 135 | | N-(adamantan-1-ylmethyl)-1-(1,3-thiazol-2-yl)-3-(trifluoromethyl)-1H-pyrazole-4-carboxamide | 411.23 | 1.39 | * |

TABLE I-continued

Representative 5-Membered Heterocyclic Amides and Related Compounds

| | Compound | Name | MS | RT | IC$_{50}$ |
|---|---|---|---|---|---|
| 136 | | N-(adamantan-1-ylmethyl)-1-pyrazin-2-yl-3-(trifluoromethyl)-1H-pyrazole-4-carboxamide | 406.27 | 1.37 | * |
| 137 | | N-(adamantan-1-ylmethyl)-1-(6-aminopyrazin-2-yl)-3-(trifluoromethyl)-1H-pyrazole-4-carboxamide | 421.28 | 1.36 | * |
| 138 | | 1-(4-amino-5-fluoropyrimidin-2-yl)-N-{[1-(6-methylpyridin-3-yl)cyclohexyl]methyl}-3-(trifluoromethyl)-1H-pyrazole-4-carboxamide | 478.29 | 1.12 | * |
| 139 | | 1-(4-amino-5-fluoropyrimidin-2-yl)-N-(4-methyl-2-pyridin-3-ylpentyl)-3-(trifluoromethyl)-1H-pyrazole-4-carboxamide | 452.27 | 1.13 | * |

TABLE I-continued

Representative 5-Membered Heterocyclic Amides and Related Compounds

| | Compound | Name | MS | RT | IC$_{50}$ |
|---|---|---|---|---|---|
| 140 | | 1-(4-amino-5-fluoropyrimidin-2-yl)-N-[2-(4-chlorophenyl)-4-methylpentyl]-3-(trifluoromethyl)-1H-pyrazole-4-carboxamide | 485.24 | 1.36 | * |
| 141 | | 1-(4-amino-5-fluoropyrimidin-2-yl)-N-{[1-(4-chlorophenyl)cyclohexyl]methyl}-3-(trifluoromethyl)-1H-pyrazole-4-carboxamide | 497.24 | 1.37 | * |
| 142 | | N-(adamantan-1-ylmethyl)-1-(1-methyl-1H-imidazol-2-yl)-3-(trifluoromethyl)-1H-pyrazole-4-carboxamide | 408.28 | 1.34 | * |
| 143 | | N-(adamantan-1-ylmethyl)-3-isopropyl-1-(6-methoxypyridazin-3-yl)-1H-pyrazole-4-carboxamide | 410.34 | 1.40 | * |

TABLE I-continued

Representative 5-Membered Heterocyclic Amides and Related Compounds

| | Compound | Name | MS | RT | IC$_{50}$ |
|---|---|---|---|---|---|
| 144 | | 1-(4-amino-5-fluoropyrimidin-2-yl)-N-[(1-morpholin-4-ylcyclohexyl)methyl]-3-(trifluoromethyl)-1H-pyrazole-4-carboxamide | 472.25 | 1.07 | * |
| 145 | | N-(adamantan-1-ylmethyl)-3-cyclopropyl-1-pyrimidin-2-yl-1H-pyrazole-4-carboxamide | 378.30 | 1.35 | * |
| 146 | | N-(adamantan-1-ylmethyl)-1-(4-aminopyrimidin-2-yl)-3-cyclopropyl-1H-pyrazole-4-carboxamide | 393.31 | 1.29 | * |
| 147 | | N-(adamantan-1-ylmethyl)-1-(3-aminopyrazin-2-yl)-3-(trifluoromethyl)-1H-pyrazole-4-carboxamide | 421.25 | 1.35 | * |
| 148 | | N-(adamantan-1-ylmethyl)-1-(5-aminopyrazin-2-yl)-3-(trifluoromethyl)-1H-pyrazole-4-carboxamide | 421.24 | 1.37 | * |

TABLE I-continued

Representative 5-Membered Heterocyclic Amides and Related Compounds

| | Compound | Name | MS | RT | IC$_{50}$ |
|---|---|---|---|---|---|
| 149 | | 1-(4-amino-5-fluoropyrimidin-2-yl)-N-[2-(4-chlorophenyl)propyl]-3-(trifluoromethyl)-1H-pyrazole-4-carboxamide | 465.15 | 1.28 | * |
| 150 | | 1-(4-amino-5-fluoropyrimidin-2-yl)-N-[2-(4-chlorophenyl)pentyl]-3-(trifluoromethyl)-1H-pyrazole-4-carboxamide | 471.18 | 1.34 | * |
| 151 | | N-[(1-pyridin-3-ylcyclohexyl)methyl]-1-pyrimidin-2-yl-3-(trifluoromethyl)-1H-pyrazole-4-carboxamide | 431.23 | 1.09 | * |
| 152 | | 1-(5-fluoropyrimidin-2-yl)-N-[(1-pyridin-3-ylcyclohexyl)methyl]-3-(trifluoromethyl)-1H-pyrazole-4-carboxamide | 449.23 | 1.09 | * |

TABLE I-continued

Representative 5-Membered Heterocyclic Amides and Related Compounds

| | Compound | Name | MS | RT | IC$_{50}$ |
|---|---|---|---|---|---|
| 153 | | N-(adamantan-1-ylmethyl)-1-(6-oxo-1,6-dihydropyrimidin-4-yl)-3-(trifluoromethyl)-1H-pyrazole-4-carboxamide | 422.21 | 1.33 | * |
| 154 | | 1-(4-amino-5-fluoropyrimidin-2-yl)-N-[(1-hydroxycycloheptyl)methyl]-3-(trifluoromethyl)-1H-pyrazole-4-carboxamide | 417.02 | 1.45 | * |
| 155 | | 1-(4-aminopyrimidin-2-yl)-N-[(1-pyridin-3-ylcyclohexyl)methyl]-3-(trifluoromethyl)-1H-pyrazole-4-carboxamide | 446.05 | 1.21 | * |
| 156 | | 1-(4-amino-5-methylpyrimidin-2-yl)-N-[(1-pyridin-3-ylcyclohexyl)methyl]-3-(trifluoromethyl)-1H-pyrazole-4-carboxamide | 460.06 | 1.26 | * |

TABLE I-continued

Representative 5-Membered Heterocyclic Amides and Related Compounds

| | Compound | Name | MS | RT | IC$_{50}$ |
|---|---|---|---|---|---|
| 157 | | 1-(3-aminopyrazin-2-yl)-N-[(1-pyridin-3-ylcyclohexyl)methyl]-3-(trifluoromethyl)-1H-pyrazole-4-carboxamide | 446.04 | 1.28 | * |
| 158 | | N-{[1-(6-methylpyridin-3-yl)cyclohexyl]methyl}-2-pyrimidin-2-yl-4-(trifluoromethyl)-1,3-thiazole-5-carboxamide | 462.16 | 1.11 | * |
| 159 | | N-[(1-morpholin-4-ylcyclohexyl)methyl]-2-pyrimidin-2-yl-4-(trifluoromethyl)-1,3-thiazole-5-carboxamide | 456.21 | 1 | * |
| 160 | | N-[2-(4-chlorophenyl)pentyl]-2-pyrimidin-2-yl-4-(trifluoromethyl)-1,3-thiazole-5-carboxamide | 455.10 | 1.34 | * |

TABLE I-continued

Representative 5-Membered Heterocyclic Amides and Related Compounds

| | Compound | Name | MS | RT | IC$_{50}$ |
|---|---|---|---|---|---|
| 161 | | N-[(1-pyridin-3-ylcyclohexyl)methyl]-2-pyrimidin-2-yl-4-(trifluoromethyl)-1,3-thiazole-5-carboxamide | 448.19 | 1.1 | * |
| 162 | Chiral | N-({1-[(3R)-3-aminopyrrolidin-1-yl]cyclohexyl}methyl)-2-pyrimidin-2-yl-4-(trifluoromethyl)-1,3-thiazole-5-carboxamide | 455.18 | 1.02 | * |
| 163 | Chiral | 2-[(3R)-3-(dimethylamino)pyrrolidin-1-yl]-N-{4-methyl-2-[4-(trifluoromethyl)phenyl]pentyl}-4-(trifluoromethyl)-1,3-thiazole-5-carboxamide | 537.27 | 1.28 | * |
| 164 | | 2-pyridin-3-yl-N-[(1-pyridin-3-ylcyclohexyl)methyl]-4-(trifluoromethyl)-1,3-thiazole-5-carboxamide | 447.20 | 1.13 | * |

TABLE I-continued

Representative 5-Membered Heterocyclic Amides and Related Compounds

| | Compound | Name | MS | RT | IC$_{50}$ |
|---|---|---|---|---|---|
| 165 | 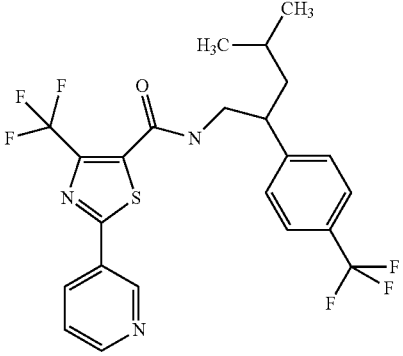 [SMILES: CC(C)CC(CNC(=O)c1sc(-c2cccnc2)nc1C(F)(F)F)c1ccc(C(F)(F)F)cc1] | N-{4-methyl-2-[4-(trifluoromethyl)phenyl]pentyl}-2-pyridin-3-yl-4-(trifluoromethyl)-1,3-thiazole-5-carboxamide | 502.20 | 1.38 | * |
| 166 | 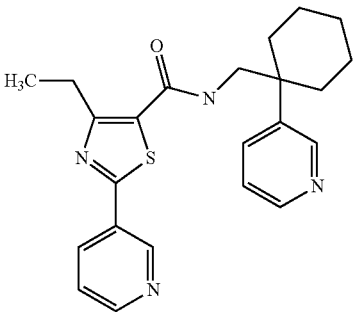 [SMILES: CCc1nc(-c2cccnc2)sc1C(=O)NCC1(c2cccnc2)CCCCC1] | 4-ethyl-2-pyridin-3-yl-N-[(1-pyridin-3-ylcyclohexyl)methyl]-1,3-thiazole-5-carboxamide | 407.21 | 1.11 | * |
| 167 | 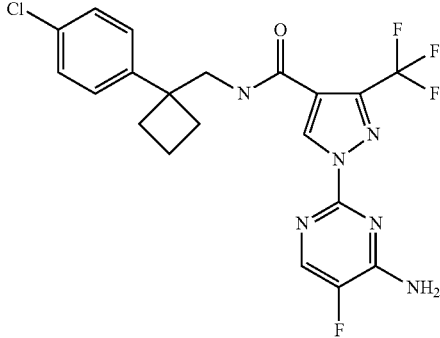 [SMILES: Nc1nc(-n2cc(C(=O)NCC3(c4ccc(Cl)cc4)CCC3)c(C(F)(F)F)n2)ncc1F] | 1-(4-amino-5-fluoropyrimidin-2-yl)-N-{[1-(4-chlorophenyl)cyclobutyl]methyl}-3-(trifluoromethyl)-1H-pyrazole-4-carboxamide | 469.18 | 1.27 | * |
| 168 | 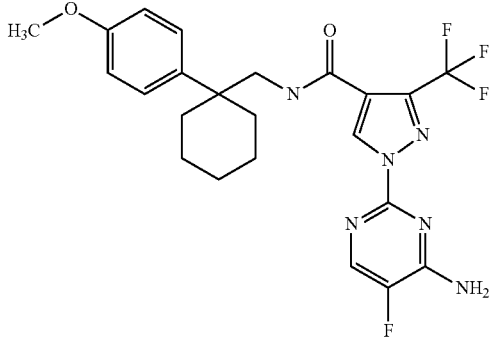 [SMILES: COc1ccc(C2(CNC(=O)c3cn(-c4ncc(F)c(N)n4)nc3C(F)(F)F)CCCCC2)cc1] | 1-(4-amino-5-fluoropyrimidin-2-yl)-N-{[1-(4-methoxyphenyl)cyclohexyl]methyl}-3-(trifluoromethyl)-1H-pyrazole-4-carboxamide | 493.27 | 1.28 | * |

TABLE I-continued

Representative 5-Membered Heterocyclic Amides and Related Compounds

| | Compound | Name | MS | RT | IC$_{50}$ |
|---|---|---|---|---|---|
| 169 | | N-(2-adamantan-1-yl-2-hydroxyethyl)-1-(4-amino-5-fluoropyrimidin-2-yl)-3-(trifluoromethyl)-1H-pyrazole-4-carboxamide | 469.26 | 1.25 | * |
| 170 | | 1-(4-amino-5-methylpyrimidin-2-yl)-3-methyl-N-({1-[4-(trifluoromethyl)phenyl]cyclohexyl}methyl)-1H-pyrazole-4-carboxamide | 473.29 | 1.27 | * |
| 171 | | 1-(4-amino-5-methylpyrimidin-2-yl)-N-{4-methyl-2-[4-(trifluoromethyl)phenyl]pentyl}-3-(trifluoromethyl)-1H-pyrazole-4-carboxamide | 515.19 | 1.36 | * |
| 172 | | 1-(4-amino-5-methylpyrimidin-2-yl)-3-(trifluoromethyl)-N-({1-[4-(trifluoromethyl)phenyl]cyclohexyl}methyl)-1H-pyrazole-4-carboxamide | 527.19 | 1.37 | * |

TABLE I-continued

Representative 5-Membered Heterocyclic Amides and Related Compounds

| | Compound | Name | MS | RT | IC$_{50}$ |
|---|---|---|---|---|---|
| 173 | | 1-(4-aminopyrimidin-2-yl)-3-methyl-N-{4-methyl-2-[4-(trifluoromethyl)phenyl]pentyl}-1H-pyrazole-4-carboxamide | 447.22 | 1.32 | * |
| 174 | | 3-methyl-N-{4-methyl-2-[4-(trifluoromethyl)phenyl]pentyl}-1-pyrazin-2-yl-1H-pyrazole-4-carboxamide | 432.19 | 1.38 | * |
| 175 | | 1-(4-aminopyrimidin-2-yl)-3-methyl-N-({1-[4-(trifluoromethyl)phenyl]cyclohexyl}methyl)-1H-pyrazole-4-carboxamide | 459.21 | 1.32 | * |
| 176 | | 1-(4-amino-5-methylpyrimidin-2-yl)-3-tert-butyl-N-{4-methyl-2-[4-(trifluoromethyl)phenyl]pentyl}-1H-pyrazole-4-carboxamide | 560.85 | 1.35 | * |

TABLE I-continued

Representative 5-Membered Heterocyclic Amides and Related Compounds

| | Compound | Name | MS | RT | IC$_{50}$ |
|---|---|---|---|---|---|
| 177 | | 1-(4-amino-5-methylpyrimidin-2-yl)-3-tert-butyl-N-({1-[4-(trifluoromethyl)phenyl]cyclohexyl}methyl)-1H-pyrazole-4-carboxamide | 515.26 | 1.33 | * |
| 178 | | 3-methyl-N-{4-methyl-2-[4-(trifluoromethyl)phenyl]pentyl}-1-pyrimidin-2-yl-1H-pyrazole-4-carboxamide | 432.19 | 1.35 | * |
| 179 | | 1-(3-aminopyrazin-2-yl)-3-methyl-N-{4-methyl-2-[4-(trifluoromethyl)phenyl]pentyl}-1H-pyrazole-4-carboxamide | 447.20 | 1.38 | * |
| 180 | | 1-(6-aminopyrazin-2-yl)-3-methyl-N-{4-methyl-2-[4-(trifluoromethyl)phenyl]pentyl}-1H-pyrazole-4-carboxamide | 447.21 | 1.36 | * |

TABLE I-continued

Representative 5-Membered Heterocyclic Amides and Related Compounds

| | Compound | Name | MS | RT | IC$_{50}$ |
|---|---|---|---|---|---|
| 181 | | 3-methyl-1-pyrimidin-2-yl-N-({1-[4-(trifluoromethyl)phenyl]cyclohexyl]methyl)-1H-pyrazole-4-carboxamide | 444.19 | 1.36 | * |
| 182 | | 1-(3-aminopyrazin-2-yl)-3-methyl-N-({1-[4-(trifluoromethyl)phenyl]cyclohexyl}methyl)-1H-pyrazole-4-carboxamide | 459.19 | 1.40 | * |
| 183 | | 1-(6-aminopyrazin-2-yl)-3-methyl-N-({1-[4-(trifluoromethyl)phenyl]cyclohexyl}methyl)-1H-pyrazole-4-carboxamide | 459.20 | 1.37 | * |
| 184 | | 3-methyl-1-pyrazin-2-yl-N-({1-[4-(trifluoromethyl)phenyl]cyclohexyl}methyl)-1H-pyrazole-4-carboxamide | 444.19 | 1.40 | * |

TABLE I-continued

Representative 5-Membered Heterocyclic Amides and Related Compounds

| Compound | Name | MS | RT | IC$_{50}$ |
|---|---|---|---|---|
| 185 | 1-(4-methoxypyrimidin-2-yl)-N-[(1-pyridin-3-ylcyclohexyl)methyl]-3-(trifluoromethyl)-1H-pyrazole-4-carboxamide | 461.24 | 1.13 | * |
| 186 | 1-(3-methylpyrazin-2-yl)-N-[(1-pyridin-3-ylcyclohexyl)methyl]-3-(trifluoromethyl)-1H-pyrazole-4-carboxamide | 445.25 | 1.15 | * |
| 187 | 1-(6-methylpyrazin-2-yl)-N-[(1-pyridin-3-ylcyclohexyl)methyl]-3-(trifluoromethyl)-1H-pyrazole-4-carboxamide | 445.25 | 1.16 | * |
| 188 | 1-(3-ethylpyrazin-2-yl)-N-[(1-pyridin-3-ylcyclohexyl)methyl]-3-(trifluoromethyl)-1H-pyrazole-4-carboxamide | 459.25 | 1.18 | * |
| 189 | 1-(3,6-dimethylpyrazin-2-yl)-N-[(1-pyridin-3-ylcyclohexyl)methyl]-3-(trifluoromethyl)-1H-pyrazole-4-carboxamide | 459.25 | 1.17 | |

TABLE I-continued

Representative 5-Membered Heterocyclic Amides and Related Compounds

| Compound | Name | MS | RT | IC$_{50}$ |
|---|---|---|---|---|
| 190 | 1-(4-amino-5-methylpyrimidin-2-yl)-N-{[1-(4-fluorophenyl)cyclohexyl]methyl}-3-(trifluoromethyl)-1H-pyrazole-4-carboxamide | 477.18 | 1.34 | * |
| 191 | 1-(5-methoxypyrimidin-2-yl)-N-[(1-pyridin-3-ylcyclohexyl)methyl]-3-(trifluoromethyl)-1H-pyrazole-4-carboxamide | 461.18 | 1.12 | * |
| 192 | 1-(5-chloropyrimidin-2-yl)-N-[(1-pyridin-3-ylcyclohexyl)methyl]-3-(trifluoromethyl)-1H-pyrazole-4-carboxamide | 465.13 | 1.14 | * |
| 193 | N-(2-adamantan-1-ylethyl)-1-pyrimidin-2-yl-3-(trifluoromethyl)-1H-pyrazole-4-carboxamide | 420.22 | 1.37 | * |

TABLE I-continued

Representative 5-Membered Heterocyclic Amides and Related Compounds

| | Compound | Name | MS | RT | IC$_{50}$ |
|---|---|---|---|---|---|
| 194 | | N-{[(2R)-6,6-dimethylbicyclo[3.1.1]hept-2-yl]methyl}-1-pyrimidin-2-yl-3-(trifluoromethyl)-1H-pyrazole-4-carboxamide | 394.20 | 1.33 | * |
| 195 | | N-{[1-(4-chlorophenyl)cyclohexyl]methyl}-1-pyrimidin-2-yl-3-(trifluoromethyl)-1H-pyrazole-4-carboxamide | 464.16 | 1.37 | * |
| 196 | | 1-pyrimidin-2-yl-3-(trifluoromethyl)-N-({1-[4-(trifluoromethyl)phenyl]cyclohexyl]methyl)-1H-pyrazole-4-carboxamide | 498.18 | 1.36 | * |
| 197 | | N-{[4-(4-chlorophenyl)tetrahydro-2H-pyran-4-yl]methyl}-1-pyrimidin-2-yl-3-(trifluoromethyl)-1H-pyrazole-4-carboxamide | 466.14 | 1.25 | * |
| 198 | | N-[(1-morpholin-4-ylcyclohexyl)methyl]-1-pyrimidin-2-yl-3-(trifluoromethyl)-1H-pyrazole-4-carboxamide | 439.22 | 1.05 | * |

TABLE I-continued

Representative 5-Membered Heterocyclic Amides and Related Compounds

| Compound | | Name | MS | RT | IC$_{50}$ |
|---|---|---|---|---|---|
| 199 | | N-{[1-(4-methoxyphenyl)cyclohexyl]methyl}-1-pyrimidin-2-yl-3-(trifluoromethyl)-1H-pyrazole-4-carboxamide | 460.20 | 1.33 | * |
| 200 | | N-{4-methyl-2-[4-(trifluoromethyl)phenyl]pentyl}-1-pyrimidin-2-yl-3-(trifluoromethyl)-1H-pyrazole-4-carboxamide | 486.18 | 1.36 | * |
| 201 | | N-[2-(4-chlorophenyl)pentyl]-1-pyrimidin-2-yl-3-(trifluoromethyl)-1H-pyrazole-4-carboxamide | 438.15 | 1.33 | * |
| 202 | | N-[2-(4-chlorophenyl)propyl]-1-pyrimidin-2-yl-3-(trifluoromethyl)-1H-pyrazole-4-carboxamide | 410.13 | 1.28 | * |
| 203 | | N-(4-methyl-2-pyridin-3-ylpentyl)-1-pyrimidin-2-yl-3-(trifluoromethyl)-1H-pyrazole-4-carboxamide | 419.19 | 1.12 | * |

TABLE I-continued

Representative 5-Membered Heterocyclic Amides and Related Compounds

| | Compound | Name | MS | RT | IC$_{50}$ |
|---|---|---|---|---|---|
| 204 | | N-{[1-(4-chlorophenyl)cyclobutyl]methyl}-1-pyrimidin-2-yl-3-(trifluoromethyl)-1H-pyrazole-4-carboxamide | 436.12 | 1.33 | * |
| 205 | | N-(2-adamantan-1-yl-2-hydroxyethyl)-1-pyrimidin-2-yl-3-(trifluoromethyl)-1H-pyrazole-4-carboxamide | 436.21 | 1.30 | * |
| 206 | | N-(3-methylbutyl)-1-pyrimidin-2-yl-3-(trifluoromethyl)-1H-pyrazole-4-carboxamide | 328.17 | 1.22 | * |
| 207 | | N-(2-phenylbutyl)-1-pyrimidin-2-yl-3-(trifluoromethyl)-1H-pyrazole-4-carboxamide | 390.18 | 1.27 | * |
| 208 | | N-(2-phenylnonyl)-1-pyrimidin-2-yl-3-(trifluoromethyl)-1H-pyrazole-4-carboxamide | 460.23 | 1.42 | * |

TABLE I-continued

Representative 5-Membered Heterocyclic Amides and Related Compounds

| | Compound | Name | MS | RT | IC$_{50}$ |
|---|---|---|---|---|---|
| 209 | 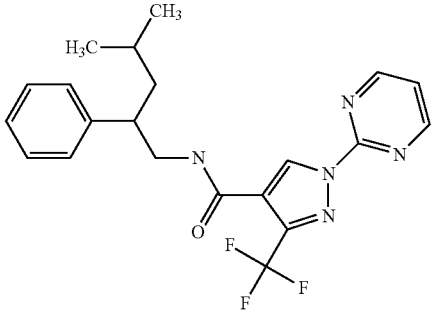 [SMILES: CC(C)CC(CNC(=O)c1cn(-c2ncccn2)nc1C(F)(F)F)c1ccccc1] | N-(4-methyl-2-phenylpentyl)-1-pyrimidin-2-yl-3-(trifluoromethyl)-1H-pyrazole-4-carboxamide | 418.20 | 1.32 | * |
| 210 | 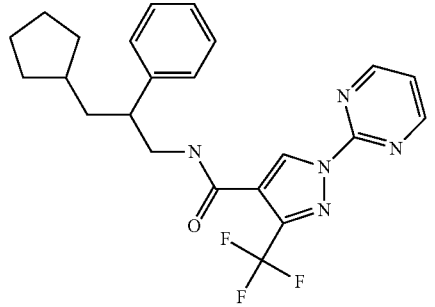 [SMILES: O=C(NCC(CC1CCCC1)c1ccccc1)c1cn(-c2ncccn2)nc1C(F)(F)F] | N-(3-cyclopentyl-2-phenylpropyl)-1-pyrimidin-2-yl-3-(trifluoromethyl)-1H-pyrazole-4-carboxamide | 444.21 | 1.36 | * |
| 211 | 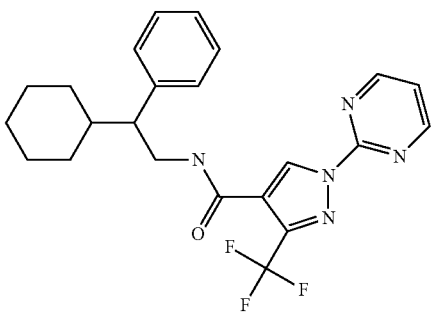 [SMILES: O=C(NCC(c1ccccc1)C1CCCCC1)c1cn(-c2ncccn2)nc1C(F)(F)F] | N-(2-cyclohexyl-2-phenylethyl)-1-pyrimidin-2-yl-3-(trifluoromethyl)-1H-pyrazole-4-carboxamide | 444.21 | 1.36 | * |
| 212 | 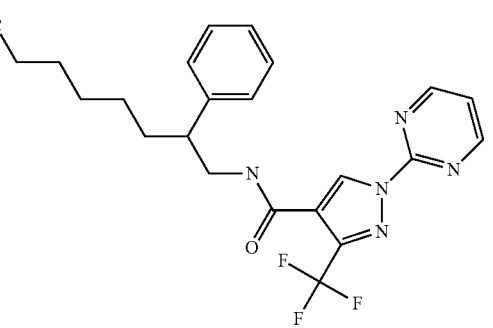 | N-(2-phenyloctyl)-1-pyrimidin-2-yl-3-(trifluoromethyl)-1H-pyrazole-4-carboxamide | 446.22 | 1.39 | * |

TABLE I-continued

Representative 5-Membered Heterocyclic Amides and Related Compounds

| Compound | | Name | MS | RT | IC$_{50}$ |
|---|---|---|---|---|---|
| 213 | | N-(3-cyclohexyl-2-phenypropyl)-1-pyrimidin-2-yl-3-(trifluoromethyl)-1H-pyrazole-4-carboxamide | 458.22 | 1.39 | * |
| 214 | | N-(4-cyclohexyl-2-phenylbutyl)-1-pyrimidin-2-yl-3-(trifluoromethyl)-1H-pyrazole-4-carboxamide | 472.24 | 1.42 | * |
| 215 | | N-(3-phenylbutyl)-1-pyrimidin-2-yl-3-(trifluoromethyl)-1H-pyrazole-4-carboxamide | 390.19 | 1.27 | * |
| 216 | | 1-pyrimidin-2-yl-3-(trifluoromethyl)-N-(3,3,5-trimethylcyclohexyl)-1H-pyrazole-4-carboxamide | 382.21 | 1.31 | * |

TABLE I-continued

Representative 5-Membered Heterocyclic Amides and Related Compounds

| Compound | | Name | MS | RT | IC$_{50}$ |
|---|---|---|---|---|---|
| 217 | | N-adamantan-2-yl-1-pyrimidin-2-yl-3-(trifluoromethyl)-1H-pyrazole-4-carboxamide | 392.18 | 1.32 | * |
| 218 | | N-[2-(2-bromophenyl)ethyl]-1-pyrimidin-2-yl-3-(trifluoromethyl)-1H-pyrazole-4-carboxamide | 440.05 | 1.26 | * |
| 219 | | 4-ethyl-N-[(1-pyridin-3-ylcyclohexyl)methyl]-2-pyrimidin-2-yl-1,3-thiazole-5-carboxamide | 408.18 | 1.1 | * |
| 220 | | 4-ethyl-N-{4-methyl-2-[4-(trifluoromethyl)phenyl]pentyl}-2-pyrimidin-2-yl-1,3-thiazole-5-carboxamide | 463.16 | 1.37 | * |
| 221 | | N-(3,4-dichlorobenzyl)-4-ethyl-2-pyrimidin-2-yl-1,3-thiazole-5-carboxamide | 393.03 | 1.3 | |

TABLE I-continued

Representative 5-Membered Heterocyclic Amides and Related Compounds

| Compound | | Name | MS | RT | IC$_{50}$ |
|---|---|---|---|---|---|
| 222 | | N-(2,3-dihydro-1H-inden-2-yl)-4-ethyl-2-pyrimidin-2-yl-1,3-thiazole-5-carboxamide | 351.13 | 1.26 | |
| 223 | | 4-ethyl-N-(4-methylcyclohexyl)-2-pyrimidin-2-yl-1,3-thiazole-5-carboxamide | 331.16 | 1.28 | |
| 224 | Chiral | 4-ethyl-N-[(1R)-1-phenylpropyl]-2-pyrimidin-2-yl-1,3-thiazole-5-carboxamide | 353.15 | 1.25 | |
| 225 | Chiral | 4-ethyl-N-[(1S)-1-phenylpropyl]-2-pyrimidin-2-yl-1,3-thiazole-5-carboxamide | 353.15 | 1.25 | |
| 226 | | N-(1,3-benzodioxol-5-ylmethyl)-4-ethyl-2-pyrimidin-2-yl-1,3-thiazole-5-carboxamide | 369.11 | 1.2 | |

TABLE I-continued

Representative 5-Membered Heterocyclic Amides and Related Compounds

| | Compound | Name | MS | RT | IC$_{50}$ |
|---|---|---|---|---|---|
| 227 | | N-(2,4-difluorobenzyl)-4-ethyl-2-pyrimidin-2-yl-1,3-thiazole-5-carboxamide | 361.10 | 1.23 | |
| 228 | | N-(3,4-difluorobenzyl)-4-ethyl-2-pyrimidin-2-yl-1,3-thiazole-5-carboxamide | 361.10 | 1.24 | |
| 229 | | 4-ethyl-2-pyrimidin-2-yl-N-[4-(trifluoromethoxy)benzyl]-1,3-thiazole-5-carboxamide | 409.10 | 1.28 | |
| 230 | | N-(2-chloro-6-methylbenzyl)-4-ethyl-2-pyrimidin-2-yl-1,3-thiazole-5-carboxamide | 373.10 | 1.27 | |

TABLE I-continued

Representative 5-Membered Heterocyclic Amides and Related Compounds

| | Compound | Name | MS | RT | IC$_{50}$ |
|---|---|---|---|---|---|
| 231 | | N-(2-chloro-4-fluorobenzyl)-4-ethyl-2-pyrimidin-2-yl-1,3-thiazole-5-carboxamide | 377.08 | 1.27 | * |
| 232 | | N-(2,4-dichlorobenzyl)-4-ethyl-2-pyrimidin-2-yl-1,3-thiazole-5-carboxamide | 393.04 | 1.31 | |
| 233 | | N-(2,4-dimethoxybenzyl)-4-ethyl-2-pyrimidin-2-yl-1,3-thiazole-5-carboxamide | 385.14 | 1.22 | |
| 234 | | N-(3,5-dimethoxybenzyl)-4-ethyl-2-pyrimidin-2-yl-1,3-thiazole-5-carboxamide | 385.15 | 1.21 | |

TABLE I-continued

Representative 5-Membered Heterocyclic Amides and Related Compounds

| Compound | | Name | MS | RT | IC$_{50}$ |
|---|---|---|---|---|---|
| 235 | | N-(4-tert-butylcyclohexyl)-4-ethyl-2-pyrimidin-2-yl-1,3-thiazole-5-carboxamide | 373.21 | 1.37 | |
| 236 | | 4-ethyl-2-pyrimidin-2-yl-N-(3,3,5-trimethylcyclohexyl)-1,3-thiazole-5-carboxamide | 359.20 | 1.34 | * |
| 237 | Chiral | N-[(1S,2S)-2-(benzyloxy)cyclohexyl]-4-ethyl-2-pyrimidin-2-yl-1,3-thiazole-5-carboxamide | 423.18 | 1.27 | |
| 238 | Chiral | N-[(1R,2R)-2-(benzyloxy)cyclopentyl]-4-ethyl-2-pyrimidin-2-yl-1,3-thiazole-5-carboxamide | 409.18 | 1.28 | |
| 239 | | 4-ethyl-2-pyrimidin-2-yl-N-{1-[4-(trifluoromethyl)pyrimidin-2-yl]piperidin-4-yl}-1,3-thiazole-5-carboxamide | 464.14 | 1.3 | |

TABLE I-continued

Representative 5-Membered Heterocyclic Amides and Related Compounds

| | Compound | Name | MS | RT | IC$_{50}$ |
|---|---|---|---|---|---|
| 240 | | N-(1-benzylpiperidin-4-yl)-4-ethyl-2-pyrimidin-2-yl-1,3-thiazole-5-carboxamide | 408.20 | 1.09 | |
| 241 | | 4-ethyl-N-[2-fluoro-4-(trifluoromethyl)benzyl]-2-pyrimidin-2-yl-1,3-thiazole-5-carboxamide | 411.10 | 1.29 | |
| 242 | | N-(4-chloro-2-fluorobenzyl)-4-ethyl-2-pyrimidin-2-yl-1,3-thiazole-5-carboxamide | 377.08 | 1.27 | |
| 243 | | N-(2,5-dichlorobenzyl)-4-ethyl-2-pyrimidin-2-yl-1,3-thiazole-5-carboxamide | 393.04 | 1.29 | |

213 214

TABLE I-continued

Representative 5-Membered Heterocyclic Amides and Related Compounds

| | Compound | Name | MS | RT | $IC_{50}$ |
|---|---|---|---|---|---|
| 244 | | N-[3,5-bis(trifluoromethyl)benzyl]-4-ethyl-2-pyrimidin-2-yl-1,3-thiazole-5-carboxamide | 461.08 | 1.33 | |
| 245 | | N-(3,5-difluorobenzyl)-4-ethyl-2-pyrimidin-2-yl-1,3-thiazole-5-carboxamide | 361.11 | 1.24 | |
| 246 | | 4-ethyl--2-pyrimidin-2-yl-N-[3-(trifluoromethoxy)benzyl]-1,3-thiazole-5-carboxamide | 409.10 | 1.28 | |
| 247 | | N-(adamantan-1-ylmethyl)-4-ethyl-2-pyrimidin-2-yl-1,3-thiazole-5-carboxamide | 383.20 | 1.36 | * |
| 248 | | N-{[(2R)-6,6-dimethylbicyclo[3.1.1]hept-2-yl]methyl}-4-ethyl-2-pyrimidin-2-yl-1,3-thiazole-5-carboxamide | 371.20 | 1.35 | * |

TABLE I-continued

Representative 5-Membered Heterocyclic Amides and Related Compounds

| Compound | | Name | MS | RT | IC$_{50}$ |
|---|---|---|---|---|---|
| 249 | 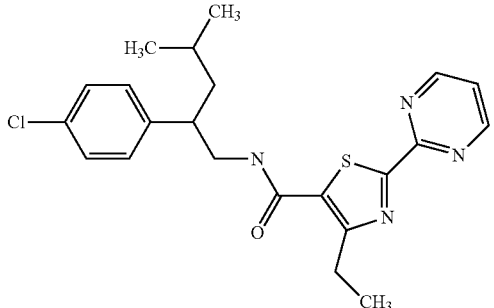 [SMILES: CCc1nc(-c2ncccn2)sc1C(=O)NCC(CC(C)C)c1ccc(Cl)cc1] | N-[2-(4-chlorophenyl)-4-methylpentyl]-4-ethyl-2-pyrimidin-2-yl-1,3-thiazole-5-carboxamide | 429.14 | 1.37 | * |
| 250 | 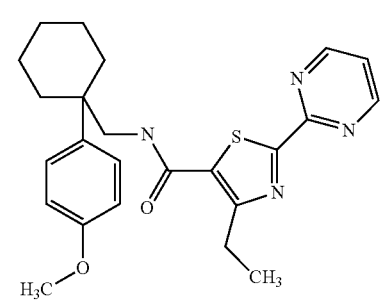 [SMILES: CCc1nc(-c2ncccn2)sc1C(=O)NCC1(c2ccc(OC)cc2)CCCCC1] | 4-ethyl-N-{[1-(4-methoxyphenyl)cyclohexyl]methyl)-2-pyrimidin-2-yl-1,3-thiazole-5-carboxamide | 437.20 | 1.35 | * |
| 251 | 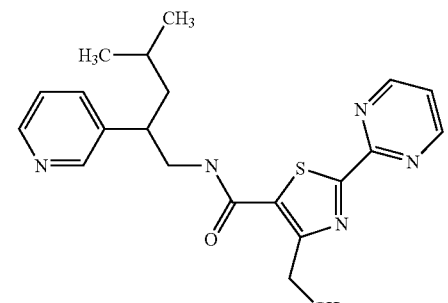 | 4-ethyl-N-(4-methyl-2-pyridin-3-ylpentyl)-2-pyrimidin-2-yl-1,3-thiazole-5-carboxamide | 396.20 | 1.13 | |
| 252 | 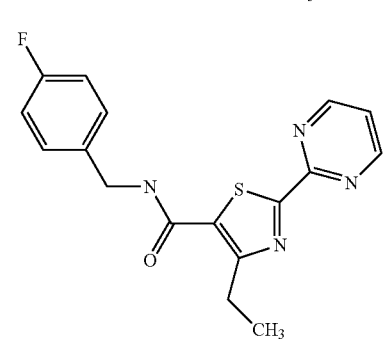 | 4-ethyl-N-(4-fluorobenzyl)-2-pyrimidin-2-yl-1,3-thiazole-5-carboxamide | 343.12 | 1.22 | |
| 253 | 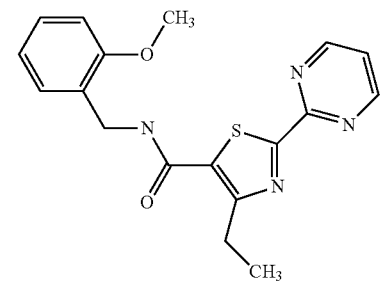 [SMILES: CCc1nc(-c2ncccn2)sc1C(=O)NCc1ccccc1OC] | 4-ethyl-N-(2-methoxybenzyl)-2-pyrimidin-2-yl-1,3-thiazole-5-carboxamide | 355.14 | 1.22 | |

TABLE I-continued

Representative 5-Membered Heterocyclic Amides and Related Compounds

| | Compound | Name | MS | RT | IC$_{50}$ |
|---|---|---|---|---|---|
| 254 | | 4-ethyl-N-(4-methoxybenzyl)-2-pyrimidin-2-yl-1,3-thiazole-5-carboxamide | 355.14 | 1.2 | |
| 255 | | N-(2-chlorobenzyl)-4-ethyl-2-pyrimidin-2-yl-1,3-thiazole-5-carboxamide | 359.09 | 1.24 | |
| 256 | | N-(4-chlorobenzyl)-4-ethyl-2-pyrimidin-2-yl-1,3-thiazole-5-carboxamide | 359.09 | 1.26 | |
| 257 | | 4-ethyl-2-pyrimidin-2-yl-N-[2-(trifluoromethyl)benzyl]-1,3-thiazole-5-carboxamide | 393.11 | 1.26 | |

TABLE I-continued

Representative 5-Membered Heterocyclic Amides and Related Compounds

| Compound | Name | MS | RT | IC$_{50}$ |
|---|---|---|---|---|
| 258 | 4-ethyl-N-(4-methyl-2-phenylpentyl)-2-pyrimidin-2-yl-1,3-thiazole-5-carboxamide | 395.20 | 1.33 | * |
| 259 | 4-ethyl-2-pyrimidin-2-yl-N-[2-(trifluoromethoxy)benzyl]-1,3-thiazole-5-carboxamide | 409.09 | 1.27 | |
| 260 | N-[3-(difluoromethoxy)benzyl]-4-ethyl-2-pyrimidin-2-yl-1,3-thiazole-5-carboxamide | 391.11 | 1.22 | |
| 261 | N-[2-(3,4-dichlorophenyl)ethyl]-4-ethyl-2-pyrimidin-2-yl-1,3-thiazole-5-carboxamide | 407.05 | 1.31 | |
| 262 | 4-ethyl-N-(2-pyridin-4-ylethyl)-2-pyrimidin-2-yl-1,3-thiazole-5-carboxamide | 340.14 | 1 | |

TABLE I-continued

Representative 5-Membered Heterocyclic Amides and Related Compounds

| | Compound | Name | MS | RT | IC$_{50}$ |
|---|---|---|---|---|---|
| 263 | | ethyl N-[(4-ethyl-2-pyrimidin-2-yl-1,3-thiazol-5-yl)carbonyl]-beta-alaninate | 335.13 | 1.15 | |
| 264 | | 4-ethyl-N-(2-morpholin-4-ylbenzyl)-2-pyrimidin-2-yl-1,3-thiazole-5-carboxamide | 410.16 | 1.21 | |
| 265 | | N-(3,3-dimethylbutyl)-4-ethyl-2-pyrimidin-2-yl-1,3-thiazole-5-carboxamide | 319.17 | 1.28 | |
| 266 | | N-(cycloheptylmethyl)-4-ethyl-2-pyrimidin-2-yl-1,3-thiazole-5-carboxamide | 345.19 | 1.31 | |
| 267 | | N-[3-(dimethylamino)-1-methyl-3-oxopropyl]-4-ethyl-2-pyrimidin-2-yl-1,3-thiazole-5-carboxamide | 348.16 | 1.1 | |

TABLE I-continued

Representative 5-Membered Heterocyclic Amides and Related Compounds

| | Compound | Name | MS | RT | IC$_{50}$ |
|---|---|---|---|---|---|
| 268 | | N-[3-(diethylamino)-3-oxopropyl]-4-ethyl-2-pyrimidin-2-yl-1,3-thiazole-5-carboxamide | 362.18 | 1.16 | |
| 269 | | 4-ethyl-N-{[1-(4-methoxyphenyl)cyclopentyl]methyl}-2-pyrimidin-2-yl-1,3-thiazole-5-carboxamide | 423.18 | 1.33 | * |
| 270 | Chiral | N-[(1S)-1-benzyl-2-hydroxyethyl]-4-ethyl-2-pyrimidin-2-yl-1,3-thiazole-5-carboxamide | 369.20 | 1.18 | |
| 271 | | N-[1-(4-chlorobenzyl)-2-hydroxyethyl]-4-ethyl-2-pyrimidin-2-yl-1,3-thiazole-5-carboxamide | 403.16 | 1.23 | |
| 272 | Chiral | 4-ethyl-N-[(1R)-1-(hydroxymethyl)pentyl]-2-pyrimidin-2-yl-1,3-thiazole-5-carboxamide | 335.21 | 1.2 | |

TABLE I-continued

Representative 5-Membered Heterocyclic Amides and Related Compounds

| | Compound | Name | MS | RT | IC$_{50}$ |
|---|---|---|---|---|---|
| 273 | | 4-ethyl-N-[(1S)-1-(hydroxymethyl)-2,2-dimethylpropyl]-2-pyrimidin-2-yl-1,3-thiazole-5-carboxamide | 335.21 | 1.18 | |
| 274 | | 4-ethyl-N-(2-hydroxy-3,3-dimethylbutyl)-2-pyrimidin-2-yl-1,3-thiazole-5-carboxamide | 335.21 | 1.2 | |
| 275 | | 4-ethyl-N-[4-methyl-2-(4-methylphenyl)pentyl]-2-pyrimidin-2-yl-1,3-thiazole-5-carboxamide | 409.25 | 1.37 | * |
| 276 | | N-{[1-(4-chlorophenyl)cyclohexyl]methyl}-4-ethyl-2-pyrimidin-2-yl-1,3-thiazole-5-carboxamide | 441.20 | 1.38 | * |
| 277 | | N-[2-(4-chlorophenyl)pentyl]-4-ethyl-2-pyrimidin-2-yl-1,3-thiazole-5-carboxamide | 415.16 | 1.35 | * |

TABLE I-continued

Representative 5-Membered Heterocyclic Amides and Related Compounds

| | Compound | Name | MS | RT | IC$_{50}$ |
|---|---|---|---|---|---|
| 278 | 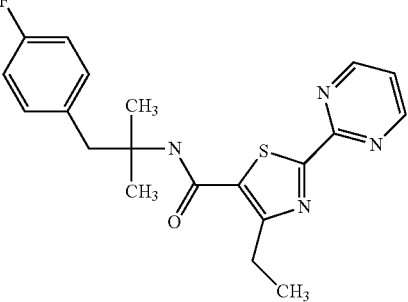 | 4-ethyl-N-[2-(4-fluorophenyl)-1,1-dimethylethyl]-2-pyrimidin-2-yl-1,3-thiazole-5-carboxamide | 385.19 | 1.29 | |
| 279 | 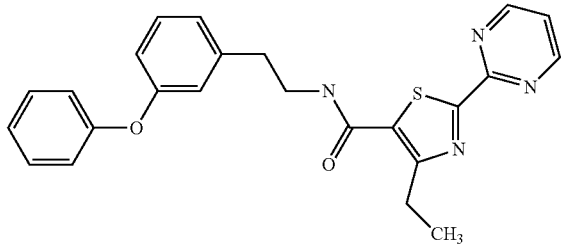 [SMILES: CCc1nc(-c2ncccn2)sc1C(=O)NCCc1cccc(Oc2ccccc2)c1] | 4-ethyl-N-[2-(3-phenoxyphenyl)ethyl]-2-pyrimidin-2-yl-1,3-thiazole-5-carboxamide | 431.17 | 1.32 | |
| 280 | 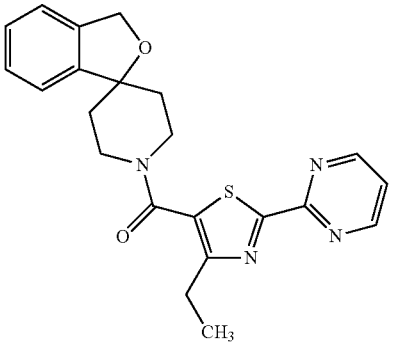 [SMILES: CCc1nc(-c2ncccn2)sc1C(=O)N1CCC2(CC1)OCc1ccccc12] | 1'-[(4-ethyl-2-pyrimidin-2-yl-1,3-thiazol-5-yl)carbonyl]-3H-spiro[2-benzofuran-1,4'-piperidine] | 407.17 | 1.28 | |
| 281 | 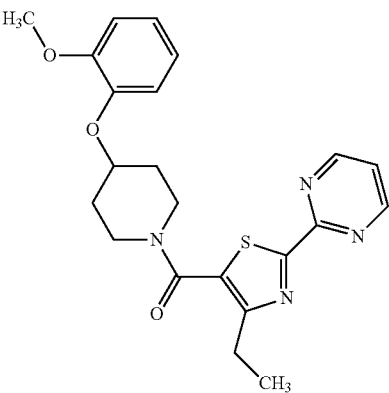 [SMILES: CCc1nc(-c2ncccn2)sc1C(=O)N1CCC(Oc2ccccc2OC)CC1] | 2-(4-ethyl-5-{[4-(2-methoxyphenoxy)piperidin-1-yl]carbonyl}-1,3-thiazol-2-yl)pyrimidine | 425.18 | 1.24 | |

TABLE I-continued

Representative 5-Membered Heterocyclic Amides and Related Compounds

| Compound | Name | MS | RT | IC$_{50}$ |
|---|---|---|---|---|
| 282 | 2-(5-{[2-(1,3-benzodioxol-5-yl)piperidin-1-yl]carbonyl}-4-ethyl-1,3-thiazol-2-yl)pyrimidine | 423.16 | 1.29 | |
| 283 | 4-{1-[(4-ethyl-2-pyrimidin-2-yl-1,3-thiazol-5-yl)carbonyl]piperidin-4-yl}morpholine | 388.22 | 0.64 | |
| 284 | 5-[(4-ethyl-2-pyrimidin-2-yl-1,3-thiazol-5-yl)carbonyl]-2-methyl-4,5,6,7-tetrahydro-2H-pyrazolo[4,3-c]pyridine | 355.16 | 1.1 | |
| 285 | N-{[1-(4-methoxyphenyl)cyclopentyl]methyl}-2-pyrimidin-2-yl-4-(trifluoromethyl)-1,3-thiazole-5-carboxamide | 463.17 | 1.31 | * |
| 286 | N-[2-(4-chlorophenyl)-2-pyrrolidin-1-ylethyl]-2-pyrimidin-2-yl-4-(trifluoromethyl)-1,3-thiazole-5-carboxamide | 482.14 | 1.13 | * |

TABLE I-continued

Representative 5-Membered Heterocyclic Amides and Related Compounds

| | Compound | Name | MS | RT | IC$_{50}$ |
|---|---|---|---|---|---|
| 287 | | N-{[1-(6-chloropyridin-3-yl)cyclopentyl]methyl}-2-pyrimidin-2-yl-4-(trifluoromethyl)-1,3-thiazole-5-carboxamide | 468.09 | 1.26 | * |
| 288 | | N-{[1-(6-chloropyridin-3-yl)cyclopentyl]methyl}-4-ethyl-2-pyrimidin-2-yl-1,3-thiazole-5-carboxamide | 428.15 | 1.26 | * |
| 289 | | 4-methyl-N-[(1-pyridin-3-ylcyclohexyl)methyl]-2-pyrimidin-2-yl-1,3-thiazole-5-carboxamide | 394.23 | 1.08 | * |
| 290 | | 4-methyl-N-{4-methyl-2-[4-(trifluoromethyl)phenyl]pentyl}-2-pyrimidin-2-yl-1,3-thiazole-5-carboxamide | 449.16 | 1.36 | * |

TABLE I-continued

Representative 5-Membered Heterocyclic Amides and Related Compounds

| | Compound | Name | MS | RT | IC$_{50}$ |
|---|---|---|---|---|---|
| 291 | | N-{[1-(6-chloropyridin-3-yl)cyclohexyl]methyl}-2-pyrimidin-2-yl-4-(trifluoromethyl)-1,3-thiazole-5-carboxamide | 482.11 | 1.28 | * |
| 292 | | N-[2-(6-chloropyridin-3-yl)-4-methylpentyl]-2-pyrimidin-2-yl-4-(trifluoromethyl)-1,3-thiazole-5-carboxamide | 470.12 | 1.28 | * |
| 293 | | 2-(2-oxopyridin-1(2H)-yl)-N-[(1-pyridin-3-ylcyclohexyl)methyl]-4-(trifluoromethyl)-1,3-thiazole-5-carboxamide | 463.14 | 1.16 | * |
| 294 | | 2-morpholin-4-yl-N-[(1-pyridin-3-ylcyclohexyl)methyl]-4-(trifluoromethyl)-1,3-thiazole-5-carboxamide | 455.20 | 1.12 | * |

TABLE I-continued

Representative 5-Membered Heterocyclic Amides and Related Compounds

| | Compound | Name | MS | RT | IC$_{50}$ |
|---|---|---|---|---|---|
| 295 | | 2-(4-hydroxypiperidin-1-yl)-N-[(1-pyridin-3-ylcyclohexyl)methyl]-4-(trifluoromethyl)-1,3-thiazole-5-carboxamide | 469.20 | 1.11 | * |
| 296 | | N-[(1-piperidin-1-ylcyclohexyl)methyl]-2-pyrimidin-2-yl-4-(trifluoromethyl)-1,3-thiazole-5-carboxamide | 454.21 | 1.1 | * |
| 297 | | N-{[1-(1-isopropyl-1H-pyrazol-4-yl)cyclohexyl]methyl}-2-pyrimidin-2-yl-4-(trifluoromethyl)-1,3-thiazole-5-carboxamide | 479.20 | 1.27 | * |
| 298 | | N-{[1-(6-chloropyridin-3-yl)cyclohexyl]methyl}-4-ethyl-2-pyrimidin-2-yl-1,3-thiazole-5-carboxamide | 442.17 | 1.27 | * |

TABLE I-continued

Representative 5-Membered Heterocyclic Amides and Related Compounds

| | Compound | Name | MS | RT | IC$_{50}$ |
|---|---|---|---|---|---|
| 299 | | N-[2-(6-chloropyridin-3-yl)-4-methylpentyl]-4-ethyl-2-pyrimidin-2-yl-1,3-thiazole-5-carboxamide | 430.17 | 1.28 | * |
| 300 | | 2-piperazin-1-yl-N-[(1-pyridin-3-ylcyclohexyl)methyl]-4-(trifluoromethyl)-1,3-thiazole-5-carboxamide | 454.22 | 1.04 | * |
| 301 | | tert-butyl {1-[5-{[(1-pyridin-3-ylcyclohexyl)methyl]carbamoyl}-4-(trifluoromethyl)-1,3-thiazol-2-yl]piperidin-4-yl}carbamate | 568.27 | 1.2 | * |
| 302 | | N-[(1-pyridin-3-ylcyclohexyl)methyl]-2-(4-pyrrolidin-1-ylpiperidin-1-yl)-4-(trifluoromethyl)-1,3-thiazole-5-carboxamide | 522.28 | 1.06 | * |

TABLE I-continued

Representative 5-Membered Heterocyclic Amides and Related Compounds

| | Compound | Name | MS | RT | IC$_{50}$ |
|---|---|---|---|---|---|
| 303 | 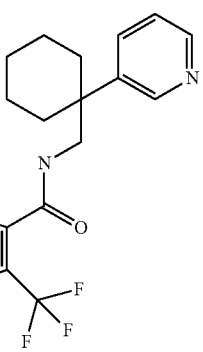 | 2-(4-aminopiperidin-1-yl)-N-[(1-pyridin-3-ylcyclohexyl)methyl]-4-(trifluoromethyl)-1,3-thiazole-5-carboxamide | 468.26 | 0.99 | * |
| 304 | 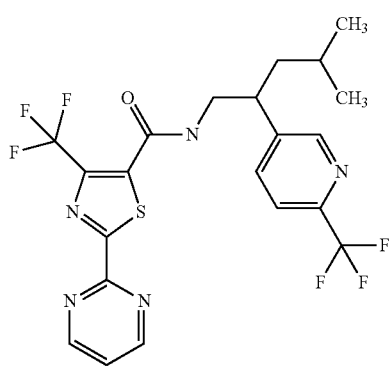 [SMILES: CC(C)CC(CNC(=O)c1sc(-c2ncccn2)nc1C(F)(F)F)c1ccc(C(F)(F)F)nc1] | N-{4-methyl-2-[6-(trifluoromethyl)pyridin-3-yl]pentyl}-2-pyrimidin-2-yl-4-(trifluoromethyl)-1,3-thiazole-5-carboxamide | 504.22 | 1.24 | * |
| 305 | 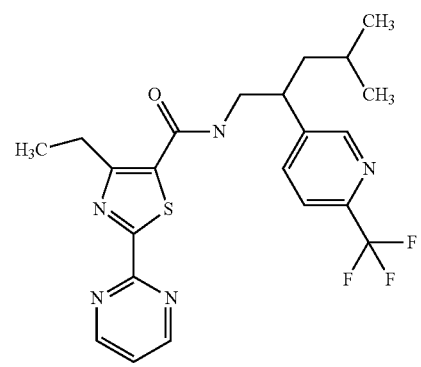 [SMILES: CCc1nc(-c2ncccn2)sc1C(=O)NCC(CC(C)C)c1ccc(C(F)(F)F)nc1] | 4-ethyl-N-{4-methyl-2-[6-(trifluoromethyl)pyridin-3-yl]pentyl}-2-pyrimidin-2-yl-1,3-thiazole-5-carboxamide | 464.25 | 1.24 | * |
| 306 | 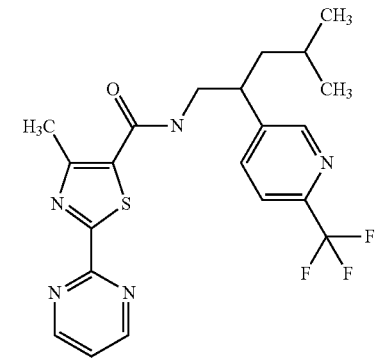 [SMILES: Cc1nc(-c2ncccn2)sc1C(=O)NCC(CC(C)C)c1ccc(C(F)(F)F)nc1] | 4-methyl-N-{4-methyl-2-[6-(trifluoromethyl)pyridin-3-yl]pentyl}-2-pyrimidin-2-yl-1,3-thiazole-5-carboxamide | 450.23 | 1.22 | * |

TABLE I-continued

Representative 5-Membered Heterocyclic Amides and Related Compounds

| | Compound | Name | MS | RT | $IC_{50}$ |
|---|---|---|---|---|---|
| 307 | | 2-(6-oxopyridazin-1(6H)-yl)-N-[(1-pyridin-3-ylcyclohexyl)methyl]-4-(trifluoromethyl)-1,3-thiazole-5-carboxamide | 464.14 | 1.02 | * |
| 308 | | N-[(1-pyridin-3-ylcyclohexyl)methyl]-2-(1H-1,2,3-triazol-1-yl)-4-(trifluoromethyl)-1,3-thiazole-5-carboxamide | 437.15 | 1.05 | * |
| 309 | | N-[(1-pyridin-3-ylcyclohexyl)methyl]-2-(2H-1,2,3-triazol-2-yl)-4-(trifluoromethyl)-1,3-thiazole-5-carboxamide | 437.14 | 1.06 | * |
| 310 | | N-[(1-pyridin-3-ylcyclohexyl)methyl]-2-(1H-1,2,4-triazol-1-yl)-4-(trifluoromethyl)-1,3-thiazole-5-carboxamide | 437.16 | 1.05 | * |

TABLE I-continued

Representative 5-Membered Heterocyclic Amides and Related Compounds

| | Compound | Name | MS | RT | IC$_{50}$ |
|---|---|---|---|---|---|
| 311 | | 4-methyl-2-pyridin-3-yl-N-[(1-pyridin-3-ylcyclohexyl)methyl]-1,3-thiazole-5-carboxamide | 393.21 | 1.02 | * |
| 312 | | N-{[1-(4-methylpiperazin-1-yl)cyclohexyl]methyl}-2-pyrimidin-2-yl-4-(trifluoromethyl)-1,3-thiazole-5-carboxamide | 469.21 | 1.06 | * |
| 313 | | N-[(1-piperazin-1-ylcyclohexyl)methyl]-2-pyrimidin-2-yl-4-(trifluoromethyl)-1,3-thiazole-5-carboxamide | 455.19 | 1.05 | * |
| 314 | | N-[2-(4-chlorophenyl)-2-morpholin-4-ylethyl]-2-pyrimidin-2-yl-4-(trifluoromethyl)-1,3-thiazole-5-carboxamide | 498.14 | 1.06 | * |

TABLE I-continued

Representative 5-Membered Heterocyclic Amides and Related Compounds

| | Compound | Name | MS | RT | IC$_{50}$ |
|---|---|---|---|---|---|
| 315 | | 4-ethyl-N-{2-[isopropyl(methyl)amino]-2-[4-(trifluoromethyl)phenyl]ethyl}-2-pyrimidin-2-yl-1,3-thiazole-5-carboxamide | 478.19 | 1.08 | * |
| 316 | | 2-pyrazin-2-yl-N-[(1-pyridin-3-ylcyclohexyl)methyl]-4-(trifluoromethyl)-1,3-thiazole-5-carboxamide | 448.17 | 1.08 | * |
| 317 | | N-[(1-pyridin-3-ylcyclohexyl)methyl]-4-(trifluoromethyl)-2,2'-bi-1,3-thiazole-5-carboxamide | 453.13 | 1.1 | * |
| 318 | | 2-(1H-indol-5-yl)-N-[(1-pyridin-3-ylcyclohexyl)methyl]-4-(trifluoromethyl)-1,3-thiazole-5-carboxamide | 485.20 | 1.13 | * |

TABLE I-continued

Representative 5-Membered Heterocyclic Amides and Related Compounds

| Compound | | Name | MS | RT | IC$_{50}$ |
|---|---|---|---|---|---|
| 319 | | N-[(1-pyridin-3-ylcyclohexyl)methyl]-2-quinolin-8-yl-4-(trifluoromethyl)-1,3-thiazole-5-carboxamide | 497.20 | 1.16 | * |
| 320 | | N-(4-methyl-2-pyridin-3-ylpentyl)-2-pyrimidin-2-yl-4-(trifluoromethyl)-1,3-thiazole-5-carboxamide | | | * |
| 321 | | 2-pyridin-2-yl-N-[(1-pyridin-3-ylcyclohexyl)methyl]-4-(trifluoromethyl)-1,3-thiazole-5-carboxamide | | | * |

Example 4

P2X7 Calcium Mobilization Assay

This Example illustrates representative calcium mobilization assays for use in evaluating test compounds for agonist and antagonist activity.

A. High Throughput Assay of P2X7 Receptors

SH-SY5Y cells, ATCC Number CRL-2266, (American Type Culture Collection, Manassas, Va.) are cultured under DMEM/High medium supplemented with 10% FBS, and 10 mM HEPES (Invitrogen Corp., Carlsbad, Calif.) in 5% $CO_2$ and at 37° C. One day prior to the experiment, cells are plated at a density of 100,000 cells/well in a 96 well black/clear TC plate (Corning® Costar®, Sigma-Aldrich Co., St. Louis, Mo.). At the beginning of the experiment, the culture medium is removed and cells are incubated with 50 µL of 2.3 µM Fluo-4 AM dye (Invitrogen Corp.) in the assay solution (5 mM KCl, 9.6 mM $NaH_2PO_4 \cdot H_2O$, 25 mM HEPES, 280 mM sucrose, 5 mM glucose, and 0.5 mM $CaCl_2$; pH is adjusted to 7.4 with NaOH) for an hour at 37° C. After one hour dye incubation, wells are rinsed once with 50 µL assay solution, and are then incubated for an hour at room temperature with 100 µL assay solution containing the test compound. The final concentration of test compound generally ranges from 1 to 2500 nM; for positive control cells, no test compound is added. After the one hour incubation, plates are transferred to a FLIPR$^{TETRA}$ instrument (Molecular Devices, Sunnyvale, Calif.) for calcium mobilization analysis.

For determination of antagonist activity, 50 µL, of P2X$_7$ agonist (2'(3)-O-(4-benzoyl-benzoyl)adenosine 5'-triphosephate (BzATP; Sigma-Aldrich) in the assay solution is transferred using the FLIPR into the plate, such that the final agonist concentration is 80 µM (about EC$_{50}$). In negative control cells, 50 µL of assay solution without agonist is added at this stage. The peak fluorescence signal over a 2 minute period is then measured.

The data is analyzed as follows. First, the average maximum relative fluorescent unit (RFU) response from the negative control wells (no agonist) is subtracted from the maximum response detected for each of the other experimental wells. Second, average maximum RFU response is calculated for the positive control wells (agonist wells). Then, percent inhibition for each compound tested is calculated using the equation:

Percent Inhibition=100−100×(Peak Signal in Test Cells/Peak Signal in Control Cells)

The % inhibition data is plotted as a function of test compound concentration and test compound $IC_{50}$ is determined using a linear regression in which x is ln(concentration of test compound) and y is ln(percent inhibition/(100−percent inhibition). Data with a percent inhibition that is greater than 90% or less than 15% are rejected and are not used in the regression. The $IC_{50}$ is $e^{(-intercept/slope)}$.

Alternatively, a sigmoidal fit can be used, such as that achieved using KALEIDAGRAPH software (Synergy Software, Reading, Pa.), which determines the best fit of the data to the equation:

$$y=m_1*(1/(1+(m_2/m_0)^{m_3})$$

where y is the percent inhibition, $m_0$ is the concentration of the agonist, $m_1$ is the maximum RFU, $m_2$ corresponds to the test compound $IC_{50}$ (the concentration required to provide a 50% decrease, relative to the response observed in the presence of agonist and without antagonist) and $m_3$ is the Hill coefficient.

For antagonists of the $P2X_7$ receptor, the calculated $IC_{50}$ is preferably below 20 micromolar, more preferably below 10 micromolar, even more preferably below 5 micromolar and most preferably below 1 micromolar.

Similar assays are performed in the absence of added agonist for the determination of agonist activity of the test compounds. Within such assays, the ability of a test compound to act as an agonist of $P2X_7$ receptor is determined by measuring the fluorescence response elicited by the test compound as a function of compound concentration. $P2X_7$ receptor antagonists that exhibit no detectable agonist activity elicit no detectable fluorescence response at a concentration of 2,500 nM.

B. Electrophysiology Assay for P2X7 Receptors

SH-SY5Y cells are cultured under DMEM/High medium supplemented with 10% FBS, and 10 mM HEPES (Invitrogen Corp., Carlsbad, Calif.) in 5% $CO_2$ and at 37° C., and are split onto 12 mm round Poly-D-Lysine (PDL) coated coverslips (BD Biosciences, San Jose, Calif.) in a 35 mm dish with a density of 130K cells/dish a day prior to the experiment. Whole cell voltage clamp recordings are made with the Axopatch-200B amplifier (Axon Instruments, Foster City, Calif.). The recording electrodes are pulled from borosilicate pipettes (World Precision Instruments, Sarasota, Fla.) on a horizontal puller (Sutter Instrument Model P-87) and have resistances ranging from 2 to 3 MΩ when backfilled with internal solution. All voltage protocols are generated using pClamp 8 (Axon Instruments) software. Data are digitized at 1 or 5 kHz and recorded onto a PC for further analysis. Data are analyzed using Clampfit (Axon Instruments), Excel (Microsoft, Redmond, Wash.), and Origin software (MicroCal, LLC; Northampton, Mass.). All whole-cell recordings are conducted at room temperature. Internal solution contains (in mM): 100 KF, 40 KCl, 5 NaCl, 10 EGTA and 10 HEPES (pH=7.4 adjusted with KOH). The external solution contains 70 mM NaCl, 0.3 mM $CaCl_2$, 5 mM KCl, 20 mM HEPES, 10 mM glucose, and 134 mM sucrose (pH=7.4 adjusted with NaOH). All chemicals are from Sigma, unless otherwise stated.

$P2X_7$ receptor is activated by 200 μM of $P2X_7$ agonist, BzATP. At a holding potential of −80 mV, the activated inward current is recorded in the presence and absence of the test compound. Then, percent inhibition for each compound tested is calculated using the equation:

% Inhibition=100−100×(Current Amplitude in Compound/Current Amplitude in Control).

To determine a test compound's $IC_{50}$ for $P2X_7$ receptor electrophysiologically, several concentrations of the compound are tested and their inhibitions on $P2X_7$ currents are calculated as above. This dose-response curve is best fitted using Origin software (Microcal, MA) with the following equation:

Percent Inhibition=$100/(1+(IC_{50}/C)^N)$ where C is the concentration of the antagonist, N is the Hill coefficient, and $IC_{50}$ represents the compound $IC_{50}$ value against $P2X_7$ receptors.

Example 5

Carrageenan-Induced Mechanical Hyperalgesia (Paw Pressure) Assay for Determining Pain Relief This Example illustrates a representative method for assessing the degree of pain relief provided by a test compound.

Adult male Sprague Dawley rats (200-300 g; obtained from Harlan Sprague Dawley, Inc., Indianapolis, Ind.) are housed under a 12 h light/dark cycle with access to food and water ad libitum. For the assay, all animals are habituated once, baselined twice and tested once, with each procedure being conducted on a separate day. Prior to each day's procedure, animals are allowed to acclimate for at least 1 hour in the testing room before the start of the procedure. For habituation, each animal is gently restrained with each hindpaw consecutively extended in front of the animal as is necessary for testing. This procedure is performed by alternating hindpaws and repeated three times for each hindpaw. Animals are then subjected to the first baseline, second baseline and testing on consecutive days. For each baseline, the animal is restrained as in the habituation session and the paw tested using the paw pressure testing apparatus (Digital Randall Selitto, IITC Inc., Woodland Hills, Calif.). Animals are baselined and tested in groups of ten, each animal being tested once on the left and right hindpaws, followed by the next consecutive animal. This procedure is repeated three times for a total of three measurements on each hindpaw. If any individual read is drastically different (varies by more than about 100 g) from the other two on a given hindpaw, the hindpaw is retested a $4^{th}$ time, and the average of the three most consistent scores is used. On test day, all animals are injected with 0.1 mL intraplantar 0.5%-1.5% carrageenan (dissolved in saline) 3 hours prior to testing. Test compounds or vehicle may be administered by various routes at various timepoints prior to testing, but for any particular assay, the routes and timepoints are the same for animals in each treatment group administered test compound (a different dosage of test compound may be administered to each such group) and those in the treatment group administered vehicle control. If a compound is orally administered, the animals are food-deprived the evening before testing. As with the baseline, each hindpaw is tested three times and the results recorded for analysis.

Hypersensitivity of nociception values are calculated for each treatment group as the mean of the left foot gram force scores on test day (left foot only or LFO score). Statistical significance between treatment groups is determined by running an ANOVA on LFO scores followed with a least significant difference (LSD) post hoc test. A p<0.05 is considered to be a statistically significant difference.

Compounds are said to relieve pain in this model if they result in a statistically significant reduction in hypersensitivity of nociception values compared to vehicle controls, determined as described above, when administered (0.01-50 mg/kg, orally, parenterally or topically) immediately prior to testing as a single bolus, or for several days: once or twice or three times daily prior to testing.

What is claimed is:

1. The compound N-[2-(4-chlorophenyl)-2-morpholin-4-ylethyl]-2-pyrimidin-2-yl-4-(trifluoromethyl)-1,3-thiazole-5-carboxamide or salt or hydrate thereof.

2. A pharmaceutical composition comprising the compound according to claim 1 in combination with a physiologically acceptable carrier or excipient.

3. A method of treating a condition responsive to $P2X_7$ receptor modulation comprising administering a therapeutically effective amount of a compound according to claim 1 to a patient in need thereof.

4. A method of treating pain or inflammation comprising administering a therapeutically effective amount of N-[2-(4-chlorophenyl)-2-morpholin-4-ylethyl]-2-pyrimidin-2-yl-4-(trifluoromethyl)-1,3-thiazole-5-carboxamide or salt or hydrate thereof to a patient in need thereof.

5. The method of claim 4 wherein the pain is arthritis-associated pain, visceral pain, dental pain, headache, stump pain, meralgia paresthetica, or burning-mouth syndrome.

6. The method of claim 4 wherein the pain is associated with nerve and root damage, causalgia, neuritis, neuronitis, or neuralgia.

7. The method of claim 4 wherein the pain is surgery-related pain, musculoskeletal pain, central nervous system pain, or spinal pain.

8. The method of claim 4 wherein the pain is Charcot's pains, ear pain, muscle pain, eye pain, or orofacial pain.

9. The method of claim 4 wherein the pain is carpel tunnel syndrome, acute back pain or chronic back pain.

10. The method of claim 4 wherein the pain is scar pain, hemorrhoidal pain, dyspeptic pains, angina, nerve root pain, or complex regional pain syndrome.

11. The method of claim 4 wherein the pain is gout-associated pain, cancer-associated pain, pain associated with venom exposure, trauma-associated pain or pain associated with autoimmune diseases or immunodeficiency disorders.

12. The method of claim 4 wherein the pain results from hot flashes, burns, sunburn, or exposure to heat, cold or external chemical stimuli.

13. A method of treating neuropathic pain comprising administering a therapeutically effective amount of N-[2-(4-chlorophenyl)-2-morpholin-4-ylethyl]-2-pyrimidin-2-yl-4-(trifluoromethyl)-1,3-thiazole-5-carboxamide or salt or hydrate thereof to a patient in need thereof.

* * * * *